(12) United States Patent
Beier et al.

(10) Patent No.: US 8,951,770 B2
(45) Date of Patent: Feb. 10, 2015

(54) GH8 XYLANASE VARIANTS

(75) Inventors: Lars Beier, Lyngby (DK); Miguel Duarte Toscano, Copenhagen (DK); Esben Peter Friis, Herlev (DK); Merete Moeller Engelsen, Frederiksberg (DK); Henrik Lundkvist, Malmo (SE); Sune Sauer Lobedanz, Lyngby (DK)

(73) Assignee: Novozymes A/S, Bagsvaerd (DK)

( * ) Notice: Subject to any disclaimer, the term of this patent is extended or adjusted under 35 U.S.C. 154(b) by 121 days.

(21) Appl. No.: 13/511,546

(22) PCT Filed: Dec. 9, 2010

(86) PCT No.: PCT/EP2010/069249
§ 371 (c)(1),
(2), (4) Date: May 23, 2012

(87) PCT Pub. No.: WO2011/070101
PCT Pub. Date: Jun. 16, 2011

(65) Prior Publication Data
US 2012/0288585 A1    Nov. 15, 2012

Related U.S. Application Data

(60) Provisional application No. 61/329,362, filed on Apr. 29, 2010.

(30) Foreign Application Priority Data

Dec. 9, 2009    (EP) .................................... 09178558

(51) Int. Cl.
| C12N 9/24 | (2006.01) |
| C12Q 1/34 | (2006.01) |
| A21D 2/26 | (2006.01) |
| A21D 8/04 | (2006.01) |
| A21D 13/00 | (2006.01) |
| A21D 10/00 | (2006.01) |

(52) U.S. Cl.
CPC ................ *A21D 8/042* (2013.01); *C12N 9/248* (2013.01)
USPC ............... 435/200; 435/18; 426/20; 426/549; 426/391; 426/496

(58) Field of Classification Search
CPC ............ C12P 19/14; C12P 19/02; C12P 7/10; C12P 21/02; C12N 9/248; C12N 9/2482; C12N 9/2485; C12Y 302/01008; C12Y 302/01032; C12Y 302/01136; C12Y 302/01156
USPC .............. 435/200, 69.1, 18; 530/350; 426/94; 424/94.61
See application file for complete search history.

(56) References Cited

PUBLICATIONS

Branden et al. (Introduction to Protein Structure, Garland Publishing Inc., New York, p. 247, 1991).*
Seffernick et al., J. Bacteriol. 183(8):2405-2410, 2001.*
Witkowski et al., Biochemistry 38:11643-11650, 1999.*
Watanabe et al., GenBank accession No. BAF49077, Mar. 16, 2007.*
Watanabe et al., Biosci. Biotechnol. Biochem. 72(4):951-958, Apr. 7, 2008.*
Collins et al., J Cereal Science, vol. 43, pp. 79-84 (2009).
Collins et al., Fems Microbiol Revs, vol. 29, No. 1, pp. 3-23 (2005).
Medigue et al., AC Q3IER3 database Uniprot (2005).
Read et al., AC C4TR35 database Uniprot (2008).
Yoon et al., Biochem Mol Biol Intl, vol. 45, No. 2, pp. 337-347 (1998).
Yoon et al., AC 052730 database Uniprot (1998).
Yoon et al., AC AF045480 database EMB (1998).
Davies et al., 1996, Structure, vol. 3, pp. 853-859.
Henrissat et al., Biochem J, vol. 280, pp. 309-316 (1991).
Henrissat et al., Biochem J, vol. 293, pp. 781-788 (1993).
Henrissat et al., Biochem J, vol. 316, pp. 695-695 (1996).

* cited by examiner

*Primary Examiner* — Delia Ramirez
(74) *Attorney, Agent, or Firm* — Kristin J. McNamara

(57) ABSTRACT

The present invention relates to isolated polypeptides having xylanase activity and isolated polynucleotides encoding the polypeptides. The invention also relates to nucleic acid constructs, vectors, and host cells comprising the polynucleotides as well as methods of producing and using the polypeptides.

20 Claims, 2 Drawing Sheets

GH8 XYLANASE VARIANTS

CROSS-REFERENCE TO RELATED APPLICATIONS

This application is a 35 U.S.C. 371 national application of PCT/EP2010/069249 filed Dec. 9, 2010, which claims priority or the benefit under 35 U.S.C. 119 of European application no. 09178558.4 filed Dec. 9, 2009 and U.S. provisional application No. 61/329,362 filed Apr. 29, 2010 the contents of which are fully incorporated herein by reference.

REFERENCE TO A SEQUENCE LISTING

This application contains a Sequence Listing in computer readable form. The computer readable form is incorporated herein by reference.

FIELD OF THE INVENTION

The present invention relates to methods of producing a variant of a parent GH8 xylanase polypeptide which retains xylanase activity. It also relates to isolated GH8 polypeptide variants having xylanase activity and isolated polynucleotides encoding the polypeptide variants. The invention further relates to nucleic acid constructs, vectors, and host cells comprising the polynucleotides as well as methods of producing and using the polypeptides, such as, in the preparation of a dough or a baked product prepared from the dough. More particularly, it relates to such a process where the dough is less sticky than if prepared with the parent GH8 xylanase and/or where the bread has an increased volume.

BACKGROUND OF THE INVENTION

Carbohydrates and glycol-conjugates are substrates for glycosyl transferases (GTs) and glycoside hydrolases (GHs). The structure of glycoside hydrolases began to be solved starting from the 1980s. At the same time, new GH proteins were discovered and their amino acid sequence determined. Two main observations emerged from the new data. 1) The classical E.C. nomenclature system for naming enzyme families was not precise enough to classify the increasing number of enzymes that had different structure yet performed the same enzymatic reaction. 2) Enzymes related by homology could have different enzymatic activity thus also making the E.C. nomenclature system confusing for these related enzymes.

A new family based nomenclature system was proposed by Bernard Henrissat in 1991 based on the structure of the enzymes (Henrissat B., A classification of glycosyl hydrolases based on amino-acid sequence similarities. Biochem. J. 280:309-316 (1991); Henrissat B., Bairoch A. New families in the classification of glycosyl hydrolases based on amino-acid sequence similarities. Biochem. J. 293:781-788 (1993); Henrissat B., Bairoch A. Updating the sequence-based classification of glycosyl hydrolases. Biochem. J. 316:695-696 (1996) and Davies G., Henrissat B. Structures and mechanisms of glycosyl hydrolases. Structure 3:853-859 (1995).). Updated classifications are available on the Carbohydrate-Active EnZymes website (CAZy).

The classification of glycoside hydrolases in families based on amino acid sequence similarities was introduced because there is a direct relationship between sequence and folding similarities, and such a classification is expected to:
 (i) reflect the structural features of the enzymes, which cannot be reflected by the substrate specificity alone,
 (ii) help to reveal the evolutionary relationships between the enzymes, and
 (iii) provide a convenient tool to derive mechanistic information.

Amino acid sequences grouped by nature of their similarity to a particular GH family can give ideas as to the activity of the new hypothetical protein. Some of these amino acid sequences, grouped in a GH family by homology have later been suggested to have certain enzymatic activity. So, in short, grouping a new amino acid sequence in a GH family does not specifically indicate the exact enzymatic activity. The enzymatic activity must be demonstrated by an activity assay of the cloned or purified protein. If the assay is difficult determination of the proteins actual function can remain un-revealed for years.

Glycoside hydrolase family 8 (GH8) comprises enzymes with several known activities; endoglucanase (EC:3.2.1.4); lichenase (EC:3.2.1.73); chitosanase (EC:3.2.1.132).

Some xylanases are inhibited by components found in flour which makes them unsuitable for the manufacture of products based on a dough. GH8 xylanases are not inhibited by components in dough and they require only a very low dosage in the dough to provide a volume increase in the baked bread. Unfortunately, as is well-known in the art of baking, use of any of the naturally occurring GH8 xylanases identified to date results in a sticky dough which is problematic to handle.

SUMMARY OF THE INVENTION

The inventors identified a characteristic amino acid motif conserved throughout a diverse range of GH8 xylanases; it comprises the glutamic acid (E) nucleophile of the active site in those xylanases:

(SEQ ID NO: 1)
[ST]E[GAS]X[GAS][YFW].

Molecular modelling was employed and a structural loop lining the active site of the GH8 xylanases was identified (see FIG. 1). The loop comprised about 20 consecutive amino acids directly flanking the conserved GH8 motif on the N-terminal side (FIG. 1).

A synthetic expression construct (SEQ ID NO:2) was manufactured encoding the mature GH8 xylanase from Bacillus sp. KK-1 (UNIPROT accession number: O52730; SEQ ID NO:4). The synthetic construct comprised a sequence encoding a heterologous signal peptide fused to a mature GH8 xylanase polypeptide coding sequence; the nucleic acid sequence of the construct was optimized for Bacillus expression. The amino acid sequences of the encoded heterologous signal peptide and the mature GH8 xylanase are shown in SEQ ID NO:3. The amino acid sequences of the mature polypeptides in SEQ ID NO:3 and SEQ ID NO:4 are identical, of course.

The conserved GH8 motif is found in amino acid positions 65-70 of the mature polypeptide shown in SEQ ID NO:3 or 4.

The loop flanking the conserved GH8 motif in SEQ ID NO:3 was mutated by site-specific mutagenesis of amino acids comprised therein. Deletions, insertions and substitutions of single amino acids were made, as well as some combinations thereof, to produce a number of GH8 variants having xylanase activity, vide infra. The activity of the variants was investigated in baking applications and they showed surprisingly interesting and promising properties.

Accordingly, in a first aspect, the present invention relates to a method of producing a variant of a parent GH8 xylanase polypeptide, said method comprising the steps of:
a) providing a polynucleotide encoding a mature parent GH8 xylanase polypeptide comprising a first conserved GH8 xylanase motif:

[ST]E[GAS]X[GAS][YFW], (SEQ ID NO: 1)

b) introducing at least one mutation into the encoding polynucleotide, whereby at least one alteration is introduced in the encoded polypeptide in one or more of the 20 amino acid positions flanking the first conserved GH8 xylanase motif on the N-terminal side, and
c) expressing the mutated polynucleotide in a suitable host cell and under conditions conducive to producing the variant,
wherein the variant has xylanase activity.

In a second aspect, the invention relates to an isolated variant of a parent GH8 xylanase polypeptide comprising a first conserved GH8 xylanase motif:

[ST]E[GAS]X[GAS][YFW], (SEQ ID NO: 1)

wherein the variant comprises at least one amino acid alteration compared to the parent in one or more of the 20 amino acid positions flanking the first conserved GH8 motif on the N-terminal side, and wherein the variant has xylanase activity.

In a third aspect, the invention relates to an isolated polynucleotide comprising a nucleotide sequence that encodes the variant polypeptide of the second aspect.

A fourth aspect relates to a nucleic acid construct comprising the polynucleotide of the third aspect.

A fifth aspect relates to a recombinant expression vector comprising the nucleic acid construct of the fourth aspect.

A sixth aspect relates to a recombinant host cell comprising the recombinant expression vector of the previous aspect, the nucleic acid construct of the fourth aspect or the polynucleotide of the third aspect operably linked to one or more control sequences that direct the production of the variant polypeptide.

A seventh aspect relates to a method of producing the variant polypeptide of the second aspect, comprising: (a) cultivating a host cell comprising a nucleic acid construct comprising a nucleotide sequence encoding the variant polypeptide under conditions conducive for production of the variant; and (b) recovering the variant.

Other aspects relate to a composition comprising the variant polypeptide of the second aspect, a method for the preparation of a baked product, said method comprising the step of adding to a dough of said baked product the variant polypeptide of the second aspect or a bread improving composition comprising the variant polypeptide of the second aspect.

Another aspect of the invention relates to a method for increasing the loaf volume of a baked product, comprising the step of adding during the mixing of the dough of said baked product, a sufficient amount of the variant polypeptide of the second aspect or a composition comprising said polypeptide.

Yet another aspect of the invention relates to a method for increasing the loaf volume of a baked product or for increasing the width of cut on the surface of a baked product, comprising the step of adding during the mixing of the dough of said baked product, a sufficient amount the variant polypeptide of the second aspect or a composition comprising said polypeptide.

In a final aspect, the invention relates to a bread improver composition for increasing the loaf volume of a baked product or for increasing the width of cut on the surface of a baked product, characterised in that it comprises at least one variant polypeptide of the second aspect.

DEFINITIONS

Xylanase activity: For the purposes of the present invention any of the commercially available xylanase activity measurement kits is suitable to determine xylanase activity. The sole purpose of the xylanase activity measurement in the present invention is as a primary screen to ensure that the GH8 xylanase variants of the invention have not inadvertently been inactivated by the amino acid alteration(s) introduced therein. One suitable way of measuring the xylanase activity is as follows:

Substrate:
  AZCL-Arabinoxylan from wheat (Megazyme).
Assay Buffer:
  50 mM B&R (50 mM $H_3PO_4$, 50 mM acetic acid, 50 mM $H_3BO_3$), 50 mM KCl, 1 mM $CaCl_2$, 0.01% Triton X-100, pH adjusted to 6.0 using NaOH.
Enzyme:
  All enzyme dilutions are made in distilled water with 0.01% Triton X-100.
Substrate Solution:
  A 0.2% (w/v) slurry of AZCL-Arabinoxylan substrate is prepared in assay buffer. Cut the tip of a 1000 uL pipette tip to siphon off homogenous aliquots.
Standard:
  BioFeed Wheat™ (Novozymes A/S), diluted in 0.01% Triton X-100. FXU/ml: 0.05; 0.10; 0.15; 0.20; 0.25; 0.30; 0.40.
Analysis:
1. Eppendorf termomixer at 37° C.
2. 750 µl substrate solution is placed on ice for 5 minutes.
3. 50 µl enzyme sample is added.
4. Incubation for 15 min. at 1400 rpm, 37° C.
5. Reaction is stopped in ice/waterbath.
6. Centrifugation 5 min. at 10.000 rpm, 4° C.
7. 200 µl supernatant is transferred to a microtiter plate
8. Endpoint absorbance is measured, OD595 nm
Note: The absorbance, OD595 nm, should be in the range of 0-1.5.

Note: In this assay, the standard curve is made from a FXU standard, but the activity measured is xylanase units. FXU is measured on azo-xylan not azcl-xylan.

Standard Curve:

A standard solution is prepared from BioFeed Wheat™ (Novozymes A/S) with a declared xylanase activity of 439 FXU(W)/g. 2.05 g BioFeed Wheat™ is dissolved up to 100 mL in 0.9% NaCl, which provides a solution with an activity of 9.0 FXU/mL (frozen stock kept at −80° C.).

Immediately prior to carrying out the assay the stock is diluted 10 times to provide the assay stock solution (stock).

| Standard | μl stock | μl buffer | dilution | std-1 FXU(W)/ml |
|---|---|---|---|---|
| 1 | — | 180 | | 0 |
| 2 | 20 | 180 | 10 | 0.09 |
| 3 | 60 | 180 | 4 | 0.225 |
| 4 | 180 | 180 | 2 | 0.45 |
| 5 | 540 | 180 | 1.33 | 0.675 |
| 6 | 60 | — | 1 | 0.9 |

Calculations:

The standard curve is made from A595 for the enzyme standard subtracted std1 (as shown below).

The activity is calculated from A595 for the enzyme subtracted a blank-value. Since the enzyme dilution often is without colour, std1 is used as blank value in these cases.

Figure 1:
FIG. 1 (landscape) shows a section of a molecular model of the parent GH8 xylanase from *Bacillus* sp. KK-1 (UNIPROT accession number: O52730; SEQ ID NO:4). A close-up of the substrate binding pocket is provided (light grey net) with the active site (dark grey net) just below the center of the figure. The loop (dark grey coil) flanking the first conserved GH8 xylanase motif (not shown) on the N-terminal side is found just above the active site, may be protruding slightly into the substrate binding pocket. The three loop amino acid residues 53 (Asp), 55 (Asn) and 59 (Gly) are indicated (dark grey) and a stick-model is shown of a substrate molecule in the substrate pocket.
Figure 2:
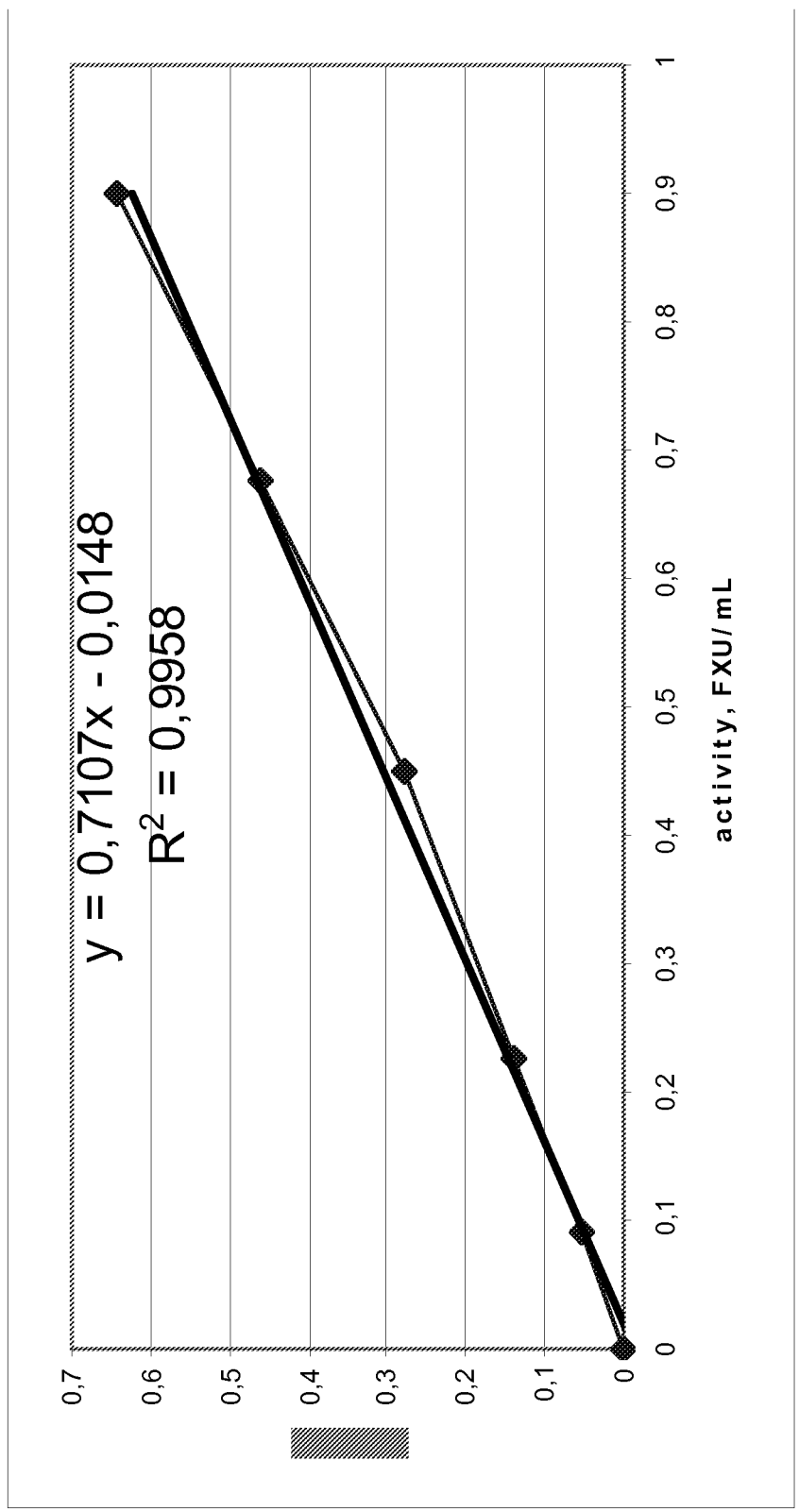
FIG. 2 (landscape) shows a xylanase activity standard curve calculated as shown in the definition section below; the x-axis is the xylanase activity in FXU/ml and the y-axis is the absorbance at 595 nm (Abs595 or OD595 nm).

Example of a standard curve calculation, the curve is shown in FIG. 2:

| Standard | μl stock | μl buffer | dilution | std-1 FXU(W)/ml | A595 | A595-std1 |
|---|---|---|---|---|---|---|
| 1 | — | 180 | | 0 | 1.1064 | 0 |
| 2 | 20 | 180 | 10 | 0.09 | 1.1588 | 0.0524 |
| 3 | 60 | 180 | 4 | 0.225 | 0.2472 | 0.1408 |
| 4 | 180 | 180 | 2 | 0.45 | 0.385 | 0.2786 |
| 5 | 540 | 180 | 1.33 | 0.675 | 0.5659 | 0.4595 |
| 6 | 60 | — | 1 | 0.9 | 0.7492 | 0.6428 |

The mature variant polypeptides of the present invention have at least 20%, preferably at least 40%, more preferably at least 50%, more preferably at least 60%, more preferably at least 70%, more preferably at least 80%, even more preferably at least 90%, most preferably at least 95%, and even most preferably at least 100% of the xylanase activity of their mature GH8 parent xylanase polypeptide.

Isolated polypeptide: The term "isolated polypeptide" as used herein refers to a polypeptide that is isolated from a source. In a preferred aspect, the polypeptide is at least 1% pure, preferably at least 5% pure, more preferably at least 10% pure, more preferably at least 20% pure, more preferably at least 40% pure, more preferably at least 60% pure, even more preferably at least 80% pure, and most preferably at least 90% pure, as determined by SDS-PAGE.

Mature polypeptide: The term "mature polypeptide" is defined herein as a polypeptide in its final form following translation and any post-translational modifications, such as N-terminal processing, C-terminal truncation, glycosylation, phosphorylation, etc. In one aspect, the mature polypeptide comprises or consists of the amino acid positions listed in table 1, vide infra.

Mature polypeptide coding sequence: The term "mature polypeptide coding sequence" is defined herein as a nucleotide sequence that encodes a mature polypeptide having xylanase activity. In one aspect, the mature polypeptide coding sequence comprises or consists of the nucleotides encoding the mature polypeptides comprising or consisting of the amino acid positions listed in table 1, vide infra.

Sequence Identity: The relatedness between two amino acid sequences or between two nucleotide sequences is described by the parameter "sequence identity".

For purposes of the present invention, the degree of sequence identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends in Genetics* 16: 276-277), preferably version 3.0.0 or later. The optional parameters used are gap open penalty of 10, gap extension penalty of 0.5, and the EBLOSUM62 (EMBOSS version of BLOSUM62) substitution matrix. The output of Needle labeled "longest identity" (obtained using the -nobrief option) is used as the percent identity and is calculated as follows:

(Identical Residues×100)/(Length of Alignment−Total Number of Gaps in Alignment)

For purposes of the present invention, the degree of sequence identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 3.0.0 or later. The optional parameters used are gap open penalty of 10, gap extension penalty of 0.5, and the EDNAFULL (EMBOSS version of NCBI NUC4.4) substitution matrix. The output of Needle labeled "longest identity" (obtained using the -nobrief option) is used as the percent identity and is calculated as follows:

(Identical Deoxyribonucleotides×100)/(Length of Alignment−Total Number of Gaps in Alignment)

Homologous sequence: The term "homologous sequence" is defined herein as a predicted protein having an E value (or expectancy score) of less than 0.001 in a tfasty search (Pearson, W. R., 1999, in *Bioinformatics Methods and Protocols*, S. Misener and S. A. Krawetz, ed., pp. 185-219) with any of the polypeptides shown in any of SEQ ID NO's: 3-154 and 159 or the mature part thereof.

Polypeptide fragment: The term "polypeptide fragment" is defined herein as a polypeptide having one or more (several) amino acids deleted from the amino and/or carboxyl terminus of the mature polypeptide of any of SEQ ID NO's: 3-154 and 159; or a homologous sequence thereof; wherein the fragment has xylanase activity.

Subsequence: The term "subsequence" is defined herein as a nucleotide sequence having one or more (several) nucleotides deleted from the 5' and/or 3' end of the mature polypeptide coding sequence or a homologous sequence thereof; wherein the subsequence encodes a polypeptide fragment having xylanase activity.

Allelic variant: The term "allelic variant" denotes herein any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

Isolated polynucleotide: The term "isolated polynucleotide" as used herein refers to a polynucleotide that is isolated from a source. In a preferred aspect, the polynucleotide is at least 1% pure, preferably at least 5% pure, more preferably at least 10% pure, more preferably at least 20% pure, more preferably at least 40% pure, more preferably at least 60% pure, even more preferably at least 80% pure, and most preferably at least 90% pure, as determined by agarose electrophoresis.

Coding sequence: When used herein the term "coding sequence" means a nucleotide sequence, which directly specifies the amino acid sequence of its protein product. The boundaries of the coding sequence are generally determined by an open reading frame, which usually begins with the ATG start codon or alternative start codons such as GTG and TTG and ends with a stop codon such as TAA, TAG, and TGA. The coding sequence may be a DNA, cDNA, synthetic, or recombinant nucleotide sequence.

cDNA: The term "cDNA" is defined herein as a DNA molecule that can be prepared by reverse transcription from a mature, spliced, mRNA molecule obtained from a eukaryotic cell. cDNA lacks intron sequences that may be present in the corresponding genomic DNA. The initial, primary RNA transcript is a precursor to mRNA that is processed through a series of steps before appearing as mature spliced mRNA. These steps include the removal of intron sequences by a process called splicing. cDNA derived from mRNA lacks, therefore, any intron sequences.

Nucleic Acid Construct: The term "nucleic acid construct" as used herein refers to a nucleic acid molecule, either single- or double-stranded, which is isolated from a naturally occurring gene or which is modified to contain segments of nucleic acids in a manner that would not otherwise exist in nature or which is synthetic. The term nucleic acid construct is synonymous with the term "expression cassette" when the nucleic acid construct contains the control sequences required for expression of a coding sequence of the present invention.

Control sequences: The term "control sequences" is defined herein to include all components necessary for the expression of a polynucleotide encoding a polypeptide of the present invention. Each control sequence may be native or foreign to the nucleotide sequence encoding the polypeptide or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the nucleotide sequence encoding a polypeptide.

Operably linked: The term "operably linked" denotes herein a configuration in which a control sequence is placed at an appropriate position relative to the coding sequence of a polynucleotide sequence such that the control sequence directs the expression of the coding sequence of a polypeptide.

Expression: The term "expression" includes any step involved in the production of a polypeptide including, but not limited to, transcription, post-transcriptional modification, translation, post-translational modification, and secretion.

Expression vector: The term "expression vector" is defined herein as a linear or circular DNA molecule that comprises a polynucleotide encoding a polypeptide of the present invention and is operably linked to additional nucleotides that provide for its expression.

Host cell: The term "host cell", as used herein, includes any cell type that is susceptible to transformation, transfection, transduction, and the like with a nucleic acid construct or expression vector comprising a polynucleotide of the present invention.

Modification: The term "modification" means herein any chemical modification of the polypeptide comprising or consisting of the mature polypeptide of SEQ ID NO: 2; or a homologous sequence thereof; as well as genetic manipulation of the DNA encoding such a polypeptide. The modification can be a substitution, a deletion and/or an insertion of one or more (several) amino acids as well as replacements of one or more (several) amino acid side chains.

Artificial variant: When used herein, the term "artificial variant" means a polypeptide having xylanase activity produced by an organism expressing a modified polynucleotide sequence encoding a variant of any of the polypeptides shown in SEQ ID NO's: 3-154 and 159 having xylanase activity, or a variant of the mature parts thereof having xylanase activity. The modified nucleotide sequence is obtained through human intervention by modification of the encoding polynucleotide sequence or complete synthesis of an polynucleotide encoding the modified variant.

DETAILED DESCRIPTION OF THE INVENTION

In its most general form, the instant invention relates to a method of producing a variant of a parent GH8 xylanase polypeptide, said method comprising the steps of:

a) providing a polynucleotide encoding a mature parent GH8 xylanase polypeptide comprising a first conserved GH8 xylanase motif:

(SEQ ID NO: 1)
[ST]E[GAS]X[GAS][YFW], b) introducing at least one mutation into the encoding polynucleotide, whereby at least one alteration is introduced in the encoded polypeptide in one or more of the 20 amino acid positions flanking the first conserved GH8 xylanase motif on the N-terminal side, and c) expressing the mutated polynucleotide in a suitable host cell and under conditions conducive to producing the variant, wherein the variant has xylanase activity.

In a preferred embodiment of the first aspect, the mature parent GH8 xylanase polypeptide comprises an amino acid sequence at least 60% identical to the mature part of a GH8 xylanase selected from the group of GH8 xylanases shown in any of SEQ ID NO:3 to SEQ ID NO:154 and SEQ ID NO:159; preferably the amino acid sequence is at least 65%, more preferably at least 70%, more preferably at least 75%, more preferably at least 80%, more preferably at least 85%, even more preferably at least 90%, most preferably at least 95%, and even most preferably at least 96%, at least 97%, at least 98%, or at least 99% identical to the mature part of a GH8 xylanase selected from the group of GH8 xylanases shown in any of SEQ ID NO:3 to SEQ ID NO:154 and SEQ ID NO:159.

In another preferred embodiment of the first aspect, the mature parent GH8 xylanase comprises a second conserved GH8 xylanase motif:

(SEQ ID NO: 155)
[ND][AS]X[RLPQ].

Preferably, the mature parent GH8 xylanase comprises or consists of amino acids 28 to 433 of SEQ ID NO: 3.

In a preferred embodiment, the at least one alteration in the encoded polypeptide comprises a substitution, deletion, and/or insertion of one or more amino acids in one or more of the 20 amino acid positions flanking the first conserved GH8 xylanase motif on the N-terminal side.

It is also preferred that the at least one alteration in the encoded polypeptide in the first aspect of the invention comprises an insertion of one or more amino acids in one or more of the 15 amino acid positions flanking the first conserved GH8 xylanase motif on the N-terminal side; preferably an insertion of one or more alanine(s).

In another preferred embodiment of the first aspect, the variant has at least one bread or dough improving property when added to the dough before or during mixing in a sufficient amount.

Preferably, the variant is capable of increasing the loaf volume of a baked product or increasing the width of cut on the surface of a baked product, when added to the dough before or during mixing in a sufficient amount; such as, when added to the dough before or during mixing in a sufficient amount, the variant provides a less sticky dough compared to the parent GH8 xylanase, determined as in the examples herein, vide infra.

Polypeptides Having Xylanase Activity

In one aspect, the invention relates to an isolated variant of a parent GH8 xylanase polypeptide comprising a first conserved GH8 xylanase motif:

[ST]E[GAS]X[GAS][YFW], (SEQ ID NO: 1)

wherein the variant comprises at least one amino acid alteration compared to the parent in one or more of the 20 amino acid positions flanking the first conserved GH8 motif on the N-terminal side, and wherein the variant has xylanase activity.

Preferably, the isolated polypeptide comprises an amino acid sequence having a degree of sequence identity to the mature polypeptide xylanase of any of SEQ ID NO's: 3-154 and 159 of at least 60%, more preferably at least 65%, more preferably at least 70%, more preferably at least 75%, more preferably at least 80%, more preferably at least 85%, even more preferably at least 90%, most preferably at least 95%, and even most preferably at least 96%, at least 97%, at least 98%, or at least 99% (hereinafter "homologous polypeptides").

In a preferred embodiment, the variant of the second aspect is selected from the group of variants consisting of:

(a) the variant polypeptide comprising an amino acid sequence having at least 60% sequence identity to the mature part of a GH8 xylanase selected from the group of GH8 xylanases shown in SEQ ID NO: 3 to SEQ ID NO: 154 and SEQ ID NO:159; preferably the amino acid sequence is at least 65%, more preferably at least 70%, more preferably at least 75%, more preferably at least 80%, more preferably at least 85%, even more preferably at least 90%, most preferably at least 95%, and even most preferably at least 96%, at least 97%, at least 98%, or at least 99% identical to the mature part of a GH8 xylanase selected from the group of GH8 xylanases shown in any of SEQ ID NO:3 to SEQ ID NO:154 and SEQ ID NO:159;

(b) the variant polypeptide encoded by a polynucleotide that hybridizes under at least medium-high stringency conditions with (i) the mature polypeptide coding sequence shown in SEQ ID NO: 2, or (ii) a full-length complementary strand of (i);

(c) the variant polypeptide encoded by a polynucleotide comprising a nucleotide sequence having at least 60% sequence identity to the mature polypeptide coding sequence shown in SEQ ID NO: 2; and (d) the variant of (a), (b) or (c) comprising a substitution, deletion, and/or insertion of one or more amino acids.

In another preferred embodiment, the parent GH8 xylanase polypeptide comprises a second conserved GH8 xylanase motif: [ND][AS]X[RLPQ] (SEQ ID NO:155).

Yet another preferred embodiment relates to the variant of the second aspect, wherein the mature parent GH8 xylanase polypeptide comprises an amino acid sequence at least 60% identical to the mature part of a GH8 xylanase shown in SEQ ID NO:3, preferably the amino acid sequence is at least 65%, more preferably at least 70%, more preferably at least 75%, more preferably at least 80%, more preferably at least 85%, even more preferably at least 90%, most preferably at least 95%, and even most preferably at least 96%, at least 97%, at least 98%, or at least 99% identical to the mature part of a GH8 xylanase shown in SEQ ID NO:3.

It is also preferred that the variant of the second aspect is encoded by a polynucleotide that hybridizes under at least medium-high stringency conditions with (i) a polynucleotide comprising a nucleotide sequence of the mature polypeptide coding sequence of SEQ ID NO: 2 or (ii) a full-length complementary strand of (i).

Preferably, the variant of the second aspect is encoded by a polynucleotide comprising a nucleotide sequence having at least 60% sequence identity to the mature polypeptide coding sequence of SEQ ID NO: 2; preferably at least 65%, more preferably at least 70%, more preferably at least 75%, more preferably at least 80%, more preferably at least 85%, even more preferably at least 90%, most preferably at least 95%, and even most preferably at least 96%, at least 97%, at least 98%, or at least 99% identity.

In an even more preferred embodiment, the variant of the second aspect is encoded by a polynucleotide comprising or consisting of the nucleotide sequence of SEQ ID NO: 2; or a subsequence thereof encoding a polypeptide fragment having xylanase activity.

Even more preferable, is where the mature polypeptide comprises or consists of amino acids 28 to 433 of SEQ ID NO: 3, or wherein the mature polypeptide is encoded by a polynucleotide comprising or consisting of nucleotides 82 to 1299 of SEQ ID NO: 2.

Another preferred embodiment relates to the variant of the second aspect, wherein the at least one amino acid alteration comprises substitution, deletion, and/or insertion of one or more amino acids; preferably the at least one amino acid alteration comprises substitution, deletion, and/or insertion of one or more amino acids at one or more position(s) 20, 19, 18, 17, 16, 15, 14, 13, 12, 11, 10, 9, 8, 7, 6, 5, 4, 3, 2 and/or 1 amino acid(s) away from the first conserved GH8 xylanase motif on the N-terminal side or at one or more position(s) corresponding to position(s) 45, 46, 47, 48, 49, 50, 51, 52, 53, 54, 55, 56, 57, 58,59, 60, 61, 62, 63 and/or 64 in the mature polypeptide of SEQ ID NO: 3.

In another preferred embodiment, the at least one amino acid alteration(s) in the variant of the second aspect is comprised in one or more of the 15 amino acid positions flanking the first conserved GH8 xylanase motif on the N-terminal side, preferably in one or more of the 12 amino acid positions flanking the first conserved GH8 xylanase motif on the N-terminal side.

It is also preferable that the at least one amino acid alteration(s) comprises one or more insertion(s) at a position corresponding to a position 12 amino acids away from the first conserved GH8 xylanase motif on the N-terminal side in the mature polypeptide of SEQ ID NO: 3 or at a position corresponding to position 53 in the mature polypeptide of SEQ ID NO: 3.

Preferably, the at least one amino acid alteration comprises one or more insertion(s) at a position corresponding to a position 10 amino acids away from the first conserved GH8 xylanase motif on the N-terminal side in the mature polypeptide of SEQ ID NO: 3 or at a position corresponding to position 55 in the mature polypeptide of SEQ ID NO: 3.

More preferably, the at least one amino acid alteration comprises one or more insertion(s) at a position corresponding to a position 8 amino acids away from the first conserved GH8 xylanase motif on the N-terminal side in the mature polypeptide of SEQ ID NO: 3 or at a position corresponding to position 57 in the mature polypeptide of SEQ ID NO: 3.

Even more preferably, the at least one amino acid alteration comprises one or more insertion(s) at a position corresponding to a position 6 amino acids away from the first conserved GH8 xylanase motif on the N-terminal side in the mature polypeptide of SEQ ID NO: 3 or at a position corresponding to position 59 in the mature polypeptide of SEQ ID NO: 3.

In another preferred embodiment, the at least one amino acid alteration comprises one or more insertion(s) at a position corresponding to a position 4 amino acids away from the first conserved GH8 xylanase motif on the N-terminal side in the mature polypeptide of SEQ ID NO: 3 or at a position corresponding to position 61 in the mature polypeptide of SEQ ID NO: 3.

Yet another preferred embodiment relates to the variant of the second aspect, wherein the one or more insertion(s) comprise the insertion of at least one alanine residue, at least one aspartic acid residue, at least one serine residue, at least one lysine residue, and/or at least one phenylalanine; preferably the one or more insertion(s) comprises the insertion of at least one alanine residue; preferably the one or more insertion(s) comprise the insertion of at least one amino acid residue and at least one additional but different amino acid residue at the same position or at a different position.

Other preferred embodiments relate to the variant of the second aspect, which has at least one bread or dough improving property when added to the dough before or during mixing in a sufficient amount; preferably it is capable of increasing the loaf volume of a baked product or increasing the width of cut on the surface of a baked product, when added to the dough before or during mixing in a sufficient amount, and more preferably it provides a less sticky dough when compared with the parent GH8 xylanase added in the same amount.

In a preferred aspect, the homologous polypeptides comprise amino acid sequences that differ by ten amino acids, preferably by five amino acids, more preferably by four amino acids, even more preferably by three amino acids, most preferably by two amino acids, and even most preferably by one amino acid from the mature polypeptide of any of SEQ ID NO's: 3-154 and 159. A polypeptide of the present invention preferably comprises the amino acid sequence of any of SEQ ID NO's: 3-154 and 159 or an allelic variant thereof; or a fragment thereof having xylanase activity. In a preferred aspect, the polypeptide comprises the amino acid sequence of any of SEQ ID NO's: 3-154 and 159. In another preferred aspect, the polypeptide comprises the mature polypeptide of any of SEQ ID NO's: 3-154 and 159. In another preferred aspect, the polypeptide consists of the amino acid sequence of any of SEQ ID NO's: 3-154 and 159. In another preferred aspect, the polypeptide consists of the mature polypeptide of any of SEQ ID NO's: 3-154 and 159.

In another aspect, the present invention relates to isolated polypeptides having xylanase activity that are encoded by polynucleotides that hybridize under preferably very low stringency conditions, more preferably low stringency conditions, more preferably medium stringency conditions, more preferably medium-high stringency conditions, even more preferably high stringency conditions, and most preferably very high stringency conditions with (i) the mature polypeptide coding sequence of SEQ ID NO: 2, (ii) the genomic DNA sequence comprising the mature polypeptide coding sequence of SEQ ID NO: 2, or (iii) a full-length complementary strand of (i) or (ii) (J. Sambrook, E. F. Fritsch, and T. Maniatis, 1989, *Molecular Cloning, A Laboratory Manual*, 2d edition, Cold Spring Harbor, N.Y.).

The nucleotide sequence of SEQ ID NO: 2; or a subsequence thereof; as well as the amino acid sequence of any of SEQ ID NO's: 3-154 and 159; or a fragment thereof; may be used to design nucleic acid probes to identify and clone DNA encoding polypeptides having xylanase activity from strains of different genera or species according to methods well known in the art. In particular, such probes can be used for hybridization with the genomic or cDNA of the genus or species of interest, following standard Southern blotting procedures, in order to identify and isolate the corresponding gene therein. Such probes can be considerably shorter than the entire sequence, but should be at least 14, preferably at least 25, more preferably at least 35, and most preferably at least 70 nucleotides in length. It is, however, preferred that the nucleic acid probe is at least 100 nucleotides in length. For example, the nucleic acid probe may be at least 200 nucleotides, preferably at least 300 nucleotides, more preferably at least 400 nucleotides, or most preferably at least 500 nucleotides in length. Even longer probes may be used, e.g., nucleic acid probes that are preferably at least 600 nucleotides, more preferably at least 700 nucleotides, even more preferably at least 800 nucleotides, or most preferably at least 900 nucleotides in length. Both DNA and RNA probes can be used. The probes are typically labeled for detecting the corresponding gene (for example, with $^{32}P$, $^{3}H$, $^{35}S$, biotin, or avidin). Such probes are encompassed by the present invention.

A genomic DNA or cDNA library prepared from such other strains may, therefore, be screened for DNA that hybridizes with the probes described above and encodes a polypeptide having xylanase activity. Genomic or other DNA from such other strains may be separated by agarose or polyacrylamide gel electrophoresis, or other separation techniques. DNA from the libraries or the separated DNA may be transferred to and immobilized on nitrocellulose or other suitable carrier material. In order to identify a clone or DNA that is homologous with SEQ ID NO: 2, or a subsequence thereof, the carrier material is preferably used in a Southern blot.

For purposes of the present invention, hybridization indicates that the nucleotide sequence hybridizes to a labeled nucleic acid probe corresponding to the mature polypeptide coding sequence of SEQ ID NO: 2; the genomic DNA sequence comprising the mature polypeptide coding sequence of SEQ ID NO: 29; its full-length complementary strand; or a subsequence thereof; under very low to very high stringency conditions. Molecules to which the nucleic acid probe hybridizes under these conditions can be detected using, for example, X-ray film.

In a preferred aspect, the nucleic acid probe is the mature polypeptide coding sequence of SEQ ID NO: 2. In another preferred aspect, the nucleic acid probe is a polynucleotide sequence that encodes the polypeptide of any of SEQ ID NO's: 3-154 and 159, or a subsequence thereof. In another preferred aspect, the nucleic acid probe is SEQ ID NO: 2.

For long probes of at least 100 nucleotides in length, very low to very high stringency conditions are defined as prehybridization and hybridization at 42° C. in 5×SSPE, 0.3% SDS, 200 µg/ml sheared and denatured salmon sperm DNA, and either 25% formamide for very low and low stringencies, 35% formamide for medium and medium-high stringencies, or 50% formamide for high and very high stringencies, following standard Southern blotting procedures for 12 to 24 hours optimally.

For long probes of at least 100 nucleotides in length, the carrier material is finally washed three times each for 15 minutes using 2×SSC, 0.2% SDS preferably at 45° C. (very low stringency), more preferably at 50° C. (low stringency), more preferably at 55° C. (medium stringency), more preferably at 60° C. (medium-high stringency), even more preferably at 65° C. (high stringency), and most preferably at 70° C. (very high stringency).

For short probes of about 15 nucleotides to about 70 nucleotides in length, stringency conditions are defined as prehybridization, hybridization, and washing post-hybridization at about 5° C. to about 10° C. below the calculated $T_m$ using the calculation according to Bolton and McCarthy (1962, *Proceedings of the National Academy of Sciences USA* 48:1390) in 0.9 M NaCl, 0.09 M Tris-HCl pH 7.6, 6 mM EDTA, 0.5% NP-40, 1×Denhardt's solution, 1 mM sodium pyrophosphate, 1 mM sodium monobasic phosphate, 0.1 mM ATP, and 0.2 mg of yeast RNA per ml following standard Southern blotting procedures for 12 to 24 hours optimally.

For short probes of about 15 nucleotides to about 70 nucleotides in length, the carrier material is washed once in 6×SCC plus 0.1% SDS for 15 minutes and twice each for 15 minutes using 6×SSC at 5° C. to 10° C. below the calculated $T_m$.

In a third aspect, the present invention relates to isolated polypeptides having xylanase activity encoded by polynucleotides comprising or consisting of nucleotide sequences having a degree of sequence identity to the mature polypeptide coding sequence of SEQ ID NO: 2 of preferably at least 60%, more preferably at least 65%, more preferably at least 70%, more preferably at least 75%, more preferably at least 80%, more preferably at least 85%, even more preferably at least 90%, most preferably at least 95%, and even most preferably at least 96%, at least 97%, at least 98%, or at least 99%, which encode a polypeptide having xylanase activity. See polynucleotide section herein.

In a fourth aspect, the isolated polypeptides having xylanase activity, comprise the following 6 amino acid long motif:

[ST]E[GAS]X[GAS][YFW], (SEQ ID NO: 1)

wherein X is any amino acid and the amino acids listed together in brackets are alternative amino acid residues that may be found in a single position, e.g., [ST] denotes that either serine or threonine may be present in the that position in the motif. In the above motif, the accepted IUPAC single letter amino acid abbreviation is employed.

In another aspect, the present invention relates to artificial variants comprising a substitution, deletion, and/or insertion of one or more (or several) amino acids of the mature polypeptide of any of SEQ ID NO's: 3-154 and 159, or a homologous sequence thereof. Preferably, amino acid changes are of a minor nature, that is conservative amino acid substitutions or insertions that do not significantly affect the folding and/or activity of the protein; small deletions, typically of one to about 30 amino acids; small amino- or carboxyl-terminal extensions, such as an amino-terminal methionine residue; a small linker peptide of up to about 20-25 residues; or a small extension that facilitates purification by changing net charge or another function, such as a poly-histidine tract, an antigenic epitope or a binding domain.

Examples of conservative substitutions are within the group of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions that do not generally alter specific activity are known in the art and are described, for example, by H. Neurath and R. L. Hill, 1979, In, *The Proteins*, Academic Press, New York. The most commonly occurring exchanges are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly.

In addition to the 20 standard amino acids, non-standard amino acids (such as 4-hydroxyproline, 6-N-methyl lysine, 2-aminoisobutyric acid, isovaline, and alpha-methyl serine) may be substituted for amino acid residues of a wild-type polypeptide. A limited number of non-conservative amino acids, amino acids that are not encoded by the genetic code, and unnatural amino acids may be substituted for amino acid residues. "Unnatural amino acids" have been modified after protein synthesis, and/or have a chemical structure in their side chain(s) different from that of the standard amino acids. Unnatural amino acids can be chemically synthesized, and preferably, are commercially available, and include pipecolic acid, thiazolidine carboxylic acid, dehydroproline, 3- and 4-methylproline, and 3,3-dimethylproline.

Alternatively, the amino acid changes are of such a nature that the physico-chemical properties of the polypeptides are altered. For example, amino acid changes may improve the thermal stability of the polypeptide, alter the substrate specificity, change the pH optimum, and the like.

Essential amino acids in the parent polypeptide can be identified according to procedures known in the art, such as site-directed mutagenesis or alanine-scanning mutagenesis (Cunningham and Wells, 1989, *Science* 244: 1081-1085). In the latter technique, single alanine mutations are introduced at every residue in the molecule, and the resultant mutant molecules are tested for biological activity (i.e., xylanase activity) to identify amino acid residues that are critical to the activity of the molecule. See also, Hilton et al., 1996, *J. Biol. Chem.* 271: 4699-4708. The active site of the enzyme or other biological interaction can also be determined by physical analysis of structure, as determined by such techniques as nuclear magnetic resonance, crystallography, electron diffraction, or photoaffinity labeling, in conjunction with mutation of putative contact site amino acids. See, for example, de Vos et al., 1992, *Science* 255: 306-312; Smith et al., 1992, *J. Mol. Biol.* 224: 899-904; Wlodaver et al., 1992, *FEBS Lett.* 309: 59-64. The identities of essential amino acids can also be inferred from analysis of identities with polypeptides that are related to a polypeptide according to the invention.

Single or multiple amino acid substitutions, deletions, and/or insertions can be made and tested using known methods of mutagenesis, recombination, and/or shuffling, followed by a relevant screening procedure, such as those disclosed by Reidhaar-Olson and Sauer, 1988, *Science* 241: 53-57; Bowie and Sauer, 1989, *Proc. Natl. Acad. Sci.* USA 86: 2152-2156; WO 95/17413; or WO 95/22625. Other methods that can be used include error-prone PCR, phage display (e.g., Lowman et al., 1991, *Biochem.* 30: 10832-10837; U.S. Pat. No. 5,223, 409; WO 92/06204), and region-directed mutagenesis (Derbyshire et al., 1986, *Gene* 46: 145; Ner et al., 1988, *DNA* 7: 127).

Mutagenesis/shuffling methods can be combined with high-throughput, automated screening methods to detect activity of cloned, mutagenized polypeptides expressed by host cells (Ness et al., 1999, *Nature Biotechnology* 17: 893-896). Mutagenized DNA molecules that encode active polypeptides can be recovered from the host cells and rapidly sequenced using standard methods in the art. These methods allow the rapid determination of the importance of individual amino acid residues in a polypeptide of interest, and can be applied to polypeptides of unknown structure.

The total number of amino acid substitutions, deletions and/or insertions of the mature polypeptide of any of SEQ ID NO's: 3-154 and 159 is 10, preferably 9, more preferably 8, more preferably 7, more preferably at most 6, more preferably 5, more preferably 4, even more preferably 3, most preferably 2, and even most preferably 1.

Sources of Parent GH8 Xylanase Polypeptides

A parent GH8 xylanase polypeptide of the present invention may be obtained from microorganisms of any genus. For purposes of the present invention, the term "obtained from" as used herein in connection with a given source shall mean that the polypeptide encoded by a nucleotide sequence is produced by the source or by a strain in which the nucleotide sequence from the source has been inserted. In a preferred aspect, the polypeptide obtained from a given source is secreted extracellularly.

A polypeptide having xylanase activity of the present invention may be a bacterial polypeptide. For example, the polypeptide may be a gram positive bacterial polypeptide such as a *Bacillus, Streptococcus, Streptomyces, Staphylococcus, Enterococcus, Lactobacillus, Lactococcus, Clostridium, Geobacillus,* or *Oceanobacillus* polypeptide having xylanase activity, or a Gram negative bacterial polypeptide such as an *E. coli, Pseudomonas, Salmonella, Campylobacter, Helicobacter, Flavobacterium, Fusobacterium, Ilyobacter, Neisseria,* or *Ureaplasma* polypeptide having xylanase activity.

In a preferred aspect, the polypeptide is a *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis,* or *Bacillus thuringiensis* polypeptide having xylanase activity.

In another preferred aspect, the polypeptide is a *Streptococcus equisimilis, Streptococcus pyogenes, Streptococcus uberis,* or *Streptococcus equi* subsp. *Zooepidemicus* polypeptide having xylanase activity.

In another preferred aspect, the polypeptide is a *Streptomyces achromogenes, Streptomyces avermitilis, Streptomyces coelicolor, Streptomyces griseus,* or *Streptomyces lividans* polypeptide having xylanase activity.

A polypeptide having xylanase activity of the present invention may also be a fungal polypeptide, and more preferably a yeast polypeptide such as a *Candida, Kluyveromyces, Pichia, Saccharomyces, Schizosaccharomyces,* or *Yarrowia* polypeptide having xylanase activity; or more preferably a filamentous fungal polypeptide such as an *Acremonium, Agaricus, Alternaria, Aspergillus, Aureobasidium, Botryospaeria, Ceriporiopsis, Chaetomidium, Chrysosporium, Claviceps, Cochliobolus, Coprinopsis, Coptotermes, Corynascus, Cryphonectria, Cryptococcus, Diplodia, Exidia, Filibasidium, Fusarium, Gibberella, Holomastigotoides, Humicola, Irpex, Lentinula, Leptospaeria, Magnaporthe, Melanocarpus, Meripilus, Mucor, Myceliophthora, Neocallimastix, Neurospora, Paecilomyces, Penicillium, Phanerochaete, Piromyces, Poitrasia, Pseudoplectania, Pseudotrichonympha, Rhizomucor, Schizophyllium, Scytalidium, Talaromyces, Thermoascus, Thielavia, Tolypocladium, Trichoderma, Trichophaea, Verticillium, Volvariella,* or *Xylaria* polypeptide having xylanase activity.

In a preferred aspect, the polypeptide is a *Saccharomyces carlsbergensis, Saccharomyces cerevisiae, Saccharomyces diastaticus, Saccharomyces douglasii, Saccharomyces kluyveri, Saccharomyces norbensis,* or *Saccharomyces oviformis* polypeptide having xylanase activity.

In another preferred aspect, the polypeptide is an *Acremonium cellulolyticus, Aspergillus aculeatus, Aspergillus awamori, Aspergillus fumigatus, Aspergillus foetidus, Aspergillus japonicus, Aspergillus nidulans, Aspergillus niger, Aspergillus oryzae, Chrysosporium keratinophilum, Chrysosporium lucknowense, Chrysosporium tropicum, Chrysosporium merdarium, Chrysosporium inops, Chrysosporium pannicola, Chrysosporium queenslandicum, Chrysosporium zonatum, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola grisea, Humicola insolens, Humicola lanuginosa, Irpex lacteus, Mucor miehei, Myceliophthora thermophila, Neurospora crassa, Penicillium funiculosum, Penicillium purpurogenum, Phanerochaete chrysosporium, Thielavia achromatica, Thielavia albomyces, Thielavia albopilosa, Thielavia australeinsis, Thielavia fimeti, Thielavia microspora, Thielavia ovispora, Thielavia peruviana, Thielavia spededonium, Thielavia setosa, Thielavia subthermophila, Thielavia terrestris, Trichoderma harzianum, Trichoderma koningii, Trichoderma longibrachiatum, Trichoderma reesei,* or *Trichoderma viride* polypeptide having xylanase activity.

It will be understood that for the aforementioned species the invention encompasses both the perfect and imperfect states, and other taxonomic equivalents, e.g., anamorphs, regardless of the species name by which they are known. Those skilled in the art will readily recognize the identity of appropriate equivalents.

Strains of these species are readily accessible to the public in a number of culture collections, such as the American Type Culture Collection (ATCC), Deutsche Sammlung von Mikroorganismen and Zellkulturen GmbH (DSM), Centraalbureau Voor Schimmelcultures (CBS), and Agricultural Research Service Patent Culture Collection, Northern Regional Research Center (NRRL).

Furthermore, such polypeptides may be identified and obtained from other sources including microorganisms isolated from nature (e.g., soil, composts, water, etc.) using the above-mentioned probes. Techniques for isolating microorganisms from natural habitats are well known in the art. The polynucleotide may then be obtained by similarly screening a genomic or cDNA library of such a microorganism. Once a polynucleotide encoding a polypeptide has been detected with the probe(s), the polynucleotide can be isolated or cloned by utilizing techniques that are well known to those of ordinary skill in the art (see, e.g., Sambrook et al., 1989, supra).

A non-exhaustive list of polypeptides having (or predicted to have) xylanase activity belonging to the GH8 family is provided in table 1, vide infra.

Polypeptides of the present invention also include fused polypeptides or cleavable fusion polypeptides in which another polypeptide is fused at the N-terminus or the C-terminus of the polypeptide or fragment thereof. A fused polypeptide is produced by fusing a nucleotide sequence (or a portion thereof) encoding another polypeptide to a nucleotide sequence (or a portion thereof) of the present invention. Techniques for producing fusion polypeptides are known in the art, and include ligating the coding sequences encoding the polypeptides so that they are in frame and that expression of the fused polypeptide is under control of the same promoter(s) and terminator.

A fusion polypeptide can further comprise a cleavage site. Upon secretion of the fusion protein, the site is cleaved releasing the polypeptide having xylanase activity from the fusion protein. Examples of cleavage sites include, but are not limited to, a Kex2 site that encodes the dipeptide Lys-Arg (Martin et al., 2003, *J. Ind. Microbiol. Biotechnol.* 3: 568-576; Svetina et al., 2000, *J. Biotechnol.* 76: 245-251; Rasmussen-Wilson et al., 1997, *Appl. Environ. Microbiol.* 63: 3488-3493; Ward et al., 1995, *Biotechnology* 13: 498-503; and Contreras et al., 1991, *Biotechnology* 9: 378-381), an Ile-(Glu or Asp)-Gly-Arg site, which is cleaved by a Factor Xa protease after the arginine residue (Eaton et al., 1986, *Biochem.* 25: 505-512); a Asp-Asp-Asp-Asp-Lys site, which is cleaved by an enterokinase after the lysine (Collins-Racie et al., 1995, *Biotechnology* 13: 982-987); a His-Tyr-Glu site or His-Tyr-Asp site, which is cleaved by Genenase I (Carter et al., 1989, *Proteins: Structure, Function, and Genetics* 6: 240-248); a Leu-Val-Pro-Arg-Gly-Ser site, which is cleaved by thrombin after the Arg (Stevens, 2003, *Drug Discovery World* 4: 35-48); a Glu-Asn-Leu-Tyr-Phe-Gln-Gly site, which is cleaved by TEV protease after the Gln (Stevens, 2003, supra); and a Leu-Glu-Val-Leu-Phe-Gln-Gly-Pro site, which is cleaved by a genetically engineered form of human rhinovirus 3C protease after the Gln (Stevens, 2003, supra).

Polynucleotides

The present invention also relates to isolated polynucleotides comprising or consisting of nucleotide sequences that encode the variant GH8 xylanase polypeptides of the present invention.

In a preferred aspect, the nucleotide sequence comprises or consists of SEQ ID NO: 2, wherein one or more mutation(s) has been introduced according to the methods of the invention. In another preferred aspect, the nucleotide sequence comprises or consists of the mature polypeptide coding sequence of SEQ ID NO: 2, wherein one or more mutation(s) has been introduced according to the methods of the invention. The present invention also encompasses nucleotide sequences that encode variant polypeptides prepared from the parent GH8 xylanase comprising or consisting of the amino acid sequence of SEQ ID NO: 3 or the mature polypeptide thereof, which differ from SEQ ID NO: 2 or the mature polypeptide coding sequence thereof by virtue of the degeneracy of the genetic code. The present invention also relates to subsequences of SEQ ID NO: 2, wherein one or more mutation(s) has been introduced according to the methods of the invention, that encode fragments of variants polypeptides prepared from the parent GH8 xylanase comprising or consisting of the amino acid sequence of SEQ ID NO: 3 having xylanase activity.

The present invention also relates to mutant polynucleotides comprising or consisting of at least one mutation in the mature polypeptide coding sequence of SEQ ID NO: 2, in which the mutant nucleotide sequence encodes the mature variant polypeptide prepared from the parent GH8 xylanase comprising or consisting of the amino acid sequence of SEQ ID NO: 3.

The techniques used to isolate or clone a polynucleotide encoding a polypeptide are known in the art and include isolation from genomic DNA, preparation from cDNA, or a combination thereof. The cloning of the polynucleotides of the present invention from such genomic DNA can be effected, e.g., by using the well known polymerase chain reaction (PCR) or antibody screening of expression libraries to detect cloned DNA fragments with shared structural features. See, e.g., Innis et al., 1990, *PCR: A Guide to Methods and Application*, Academic Press, New York. Other nucleic acid amplification procedures such as ligase chain reaction (LCR), ligated activated transcription (LAT) and nucleotide sequence-based amplification (NASBA) may be used.

The present invention also relates to isolated polynucleotides comprising or consisting of nucleotide sequences having a degree of sequence identity to the mature polypeptide coding sequence of SEQ ID NO: 2 of preferably at least 60%, more preferably at least 65%, more preferably at least 70%, more preferably at least 75%, more preferably at least 80%, more preferably at least 85%, even more preferably at least 90%, most preferably at least 95%, and even most preferably at least 96%, at least 97%, at least 98%, or at least 99%, which encode a variant polypeptide having xylanase activity according to the present invention.

Modification of a nucleotide sequence encoding a polypeptide of the present invention may be necessary for the synthesis of polypeptides substantially similar to the polypeptide. The term "substantially similar" to the polypeptide refers to non-naturally occurring forms of the polypeptide. These polypeptides may differ in some engineered way from the polypeptide isolated from its native source, e.g., artificial variants that differ in specific activity, thermostability, pH optimum, or the like. The variant sequence may be constructed on the basis of the nucleotide sequence presented as the mature polypeptide coding sequence of SEQ ID NO: 2, e.g., a subsequence thereof, and/or by introduction of nucleotide substitutions that do not give rise to another amino acid sequence of the polypeptide encoded by the nucleotide sequence, but which correspond to the codon usage of the host organism intended for production of the enzyme, or by introduction of nucleotide substitutions that may give rise to a different amino acid sequence. For a general description of nucleotide substitution, see, e.g., Ford et al., 1991, *Protein Expression and Purification* 2: 95-107.

It will be apparent to those skilled in the art that such substitutions can be made outside the regions critical to the function of the molecule and still result in an active polypeptide. Amino acid residues essential to the activity of the polypeptide encoded by an isolated polynucleotide of the invention, and therefore preferably not subject to substitution, may be identified according to procedures known in the art, such as site-directed mutagenesis or alanine-scanning mutagenesis (see, e.g., Cunningham and Wells, 1989, supra). In the latter technique, mutations are introduced at every positively charged residue in the molecule, and the resultant mutant molecules are tested for xylanase activity to identify amino acid residues that are critical to the activity of the molecule. Sites of substrate-enzyme interaction can also be determined by analysis of the three-dimensional structure as determined by such techniques as nuclear magnetic resonance analysis, crystallography or photoaffinity labeling (see, e.g., de Vos et al., 1992, supra; Smith et al., 1992, supra; Wlodaver et al., 1992, supra).

The present invention also relates to isolated polynucleotides encoding polypeptides of the present invention, which hybridize under very low stringency conditions, preferably low stringency conditions, more preferably medium stringency conditions, more preferably medium-high stringency conditions, even more preferably high stringency conditions, and most preferably very high stringency conditions with (i) the mature polypeptide coding sequence of SEQ ID NO: 2, (ii) the genomic DNA sequence comprising the mature polypeptide coding sequence of SEQ ID NO: 2, or (iii) a full-length complementary strand of (i) or (ii); or allelic variants and subsequences thereof (Sambrook et al., 1989, supra), as defined herein.

The present invention also relates to isolated polynucleotides obtained by (a) hybridizing a population of DNA under very low, low, medium, medium-high, high, or very high stringency conditions with (i) the mature polypeptide coding sequence of SEQ ID NO: 2, (ii) the genomic DNA sequence comprising the mature polypeptide coding sequence of SEQ ID NO: 2, or (iii) a full-length complementary strand of (i) or (ii); and (b) isolating the hybridizing polynucleotide, which encodes a polypeptide having xylanase activity.

Nucleic Acid Constructs

The present invention also relates to nucleic acid constructs comprising an isolated polynucleotide of the present invention operably linked to one or more (several) control sequences that direct the expression of the coding sequence in a suitable host cell under conditions compatible with the control sequences.

An isolated polynucleotide encoding a polypeptide of the present invention may be manipulated in a variety of ways to provide for expression of the polypeptide. Manipulation of the polynucleotide's sequence prior to its insertion into a vector may be desirable or necessary depending on the expression vector. The techniques for modifying polynucleotide sequences utilizing recombinant DNA methods are well known in the art.

The control sequence may be an appropriate promoter sequence, a nucleotide sequence that is recognized by a host cell for expression of a polynucleotide encoding a polypeptide of the present invention. The promoter sequence contains transcriptional control sequences that mediate the expression of the polypeptide. The promoter may be any nucleotide sequence that shows transcriptional activity in the host cell of choice including mutant, truncated, and hybrid promoters, and may be obtained from genes encoding extracellular or intracellular polypeptides either homologous or heterologous to the host cell.

Examples of suitable promoters for directing the transcription of the nucleic acid constructs of the present invention, especially in a bacterial host cell, are the promoters obtained from the E. coli lac operon, Streptomyces coelicolor agarase gene (dagA), Bacillus subtilis levansucrase gene (sacB), Bacillus licheniformis alpha-amylase gene (amyL), Bacillus stearothermophilus maltogenic amylase gene (amyM), Bacillus amyloliquefaciens alpha-amylase gene (amyQ), Bacillus licheniformis penicillinase gene (penP), Bacillus subtilis xylA and xylB genes, and prokaryotic beta-lactamase gene (Villa-Kamaroff et al., 1978, Proceedings of the National Academy of Sciences USA 75: 3727-3731), as well as the tac promoter (DeBoer et al., 1983, Proceedings of the National Academy of Sciences USA 80: 21-25). Further promoters are described in "Useful proteins from recombinant bacteria" in Scientific American, 1980, 242: 74-94; and in Sambrook et al., 1989, supra.

Examples of suitable promoters for directing the transcription of the nucleic acid constructs of the present invention in a filamentous fungal host cell are promoters obtained from the genes for Aspergillus oryzae TAKA amylase, Rhizomucor miehei aspartic proteinase, Aspergillus niger neutral alpha-amylase, Aspergillus niger acid stable alpha-amylase, Aspergillus niger or Aspergillus awamori glucoamylase (glaA), Rhizomucor miehei lipase, Aspergillus oryzae alkaline protease, Aspergillus oryzae triose phosphate isomerase, Aspergillus nidulans acetamidase, Fusarium venenatum amyloglucosidase (WO 00/56900), Fusarium venenatum Daria (WO 00/56900), Fusarium venenatum Quinn (WO 00/56900), Fusarium oxysporum trypsin-like protease (WO 96/00787), Trichoderma reesei beta-glucosidase, Trichoderma reesei cellobiohydrolase I, Trichoderma reesei cellobiohydrolase II, Trichoderma reesei endoglucanase I, Trichoderma reesei endoglucanase II, Trichoderma reesei endoglucanase III, Trichoderma reesei endoglucanase IV, Trichoderma reesei endoglucanase V, Trichoderma reesei xylanase I, Trichoderma reesei xylanase II, Trichoderma reesei beta-xylosidase, as well as the NA2-tpi promoter (a modified promoter from the gene encoding neutral alpha-amylase in Aspergillus niger in which the untranslated leader has been replaced by an untranslated leader from the gene encoding triose phosphate isomerase in Aspergillus nidulans); and mutant, truncated, and hybrid promoters thereof.

In a yeast host, useful promoters are obtained from the genes for Saccharomyces cerevisiae enolase (ENO-1), Saccharomyces cerevisiae galactokinase (GAL1), Saccharomyces cerevisiae alcohol dehydrogenase/glyceraldehyde-3-phosphate dehydrogenase (ADH1, ADH2/GAP), Saccharomyces cerevisiae triose phosphate isomerase (TPI), Saccharomyces cerevisiae metallothionein (CUP1), and Saccharomyces cerevisiae 3-phosphoglycerate kinase. Other useful promoters for yeast host cells are described by Romanos et al., 1992, Yeast 8: 423-488.

The control sequence may also be a suitable transcription terminator sequence, a sequence recognized by a host cell to terminate transcription. The terminator sequence is operably linked to the 3' terminus of the nucleotide sequence encoding the polypeptide. Any terminator that is functional in the host cell of choice may be used in the present invention.

Preferred terminators for filamentous fungal host cells are obtained from the genes for Aspergillus oryzae TAKA amylase, Aspergillus niger glucoamylase, Aspergillus nidulans anthranilate synthase, Aspergillus niger alpha-glucosidase, and Fusarium oxysporum trypsin-like protease.

Preferred terminators for yeast host cells are obtained from the genes for Saccharomyces cerevisiae enolase, Saccharomyces cerevisiae cytochrome C (CYC1), and Saccharomyces cerevisiae glyceraldehyde-3-phosphate dehydrogenase. Other useful terminators for yeast host cells are described by Romanos et al., 1992, supra.

The control sequence may also be a suitable leader sequence, a nontranslated region of an mRNA that is important for translation by the host cell. The leader sequence is operably linked to the 5' terminus of the nucleotide sequence encoding the polypeptide. Any leader sequence that is functional in the host cell of choice may be used in the present invention.

Preferred leaders for filamentous fungal host cells are obtained from the genes for Aspergillus oryzae TAKA amylase and Aspergillus nidulans triose phosphate isomerase.

Suitable leaders for yeast host cells are obtained from the genes for Saccharomyces cerevisiae enolase (ENO-1), Saccharomyces cerevisiae 3-phosphoglycerate kinase, Saccharomyces cerevisiae alpha-factor, and Saccharomyces cerevisiae alcohol dehydrogenase/glyceraldehyde-3-phosphate dehydrogenase (ADH2/GAP).

The control sequence may also be a polyadenylation sequence, a sequence operably linked to the 3' terminus of the nucleotide sequence and, when transcribed, is recognized by the host cell as a signal to add polyadenosine residues to transcribed mRNA. Any polyadenylation sequence that is functional in the host cell of choice may be used in the present invention.

Preferred polyadenylation sequences for filamentous fungal host cells are obtained from the genes for *Aspergillus oryzae* TAKA amylase, *Aspergillus niger* glucoamylase, *Aspergillus nidulans* anthranilate synthase, *Fusarium oxysporum* trypsin-like protease, and *Aspergillus niger* alpha-glucosidase.

Useful polyadenylation sequences for yeast host cells are described by Guo and Sherman, 1995, *Molecular Cellular Biology* 15: 5983-5990.

The control sequence may also be a signal peptide coding sequence that encodes a signal peptide linked to the amino terminus of a polypeptide and directs the encoded polypeptide into the cell's secretory pathway. The 5' end of the coding sequence of the nucleotide sequence may inherently contain a signal peptide coding sequence naturally linked in translation reading frame with the segment of the coding sequence that encodes the secreted polypeptide. Alternatively, the 5' end of the coding sequence may contain a signal peptide coding sequence that is foreign to the coding sequence. The foreign signal peptide coding sequence may be required where the coding sequence does not naturally contain a signal peptide coding sequence. Alternatively, the foreign signal peptide coding sequence may simply replace the natural signal peptide coding sequence in order to enhance secretion of the polypeptide. However, any signal peptide coding sequence that directs the expressed polypeptide into the secretory pathway of a host cell of choice, i.e., secreted into a culture medium, may be used in the present invention.

Effective signal peptide coding sequences for bacterial host cells are the signal peptide coding sequences obtained from the genes for *Bacillus* NCIB 11837 maltogenic amylase, *Bacillus stearothermophilus* alpha-amylase, *Bacillus licheniformis* subtilisin, *Bacillus licheniformis* beta-lactamase, *Bacillus stearothermophilus* neutral proteases (nprT, nprS, nprM), and *Bacillus subtilis* prsA. Further signal peptides are described by Simonen and Palva, 1993, *Microbiological Reviews* 57: 109-137.

Effective signal peptide coding sequences for filamentous fungal host cells are the signal peptide coding sequences obtained from the genes for *Aspergillus oryzae* TAKA amylase, *Aspergillus niger* neutral amylase, *Aspergillus niger* glucoamylase, *Rhizomucor miehei* aspartic proteinase, *Humicola insolens* cellulase, *Humicola insolens* endoglucanase V, and *Humicola lanuginosa* lipase.

Useful signal peptides for yeast host cells are obtained from the genes for *Saccharomyces cerevisiae* alpha-factor and *Saccharomyces cerevisiae* invertase. Other useful signal peptide coding sequences are described by Romanos et al., 1992, supra.

In a preferred aspect, the signal peptide comprises or consists of amino acids −27 to −1 of SEQ ID NO: 3 or −28 to −1 in SEQ ID NO:4. In another preferred aspect, the signal peptide coding sequence comprises or consists of nucleotides 1 to 81 of SEQ ID NO: 2.

The control sequence may also be a propeptide coding sequence that encodes a propeptide positioned at the amino terminus of a polypeptide. The resultant polypeptide is known as a proenzyme or propolypeptide (or a zymogen in some cases). A propeptide is generally inactive and can be converted to a mature active polypeptide by catalytic or autocatalytic cleavage of the propeptide from the propolypeptide. The propeptide coding sequence may be obtained from the genes for *Bacillus subtilis* alkaline protease (aprE), *Bacillus subtilis* neutral protease (nprT), *Saccharomyces cerevisiae* alpha-factor, *Rhizomucor miehei* aspartic proteinase, and *Myceliophthora thermophila* laccase (WO 95/33836).

Where both signal peptide and propeptide sequences are present at the amino terminus of a polypeptide, the propeptide sequence is positioned next to the amino terminus of a polypeptide and the signal peptide sequence is positioned next to the amino terminus of the propeptide sequence.

It may also be desirable to add regulatory sequences that allow the regulation of the expression of the polypeptide relative to the growth of the host cell. Examples of regulatory systems are those that cause the expression of the gene to be turned on or off in response to a chemical or physical stimulus, including the presence of a regulatory compound. Regulatory systems in prokaryotic systems include the lac, tac, and trp operator systems. In yeast, the ADH2 system or GAL1 system may be used. In filamentous fungi, the TAKA alpha-amylase promoter, *Aspergillus niger* glucoamylase promoter, and *Aspergillus oryzae* glucoamylase promoter may be used as regulatory sequences. Other examples of regulatory sequences are those that allow for gene amplification. In eukaryotic systems, these regulatory sequences include the dihydrofolate reductase gene that is amplified in the presence of methotrexate, and the metallothionein genes that are amplified with heavy metals. In these cases, the nucleotide sequence encoding the polypeptide would be operably linked with the regulatory sequence.

Expression Vectors

The present invention also relates to recombinant expression vectors comprising a polynucleotide of the present invention, a promoter, and transcriptional and translational stop signals. The various nucleic acids and control sequences described herein may be joined together to produce a recombinant expression vector that may include one or more (several) convenient restriction sites to allow for insertion or substitution of the nucleotide sequence encoding the polypeptide at such sites. Alternatively, a polynucleotide sequence of the present invention may be expressed by inserting the nucleotide sequence or a nucleic acid construct comprising the sequence into an appropriate vector for expression. In creating the expression vector, the coding sequence is located in the vector so that the coding sequence is operably linked with the appropriate control sequences for expression.

The recombinant expression vector may be any vector (e.g., a plasmid or virus) that can be conveniently subjected to recombinant DNA procedures and can bring about expression of the nucleotide sequence. The choice of the vector will typically depend on the compatibility of the vector with the host cell into which the vector is to be introduced. The vectors may be linear or closed circular plasmids.

The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one that, when introduced into the host cell, is integrated into the genome and replicated together with the chromosome(s) into which it has been integrated. Furthermore, a single vector or plasmid or two or more vectors or plasmids that together contain the total DNA to be introduced into the genome of the host cell, or a transposon, may be used.

The vectors of the present invention preferably contain one or more (several) selectable markers that permit easy selection of transformed, transfected, transduced, or the like cells. A selectable marker is a gene the product of which provides for biocide or viral resistance, resistance to heavy metals, prototrophy to auxotrophs, and the like.

Examples of bacterial selectable markers are the dal genes from *Bacillus subtilis* or *Bacillus licheniformis*, or markers that confer antibiotic resistance such as ampicillin, kanamycin, chloramphenicol, or tetracycline resistance. Suitable markers for yeast host cells are ADE2, HIS3, LEU2, LYS2, MET3, TRP1, and URA3. Selectable markers for use in a filamentous fungal host cell include, but are not limited to, amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Preferred for use in an *Aspergillus* cell are the amdS and pyrG genes of *Aspergillus nidulans* or *Aspergillus oryzae* and the bar gene of *Streptomyces hygroscopicus*.

The vectors of the present invention preferably contain an element(s) that permits integration of the vector into the host cell's genome or autonomous replication of the vector in the cell independent of the genome.

For integration into the host cell genome, the vector may rely on the polynucleotide's sequence encoding the polypeptide or any other element of the vector for integration into the genome by homologous or nonhomologous recombination. Alternatively, the vector may contain additional nucleotide sequences for directing integration by homologous recombination into the genome of the host cell at a precise location(s) in the chromosome(s). To increase the likelihood of integration at a precise location, the integrational elements should preferably contain a sufficient number of nucleic acids, such as 100 to 10,000 base pairs, preferably 400 to 10,000 base pairs, and most preferably 800 to 10,000 base pairs, which have a high degree of sequence identity to the corresponding target sequence to enhance the probability of homologous recombination. The integrational elements may be any sequence that is homologous with the target sequence in the genome of the host cell. Furthermore, the integrational elements may be non-encoding or encoding nucleotide sequences. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication that functions in a cell. The term "origin of replication" or "plasmid replicator" is defined herein as a nucleotide sequence that enables a plasmid or vector to replicate in vivo.

Examples of bacterial origins of replication are the origins of replication of plasmids pBR322, pUC19, pACYC177, and pACYC184 permitting replication in *E. coli*, and pUB110, pE194, pTA1060, and pAMβ1 permitting replication in *Bacillus*.

Examples of origins of replication for use in a yeast host cell are the 2 micron origin of replication, ARS1, ARS4, the combination of ARS1 and CEN3, and the combination of ARS4 and CEN6.

Examples of origins of replication useful in a filamentous fungal cell are AMA1 and ANS1 (Gems et al., 1991, *Gene* 98: 61-67; Cullen et al., 1987, *Nucleic Acids Research* 15: 9163-9175; WO 00/24883). Isolation of the AMA1 gene and construction of plasmids or vectors comprising the gene can be accomplished according to the methods disclosed in WO 00/24883.

More than one copy of a polynucleotide of the present invention may be inserted into a host cell to increase production of the gene product. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to recombinant host cells, comprising an isolated polynucleotide of the present invention operably linked to one or more (several) control sequences that direct the production of a polypeptide having xylanase activity. A construct or vector comprising a polynucleotide of the present invention is introduced into a host cell so that the construct or vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the polypeptide and its source.

The host cell may be any cell useful in the recombinant production of a polypeptide of the present invention, e.g., a prokaryote or a eukaryote.

The prokaryotic host cell may be any Gram positive bacterium or a Gram negative bacterium. Gram positive bacteria include, but not limited to, *Bacillus, Streptococcus, Streptomyces, Staphylococcus, Enterococcus, Lactobacillus, Lactococcus, Clostridium, Geobacillus*, and *Oceanobacillus*. Gram negative bacteria include, but not limited to, *E. coli, Pseudomonas, Salmonella, Campylobacter, Helicobacter, Flavobacterium, Fusobacterium, Ilyobacter, Neisseria*, and *Ureaplasma*.

The bacterial host cell may be any *Bacillus* cell. *Bacillus* cells useful in the practice of the present invention include, but are not limited to, *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis*, and *Bacillus thuringiensis* cells.

In a preferred aspect, the bacterial host cell is a *Bacillus amyloliquefaciens, Bacillus lentus, Bacillus licheniformis, Bacillus stearothermophilus* or *Bacillus subtilis* cell. In a more preferred aspect, the bacterial host cell is a *Bacillus amyloliquefaciens* cell. In another more preferred aspect, the bacterial host cell is a *Bacillus clausii* cell. In another more preferred aspect, the bacterial host cell is a *Bacillus licheniformis* cell. In another more preferred aspect, the bacterial host cell is a *Bacillus subtilis* cell.

The bacterial host cell may also be any *Streptococcus* cell. *Streptococcus* cells useful in the practice of the present invention include, but are not limited to, *Streptococcus equisimilis, Streptococcus pyogenes, Streptococcus uberis*, and *Streptococcus equi* subsp. *Zooepidemicus* cells.

In a preferred aspect, the bacterial host cell is a *Streptococcus equisimilis* cell. In another preferred aspect, the bacterial host cell is a *Streptococcus pyogenes* cell. In another preferred aspect, the bacterial host cell is a *Streptococcus uberis* cell. In another preferred aspect, the bacterial host cell is a *Streptococcus equi* subsp. *Zooepidemicus* cell.

The bacterial host cell may also be any *Streptomyces* cell. *Streptomyces* cells useful in the practice of the present invention include, but are not limited to, *Streptomyces achromogenes, Streptomyces avermitilis, Streptomyces coelicolor, Streptomyces griseus*, and *Streptomyces lividans* cells.

In a preferred aspect, the bacterial host cell is a *Streptomyces achromogenes* cell. In another preferred aspect, the bacterial host cell is a *Streptomyces avermitilis* cell. In another preferred aspect, the bacterial host cell is a *Streptomyces coelicolor* cell. In another preferred aspect, the bacterial host cell is a *Streptomyces griseus* cell. In another preferred aspect, the bacterial host cell is a *Streptomyces lividans* cell.

The introduction of DNA into a *Bacillus* cell may, for instance, be effected by protoplast transformation (see, e.g., Chang and Cohen, 1979, *Molecular General Genetics* 168: 111-115), by using competent cells (see, e.g., Young and Spizizen, 1961, *Journal of Bacteriology* 81: 823-829, or Dubnau and Davidoff-Abelson, 1971, *Journal of Molecular Biology* 56: 209-221), by electroporation (see, e.g., Shigekawa and Dower, 1988, *Biotechniques* 6: 742-751), or by conjugation (see, e.g., Koehler and Thorne, 1987, *Journal of Bacteriology* 169: 5271-5278). The introduction of DNA into an *E coli* cell may, for instance, be effected by protoplast transformation (see, e.g., Hanahan, 1983, *J. Mol. Biol.* 166: 557-580) or electroporation (see, e.g., Dower et al., 1988, *Nucleic Acids Res.* 16: 6127-6145). The introduction of DNA into a Streptomyces cell may, for instance, be effected by protoplast transformation and electroporation (see, e.g., Gong et al., 2004, *Folia Microbiol. (Praha)* 49: 399-405), by conjugation (see, e.g., Mazodier et al., 1989, *J. Bacteriol.* 171: 3583-3585), or by transduction (see, e.g., Burke et al., 2001, *Proc. Natl. Acad. Sci.* USA 98: 6289-6294). The introduction of DNA into a *Pseudomonas* cell may, for instance, be effected by electroporation (see, e.g., Choi et al., 2006, *J. Microbiol. Methods* 64: 391-397) or by conjugation (see, e.g., Pinedo and Smets, 2005, *Appl. Environ. Microbiol.* 71: 51-57). The introduction of DNA into a *Streptococcus* cell may, for instance, be effected by natural competence (see, e.g., Perry and Kuramitsu, 1981, *Infect. Immun.* 32: 1295-1297), by protoplast transformation (see, e.g., Catt and Jollick, 1991, *Microbios.* 68: 189-207, by electroporation (see, e.g., Buckley et al., 1999, *Appl. Environ. Microbiol.* 65: 3800-3804) or by conjugation (see, e.g., Clewell, 1981, *Microbiol. Rev.* 45: 409-436). However, any method known in the art for introducing DNA into a host cell can be used.

The host cell may also be a eukaryote, such as a mammalian, insect, plant, or fungal cell.

In a preferred aspect, the host cell is a fungal cell. "Fungi" as used herein includes the phyla Ascomycota, Basidiomycota, Chytridiomycota, and Zygomycota (as defined by Hawksworth et al., In, *Ainsworth and Bisby's Dictionary of The Fungi*, 8th edition, 1995, CAB International, University Press, Cambridge, UK) as well as the Oomycota (as cited in Hawksworth et al., 1995, supra, page 171) and all mitosporic fungi (Hawksworth et al., 1995, supra).

In a more preferred aspect, the fungal host cell is a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in *Biology and Activities of Yeast* (Skinner, F. A., Passmore, S. M., and Davenport, R. R., eds, *Soc. App. Bacteriol. Symposium Series No. 9*, 1980).

In an even more preferred aspect, the yeast host cell is a *Candida, Hansenula, Kluyveromyces, Pichia, Saccharomyces, Schizosaccharomyces*, or *Yarrowia* cell.

In a most preferred aspect, the yeast host cell is a *Saccharomyces carlsbergensis, Saccharomyces cerevisiae, Saccharomyces diastaticus, Saccharomyces douglasii, Saccharomyces kluyveri, Saccharomyces norbensis*, or *Saccharomyces oviformis* cell. In another most preferred aspect, the yeast host cell is a *Kluyveromyces lactis* cell. In another most preferred aspect, the yeast host cell is a *Yarrowia lipolytica* cell.

In another more preferred aspect, the fungal host cell is a filamentous fungal cell. "Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

In an even more preferred aspect, the filamentous fungal host cell is an *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes*, or *Trichoderma* cell.

In a most preferred aspect, the filamentous fungal host cell is an *Aspergillus awamori, Aspergillus fumigatus, Aspergillus foetidus, Aspergillus japonicus, Aspergillus nidulans, Aspergillus niger* or *Aspergillus oryzae* cell. In another most preferred aspect, the filamentous fungal host cell is a *Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides*, or *Fusarium venenatum* cell. In another most preferred aspect, the filamentous fungal host cell is a *Bjerkandera adusta, Ceriporiopsis aneirina, Ceriporiopsis aneirina, Ceriporiopsis caregiea, Ceriporiopsis gilvescens, Ceriporiopsis pannocinta, Ceriporiopsis rivulosa, Ceriporiopsis subrufa, Ceriporiopsis subvermispora, Chrysosporium keratinophilum, Chrysosporium lucknowense, Chrysosporium tropicum, Chrysosporium merdarium, Chrysosporium inops, Chrysosporium pannicola, Chrysosporium queenslandicum, Chrysosporium zonatum, Coprinus cinereus, Coriolus hirsutus, Humicola insolens, Humicola lanuginosa, Mucor miehei, Myceliophthora thermophila, Neurospora crassa, Penicillium purpurogenum, Phanerochaete chrysosporium, Phlebia radiata, Pleurotus eryngii, Thielavia terrestris, Trametes villosa, Trametes versicolor, Trichoderma harzianum, Trichoderma koningii, Trichoderma longibrachiatum, Trichoderma reesei*, or *Trichoderma viride* cell.

Fungal cells may be transformed by a process involving protoplast formation, transformation of the protoplasts, and regeneration of the cell wall in a manner known per se. Suitable procedures for transformation of *Aspergillus* and *Trichoderma* host cells are described in EP 238 023 and Yelton et al., 1984, *Proceedings of the National Academy of Sciences USA* 81: 1470-1474. Suitable methods for transforming *Fusarium* species are described by Malardier et al., 1989, *Gene* 78: 147-156, and WO 96/00787. Yeast may be transformed using the procedures described by Becker and Guarente, In Abelson, J. N. and Simon, M. I., editors, *Guide to Yeast Genetics and Molecular Biology, Methods in Enzymology*, Volume 194, pp 182-187, Academic Press, Inc., New York; Ito et al., 1983, *Journal of Bacteriology* 153: 163; and Hinnen et al., 1978, *Proceedings of the National Academy of Sciences USA* 75: 1920.

Methods of Production

The present invention also relates to methods of producing a variant polypeptide of the present invention, comprising: (a) cultivating a cell, which produces the polypeptide, under conditions conducive for production of the polypeptide; and (b) recovering the polypeptide. In a preferred aspect, the cell is of the genus *Bacillus*. In a more preferred aspect, the cell is *Bacillus licheniformis*.

The present invention also relates to methods of producing a variant polypeptide of the present invention, comprising: (a) cultivating a recombinant host cell, as described herein, under conditions conducive for production of the polypeptide; and (b) recovering the polypeptide.

The present invention also relates to methods of producing a variant polypeptide of the present invention, comprising: (a) cultivating a recombinant host cell under conditions conducive for production of the polypeptide, wherein the host cell comprises a mutant nucleotide sequence having at least one mutation in the mature polypeptide coding sequence of SEQ ID NO: 2, wherein the mutant nucleotide sequence encodes a variant of any of the mature polypeptides of SEQ ID NO's: 3-154 and 159 according to the invention; and (b) recovering the polypeptide.

In the production methods of the present invention, the cells are cultivated in a nutrient medium suitable for production of the polypeptide using methods well known in the art. For example, the cell may be cultivated by shake flask cultivation, and small-scale or large-scale fermentation (including continuous, batch, fed-batch, or solid state fermentations) in laboratory or industrial fermentors performed in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted into the medium, it can be recovered from cell lysates.

The polypeptides may be detected using methods known in the art that are specific for the polypeptides. These detection methods may include use of specific antibodies, formation of an enzyme product, or disappearance of an enzyme substrate. For example, an enzyme assay may be used to determine the activity of the polypeptide as described herein.

The resulting polypeptide may be recovered using methods known in the art. For example, the polypeptide may be recovered from the nutrient medium by conventional procedures including, but not limited to, centrifugation, filtration, extraction, spray-drying, evaporation, or precipitation.

The polypeptides of the present invention may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, J.-C. Janson and Lars Ryden, editors, VCH Publishers, New York, 1989) to obtain substantially pure polypeptides.

Compositions

The present invention also relates to compositions comprising a variant polypeptide of the present invention. Preferably, the compositions are enriched in such a polypeptide. The term "enriched" indicates that the variant GH8 xylanase activity of the composition has been increased, e.g., with an enrichment factor of at least 1.1.

The composition may comprise a polypeptide of the present invention as the major enzymatic component, e.g., a mono-component composition. Alternatively, the composition may comprise multiple enzymatic activities, such as an aminopeptidase, amylase, carbohydrase, carboxypeptidase, catalase, cellulase, chitinase, cutinase, cyclodextrin glycosyltransferase, deoxyribonuclease, esterase, alpha-galactosidase, beta-galactosidase, glucoamylase, alpha-glucosidase, beta-glucosidase, haloperoxidase, invertase, laccase, lipase, mannosidase, oxidase, pectinolytic enzyme, peptidoglutaminase, peroxidase, phytase, polyphenoloxidase, proteolytic enzyme, ribonuclease, transglutaminase, or xylanase. The additional enzyme(s) may be produced, for example, by a microorganism belonging to the genus *Aspergillus*, preferably *Aspergillus aculeatus*, *Aspergillus awamori*, *Aspergillus fumigatus*, *Aspergillus foetidus*, *Aspergillus japonicus*, *Aspergillus nidulans*, *Aspergillus niger*, or *Aspergillus oryzae*; *Fusarium*, preferably *Fusarium bactridioides*, *Fusarium cerealis*, *Fusarium crookwellense*, *Fusarium culmorum*, *Fusarium graminearum*, *Fusarium graminum*, *Fusarium heterosporum*, *Fusarium negundi*, *Fusarium oxysporum*, *Fusarium reticulatum*, *Fusarium roseum*, *Fusarium sambucinum*, *Fusarium sarcochroum*, *Fusarium sulphureum*, *Fusarium toruloseum*, *Fusarium trichothecioides*, or *Fusarium venenatum*; *Humicola*, preferably *Humicola insolens* or *Humicola lanuginosa*; or *Trichoderma*, preferably *Trichoderma harzianum*, *Trichoderma koningii*, *Trichoderma longibrachiatum*, *Trichoderma reesei*, or *Trichoderma viride*.

The polypeptide compositions may be prepared in accordance with methods known in the art and may be in the form of a liquid or a dry composition. For instance, the polypeptide composition may be in the form of a granulate or a microgranulate. The polypeptide to be included in the composition may be stabilized in accordance with methods known in the art.

Examples are given below of preferred uses of the polypeptide compositions of the invention. The dosage of the polypeptide composition of the invention and other conditions under which the composition is used may be determined on the basis of methods known in the art.

Uses

The present invention is also directed to methods for using the variant polypeptides having GH8 xylanase activity, or compositions thereof, including baking applications.

In one aspect the invention relates to a method for the preparation of a baked product, said method comprising the step of adding to a dough of said baked product the variant polypeptide of the second aspect or a bread improving composition comprising said variant polypeptide.

In one preferred embodiment, said variant polypeptide or bread improving composition is added during the mixing of the dough.

In another preferred embodiment, said bread improving composition further comprises one or more bread-improving agent selected from the list consisting of enzymes, emulsifiers, oxidants, milk powder, fats, sugars, amino acids, salts, proteins (gluten, cellulose binding sites) or a mixture thereof; preferably said enzymes are selected from the list consisting of alpha-amylases, beta-amylases, maltogenic amylases, other xylanases, proteases, glucose oxidase, oxidoreductases, glucanases, cellulases, transglutaminases, isomerases, lipases, phospholipases, pectinases or a mixture thereof.

It is preferred that said variant polypeptide is present as a cell extract, a cell-free extract or as a purified protein.

In another preferred embodiment, said variant polypeptide is mixed with other ingredients in the form of a dry powder or a granulate, in particular a non-dusting granulate, or in the form of a liquid, preferably with one or more stabilizer(s) such as polyols, sugars, organic acids or sugar alcohols.

Baked Product

The process or the GH8 xylanase variants of the invention may be used for any kind of baked product pre-pared from dough, either of a soft or a crisp character, either of a white, light or dark type. Examples are bread (in particular white, whole-meal or rye bread), typically in the form of loaves or rolls, French baguette-type bread, flat bread, pita bread, tortillas, cakes, pancakes, biscuits, cookies, pie crusts, crisp bread, steamed bread, pizza and the like.

Pre-mix

The present invention further relates to a pre-mix comprising flour together with a GH8 variant xylanase polypeptide according to the invention. The pre-mix may contain other dough-improving and/or bread-improving additives, e.g. any of the additives, including enzymes, mentioned above.

Enzyme Preparation

The invention provides an enzyme preparation comprising a GH8 variant xylanase according to the invention, for use as a baking additive in the process of the invention. The enzyme preparation is preferably in the form of a granulate or agglomerated powder. It preferably has a narrow particle size distribution with more than 95% (by weight) of the particles in the range from 25 to 500 µm.

Granulates and agglomerated powders may be prepared by conventional methods, e.g. by spraying the xylanase onto a carrier in a fluid-bed granulator. The carrier may consist of particulate cores having a suitable particle size. The carrier may be soluble or insoluble, e.g. a salt (such as NaCl or sodium sulfate), a sugar (such as sucrose or lactose), a sugar alcohol (such as sorbitol), starch, rice, corn grits, or soy.

The present invention is further described by the following examples that should not be construed as limiting the scope of the invention.

EXAMPLES

The invention described and claimed herein is not to be limited in scope by the specific aspects herein disclosed, since these aspects are intended as illustrations of several aspects of the invention. Any equivalent aspects are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

Chemicals used as buffers and substrates were commercial products of at least reagent grade.

Example 1

Parent GH8 Xylanases

A non-limiting and non-exhaustive list of diverse potential parent GH8 xylanases is provided in table 1 below. Each of the GH8 xylanases listed comprises the conserved GH8-motif of SEQ ID NO:1, the amino acid position of which is indicated in the rightmost column for each sequence. The sequence identifiers (SEQ ID NO's) are indicated in the leftmost column of the table, the organism name and the UniProtKB accession numbers are shown in the second and third columns, respectively. Where applicable, the amino acids predicted or shown to be part of a signal peptide are indicated, as are the amino acids predicted or shown as comprised in the mature GH8 polypeptide. The amino acids in a signal peptide are labeled with '-' in the accompanying sequence list, but in the table below they are numbered from the start codon of the full polypeptide. Not all the listed polypeptides are secreted. A few of the listed polypeptides may also comprise a prepro sequence that is cleaved off to produce the mature polypeptide, but is shown here in most cases as part of the mature polypeptide—this may be determined by standard practices in the art, such as, N-terminal amino acid sequencing of the mature polypeptide.

TABLE 1

Potential parent GH8 xylanases; the G8 motif 1 is indicated in the mature sequence numbering, where the signal has been included as a feature in the sequence listing (with negative numbers), otherwise it is indicated from the start of the signal.

| SEQ ID | Organism | UniProt | Signal | Mature | G8 Motif 1 |
|---|---|---|---|---|---|
| 3 | Bacillus sp. KK-1 (artificial signal) | | 1-27 | 28-433 | 65-70 |
| 4 | Bacillus sp. KK-1 (native signal) | O52730 | 1-28 | 29-434 | 65-70 |
| 5 | Burkholderia phymatum | B2JFS8 | 1-39 | 40-388 | 81-86 |
| 6 | Labrenzia aggregata | A0NZ93 | 1-21 | 22-400 | 79-84 |
| 7 | Alteromonadales bacterium TW-7 | A0XXD5 | 1-21 | 22-376 | 58-63 |
| 8 | Yersinia enterocolitica | A1JST6 | 1-23 | 24-375 | 55-60 |
| 9 | Mycobacterium vanbaalenii | A1TEN4 | 1-28 | 29-376 | 75-80 |
| 10 | Lactococcus lactis | A2RKE9 | | 1-298 | 54-59 |
| 11 | Burkholderia cenocepacia | A2VR29 | 1-40 | 41-409 | 86-91 |
| 12 | Streptococcus sanguinis | A3CKD9 | | 1-342 | 42-47 |
| 13 | Leptospirillum rubarum | A3ER07 | 1-23 | 24-366 | 55-60 |
| 14 | Sagittula stellata | A3K4W8 | 1-25 | 26-416 | 99-104 |
| 15 | Burkholderia mallei | A3MCA1 | 1-23 | 24-437 | 113-118 |
| 16 | Rhodobacter sphaeroides | A3PL64 | 1-25 | 26-356 | 66-71 |
| 17 | Rhodobacterales bacterium | A3VA52 | 1-27 | 28-342 | 58-63 |

TABLE 1-continued

Potential parent GH8 xylanases; the G8 motif 1 is indicated in the mature sequence numbering, where the signal has been included as a feature in the sequence listing (with negative numbers), otherwise it is indicated from the start of the signal.

| SEQ ID | Organism | UniProt | Signal | Mature | G8 Motif 1 |
|---|---|---|---|---|---|
| 18 | Paenibacillus sp. W-61 | A4F259 | | 1-380 | 69-74 |
| 19 | Cronobacter sakazakii | A4H2S1 | 1-21 | 22-371 | 54-59 |
| 20 | Burkholderia vietnamiensis | A4JDK7 | 1-32 | 33-407 | 84-89 |
| 21 | Polynucleobacter necessarius | A4SY19 | 1-27 | 28-337 | 64-69 |
| 22 | Enterobacter sp. 638 | A4WFV3 | 1-13 | 14-360 | 56-61 |
| 23 | Enterobacter sp. 638 | A4WFW1 | 1-24 | 25-330 | 52-57 |
| 24 | Rhodobacter sphaeroides | A4WR51 | 1-25 | 26-356 | 65-70 |
| 25 | Rhodobacter sphaeroides | A4X062 | 1-24 | 25-362 | 67-72 |
| 26 | Flavobacterium johnsoniae | A5FD37 | 1-33 | 34-430 | 100-105 |
| 27 | Flavobacterium johnsoniae | A5FL64 | 1-19 | 20-465 | 75-80 |
| 28 | Acidiphilium cryptum | A5FW12 | 1-26 | 27-376 | 60-65 |
| 29 | Vibrio fischeri | A5JJ40 | 1-23 | 24-392 | 74-79 |
| 30 | Vibrionales bacterium SWAT-3 | A5L0Z5 | 1-18 | 19-369 | 51-56 |
| 31 | Pseudomonas putida | A5W2B7 | 1-16 | 17-367 | 51-56 |
| 32 | Vibrio harveyi | A6ARS3 | 1-18 | 19-369 | 51-56 |
| 33 | Plesiocystis pacifica | A6FX48 | 1-8 | 9-452 | 127-132 |
| 34 | Limnobacter | A6GMN1 | 1-31 | 32-383 | 61-66 |
| 35 | Limnobacter | A6GNP5 | 1-25 | 26-380 | 62-67 |
| 36 | Klebsiella pneumoniae | A6TFD4 | 1-22 | 23-369 | 56-60 |
| 37 | Klebsiella pneumoniae | A6TFE2 | 1-23 | 24-333 | 52-57 |
| 38 | Sinorhizobium medicae | A6UK07 | 1-19 | 20-344 | 54-59 |
| 39 | Marimonas | A6W1N6 | 1-27 | 27-417 | 91-96 |
| 40 | Bifidobacterium adolescentis | A7A3Z7 | 1-22 | 23-379 | 65-70 |
| 41 | Yersinia pseudotuberculosis | A7FP36 | 1-22 | 23-371 | 55-60 |
| 42 | Asaia bogorensis | A7M789 | 1-25 | 26-345 | 60-65 |
| 43 | Escherichia coli | A7ZT72 | 1-18 | 19-365 | 51-56 |
| 44 | Citrobacter koseri | A8ARA5 | 1-22 | 23-369 | 55-60 |
| 45 | Serratia proteamaculans | A8G820 | 1-23 | 24-370 | 55-60 |
| 46 | Vibrio campbellii | A8T846 | 1-18 | 19-369 | 51-56 |
| 47 | Burkholderia multivorans | A9ACB8 | 1-38 | 39-414 | 91-96 |
| 48 | Herpetosiphon aurantiacus | A9AYU3 | 1-39 | 40-543 | 110-115 |
| 49 | Herpetosiphon aurantiacus | A9B7H2 | 1-29 | 30-511 | 88-93 |
| 50 | Herpetosiphon aurantiacus | A9B7H3 | 1-27 | 28-609 | 88-93 |
| 51 | Agrobacterium tumefaciens | A9CEZ6 | 1-28 | 29-351 | 61-66 |
| 52 | Sorangium cellulosum | A9G2N6 | | 1-383 | 58-62 |
| 53 | Sorangium cellulosum | A9GFS5 | 1-22 | 23-467 | 134-139 |
| 54 | Sorangium cellulosum | A9GJA6 | 1-23 | 24-497 | 142-147 |
| 55 | Clostridium phytofermentans | A9KRR7 | | 1-381 | 65-70 |
| 56 | Salmonella arizonae | A9MLJ1 | 1-22 | 23-369 | 55-60 |
| 57 | Salmonella paratyphi | A9MUP9 | 1-21 | 22-368 | 54-59 |
| 58 | Bacillus thuringiensis | A9P7F6 | 1-27 | 28-453 | 121-126 |
| 59 | Lactococcus lactis | A9QS66 | | 1-377 | 54-59 |
| 60 | Lactococcus lactis | A9QSM5 | 1-25 | 26-371 | 68-73 |
| 61 | Methylobacterium extorquens | A9W2G4 | 1-29 | 30-419 | 124-129 |
| 62 | Pseudomonas putida | B0KHK5 | 1-21 | 22-371 | 55-60 |
| 63 | Methylobacterium sp. 4-46 | B0UPS6 | 1-28 | 29-393 | 97-102 |
| 64 | Escherichia albertii | B1EHK5 | 1-22 | 23-369 | 55-60 |
| 65 | Burkholderia graminis | B1FXP2 | 1-58 | 59-476 | 152-157 |
| 66 | Burkholderia pseudomallei | B1H9R8 | | 1-513 | 189-194 |
| 67 | Yersinia pseudotuberculosis | B1JH76 | 1-22 | 23-371 | 55-60 |
| 68 | Burkholderia cenocepacia | B1JZP0 | 1-40 | 41-409 | 86-91 |
| 69 | Escherichia coli | B1LJ80 | 1-23 | 24-370 | 56-61 |
| 70 | Methylobacterium radiotolerans | B1LS51 | 1-24 | 25-385 | 89-94 |
| 71 | Methylobacterium radiotolerans | B1M836 | 1-29 | 30-367 | 71-76 |
| 72 | Burkholderia ambifaria | B1TH37 | | 1-359 | 36-41 |
| 73 | Leptothrix cholodnii | B1Y239 | | 1-379 | 48-53 |
| 74 | Burkholderia ambifaria | B1YNG4 | 1-41 | 42-406 | 83-88 |
| 75 | Methylobacterium populi | B1ZDE2 | 1-34 | 35-421 | 126-131 |
| 76 | Opitutus terrae | B1ZP97 | 1-22 | 23-412 | 101-106 |
| 77 | Opitutus terrae | B1ZP98 | | 1-445 | 121-126 |
| 78 | Cupriavidus taiwanensis | B2AI90 | 1-23 | 24-393 | 72-77 |
| 79 | Burkholderia phymatum | B2JFS8 | 1-40 | 41-388 | 71-76 |
| 80 | Burkholderia phymatum | B2JS35 | 1-42 | 43-410 | 76-81 |
| 81 | Escherichia coli | B2N7Y3 | 1-18 | 19-365 | 51-56 |
| 82 | Burkholderia phytofirmans | B2TFR8 | 1-25 | 26-393 | 71-76 |
| 83 | Shigella boydii | B2U4J9 | 1-18 | 19-365 | 51-56 |
| 84 | Erwinia tasmaniensis | B2VCL4 | 1-23 | 24-333 | 52-57 |
| 85 | Bacteroides intestinalis | B3C8W4 | 1-20 | 21-419 | 89-94 |
| 86 | Bacteroides intestinalis | B3CES9 | 1-26 | 27-418 | 103-108 |
| 87 | Geobacillus | B3K473 | 1-30 | 31-407 | 92-97 |
| 88 | Rhizobium etli | B3PVE9 | 1-24 | 25-348 | 59-64 |
| 89 | Escherichia coli | B3WP91 | 1-23 | 24-370 | 56-61 |

TABLE 1-continued

Potential parent GH8 xylanases; the G8 motif 1 is indicated in the mature sequence numbering, where the signal has been included as a feature in the sequence listing (with negative numbers), otherwise it is indicated from the start of the signal.

| SEQ ID | Organism | UniProt | Signal | Mature | G8 Motif 1 |
|---|---|---|---|---|---|
| 90 | *Lactobacillus reuteri* | B3XPX3 | 1-23 | 24-380 | 78-83 |
| 91 | *Salmonella enterica* | B3YCW2 | 1-22 | 23-369 | 55-60 |
| 92 | *Bacillus cereus* | B3ZAY7 | 1-27 | 28-453 | 121-126 |
| 93 | *Bacillus cereus* | B3ZAZ1 | | 1-412 | 95-99 |
| 94 | *Clostridium thermocellum* | B4BE17 | 1-33 | 34-477 | 94-98 |
| 95 | *Burkholderia cenocepacia* | B4E6B0 | 1-14 | 15-383 | 60-65 |
| 96 | *Proteus mirabilis* | B4F0R7 | 1-31 | 32-345 | 63-68 |
| 97 | *Alteromonas macleodii* | B4RSC3 | 1-26 | 27-366 | 59-64 |
| 98 | *Anaeromyxobacter* | B4UAH9 | 1-29 | 30-1140 | 70-75 |
| 99 | *Microcoleus chthonoplastes* | B4W0R5 | | 1-454 | 116-121 |
| 100 | *Microbacteriaceae* | B5BUR0 | 1-14 | 15-326 | 44-49 |
| 101 | *Verrucomicrobiae* | B5JFU0 | | 1-387 | 76-81 |
| 102 | *Verrucomicrobiae* | B5JIL3 | 1-18 | 19-431 | 88-93 |
| 103 | *Methylobacterium chloromethanicum* | B7KRP7 | 1-26 | 27-385 | 89-94 |
| 104 | *Clostridium cellulolyticum* | B8I0N9 | | 1-376 | 65-70 |
| 105 | *Clostridium cellulolyticum* | B8I0S8 | 1-26 | 27-477 | 92-97 |
| 106 | *Stenotrophomonas* | B8L0W8 | 1-29 | 30-380 | 67-72 |
| 107 | *Rhodobacter sphaeroides* | B9KK73 | 1-24 | 25-356 | 66-71 |
| 108 | *Bifidobacterium pseudocatenulatum* | C0BQ52 | | 1-384 | 70-75 |
| 109 | *Subdoligranulum variabile* | C0CBU5 | | 1-388 | 67-72 |
| 110 | *Halomonas* | C0JSK6 | 1-32 | 33-350 | 66-71 |
| 111 | *Geodermatophilus obscurus* | C0U1B3 | 1-22 | 23-390 | 88-93 |
| 112 | *Lactobacillus gasseri* | C0XE89 | | 1-372 | 67-72 |
| 113 | *Azotobacter vinelandii* | C1DJH4 | 1-24 | 25-337 | 54-59 |
| 114 | *Sulfurihydrogenibium azorense* | C1DW55 | 1-19 | 20-320 | 50-55 |
| 115 | *Acidobacterium capsulatum* | C1F831 | 1-29 | 30-388 | 60-65 |
| 116 | *Lactobacillus jensenii* | C2DZT7 | | 1-381 | 71-76 |
| 117 | *Spirosoma linguale* | C4CS14 | 1-31 | 32-432 | 101-106 |
| 118 | *Edwardsiella ictaluri* | C5BB42 | 1-24 | 25-373 | 57-62 |
| 119 | *Teredinibacter turnerae* | C5BJ89 | 1-29 | 30-436 | 109-114 |
| 120 | *Aquifex aeolicus* | O67401 | 1-16 | 17-325 | 50-55 |
| 121 | *Acetobacter xylinus* | O82857 | 1-16 | 17-341 | 55-60 |
| 122 | *Cellulomonas uda* | P18336 | 1-23 | 24-359 | 52-57 |
| 123 | *Erwinia chrysanthemi* | P27032 | 1-23 | 24-332 | 52-57 |
| 124 | *Bacillus* sp. KSM-330 | P29019 | 1-27 | 56-463 | 129-134 |
| 125 | *Acetobacter xylinus* | P37696 | 1-20 | 21-342 | 56-61 |
| 126 | *Xanthomonas axonopodis* | P58935 | 1-25 | 26-384 | 62-67 |
| 127 | *Fulvimarina pelagi* | Q0FZX6 | 1-23 | 24-365 | 73-78 |
| 128 | *Chlorobium ferrooxidans* | Q0YP21 | 1-23 | 24-376 | 59-64 |
| 129 | *Cytophaga hutchinsonii* | Q11NQ3 | 1-25 | 26-1223 | 59-64 |
| 130 | *Pseudoalteromonas atlantica* | Q15WZ3 | 1-44 | 45-912 | 585-590 |
| 131 | *Deinococcus geothermalis* | Q1J317 | 1-26 | 27-292 | 101-106 |
| 132 | *Ralstonia metallidurans* | Q1LL46 | 1-31 | 32-387 | 60-65 |
| 133 | *Candidatus Kuenenia stuttgartiensis* | Q1Q2C1 | 1-24 | 25-344 | 55-60 |
| 134 | *Vibrio alginolyticus* | Q1V8W2 | 1-18 | 19-368 | 51-56 |
| 135 | *Aurantimonas* sp. SI85-9A1 | Q1YMU9 | 1-25 | 26-364 | 72-77 |
| 136 | *Photobacterium profundum* | Q1Z1X9 | 1-18 | 19-369 | 51-56 |
| 137 | *Lysobacter* sp. IB-9374 | Q25C15 | 1-33 | 34-414 | 98-103 |
| 138 | *Bordetella avium* | Q2KWR4 | 1-31 | 32-398 | 67-72 |
| 139 | *Hahella chejuensis* | Q2S7F9 | 1-30 | 31-555 | 127-132 |
| 140 | *Chlorobium chlorochromatii* | Q3ATR3 | 1-22 | 23-398 | 60-65 |
| 141 | *Pelodictyon luteolum* | Q3B476 | 1-23 | 24-376 | 56-61 |
| 142 | *Xanthomonas euvesicatoria* | Q3BPE1 | 1-34 | 35-393 | 71-76 |
| 143 | *Pseudoalteromonas haloplanktis* | Q3IER3 | 1-21 | 22-376 | 66-71 |
| 144 | *Cupriavidus pinatubonensis* | Q46VF0 | 1-29 | 30-392 | 63-68 |
| 145 | *Ustilago maydis* | Q4PG97 | | 1-361 | 37-42 |
| 146 | *Zymomonas mobilis* | Q5NNK0 | 1-20 | 21-339 | 56-61 |
| 147 | *Erwinia carotovora* | Q6CYY2 | 1-22 | 23-371 | 56-61 |
| 148 | *Photobacterium profundum* | Q6LRE7 | 1-18 | 19-369 | 51-56 |
| 149 | *Acetobacter xylinus* | Q76KK1 | 1-20 | 21-342 | 56-61 |
| 150 | *Chromobacterium violaceum* | Q7NUM1 | 1-21 | 22-382 | 56-61 |
| 151 | *Pseudomonas syringae* | Q888J5 | 1-29 | 30-403 | 67-72 |
| 152 | *Pseudomonas putida* | Q88JL2 | 1-19 | 20-370 | 54-59 |
| 153 | *Bacillus circulans* | Q93HV0 | 1-30 | 31-407 | 92-97 |
| 154 | *Paenibacillus fukuinensis* | Q93IE7 | 1-41 | 42-797 | 114-119 |
| 159 | *Pseudoalteromonas haloplanktis* | | 1-27 | 29-402 | 77-82 |

Example 2

Construction of Variants by Site-directed Mutagenesis

Site-directed variants were constructed of the *Bacillus* sp. KK-1 GH8 xylanase (SEQ ID NO:3 or 4) comprising specific insertions/deletions/substitutions in the loop flanking the conserved GH8 motif on the N-terminal side according to the invention. The variants were made by traditional cloning of DNA fragments (Sambrook et al., Molecular Cloning: A Laboratory Manual, 2nd Ed., Cold Spring Harbor, 1989) using PCR together with properly designed mutagenic oligonucleotides that introduced the desired mutations in the resulting sequence.

Mutagenic oligos were synthesized corresponding to the DNA sequence flanking the desired site(s) of mutation, separated by the DNA base pairs defining the insertions/deletions/substitutions. In this manner, the variants listed in table 2 below were constructed and produced.

As an example, the mutagenic primers for the construction of variant LBei411, which has a single alanine amino acid insertion in position 53 of the mature polypeptide (*53aA), were designed as follows:

```
LBei411f (SEQ ID NO: 156):
5'-gcttctacaacagacgctgacaaccttggcaacggctattac

LBei411r (SEQ ID NO: 157):
5'-gtaatagccgttgccaaggttgtcagcgtctgttgtagaagc
```

In order to purify GH8 xylanase variants of the invention, the mutated DNA comprising a variant of the invention was transformed into a competent *B. subtilis* strain and fermented using standard protocols (PS-1 media, 3-4 days, 30° C.).

TABLE 2

Loop variants of Bacillus sp. KK-1 GH8 xylanase (SEQ ID NO: 3 or 4), where the amino acid mutation(s) is listed for each variant.

| Variant | Mutation(s) |
|---|---|
| LBei386 | D53* |
| LBei388 | L56* |
| LBei390 | N58* |
| LBei411 | *53aA |
| LBei413 | *55aA |
| LBei417 | *59aA |
| LBei418 | N55A, L56*, G57N, N58L |
| LBei440 | *61aA |
| MDTo253 | *60aA |
| MDTo254 | *62aA |
| MDTo255 | *53aS |
| MDTo256 | *53aD |
| MDTo257 | *53aK |
| MDTo258 | *53aF |
| MDTo259 | *53aL |
| MDTo260 | *55aS |
| MDTo262 | *55aK |
| MDTo263 | *55aF |
| MDTo264 | *55aL |
| MDTo265 | *59aS |
| MDTo266 | *59aD |
| MDTo267 | *59aK |
| MDTo268 | *59aF |
| MDTo269 | *59aL |
| MDTo298 | *53aA, *55aA |
| MDTo299 | *55aA, *59aA |
| MDTo300 | *53aA, *59aA |
| MDTO301 | *53aA, *55aA, *59aA |
| MDTo323 | *53aA, *55aL |
| MDTo324 | *55aA, *59aD |
| MDTo325 | *55aL, *59aA |
| MDTo326 | *55aL, *59aS |
| MDTo327 | *55aL, *59aD |
| MDTo328 | *53aA, *59aS |
| MDTo329 | *53aA, *59aD |
| MDTo330 | *53aA, *55aL, *59aA |
| MDTo331 | *53aA, *55aA, *59aS |
| MDTo332 | *53aA, *55aA, *59aD |
| MDTo333 | *53aA, *55aA, *59aF |
| MDTo334 | *53aA, *55aL, *59aS |
| MDTo335 | *53aA, *55aL, *59aD |
| MDTo336 | *53aA, *55aL, *59aF |

Amino acid position numbers 53-62 refer to the mature polypeptide of SEQ ID NO: 3 or 4.
An amino acid deletion is shown as the deleted amino acid, its position number and an asterisk, e.g., "D53*" denotes the deletion of an aspartic acid residue (D) from position 53.
An insertion is shown as an asterisk followed by the position number, a lowercase "a" to denote the amino acid already present in that position and finally the inserted amino acid, e.g., "*53aA" denotes the insertion of an alanine (A) residue in the polypeptide following the aspartic acid (D) in position 53.
An amino acid substitution is shown as the amino acid, its position number and the new amino acid replacing or substituting the first mentioned, e.g., "N55A" denotes that the asparagine (N) residue in position 55 was replaced with an alanine (A) residue.

Example 3

Straight Dough Procedure

Recipe

| Dough | % on flour basis |
|---|---|
| Ascorbic acid | to be optimized for each flour (40 ppm in this trial) |
| Cream yeast | 4 (73% water) |
| Salt | 1.5 |
| Sugar | 1.5 |
| Water | to be optimized for each flour (57% in this trial) |
| Wheat flour + Enzyme | 100 (Kolibri flour from Meneba or Kluut flour with lower gluten content from Meneba) |

Procedure

1. Scaling of ingredients, addition of flour, yeast, salt, sugar, ascorbic acid and enzyme
2. Enzyme was dosed from 0.02 to 0.2 mg protein enzyme/kg flour; excl. the negative control (no enzyme)
3. Temperature adjustment of water in order to reach a dough temperature of 27° C. after mixing, scaling and addition of water into mixer bowl
4. Mixing: 3 min at 78 rpm and 6 min at 138 rpm using a Diosna spiral mixer
5. The dough is taken from the mixer bowl and the dough temperature is determined, the dough parameters are determined (dough evaluation after mixing) and the dough is molded by the baker
6. The dough is given 20 min. floor-time under plastic cover and the second dough evaluation is performed (dough evaluation after floor time)
7. The dough is scaled at 1500 g (30 rolls) and 6×350 g (bread)
8. The molded rolls and bread dough is given 10 min bench-time covered in plastic
9. The dough for rolls is formed to a ~34 cm round plate and put on a roll maker plate and rolls are formed in a rounder.
    a. The rolls are transferred to a silicone covered baking sheet.
    b. The dough for bread are shaped in a sheeter and transferred to pans which are put in baking sheet 10. The bread and rolls are proofed at 32° C., 86% RH.
    a. The proofing time for rolls is 45 min. and 70 min. (overproofing)
    b. The proofing time for bread is 55 min and 80 min. (overproofing)
11. The bread and rolls are baked at 230° C. with steam
    a. The rolls are baked for 22 min (damper opens after 12 min in order to let out the steam from the oven)
    b. The bread is baked for 35 min (damper opens after 25 min in order to let out the steam from the oven)
12. The bread is taken out of the pan after baking and put on a baking sheet
13. The bread and rolls are allowed to cool down
14. The bread and rolls are evaluated Example 4

Chorleywood Baking Procedure (CBP)

Recipe

| Dough | % on flour basis |
|---|---|
| Ascorbic acid | to be optimized for each flour (150 ppm in this trial) |
| Cream yeast | 4.5 (73% water) |
| Salt | 2.0 |
| Soy flour | 0.5 (contains active enzymes) |
| Water | to be optimized for each flour (58% in this trial) |
| Wheat flour + Enzyme | 100 (Kolibri flour from Meneba) |

Procedure
1. Scaling of ingredients, addition of flour, water, cream yeast, salt, soy flour, ascorbic acid and enzyme
2. Enzyme was dosed from 0.02 to 0.2 mg protein enzyme/kg flour; excl. the negative control (no enzyme)
3. All ingredients is put in a Pentagon K5 High speed mixer
4. The dough is mixed to a energy input of 11 w/kg dough at a speed of 425 rpm (30% of the mixing time with 0.6 bar atmosphere pressure and 70% of the mixing time at 18 hg vacuum)
5. The dough parameters are evaluated (dough evaluation after mixing)
6. The dough is resting (first) for 5 min. covered in plastic
7. The dough is scaled at 4×600 g
8. The dough is resting (second) for 10 min. covered in plastic
9. The dough is moulded and shaped in a sheeter and transferred to lidded pans which are put in baking sheet
10. The dough is proofed at 40° C., 80 RH in Termaks proof box
    a. The proofing time for pan bread is 55 min.
    b. The proofing time for 3-cut-bread is 45 min.
11. The bread is baked at 220° C. in Reed Trap oven with no steam
12. The bread is evaluated Example 5

Dough and Bread Evaluation Parameters

Stickiness: The dough stickiness is the degree to which a dough adheres to ones hands or other surfaces. This is a sensory evaluation performed by an experienced baker where the control dough without enzyme is given the value 5 and the other doughs are judged compared to the control on a scale from 0 to 10, where 0 is very little stickiness and 10 is very sticky.

Softness: The dough softness is the ease with which a dough will compress. This is a sensory evaluation performed by an experienced baker where the control dough without enzyme is given the value 5 and the other doughs are judged compared to the control on a scale from 0 to 10, where 0 is less soft and 10 is more soft.

Extensibility: The dough extensibility is the degree to which a dough can be stretched without tearing. This is a sensory evaluation performed by an experienced baker where the control dough without enzyme is given the value 5 and the other doughs are judged compared to the control on a scale from 0 to 10, where 0 is low/short extensibility and 10 is high/long extensibility.

Elasticity: The dough elasticity is the ability of a dough to resist stretching as well as to return to its original size and shape when the force is removed. This is a sensory evaluation performed by an experienced baker where the control dough without enzyme is given the value 5 and the other doughs are judged compared to the control on a scale from 0 to 10, where 0 is low/weak extensibility and 10 is high/strong extensibility.

Machinability: The machinability is the degree to which a dough tends to retain its original surface without damages after work up in machinery. This is evaluated by an experienced baker where the control dough without enzyme is given the value 5 and the other doughs are judged compared to the control on a scale from 0 to 10, where 0 is low machinability and 10 is high machinability.

Volume: The volume of baked rolls and bread is determined through rape seed displacement. The specific volume index is calculated as follows:

Specific volume=specific volume of bread with enzyme (in ml/g)/specific volume of bread without enzyme (in ml/g)

The average specific volume of two control doughs is set to 100%. The specific volumes of bread or rolls prepared from dough with added enzyme are averages of double samples.

Example 6

Evaluating the Performance of the GH8 Xylanase Parent

Determining the dough and bread parameters described above, in most cases, involves a sensory evaluation by an experienced baker, but even so, there will likely be some natural variation, depending on which day the test is carried out and on which baker does the test etc.

The mature parent GH8 xylanase of Bacillus sp. KK-1 (SEQ ID NO:3 or 4) was tested in twelve experiments over several days by at least two bakers, using an enzyme dosage of 0.05 mg/kg in the straight dough procedure with Kolibri flour from Meneba. The dough was evaluated after floor time for stickiness, softness, extensability, elasticity and machinability. The specific volume of the resulting bread was also determined, both after normal proofing and long proofing. The results are shown in table 3 below.

TABLE 3

Dough evaluation of example 6; results.

| Test | Sticki-ness | Softness | Extens-ability | Elastic-ity | Machin-ability | Vol. | Vol. long proof |
|---|---|---|---|---|---|---|---|
| 1 | 7 | 7 | 6 | 4 | 4 | 108 | 112 |
| 2 | 7 | 7 | 6 | 4 | 4 | 106 | 108 |

TABLE 3-continued

Dough evaluation of example 6; results.

| Test | Sticki-ness | Softness | Extens-ability | Elastic-ity | Machin-ability | Vol. | Vol. long proof |
|---|---|---|---|---|---|---|---|
| 3 | 6 | 6 | 5 | 5 | 5 | 105 | 106 |
| 4 | 6 | 5 | 5 | 5 | 5 | 98 | 99 |
| 5 | 7 | 6 | 6 | 4 | 4 | 118 | 114 |
| 6 | 7 | 7 | 6 | 4 | 4 | 115 | 111 |
| 7 | 6 | 6 | 6 | 4 | 4 | 106 | 116 |
| 8 | 6 | 6 | 5 | 4 | 5 | 110 | 113 |
| 9 | 6 | 6 | 6 | 5 | 5 | 110 | 113 |
| 10 | 6 | 6 | 6 | 5 | 5 | 109 | 109 |
| 11 | 7 | 7 | 6 | 4 | 4 | 110 | 115 |
| 12 | 6 | 6 | 5 | 5 | 5 | 111 | 116 |

Example 7

Stickiness of Doughs Prepared Using the GH8 Xylanase Variants

The stickiness of doughs prepared using the GH8 xylanase variants in the straight dough procedure with Kolibri flour from Meneba at an enzyme dosage of 0.05 mg/kg was evaluated after floor time. For some of the more interesting variants that provided a significantly less sticky dough, the evaluations after floor time were also done for higher enzyme dosages of 0.1 mg/kg, 4 times overdose (4×OD) and 10 times overdose (10×OD). The results are shown in table 4 below.

There is a trend that the GH8 variants of the invention provide less sticky doughs than the parent GH8 xylanase; some of them even at very high enzyme dosages.

TABLE 4

Dough evaluation of example 7; results of stickiness score by bakers.

| Variant | Mutation | 0.05 mg/kg | 0.1 mg/kg | 4 × OD | 10 × OD |
|---|---|---|---|---|---|
| LBei386 | D53* | 6 | | | |
| LBei388 | L56* | 5 | | | |
| LBei390 | N58* | 7 | | | |
| LBei411 | *53aA | 6 | | | |
| LBei411 | *53aA | 5 | 5 | 6 | 6 |
| LBei411 | *53aA | 5 | | | |
| LBei413 | *55aA | 6 | 6 | | |
| LBei413 | *55aA | 5 | 6 | 6 | 7 |
| LBei413 | *55aA | 5 | | | |
| LBei417 | *59aA | 5 | 6 | | |
| LBei417 | *59aA | 5 | 6 | 6 | 6 |
| LBei417 | *59aA | 5 | | | |
| LBei418 | N55A, L56*, G57N, N58L | 6 | | | |
| LBei440 | *61aA | 6 | | | |
| MDTo253 | *60aA | 6 | 7 | | |
| MDTo254 | *62aA | 5 | 6 | | |
| MDTo255 | *53aS | 6 | 7 | | |
| MDTo256 | *53aD | 6 | 8 | | |
| MDTo257 | *53aK | 6 | 7 | | |
| MDTo258 | *53aF | 6 | 6 | | |
| MDTo259 | *53aL | 7 | 7 | | |
| MDTo260 | *55aS | 6 | 7 | | |
| MDTo262 | *55aK | 6 | 8 | | |
| MDTo263 | *55aF | 6 | 6 | | |
| MDTo264 | *55aL | 5 | 5 | | |
| MDTo264 | *55aL | 5 | | 6 | 6 |
| MDTo265 | *59aS | 5 | 6 | | |
| MDTo265 | *59aS | 6 | | 8 | 7 |
| MDTo266 | *59aD | 5 | 6 | | |
| MDTo266 | *59aD | 6 | | 6 | 7 |
| MDTo267 | *59aK | 5 | 6 | | |
| MDTo268 | *59aF | 5 | 6 | | |
| MDTo268 | *59aF | 6 | | 8 | 9 |
| MDTo269 | *59aL | 5 | 6 | | |
| MDTo298 | *53aA, *55aA | 6 | | | |
| MDTo298 | *53aA, *55aA | 6 | | 8 | 7 |
| MDTo299 | *55aA, *59aA | 6 | | | |
| MDTo299 | *55aA, *59aA | 6 | | 7 | 7 |
| MDTo300 | *53aA, *59aA | 6 | | | |
| MDTo300 | *53aA, *59aA | 6 | | 6 | 7 |
| MDTO301 | *53aA, *55aA, *59aA | 6 | | | |
| MDTO301 | *53aA, *55aA, *59aA | 5 | | 6 | 7 |
| MDTo323 | *53aA, *55aL | 6 | 8 | | |
| MDTo324 | *55aA, *59aD | 6 | 6 | | |
| MDTo325 | *55aL, *59aA | 6 | 7 | | |
| MDTo326 | *55aL, *59aS | 6 | 7 | | |
| MDTo327 | *55aL, *59aD | 6 | 7 | 8 | |
| MDTo328 | *53aA, *59aS | 6 | 6 | | |
| MDTo329 | *53aA, *59aD | 6 | 7 | | |
| MDTo330 | *53aA, *55aL, *59aA | 6 | 7 | | |
| MDTo331 | *53aA, *55aA, *59aS | 6 | 7 | | |
| MDTo332 | *53aA, *55aA, *59aD | 6 | 7 | | |
| MDTo333 | *53aA, *55aA, *59aF | 6 | 7 | | |
| MDTo334 | *53aA, *55aL, *59aS | 6 | 7 | | |
| MDTo335 | *53aA, *55aL, *59aD | 6 | 7 | | |
| MDTo336 | *53aA, *55aL, *59aF | 6 | 7 | | |

Example 8

Volume Increase in Bread Made with GH8 Xylanase Variants

Breads were baked from doughs made with the GH8 xylanase variants in the straight dough procedure with Kolibri flour from Meneba at enzyme dosages of 0.05 mg/kg using both normal and long proofing. The specific volumes of the breads were determined.

For some of the more interesting variants baking tests were also done using dough with higher enzyme dosages of 0.1 mg/kg, 4 times overdose (4×OD) and 10 times overdose (10× OD) with both normal and long proofing. The results are shown in table 5 below.

TABLE 5

Specific bread volumes of example 8; results.

| Variant | Mutation | 0.05 mg/kg | | 0.1 mg/kg | | 4 × OD | | 10 × OD | |
|---|---|---|---|---|---|---|---|---|---|
| | | Vol | Vol. long proof | Vol. | Vol. long proof | Vol. | Vol. long proof | Vol. | Vol. long prop |
| LBei386 | D53* | 102 | 103 | | | | | | |
| LBei388 | L56* | 108 | 117 | | | | | | |

TABLE 5-continued

Specific bread volumes of example 8; results.

| Variant | Mutation | 0.05 mg/kg Vol | 0.05 mg/kg Vol. long proof | 0.1 mg/kg Vol | 0.1 mg/kg Vol. long proof | 4 × OD Vol. | 4 × OD Vol. long proof | 10 × OD Vol. | 10 × OD Vol. long prop |
|---|---|---|---|---|---|---|---|---|---|
| LBei390 | N58* | 109 | 115 | | | | | | |
| LBei411 | *53aA | 100 | 100 | | | | | | |
| LBei411 | *53aA | 110 | 114 | 109 | 104 | 119 | 132 | 127 | 132 |
| LBei411 | *53aA | 111 | 120 | | | | | | |
| LBei413 | *55aA | 109 | 110 | 107 | 109 | | | | |
| LBei413 | *55aA | 109 | 113 | 107 | 108 | 127 | 133 | 123 | 126 |
| LBei413 | *55aA | 108 | 117 | | | | | | |
| LBei417 | *59aA | 108 | 110 | 110 | 109 | | | | |
| LBei417 | *59aA | 111 | 107 | 104 | 105 | 128 | 135 | 121 | 129 |
| LBei417 | *59aA | 105 | 118 | | | | | | |
| LBei418 | N55A, L56*, G57N, N58L | 97 | 98 | | | | | | |
| LBei440 | *61aA | 97 | 99 | | | | | | |
| MDTo253 | *60aA | 114 | 124 | 114 | 125 | | | | |
| MDTo254 | *62aA | 102 | 102 | 115 | 122 | | | | |
| MDTo255 | *53aS | 108 | 113 | 108 | 113 | | | | |
| MDTo256 | *53aD | 107 | 112 | 106 | 108 | | | | |
| MDTo257 | *53aK | 120 | 126 | 116 | 117 | | | | |
| MDTo258 | *53aF | 113 | 112 | 118 | 120 | | | | |
| MDTo259 | *53aL | 111 | 119 | 116 | 121 | | | | |
| MDTo260 | *55aS | 110 | 118 | 114 | 124 | | | | |
| MDTo262 | *55aK | 111 | 118 | 112 | 122 | | | | |
| MDTo263 | *55aF | 101 | 94 | 99 | 104 | | | | |
| MDTo264 | *55aL | 108 | 123 | 116 | 139 | | | | |
| MDTo264 | *55aL | 110 | 125 | | | 117 | 133 | 124 | 130 |
| MDTo265 | *59aS | 110 | 123 | 116 | 136 | | | | |
| MDTo265 | *59aS | 110 | 120 | | | 117 | 127 | 129 | 131 |
| MDTo266 | *59aD | 109 | 129 | 122 | 136 | | | | |
| MDTo266 | *59aD | 109 | 116 | | | 120 | 122 | 126 | 128 |
| MDTo267 | *59aK | 108 | 120 | 116 | 128 | | | | |
| MDTo268 | *59aF | 115 | 128 | 122 | 144 | | | | |
| MDTo268 | *59aF | 111 | 123 | | | 114 | 127 | 128 | 134 |
| MDTo269 | *59aL | 104 | 115 | 110 | 118 | | | | |
| MDTo298 | *53aA, *55aA | 110 | 125 | | | | | | |
| MDTo298 | *53aA, *55aA | 111 | 126 | | | 125 | 134 | 123 | 137 |
| MDTo299 | *55aA, *59aA | 115 | 124 | | | | | | |
| MDTo299 | *55aA, *59aA | 112 | 131 | | | 119 | 134 | 124 | 137 |
| MDTo300 | *53aA, *59aA | 111 | 123 | | | | | | |
| MDTo300 | *53aA, *59aA | 113 | 130 | | | 118 | 137 | 121 | 137 |
| MDTO301 | *53aA, *55aA, *59aA | 115 | 119 | | | | | | |
| MDTO301 | *53aA, *55aA, *59aA | 114 | 115 | | | 123 | 128 | 119 | 136 |
| MDTo323 | *53aA, *55aL | 108 | 121 | 109 | 130 | 111 | 123 | | |
| MDTo324 | *55aA, *59aD | 113 | 124 | 114 | 127 | | | | |
| MDTo325 | *55aL, *59aA | 107 | 114 | 111 | 117 | | | | |
| MDTo326 | *55aL, *59aS | 107 | 107 | 107 | 114 | | | | |
| MDTo327 | *55aL, *59aD | 113 | 115 | 113 | 115 | 111 | 126 | | |
| MDTo328 | *53aA, *59aS | 106 | 122 | 110 | 130 | | | | |
| MDTo329 | *53aA, *59aD | 111 | 126 | 114 | 125 | | | | |
| MDTo330 | *53aA, *55aL, *59aA | 112 | 132 | 111 | 131 | | | | |
| MDTo331 | *53aA, *55aA, *59aS | | | 115 | 126 | | | | |
| MDTo332 | *53aA, *55aA, *59aD | 114 | 120 | 117 | 132 | | | | |
| MDTo333 | *53aA, *55aA, *59aF | 115 | 129 | 118 | 126 | | | | |
| MDTo334 | *53aA, *55aL, *59aS | 115 | 118 | 117 | 126 | | | | |
| MDTo335 | *53aA, *55aL, *59aD | 110 | 127 | 117 | 126 | | | | |
| MDTo336 | *53aA, *55aL, *59aF | 114 | 125 | 116 | 128 | | | | |

Example 9

Softness etc. of Doughs Prepared Using the GH8 Xylanase Variants

The softness, extensability, elasticity and machinability of doughs prepared using the GH8 xylanase variants in the straight dough procedure with Kolibri flour from Meneba at an enzyme dosage of 0.05 mg/kg was evaluated after floor time. The results are shown in table 6 below.

TABLE 6

Enzyme dosage of 0.05 mg/kg.

| Variant | Mutation(s) | Softness | Extensability | Elasticity | Machinability |
|---|---|---|---|---|---|
| LBei386 | D53* | 5 | 5 | 5 | 4 |
| LBei388 | L56* | 5 | 5 | 5 | 5 |
| LBei390 | N58* | 7 | 6 | 4 | 5 |
| LBei411 | *53aA | 6 | 4 | 6 | 5 |
| LBei411 | *53aA | 6 | 5 | 5 | 4 |
| LBei411 | *53aA | 6 | 5 | 5 | 4 |
| LBei413 | *55aA | 6 | 5 | 5 | 5 |
| LBei413 | *55aA | 5 | 4 | 6 | 4 |

TABLE 6-continued

Enzyme dosage of 0.05 mg/kg.

| Variant | Mutation(s) | Soft-ness | Extens-ability | Elas-ticity | Machin-ability |
|---|---|---|---|---|---|
| LBei413 | *55aA | 5 | 5 | 5 | 5 |
| LBei417 | *59aA | 5 | 5 | 5 | 5 |
| LBei417 | *59aA | 6 | 5 | 5 | 4 |
| LBei417 | *59aA | 5 | 5 | 5 | 5 |
| LBei418 | N55A, L56*, G57N, N58L | 6 | 5 | 5 | 4 |
| LBei440 | *61aA | 5 | 4 | 6 | 4 |
| MDTo253 | *60aA | 6 | 5 | 5 | 5 |
| MDTo254 | *62aA | 4 | 5 | 5 | 5 |
| MDTo255 | *53aS | 6 | 5 | 4 | 5 |
| MDTo256 | *53aD | 6 | 6 | 5 | 3 |
| MDTo257 | *53aK | 6 | 6 | 4 | 4 |
| MDTo258 | *53aF | 6 | 5 | 5 | 4 |
| MDTo259 | *53aL | 7 | 6 | 4 | 5 |
| MDTo260 | *55aS | 6 | 5 | 5 | 4 |
| MDTo262 | *55aK | 6 | 7 | 4 | 5 |
| MDTo263 | *55aF | 5 | 6 | 5 | 5 |
| MDTo264 | *55aL | 5 | 5 | 5 | 5 |
| MDTo264 | *55aL | 6 | 4 | 6 | 5 |
| MDTo265 | *59aS | 5 | 5 | 5 | 5 |
| MDTo265 | *59aS | 7 | 6 | 5 | 5 |
| MDTo266 | *59aD | 6 | 6 | 6 | 4 |
| MDTo266 | *59aD | 6 | 5 | 5 | 5 |
| MDTo267 | *59aK | 5 | 5 | 5 | 5 |
| MDTo268 | *59aF | 6 | 6 | 4 | 5 |
| MDTo268 | *59aF | 7 | 5 | 4 | 5 |
| MDTo269 | *59aL | 5 | 4 | 5 | 5 |
| MDTo298 | *53aA, *55aA | 5 | 5 | 5 | 5 |
| MDTo298 | *53aA, *55aA | 6 | 6 | 6 | 5 |
| MDTo299 | *55aA, *59aA | 6 | 5 | 5 | 5 |
| MDTo299 | *55aA, *59aA | 6 | 6 | 4 | 4 |
| MDTo300 | *53aA, *59aA | 6 | 5 | 5 | 5 |
| MDTo300 | *53aA, *59aA | 6 | 6 | 4 | 5 |
| MDTO301 | *53aA, *55aA, *59aA | 5 | 5 | 5 | 5 |
| MDTO301 | *53aA, *55aA, *59aA | 5 | 5 | 5 | 5 |
| MDTo323 | *53aA, *55aL | 6 | 6 | 5 | 5 |
| MDTo324 | *55aA, *59aD | 6 | 6 | 5 | 5 |
| MDTo325 | *55aL, *59aA | 7 | 5 | 5 | 5 |
| MDTo326 | *55aL, *59aS | 7 | 5 | 5 | 5 |
| MDTo327 | *55aL, *59aD | 7 | 5 | 5 | 5 |
| MDTo328 | *53aA, *59aS | 6 | 6 | 5 | 5 |
| MDTo329 | *53aA, *59aD | 6 | 6 | 5 | 5 |
| MDTo330 | *53aA, *55aL, *59aA | 6 | 6 | 4 | 5 |
| MDTo331 | *53aA, *55aA, *59aS | 6 | 6 | 5 | 5 |
| MDTo332 | *53aA, *55aA, *59aD | 6 | 5 | 5 | 5 |
| MDTo333 | *53aA, *55aA, *59aF | 6 | 5 | 5 | 5 |
| MDTo334 | *53aA, *55aL, *59aS | 6 | 6 | 5 | 5 |
| MDTo335 | *53aA, *55aL, *59aD | 7 | 6 | 4 | 5 |
| MDTo336 | *53aA, *55aL, *59aF | 7 | 6 | 5 | 5 |

As already mentioned, for some of the more interesting variants that provided a significantly less sticky dough, the evaluations after floor time were also done for higher enzyme dosages of 0.1 mg/kg, 4 times overdose (4×OD) and 10 times overdose (10×OD). Those results with respect to softness, extensability, elasticity and machinability are shown in tables 7-9 below.

TABLE 7

Enzyme dosage of 0.1 mg/kg.

| Variant | Mutation(s) | Soft-ness | Extens-ability | Elas-ticity | Machin-ability |
|---|---|---|---|---|---|
| LBei411 | *53aA | 6 | 5 | 5 | 4 |
| LBei413 | *55aA | 6 | 4 | 6 | 5 |
| LBei413 | *55aA | 6 | 5 | 5 | 4 |
| LBei417 | *59aA | 6 | 4 | 6 | 5 |
| LBei417 | *59aA | 6 | 5 | 5 | 4 |
| MDTo253 | *60aA | 7 | 6 | 4 | 4 |
| MDTo254 | *62aA | 6 | 5 | 5 | 4 |

TABLE 7-continued

Enzyme dosage of 0.1 mg/kg.

| Variant | Mutation(s) | Soft-ness | Extens-ability | Elas-ticity | Machin-ability |
|---|---|---|---|---|---|
| MDTo255 | *53aS | 7 | 5 | 5 | 5 |
| MDTo256 | *53aD | 7 | 6 | 4 | 2 |
| MDTo257 | *53aK | 6 | 6 | 4 | 4 |
| MDTo258 | *53aF | 6 | 5 | 5 | 4 |
| MDTo259 | *53aL | 7 | 6 | 4 | 4 |
| MDTo260 | *55aS | 7 | 6 | 4 | 4 |
| MDTo262 | *55aK | 8 | 7 | 4 | 4 |
| MDTo263 | *55aF | 6 | 6 | 5 | 5 |
| MDTo264 | *55aL | 6 | 6 | 4 | 5 |
| MDTo265 | *59aS | 6 | 5 | 5 | 5 |
| MDTo266 | *59aD | 6 | 6 | 4 | 5 |
| MDTo267 | *59aK | 6 | 6 | 4 | 5 |
| MDTo268 | *59aF | 6 | 6 | 4 | 5 |
| MDTo269 | *59aL | 6 | 6 | 4 | 5 |
| MDTo323 | *53aA, *55aL | 7 | 6 | 4 | 4 |
| MDTo324 | *55aA, *59aD | 7 | 6 | 4 | 4 |
| MDTo325 | *55aL, *59aA | 8 | 6 | 4 | 5 |
| MDTo326 | *55aL, *59aS | 8 | 6 | 4 | 5 |
| MDTo327 | *55aL, *59aD | 8 | 6 | 4 | 5 |
| MDTo328 | *53aA, *59aS | 7 | 6 | 4 | 4 |
| MDTo329 | *53aA, *59aD | 7 | 6 | 4 | 5 |
| MDTo330 | *53aA, *55aL, *59aA | 7 | 6 | 4 | 5 |
| MDTo331 | *53aA, *55aA, *59aS | 8 | 6 | 4 | 5 |
| MDTo332 | *53aA, *55aA, *59aD | 8 | 6 | 4 | 5 |
| MDTo333 | *53aA, *55aA, *59aF | 7 | 7 | 4 | 5 |
| MDTo334 | *53aA, *55aL, *59aS | 8 | 7 | 4 | 5 |
| MDTo335 | *53aA, *55aL, *59aD | 7 | 6 | 4 | 4 |
| MDTo336 | *53aA, *55aL, *59aF | 7 | 6 | 4 | 4 |

TABLE 8

Enzyme dosage of 4 times overdose (4 × OD).

| Variant | Mutation(s) | Softness | Extensability | Elas-ticity | Machin-ability |
|---|---|---|---|---|---|
| LBei411 | *53aA | 6 | 5 | 5 | 4 |
| LBei413 | *55aA | 6 | 4 | 6 | 5 |
| LBei413 | *55aA | 6 | 5 | 5 | 4 |
| LBei417 | *59aA | 6 | 4 | 6 | 5 |
| LBei417 | *59aA | 6 | 5 | 5 | 4 |
| MDTo253 | *60aA | 7 | 6 | 4 | 4 |
| MDTo254 | *62aA | 6 | 5 | 5 | 4 |
| MDTo255 | *53aS | 7 | 5 | 5 | 5 |
| MDTo256 | *53aD | 7 | 6 | 4 | 2 |
| MDTo257 | *53aK | 6 | 6 | 4 | 4 |
| MDTo258 | *53aF | 6 | 5 | 5 | 4 |
| MDTo259 | *53aL | 7 | 6 | 4 | 4 |
| MDTo260 | *55aS | 7 | 6 | 4 | 4 |
| MDTo262 | *55aK | 8 | 7 | 4 | 4 |
| MDTo263 | *55aF | 6 | 6 | 5 | 5 |
| MDTo264 | *55aL | 6 | 6 | 4 | 5 |
| MDTo265 | *59aS | 6 | 5 | 5 | 5 |
| MDTo266 | *59aD | 6 | 6 | 4 | 5 |
| MDTo267 | *59aK | 6 | 6 | 4 | 5 |
| MDTo268 | *59aF | 6 | 6 | 4 | 5 |
| MDTo269 | *59aL | 6 | 6 | 4 | 5 |
| MDTo323 | *53aA, *55aL | 8 | 6 | 4 | 4 |
| MDTo327 | *55aL, *59aD | 8 | 6 | 4 | 4 |

TABLE 9

Enzyme dosage of 10 times overdose (10 × OD).

| Variant | Mutation(s) | Softness | Extensability | Elasticity | Machinability |
|---|---|---|---|---|---|
| LBei411 | *53aA | 6 | 5 | 5 | 4 |
| LBei413 | *55aA | 6 | 4 | 6 | 5 |
| LBei413 | *55aA | 6 | 5 | 5 | 4 |
| LBei417 | *59aA | 6 | 4 | 6 | 5 |
| LBei417 | *59aA | 6 | 5 | 5 | 4 |
| MDTo253 | *60aA | 7 | 6 | 4 | 4 |
| MDTo254 | *62aA | 6 | 5 | 5 | 4 |
| MDTo255 | *53aS | 7 | 5 | 5 | 5 |
| MDTo256 | *53aD | 7 | 6 | 4 | 2 |
| MDTo257 | *53aK | 6 | 6 | 4 | 4 |
| MDTo258 | *53aF | 6 | 5 | 5 | 4 |
| MDTo259 | *53aL | 7 | 6 | 4 | 4 |
| MDTo260 | *55aS | 7 | 6 | 4 | 4 |
| MDTo262 | *55aK | 8 | 7 | 4 | 4 |
| MDTo263 | *55aF | 6 | 6 | 5 | 5 |
| MDTo264 | *55aL | 6 | 6 | 4 | 5 |
| MDTo265 | *59aS | 6 | 5 | 5 | 5 |
| MDTo266 | *59aD | 6 | 6 | 4 | 5 |
| MDTo267 | *59aK | 6 | 6 | 4 | 5 |
| MDTo268 | *59aF | 6 | 6 | 4 | 5 |
| MDTo269 | *59aL | 6 | 6 | 4 | 5 |

Bread was baked from both enzyme dosages using both normal and long proofing time and the specific volumes were determined. The results are summarized in tables 10 and 11 below.

TABLE 10

Dough stickiness after floor time and specific bread volumes after normal and long proofing, respectively, at enzyme dosages of 0.05 mg/kg and 0.1 mg/kg in the straight dough procedure using flour with a lower gluten content.

| Variant | Mutation(s) | Sticky 0.05 | Sticky 0.1 | Vol. 0.05 norm | Vol. 0.05 long | Vol. 0.1 norm | Vol. 0.1 long |
|---|---|---|---|---|---|---|---|
| LBei411 | *53aA | 6 | 6 | 110 | 114 | 115 | 114 |
| LBei413 | *55aA | 5 | 5 | 110 | 112 | 112 | 114 |
| LBei417 | *59aA | 5 | 5 | 112 | 112 | 113 | 115 |
| MDTo264 | *55aL | 5 | 6 | 108 | 118 | 109 | 120 |
| MDTo265 | *59aS | 6 | 7 | 107 | 118 | 111 | 125 |
| MDTo266 | *59aD | 6 | 7 | 108 | 120 | 112 | 121 |
| MDTo268 | *59aF | 6 | 7 | 113 | 119 | 112 | 123 |
| MDTO298 | *53aA, *55aA | 6 | 6 | 109 | 114 | 114 | 123 |
| MDTO299 | *55aA, *59aA | 6 | 6 | 107 | 113 | 111 | 124 |
| MDTO300 | *53aA, *59aA | 5 | 6 | 109 | 116 | 116 | 126 |
| MDTO301 | *53aA, *55aA, *59aA | 6 | 7 | 112 | 110 | 119 | 120 |

TABLE 11

Softness (Soft), Extensability (Ext), Elasticity (Elas) and Machinability (Mach) of dough made with enzyme dosages of 0.05 mg/kg and 0.1 mg/kg in the straight dough procedure using flour with a lower gluten content.

| Variant | Mutation(s) | 0.05 mg/kg Soft | Ext | Elas | Mach | 0.1 mg/kg Soft | Ext | Elas | Mach |
|---|---|---|---|---|---|---|---|---|---|
| LBei411 | *53aA | 6 | 4 | 6 | 4 | 7 | 5 | 5 | 3 |
| LBei413 | *55aA | 6 | 5 | 5 | 5 | 6 | 5 | 5 | 5 |
| LBei417 | *59aA | 5 | 5 | 5 | 5 | 6 | 5 | 5 | 5 |
| MDTo264 | *55aL | 5 | 5 | 5 | 5 | 7 | 5 | 4 | 5 |
| MDTo265 | *59aS | 7 | 6 | 4 | 5 | 7 | 6 | 4 | 4 |
| MDTo266 | *59aD | 7 | 6 | 5 | 4 | 7 | 6 | 4 | 3 |
| MDTo268 | *59aF | 7 | 6 | 5 | 4 | 7 | 6 | 4 | 3 |
| MDTO298 | *53aA, *55aA | 6 | 6 | 5 | 5 | 6 | 6 | 5 | 5 |
| MDTO299 | *55aA, *59aA | 6 | 6 | 5 | 5 | 6 | 6 | 5 | 5 |
| MDTO300 | *53aA, *59aA | 5 | 5 | 5 | 5 | 6 | 6 | 5 | 5 |
| MDTO301 | *53aA, *55aA, *59aA | 5 | 5 | 5 | 5 | 8 | 7 | 4 | 5 |

Example 10

GH8 Variants in the Straight Dough Procedure Using Low Quality Flour

Ten GH8 variants were also tested in the straight dough procedure but with low quality flour. Enzyme dosages were 0.05 mg/kg or 0.1 mg/kg.

Example 11

GH8 Variants in the Chorleywood Baking Procedure

Eleven GH8 variants of the invention were also tested in the Chorleywood baking procedure (CBP) for dough stickiness after mixing and specific volume increase of the baked bread after normal proofing using enzyme dosages of 0.05 and 0.1 mg/kg. Results are shown in table 12.

TABLE 12

Dough stickiness after mixing in the Chorleywood baking procedure using 0.05 mg/kg (0.05) or 0.1 mg/kg (0.01) enzyme dosage.

| Variant | Mutation(s) | Sticky 0.05 | Sticky 0.1 | Vol. 0.05 | Vol. 0.1 |
|---|---|---|---|---|---|
| LBei411 | *53aA | 5 | 6 | 112 | 115 |
| LBei413 | *55aA | 5 | 5 | 114 | 112 |
| LBei417 | *59aA | 5 | 5 | 110 | 113 |
| MDTo264 | *55aL | 5 | 5 | 113 | 113 |
| MDTo265 | *59aS | 5 | 5 | 103 | 117 |
| MDTo266 | *59aD | 5 | 5 | 115 | 115 |
| MDTo268 | *59aF | 5 | 5 | 114 | 121 |
| MDTO298 | *53aA, *55aA | 6 | 6 | 113 | 116 |
| MDTO299 | *55aA, *59aA | 5 | 5 | 104 | 114 |
| MDTO300 | *53aA, *59aA | 6 | 6 | 106 | 123 |
| MDTO301 | *53aA, *55aA, *59aA | 5 | 5 | 115 | 125 |

TABLE 13

Softness (Soft), Extensability (Ext), Elasticity (Elas) and Machinability (Mach) of dough made with enzyme dosages of 0.05 mg/kg and 0.1 mg/kg in the Chorleywood procedure.

| | | 0.05 mg/kg | | | | 0.1 mg/kg | | | |
|---|---|---|---|---|---|---|---|---|---|
| Variant | Mutation(s) | Soft | Ext | Elas | Mach | Soft | Ext | Elas | Mach |
| LBei411 | *53aA | 5 | 5 | 5 | 5 | 6 | 5 | 5 | 4 |
| LBei413 | *55aA | 5 | 5 | 5 | 5 | 5 | 5 | 5 | 5 |
| LBei417 | *59aA | 5 | 5 | 5 | 5 | 5 | 5 | 5 | 5 |
| MDTo264 | *55aL | 5 | 5 | 5 | 5 | 5 | 5 | 5 | 5 |
| MDTo265 | *59aS | 5 | 5 | 5 | 5 | 5 | 5 | 5 | 5 |
| MDTo266 | *59aD | 5 | 5 | 5 | 5 | 5 | 5 | 5 | 5 |
| MDTo268 | *59aF | 5 | 5 | 5 | 5 | 5 | 5 | 5 | 5 |
| MDTO298 | *53aA, *55aA | 6 | 5 | 5 | 5 | 7 | 6 | 4 | 5 |
| MDTO299 | *55aA, *59aA | 5 | 5 | 5 | 5 | 5 | 5 | 5 | 5 |
| MDTO300 | *53aA, *59aA | 6 | 5 | 5 | 5 | 6 | 5 | 5 | 5 |
| MDTO301 | *53aA, *55aA, *59aA | 6 | 5 | 5 | 5 | 5 | 5 | 5 | 5 |

The invention claimed is:

1. An isolated variant of a parent GH8 xylanase polypeptide, wherein said variant comprises a conserved GH8 xylanase motif [ST]E[GAS]X[GAS][YFW] (SEQ ID NO: 1); the variant comprises an amino acid sequence having at least 90% sequence identity to amino acids 1-406 of the GH8 xylanase of SEQ ID NO: 3; the variant comprises at least one amino acid alteration which is a substitution, deletion, and/or insertion of one or more amino acids at one or more position(s) corresponding to position(s) 53, 55, 56, 58, 59, 60, 61, and/or 62 of SEQ ID NO: 3, and the variant has xylanase activity.

2. The variant of claim 1, wherein the at least one amino acid alteration comprises one or more insertion(s) at a position corresponding to a position 12 amino acids away from the conserved GH8 xylanase motif on the N-terminal side in amino acids 1-406 of SEQ ID NO: 3 or at a position corresponding to position 53 of SEQ ID NO: 3.

3. The variant claim 1, wherein the at least one amino acid alteration comprises one or more insertion(s) at a position corresponding to a position 10 amino acids away from the conserved GH8 xylanase motif on the N-terminal side in amino acids 1-406 of SEQ ID NO: 3 or at a position corresponding to position 55 of SEQ ID NO: 3.

4. The variant of claim 1, wherein the at least one amino acid alteration comprises one or more insertion(s) at a position corresponding to a position 8 amino acids away from the conserved GH8 xylanase motif on the N-terminal side in amino acids 1-406 of SEQ ID NO: 3 or at a position corresponding to position 57 of SEQ ID NO: 3.

5. The variant of claim 1, wherein the at least one amino acid alteration comprises one or more insertion(s) at a position corresponding to a position 6 amino acids away from the conserved GH8 xylanase motif on the N-terminal side in amino acids 1-406 of SEQ ID NO: 3 or at a position corresponding to position 59 of SEQ ID NO: 3.

6. The variant of claim 1, wherein the at least one amino acid alteration comprises one or more insertion(s) at a position corresponding to a position 4 amino acids away from the conserved GH8 xylanase motif on the N-terminal side in amino acids 1-406 of SEQ ID NO: 3 or at a position corresponding to position 61 of SEQ ID NO: 3.

7. The variant of claim 1, wherein the one or more insertion(s) comprise the insertion of at least one alanine residue, at least one aspartic acid residue, at least one serine residue, at least one lysine residue, and/or at least one phenylalanine residue.

8. The variant of claim 1, which has at least one bread improving property when added to a dough before or during mixing in a sufficient amount.

9. The variant of claim 1, which is capable of increasing the loaf volume of a baked product or increasing the width of cut on the surface of a baked product, when added to a dough before or during mixing in a sufficient amount.

10. The variant of claim 9, which provides a less sticky dough when compared with a dough to which the parent GH8 xylanase has been added in the same amount.

11. The variant of claim 1, wherein said variant comprises one or more alterations selected from the group consisting of D53*, L56*, N58*, *53aA, *55aA, *59aA, N55A +L56*+ G57N+N58L, *61aA, *60aA, *62aA, *53aS, *53aD, *53aK, *53aF, *53aL, *55aS, *55aK, *55aF, *55aL, *59aS, *59aD, *59aK, *59aF, *59aL, *53aA+*55aA, *55aA+*59aA, *53aA+*59aA, *53aA+*55aA+*59aA, *53aA+*55aL, *55aA+*59aD, *55aL+*59aA, *55aL +*59aS, *55aL+ *59aD, *53aA+*59aS, *53aA+*59aD, *53aA+*55aL+ *59aA, *53aA+*55aA+*59aS, *53aA+*55aA+*59aD, *53aA+*55aA+*59aF, *53aA+*55aL+*59aS, *53aA+ *55aL+*59aD, and *53aA+*55aL+*59aF.

12. A composition comprising the variant of claim 1.

13. A method for the preparation of a baked product, said method comprising the step of adding to a dough of said baked product the composition of claim 12.

14. The method of claim 13, wherein said composition further comprises one or more bread-improving agents selected from the group consisting of enzymes, emulsifiers, oxidants, milk powder, fats, sugars, amino acids, salts, proteins, and a mixture thereof.

15. The method of claim 14, wherein said enzymes are selected from the group consisting of alpha-amylases, beta-amylases, maltogenic amylases, additional xylanases, proteases, glucose oxidases, oxidoreductases, glucanases, cellulases, transglutaminases, isomerases, lipases, phospholipases, pectinases, and a mixture thereof.

16. The method of claim 13, wherein said variant is mixed with other ingredients in the form of a dry powder, a granulate, or a liquid.

17. A method for increasing the loaf volume of a baked product, comprising the step of adding during the mixing of the dough of said baked product, a sufficient amount of the variant of claim 1.

18. A method for increasing the loaf volume of a baked product or for increasing the width of cut on the surface of a baked product, comprising the step of adding during the mixing of the dough of said baked product, a sufficient amount of the variant of claim 1.

19. A bread improver composition for increasing the loaf volume of a baked product or for increasing the width of cut on the surface of a baked product, wherein said composition comprises the variant of claim 1.

20. The variant of claim 1, comprising an amino acid sequence having at least 95% sequence identity to amino acids 1-406 of the GH8 xylanase of SEQ ID NO: 3.

* * * * *

SEQUENCE LISTING

```
<160> NUMBER OF SEQ ID NOS: 159

<210> SEQ ID NO 1
<211> LENGTH: 6
<212> TYPE: PRT
<213> ORGANISM: artificial sequence
<220> FEATURE:
<223> OTHER INFORMATION: GH8 xylanase conserved motif 1
<220> FEATURE:
<221> NAME/KEY: NON_CONS
<222> LOCATION: (1)..(1)
<223> OTHER INFORMATION: The amino acid in position 1 of the conserved
      motif is either Serine (S) or Threonine (T).
<220> FEATURE:
<221> NAME/KEY: NON_CONS
<222> LOCATION: (3)..(3)
<223> OTHER INFORMATION: The amino acid in position 3 is Glycine (G),
      Alanine (A) or Serine (S).
<220> FEATURE:
<221> NAME/KEY: NON_CONS
<222> LOCATION: (4)..(4)
<223> OTHER INFORMATION: The amino acid in position 4 is any amino acid.
<220> FEATURE:
<221> NAME/KEY: NON_CONS
<222> LOCATION: (5)..(5)
<223> OTHER INFORMATION: The amino acid in position 5 is Glycine (G),
      Alanine (A) or Serine (S).
<220> FEATURE:
<221> NAME/KEY: NON_CONS
<222> LOCATION: (6)..(6)
<223> OTHER INFORMATION: The amino acid in position 6 is Tyrosine (Y),
      Phenylalanine (F) or Tryptophan (W).
```

<400> SEQUENCE: 1

Xaa Glu Xaa Xaa Xaa Xaa
1               5

<210> SEQ ID NO 2
<211> LENGTH: 1302
<212> TYPE: DNA
<213> ORGANISM: artificial sequence
<220> FEATURE:
<223> OTHER INFORMATION: Synthetic Coding DNA Sequence optimized for
      Bacillus expression
<220> FEATURE:
<221> NAME/KEY: CDS
<222> LOCATION: (1)..(1299)
<220> FEATURE:
<221> NAME/KEY: sig_peptide
<222> LOCATION: (1)..(81)
<220> FEATURE:
<221> NAME/KEY: mat_peptide
<222> LOCATION: (82)..(1299)

<400> SEQUENCE: 2

| atg aag aaa ccg ttg ggg aaa att gtc gca agc acc gca cta ctc att | 48 |
| Met Lys Lys Pro Leu Gly Lys Ile Val Ala Ser Thr Ala Leu Leu Ile | |
|         -25                 -20                 -15             | |

| tct gtt gct ttt agt tca tcg atc gca tcg gct gct gta cat tca aag | 96 |
| Ser Val Ala Phe Ser Ser Ser Ile Ala Ser Ala Ala Val His Ser Lys | |
|     -10                 -5                  -1  1           5   | |

| act cca gac atc ctt ggc aca act ggc aag aac aac ctt aac cag gct | 144 |
| Thr Pro Asp Ile Leu Gly Thr Thr Gly Lys Asn Asn Leu Asn Gln Ala | |
|                     10                  15                  20  | |

| tac aag aag tat ttc gac aca aag ggc gac ggc aaa ggt ggc tct ctt | 192 |
| Tyr Lys Lys Tyr Phe Asp Thr Lys Gly Asp Gly Lys Gly Gly Ser Leu | |
|             25                  30                  35          | |

| ttt cac tat atg aag gac ggc tct gct tac atc gct tct aca aca gac | 240 |
| Phe His Tyr Met Lys Asp Gly Ser Ala Tyr Ile Ala Ser Thr Thr Asp | |
|         40                  45                  50              | |

| gac aac ctt ggc aac ggc tat tac tct gta aag act gag ggc atg tca | 288 |
| Asp Asn Leu Gly Asn Gly Tyr Tyr Ser Val Lys Thr Glu Gly Met Ser | |
| 55                  60                  65                      | |

| tac ggc atg atg atc acg ctt caa atg aac gac gag tac aag ttt caa | 336 |
| Tyr Gly Met Met Ile Thr Leu Gln Met Asn Asp Glu Tyr Lys Phe Gln | |
| 70                  75                  80                  85  | |

| aag ctt tgg gac ttc gtt cgc aag tac atg cgc cat tca gac cgc aac | 384 |
| Lys Leu Trp Asp Phe Val Arg Lys Tyr Met Arg His Ser Asp Arg Asn | |
|             90                  95                  100         | |

| gac agc ctt tac ggc tat cac tct tgg cat atg aaa aca aac ggc tca | 432 |
| Asp Ser Leu Tyr Gly Tyr His Ser Trp His Met Lys Thr Asn Gly Ser | |
|                 105                 110                 115     | |

| gac gtt caa acg atc gac caa aac gtt gcg tca gac ggc gag gta tgg | 480 |
| Asp Val Gln Thr Ile Asp Gln Asn Val Ala Ser Asp Gly Glu Val Trp | |
|                     120                 125                 130 | |

| ttt gca gct gca ctt atg atg gct tct ggt cgc tgg ggt gac aag aag | 528 |
| Phe Ala Ala Ala Leu Met Met Ala Ser Gly Arg Trp Gly Asp Lys Lys | |
|             135                 140                 145         | |

| tac cct tac gac tac aag gca cgc gct caa gac atg ctt gac gca ctt | 576 |
| Tyr Pro Tyr Asp Tyr Lys Ala Arg Ala Gln Asp Met Leu Asp Ala Leu | |
| 150                 155                 160                 165 | |

| gca ggc gac ggc gag tac gct aac aca ggc aag gag tct cgc gtt ttc | 624 |
| Ala Gly Asp Gly Glu Tyr Ala Asn Thr Gly Lys Glu Ser Arg Val Phe | |
|                 170                 175                 180     | |

| atc aaa aac agc aag gac caa cgc tat gct atg gta cgc ttt ggc cct | 672 |

```
Ile Lys Asn Ser Lys Asp Gln Arg Tyr Ala Met Val Arg Phe Gly Pro
            185                 190                 195 tac gtt aac tgg act gac cca tct tat cat gtt ccg gct ttc ttc gag      720
Tyr Val Asn Trp Thr Asp Pro Ser Tyr His Val Pro Ala Phe Phe Glu
        200                 205                 210 ctt ttc gcc aag tca gct aag tca tca caa caa tac ttc tgg aag gac      768
Leu Phe Ala Lys Ser Ala Lys Ser Ser Gln Gln Tyr Phe Trp Lys Asp
215                 220                 225 gca gct aac aaa tct cgc acg tac ctt agc gag aca act ttc aag tct      816
Ala Ala Asn Lys Ser Arg Thr Tyr Leu Ser Glu Thr Thr Phe Lys Ser
230                 235                 240                 245 gta ctt aac aac ggc tca aca gtt act aac gct gct act ggc ctt ttt      864
Val Leu Asn Asn Gly Ser Thr Val Thr Asn Ala Ala Thr Gly Leu Phe
            250                 255                 260 cct gac gag gct ggc ttt gac ggc gtt tca gac gct gct cat tct tca      912
Pro Asp Glu Ala Gly Phe Asp Gly Val Ser Asp Ala Ala His Ser Ser
        265                 270                 275 aca gag aca gac cgc aac ttc tct tac gac gct tgg cgc act gta tct      960
Thr Glu Thr Asp Arg Asn Phe Ser Tyr Asp Ala Trp Arg Thr Val Ser
            280                 285                 290 cat atc gct atg gac cat act ctt tgg agc tca gct gac aac gca tat     1008
His Ile Ala Met Asp His Thr Leu Trp Ser Ser Ala Asp Asn Ala Tyr
295                 300                 305 cgc gca tct gag caa aag gct gtt aac aag ttt ctt aca ttc atg aag     1056
Arg Ala Ser Glu Gln Lys Ala Val Asn Lys Phe Leu Thr Phe Met Lys
310                 315                 320                 325 cgc gag aac tat ggt cgc act gct cat gag tat aca ctt aac ggc aca     1104
Arg Glu Asn Tyr Gly Arg Thr Ala His Glu Tyr Thr Leu Asn Gly Thr
            330                 335                 340 gca gta aag aaa ggc tct cct gtt ggc ctt atc gca gca aac gct ggt     1152
Ala Val Lys Lys Gly Ser Pro Val Gly Leu Ile Ala Ala Asn Ala Gly
        345                 350                 355 ggc gca acg gca gca tct gac gca tca ctt cgc acg ggc ttc gct aac     1200
Gly Ala Thr Ala Ala Ser Asp Ala Ser Leu Arg Thr Gly Phe Ala Asn
            360                 365                 370 gcg ttt aac tct aca tac atc cca gag gac tac tac ggc tct tgt ctt     1248
Ala Phe Asn Ser Thr Tyr Ile Pro Glu Asp Tyr Tyr Gly Ser Cys Leu
375                 380                 385 tac atg ctt aac tct ctt gtt gcg aac ggc aag ttc gca atg tat ctt     1296
Tyr Met Leu Asn Ser Leu Val Ala Asn Gly Lys Phe Ala Met Tyr Leu
390                 395                 400                 405 cca taa                                                             1302
Pro

<210> SEQ ID NO 3
<211> LENGTH: 433
<212> TYPE: PRT
<213> ORGANISM: artificial sequence
<220> FEATURE:
<223> OTHER INFORMATION: Synthetic Construct

<400> SEQUENCE: 3

Met Lys Lys Pro Leu Gly Lys Ile Val Ala Ser Thr Ala Leu Leu Ile
        -25                 -20                 -15

Ser Val Ala Phe Ser Ser Ile Ala Ser Ala Ala Val His Ser Lys
    -10                 -5              -1   1               5

Thr Pro Asp Ile Leu Gly Thr Thr Gly Lys Asn Asn Leu Asn Gln Ala
                10                  15                  20

Tyr Lys Lys Tyr Phe Asp Thr Lys Gly Asp Gly Lys Gly Gly Ser Leu
            25                  30                  35
```

Phe His Tyr Met Lys Asp Gly Ser Ala Tyr Ile Ala Ser Thr Thr Asp
           40                  45                  50

Asp Asn Leu Gly Asn Gly Tyr Tyr Ser Val Lys Thr Glu Gly Met Ser
        55                  60                  65

Tyr Gly Met Met Ile Thr Leu Gln Met Asn Asp Glu Tyr Lys Phe Gln
 70                  75                  80                  85

Lys Leu Trp Asp Phe Val Arg Lys Tyr Met Arg His Ser Asp Arg Asn
             90                  95                 100

Asp Ser Leu Tyr Gly Tyr His Ser Trp His Met Lys Thr Asn Gly Ser
                105                 110                 115

Asp Val Gln Thr Ile Asp Gln Asn Val Ala Ser Asp Gly Glu Val Trp
        120                 125                 130

Phe Ala Ala Leu Met Met Ala Ser Gly Arg Trp Gly Asp Lys Lys
135                 140                 145

Tyr Pro Tyr Asp Tyr Lys Ala Arg Ala Gln Asp Met Leu Asp Ala Leu
150                 155                 160                 165

Ala Gly Asp Gly Glu Tyr Ala Asn Thr Gly Lys Glu Ser Arg Val Phe
            170                 175                 180

Ile Lys Asn Ser Lys Asp Gln Arg Tyr Ala Met Val Arg Phe Gly Pro
                185                 190                 195

Tyr Val Asn Trp Thr Asp Pro Ser Tyr His Val Pro Ala Phe Phe Glu
        200                 205                 210

Leu Phe Ala Lys Ser Ala Lys Ser Ser Gln Gln Tyr Phe Trp Lys Asp
215                 220                 225

Ala Ala Asn Lys Ser Arg Thr Tyr Leu Ser Glu Thr Thr Phe Lys Ser
230                 235                 240                 245

Val Leu Asn Asn Gly Ser Thr Val Thr Asn Ala Ala Thr Gly Leu Phe
            250                 255                 260

Pro Asp Glu Ala Gly Phe Asp Gly Val Ser Asp Ala Ala His Ser Ser
        265                 270                 275

Thr Glu Thr Asp Arg Asn Phe Ser Tyr Asp Ala Trp Arg Thr Val Ser
    280                 285                 290

His Ile Ala Met Asp His Thr Leu Trp Ser Ser Ala Asp Asn Ala Tyr
    295                 300                 305

Arg Ala Ser Glu Gln Lys Ala Val Asn Lys Phe Leu Thr Phe Met Lys
310                 315                 320                 325

Arg Glu Asn Tyr Gly Arg Thr Ala His Glu Tyr Thr Leu Asn Gly Thr
            330                 335                 340

Ala Val Lys Lys Gly Ser Pro Val Gly Leu Ile Ala Ala Asn Ala Gly
            345                 350                 355

Gly Ala Thr Ala Ala Ser Asp Ala Ser Leu Arg Thr Gly Phe Ala Asn
        360                 365                 370

Ala Phe Asn Ser Thr Tyr Ile Pro Glu Asp Tyr Tyr Gly Ser Cys Leu
    375                 380                 385

Tyr Met Leu Asn Ser Leu Val Ala Asn Gly Lys Phe Ala Met Tyr Leu
390                 395                 400                 405

Pro

<210> SEQ ID NO 4
<211> LENGTH: 434
<212> TYPE: PRT
<213> ORGANISM: Bacillus sp. KK-1
<220> FEATURE:
<221> NAME/KEY: SIGNAL -continued

```
<222> LOCATION: (1)..(28)
<220> FEATURE:
<221> NAME/KEY: mat_peptide
<222> LOCATION: (29)..(434)

<400> SEQUENCE: 4
```

Met Arg Lys Ser Leu Lys Trp Ile Met Ala Val Phe Ile Gly Leu Thr
               -25                 -20                 -15

Cys Phe Cys Thr Ala Tyr Ser Gln Thr Ala Met Ala Ala Val His Ser
        -10                  -5                  -1   1

Lys Thr Pro Asp Ile Leu Gly Thr Thr Gly Lys Asn Asn Leu Asn Gln
 5                   10                  15                  20

Ala Tyr Lys Lys Tyr Phe Asp Thr Lys Gly Asp Gly Lys Gly Gly Ser
                 25                  30                  35

Leu Phe His Tyr Met Lys Asp Gly Ser Ala Tyr Ile Ala Ser Thr Thr
                 40                  45                  50

Asp Asp Asn Leu Gly Asn Gly Tyr Tyr Ser Val Lys Thr Glu Gly Met
                 55                  60                  65

Ser Tyr Gly Met Met Ile Thr Leu Gln Met Asn Asp Glu Tyr Lys Phe
 70                  75                  80

Gln Lys Leu Trp Asp Phe Val Arg Lys Tyr Met Arg His Ser Asp Arg
 85                  90                  95                 100

Asn Asp Ser Leu Tyr Gly Tyr His Ser Trp His Met Lys Thr Asn Gly
                105                 110                 115

Ser Asp Val Gln Thr Ile Asp Gln Asn Val Ala Ser Asp Gly Glu Val
                120                 125                 130

Trp Phe Ala Ala Ala Leu Met Met Ala Ser Gly Arg Trp Gly Asp Lys
                135                 140                 145

Lys Tyr Pro Tyr Asp Tyr Lys Ala Arg Ala Gln Asp Met Leu Asp Ala
                150                 155                 160

Leu Ala Gly Asp Gly Glu Tyr Ala Asn Thr Gly Lys Glu Ser Arg Val
165                 170                 175                 180

Phe Ile Lys Asn Ser Lys Asp Gln Arg Tyr Ala Met Val Arg Phe Gly
                185                 190                 195

Pro Tyr Val Asn Trp Thr Asp Pro Ser Tyr His Val Pro Ala Phe Phe
                200                 205                 210

Glu Leu Phe Ala Lys Ser Ala Lys Ser Ser Gln Gln Tyr Phe Trp Lys
                215                 220                 225

Asp Ala Ala Asn Lys Ser Arg Thr Tyr Leu Ser Glu Thr Thr Phe Lys
                230                 235                 240

Ser Val Leu Asn Asn Gly Ser Thr Val Thr Asn Ala Ala Thr Gly Leu
245                 250                 255                 260

Phe Pro Asp Glu Ala Gly Phe Asp Gly Val Ser Asp Ala Ala His Ser
                265                 270                 275

Ser Thr Glu Thr Asp Arg Asn Phe Ser Tyr Asp Ala Trp Arg Thr Val
                280                 285                 290

Ser His Ile Ala Met Asp His Thr Leu Trp Ser Ser Ala Asp Asn Ala
                295                 300                 305

Tyr Arg Ala Ser Glu Gln Lys Ala Val Asn Lys Phe Leu Thr Phe Met
                310                 315                 320

Lys Arg Glu Asn Tyr Gly Arg Thr Ala His Glu Tyr Thr Leu Asn Gly
325                 330                 335                 340

Thr Ala Val Lys Lys Gly Ser Pro Val Gly Leu Ile Ala Ala Asn Ala
                345                 350                 355

```
Gly Gly Ala Thr Ala Ala Ser Asp Ala Ser Leu Arg Thr Gly Phe Ala
            360                 365                 370

Asn Ala Phe Asn Ser Thr Tyr Ile Pro Glu Asp Tyr Tyr Gly Ser Cys
            375                 380                 385

Leu Tyr Met Leu Asn Ser Leu Val Ala Asn Gly Lys Phe Ala Met Tyr
            390                 395                 400

Leu Pro
405

<210> SEQ ID NO 5
<211> LENGTH: 388
<212> TYPE: PRT
<213> ORGANISM: Burkholderia phymatum

<400> SEQUENCE: 5

Met Arg Arg Lys Arg Leu Leu Thr Gln Arg Phe Ala Arg Ile Pro Lys
1               5                   10                  15

Cys Gly Ala Val Arg Arg Leu Val Gly Leu Ala Val Ala Cys Leu Gln
            20                  25                  30

Val Ser Val Ala Ala His Ala Asp Cys Arg Trp Pro Leu Trp Glu Arg
        35                  40                  45

Tyr Ala Gln Gln Gln Ile Ser Lys Asp Gly Arg Ile Val Glu Pro Gly
    50                  55                  60

Lys Gly Asp Arg Thr Thr Ser Glu Ala Gln Ala Tyr Ala Met Phe Phe
65                  70                  75                  80

Ala Val Val Gly Asp Asp Arg Val Arg Phe Asp Ser Leu Leu Asn Trp
                85                  90                  95

Ala Leu Ala His Thr Trp Ala Thr Thr Gly His Pro Pro Ala Trp Leu
            100                 105                 110

Trp Ala Lys Arg Ala Asp Gly Thr Phe Asp Val Leu Asp Asp Asn Ser
        115                 120                 125

Ala Thr Asp Ala Asp Leu Trp Met Ala Tyr Ala Met Leu Glu Ala Ala
    130                 135                 140

Arg Arg Trp Ser Glu Pro Arg Tyr Arg Ala Leu Gly Leu Arg Leu Leu
145                 150                 155                 160

Asp Gln Ile Thr Ala Thr Glu Val Val Trp Gln Asp Glu Thr Ser Ala
                165                 170                 175

Phe Leu Ile Pro Gly Arg Leu Gly Phe Arg Leu Ser Glu His Ala Tyr
            180                 185                 190

Leu Val Asn Pro Ser Tyr Ala Pro Ile Gln Leu Leu Arg Arg Phe Ile
        195                 200                 205

Lys Glu Gln Pro His Gly Pro Trp Val Ser Val Leu Asn His Gln Val
    210                 215                 220

Asp Leu Leu Val Ala Ser Ala Pro Gln Gly Phe Val Pro Asp Trp Tyr
225                 230                 235                 240

Arg Phe Asp Thr Phe Lys Gly Tyr Met Leu Glu Pro Ser Lys Gly Pro
                245                 250                 255

Thr Gly Gly Phe Asp Ala Val Arg Thr Tyr Met Trp Ala Gly Met Leu
            260                 265                 270

Asp Pro Thr Asp Pro Ala Arg Gly Glu Val Ile Pro Ala Leu Ser Gly
        275                 280                 285

Met Ala Asp Leu Val Ala Gln Thr Gly Arg Met Pro Leu Tyr Val Asn
    290                 295                 300

Ile Glu Ser Gly Glu Thr Phe Asp Glu Gly Ser Ala Gly Phe Arg Ala
305                 310                 315                 320
```

Ala Val Ile Pro Leu Leu Phe Val Thr Gly His Pro Ser Ala Ala Ser
            325                 330                 335

Arg Leu Ala Gln Glu Thr Lys Val Met Gln Gln Ala Arg Glu Trp Asp
            340                 345                 350

Gly Leu His Tyr Tyr Asp Arg Asn Leu Leu Phe Ala Ala Gly Trp
            355                 360                 365

Leu Glu Gly Arg Tyr Arg Phe Asp His Glu Gly Thr Leu Gln Leu Lys
370                 375                 380

Pro Cys Arg Pro
385

<210> SEQ ID NO 6
<211> LENGTH: 400
<212> TYPE: PRT
<213> ORGANISM: Labrenzia aggregata

<400> SEQUENCE: 6

Met Leu Phe Arg Phe Leu Ala Thr Leu Val Trp Cys Leu Leu Leu Leu
1               5                   10                  15

Leu Pro Val Ala Ala Arg Pro Leu Phe Pro Ser Gln Pro Gln Ala Glu
            20                  25                  30

Arg Leu Ala Ala Leu Asp Arg Phe Trp Ala Asp Trp Lys Lys Thr Tyr
        35                  40                  45

Leu His Glu Gly Cys Gly Gly Ala Tyr Val Asp Thr Ser Gly Asp Glu
    50                  55                  60

Lys Pro Thr Trp Gly Gly Ser Ala Thr Gly Thr Leu Thr Val Ser Glu
65                  70                  75                  80

Ala His Gly Tyr Gly Met Leu Thr Leu Val Lys Met Ala Ser Arg Asp
                85                  90                  95

Pro Glu Ala Gln Glu Asn Phe Ala Ser Met Val Ala Phe Tyr His Ala
            100                 105                 110

His Gln Ala Ala Ser Gly Pro Gly Leu Met Ala Trp Asn Gln Thr Arg
        115                 120                 125

Asp Cys Lys Asp Ala Pro Asn Gly Gly Asp Met Ser Ala Thr Asp Gly
130                 135                 140

Asp Leu Asp Thr Ala Leu Ala Leu Leu Ala Asp Lys Lys Trp Gly
145                 150                 155                 160

Gly Tyr Arg Glu Ala Phe Asp Gln Ala Gln Gln Ala Ile Leu Glu Arg
                165                 170                 175

Glu Val Thr Ala Asp Gly Met Met Arg Leu Gly Asp Trp Ala Val Asp
            180                 185                 190

Glu Asp Tyr Ser Gly Thr Ser Arg Ser Ser Asp Phe Met Pro Ala Ser
        195                 200                 205

Phe Ala Ala Phe Ala Lys Ala Ala Asp Asp Leu Ser Pro Arg Trp Thr
210                 215                 220

Ser Ile Arg Asp Arg Gly Tyr Arg Val Trp Gly Asp Ile Ala Glu Asn
225                 230                 235                 240

Tyr Ala Gly Asn Thr Gly Leu Val Pro Asp Phe Leu Val Gly Leu Pro
                245                 250                 255

Glu His Pro Arg Pro Ala Glu Ala Asp Phe Leu Glu Gly Ala Gly Asp
            260                 265                 270

Gly Gln Tyr Ser Trp Asn Ala Leu Arg Phe Pro Trp Arg Leu Ser Leu
        275                 280                 285

Asp Leu Leu Glu Thr Asp Asp Thr Arg Ala Ala Asp His Leu Met Val

```
                290                 295                 300
Ile Asn Arg Trp Ile Arg Gly Ala Ala Lys Glu Asp Pro Phe Arg Ile
305                 310                 315                 320

Ala Thr Thr Tyr Arg Leu Asp Gly Ser Ile Pro Glu Asp Gln Ser Thr
                325                 330                 335

Gly Ser Ala Ala Phe Ile Ala Met Phe Ala Ala Ala Ile Ala Gly
                340                 345                 350

Ser Gly Asp Pro Asp Gly Asp Gln Val Trp Leu Asp Ala Leu Trp Ser
                355                 360                 365

Ala Leu Ile Ser Ile Pro Leu Ala Asp Glu Asp Tyr Tyr Gly Asn Thr
                370                 375                 380

Leu Lys Leu Leu Ala Met Ile Glu Leu Ser Gly Gln Trp Gln Glu Asn
385                 390                 395                 400

<210> SEQ ID NO 7
<211> LENGTH: 376
<212> TYPE: PRT
<213> ORGANISM: Alteromonadales bacterium TW-7

<400> SEQUENCE: 7

Met Lys Ser Leu Val Asn Met Phe Phe Thr Val Met Ala Leu Phe Ala
1               5                   10                  15

Phe Asn Ala Asn Ala Gln Val Glu Gln Cys Glu Pro Trp Gln Ser Trp
                20                  25                  30

Gln Val Phe Lys Asn His Phe Ile Ser Gln Asp Gly Arg Val Ile Asp
                35                  40                  45

Leu Gly Ser Asp Gln Ser Ile Thr Thr Ser Glu Gly Ser Tyr Ala
    50                  55                  60

Leu Phe Phe Ala Leu Ile Ala Asn Asp Lys Ala Ala Phe Asp Ser Val
65                  70                  75                  80

Leu Asn Trp Thr Gln Glu His Leu Ser Glu Gly Asp Leu Ser Thr Arg
                85                  90                  95

Leu Pro Ala Trp Lys Trp Gly Leu Asp Lys Asn Arg Val Gly Gly Ile
                100                 105                 110

Leu Asp Ser Asn Pro Ala Ser Asp Ser Asp Leu Trp Ile Ala Tyr Ser
                115                 120                 125

Leu Ser Gln Ala Ala Ile Leu Trp Asp Glu Arg Arg Tyr Ser Ile Leu
                130                 135                 140

Ala Ala Val Leu Ala Gln Arg Ile Ile Arg Glu Glu Thr Ala Tyr Ile
145                 150                 155                 160

Thr Gly Leu Gly Leu Ser Leu Leu Pro Ala Pro Ala Gly Phe Glu Phe
                165                 170                 175

Asp Asn Glu Arg Tyr Lys Leu Asn Pro Ser Tyr Ser Pro Leu Phe Ile
                180                 185                 190

Tyr Gln Gln Phe Lys Lys Leu Tyr Pro His Ser Pro Trp His Gln Leu
                195                 200                 205

His Glu Gly Ser Ala Lys Leu Ile Leu Asp Thr Ala Gln Gln Gly Val
                210                 215                 220

Ser Pro Asp Trp Val Met Phe Asp Ser Asn Arg Gly Phe Tyr Tyr Asp
225                 230                 235                 240

Arg Lys Asn Thr Asp Leu Gly Ser Tyr Asn Ala Ile Arg Val Tyr Leu
                245                 250                 255

Trp Ala Ser Met Met Ala Lys Asp Ala Pro Tyr Lys Gln Glu Leu Leu
                260                 265                 270
```

```
Ala Gln Phe Ala Pro Phe Val Asp Thr Ile Lys Glu Arg Ser His Val
        275                 280                 285

Pro Leu Asn Thr Tyr Ala Gln Ser Gly Lys Ser Glu Lys Arg Gly Pro
    290                 295                 300

Leu Gly Phe Asn Ala Ala Leu Leu Pro Leu Leu Ala Glu Gln Gly Asn
305                 310                 315                 320

Asp Glu Leu Val Met Ala Ile Gln Gln Lys Leu Met Ile Asp Lys Ser
                325                 330                 335

Phe Thr Gln Thr Arg Tyr Tyr Asp Ser Val Leu His Leu Phe Gly Glu
            340                 345                 350

Ser Ala Val Asn Lys Arg Phe Lys Ile Thr Ala Asp Gly Thr Leu Gln
        355                 360                 365

Pro Thr Trp Ser Thr Glu Cys Arg
    370                 375

<210> SEQ ID NO 8
<211> LENGTH: 375
<212> TYPE: PRT
<213> ORGANISM: Yersinia enterocolitica

<400> SEQUENCE: 8

Met Val Val Met Phe Lys Arg Leu Val Cys Ile Leu Leu Leu Leu Ala
1               5                   10                  15

Ser Phe Gly Thr Ala Ala Ala Cys Asp Trp Pro Ala Trp Gln Gln Phe
            20                  25                  30

Lys Gln His Tyr Ile Ser Glu Ser Gly Arg Val Ile Asp Pro Ser Asn
        35                  40                  45

Pro Arg Lys Val Thr Thr Ser Glu Gly Gln Ser Tyr Gly Leu Phe Phe
    50                  55                  60

Ala Leu Val Ala Asp Asp Arg Glu Thr Phe Asp Arg Leu Leu Thr Trp
65                  70                  75                  80

Thr Glu Asn Asn Leu Ser Ala Gly Asp Leu Thr Ala Arg Leu Pro Ala
                85                  90                  95

Trp Leu Trp Gly Gln Arg Asn Glu His Ser Trp Asp Ile Leu Asp Pro
            100                 105                 110

Asn Ser Ala Ser Asp Ala Asp Leu Trp Ile Ala Tyr Ser Leu Leu Glu
        115                 120                 125

Ala Gly Arg Leu Trp Asp Thr Arg Arg Tyr Gln Thr Ile Gly Thr Leu
    130                 135                 140

Leu Leu Gln Arg Ile Ala Lys Glu Glu Val Val Asn Ile Pro Gly Leu
145                 150                 155                 160

Gly Glu Met Leu Leu Pro Gly Lys Ile Gly Phe Asn Asn Glu Glu Arg
                165                 170                 175

Trp Arg Leu Asn Pro Ser Tyr Leu Pro Pro Gln Leu Leu Ala Arg Phe
            180                 185                 190

Ala Ser Leu Ala Gly Pro Trp Lys Ala Met Val Lys Thr Asn Gln Arg
        195                 200                 205

Leu Trp Leu Glu Thr Ala Pro Arg Gly Phe Ser Pro Asp Trp Val Val
    210                 215                 220

Trp Gln Lys Asp Lys Gly Trp Gln Pro Asp Glu Thr His Pro Asn Leu
225                 230                 235                 240

Gly Ser Tyr Asp Ala Ile Arg Thr Tyr Leu Trp Ala Gly Met Leu Ser
                245                 250                 255

Asn Asn Ser Pro Gln Lys Ala Ala Leu Ile Gln His Phe Gln Pro Met
            260                 265                 270
```

```
Ala Glu Val Thr Gln Gln Gly Leu Pro Pro Glu Lys Ala Asp Thr
        275                 280                 285

Leu Thr Gly Lys Thr Thr Gly Asp Gly Pro Val Gly Phe Ser Ala Ala
    290                 295                 300

Leu Leu Pro Phe Leu Ala Ser Gly Pro Ala Pro Phe Asn Gln Gln Ala
305                 310                 315                 320

Leu Ser Gln Gln Gln Lys Arg Val Gln Asp Ser Pro Pro Gly Ala Asp
                325                 330                 335

Ala Tyr Tyr Ser Ala Val Leu Thr Leu Phe Gly Gln Gly Trp Ala Gln
                340                 345                 350

His Arg Tyr Ser Phe Asn Arg Gln Gly Glu Leu Gln Pro Ser Trp Asn
                355                 360                 365

Ser Gln Cys Ala Thr Leu Lys
                370                 375

<210> SEQ ID NO 9
<211> LENGTH: 376
<212> TYPE: PRT
<213> ORGANISM: Mycobacterium vanbaalenii

<400> SEQUENCE: 9

Met Val Ser Arg Leu Arg Lys Ala Met Leu Leu Val Ala Leu Leu
1               5                   10                  15

Leu Val Val Gly Ala Gly Trp Ala Ala Gln Ala Val Asp Pro Arg
                20                  25                  30

Met Ser Asp Asp Val Arg Gly Met Arg Glu Gln Ala Ala Arg Gln
                35                  40                  45

Ala Gly Glu Asp Phe Leu Ser Arg Tyr Val Glu Ser Asp Gly Arg Val
    50                  55                  60

Val Arg Arg Asp Glu Gly Gly Asp Val Val Ser Glu Gly Gln Ala Tyr
65                  70                  75                  80

Gly Met Leu Ile Ala Ala Ala Leu Gly Asp Glu Pro Arg Phe Arg Ala
                85                  90                  95

Ile Trp Asp Trp Thr Arg Thr His Leu Arg Arg Pro Asp Gly Leu Leu
                100                 105                 110

Ser Trp Arg Trp Ala Asp Gly Arg Val Thr Asp Pro Ser Ser Ala Thr
            115                 120                 125

Asp Ala Asp Leu Asp Ala Ala Arg Ser Leu Leu Leu Ala Ala Arg Arg
    130                 135                 140

Phe Ala Ala Pro Glu Leu Ala Glu Asp Gly Lys Arg Leu Gly Ala Asp
145                 150                 155                 160

Val Leu Arg Gly Glu Thr Val Thr Val Gly Ala Ala Pro Ser Pro Ala
                165                 170                 175

Met Ala Arg Pro Gly Leu Ile Thr Val Ala Gly Asn Trp Ala Thr Ala
                180                 185                 190

Pro Pro His Ala Val Asp Pro Gly Tyr Phe Ser Arg Arg Ala Glu Arg
            195                 200                 205

Glu Leu Leu Asp Ala Ser Ala Asp Arg Arg Trp Leu Asp Val Ser Arg
    210                 215                 220

Thr Gln Arg Val Leu Val Trp Gln Leu Ile Gly Thr Ala Ser Leu Pro
225                 230                 235                 240

Pro Asp Trp Ala Ser Val Asp Pro Ala Gly Arg Ala Val Pro Thr Gly
                245                 250                 255

Pro Pro Asp Gly Gly Pro Thr Arg Phe Gly Leu Asp Ala Ala Arg Leu
```

```
                260             265              270
Pro Ile Arg Phe Ala Glu Ser Cys Asp Pro Ala Asp Arg Ala Val Ala
            275                 280                 285

Val Ser Leu Arg Arg Val Val Ala Ala Ser Arg Asp Ile Pro Ala Thr
        290                 295                 300

Arg Asn Leu Asp Gly Ser Ala Ala Gly Glu Trp Gln His Pro Val Ala
305                 310                 315                 320

Leu Val Ser Ala Ala Thr Asp His Ala Ala Gly Asp Arg Glu Ala
                325                 330                 335

Gly Ala Ala Arg Leu Asp Gln Ala Ser Ala Leu Gln Gln Arg Tyr Pro
                340                 345                 350

Thr Tyr Phe Gly Ala Ala Trp Val Ala Leu Gly Arg Ile Met Leu Asp
        355                 360                 365

Thr Ser Leu Leu Gly Glu Cys Ala
        370                 375

<210> SEQ ID NO 10
<211> LENGTH: 298
<212> TYPE: PRT
<213> ORGANISM: Lactococcus lactis

<400> SEQUENCE: 10

Met Lys Asn Leu Leu Lys Val Ala Ser Lys Glu Ala Ile Asp Lys
1               5                   10                  15

Lys Val Glu Lys Val Phe Glu Ile Leu Phe Gly Gln Asp Ser Pro Glu
            20                  25                  30

Arg Leu Tyr Phe Glu Glu Asp Lys Ala Tyr Ile Val Asp Thr Gly
        35                  40                  45

Asn Asp Asp Val Arg Thr Glu Gly Met Ser Tyr Gly Met Met Ile Ala
50                  55                  60

Leu Gln Leu Asp Lys Pro Glu Ile Phe Ser Arg Leu Trp Ala Trp Val
65                  70                  75                  80

Lys Thr Tyr Met Thr Val Pro Lys Gly His Glu Asn Glu Gly Tyr Phe
                85                  90                  95

Ile Trp Ser Cys Gly Leu Asp Gly His Pro Asn Ser Asp Gly Pro Ala
            100                 105                 110

Pro Asp Gly Glu Glu Tyr Phe Ala Ala Ala Leu Leu Leu Ala Glu Lys
        115                 120                 125

Arg Trp Lys Ile Lys Glu Tyr Gly Asp Glu Ala Arg Ala Leu Leu His
130                 135                 140

Ala Met Val His Lys Gly Glu Asn Gln Asp Gly Tyr Pro Met Phe Glu
145                 150                 155                 160

Pro Lys Asn Thr Tyr Ile Lys Phe Val Ala Asn Arg Gln Met Thr Asp
                165                 170                 175

Pro Ser Tyr His Leu Leu His Phe Tyr Gln Leu Tyr Ala Lys Tyr Gly
            180                 185                 190

Asn Pro Glu Asp Ser Ala Phe Phe Leu Lys Ala Glu Glu Ala Arg
        195                 200                 205

Lys Tyr Trp Leu Lys Ser Ala Asn Ala Lys Thr Gly Leu Thr Pro Glu
210                 215                 220

Tyr Ala Asp Tyr Asp Gly Lys Pro Tyr Asp Ile Asp Gly His Trp Thr
225                 230                 235                 240

Phe Phe Ser Asp Ala Tyr Arg Thr Ala Ala Asn Ile Gly Leu Asp Trp
                245                 250                 255
```

```
Ile Trp Glu His Lys Asp Ile Gly Gln Ser Gln Ile Ala Leu Asn Ile
            260                 265                 270

Gln Lys Phe Phe Glu Ile Tyr Leu Asn Ser Asp Lys Glu Ile Pro Val
        275                 280                 285

Phe Lys Ile Asn Gly Gln Pro Leu Arg Lys
        290                 295

<210> SEQ ID NO 11
<211> LENGTH: 409
<212> TYPE: PRT
<213> ORGANISM: Burkholderia cenocepacia

<400> SEQUENCE: 11

Met Ala Arg Ala Met Thr Lys Arg Arg Ala Thr Gln Pro Ala Arg Arg
1               5                   10                  15

Val Gly Ala Thr Leu Ala Leu Ala Val Ala Val Thr Cys Ala Ala Ala
            20                  25                  30

Gly Met Ala Thr Arg Thr His Ala Ala Ala Ser Ala Ala Asp Ala
            35                  40                  45

Ala Ser Thr Gly Cys Ser Val Ala Trp Pro Arg Trp Asp Ala Phe Lys
50                  55                  60

Arg Asp Phe Ile Ser Ala Asp Gly Arg Val Ile Asp Val Gly Ser Ala
65                  70                  75                  80

Asp Ser Arg Thr Val Ser Glu Gly Gln Ala Tyr Gly Leu Phe Leu Ala
                85                  90                  95

Leu Val Ala Asn Asp Arg Arg Met Phe Asp Thr Ile Leu Ala Trp Thr
            100                 105                 110

Glu Asn Asn Leu Ala Gln Gly Asp Leu Ser Ala His Leu Pro Ala Trp
        115                 120                 125

Leu Trp Gly Arg Ala Pro Asp Gly Ala Trp Arg Val Leu Asp Ala Asn
    130                 135                 140

Pro Ala Ser Asp Ala Asp Leu Trp Ile Ala Tyr Ala Leu Val Glu Ala
145                 150                 155                 160

Gly Arg Leu Trp His Glu Arg Ser Tyr Thr Ala Arg Gly Ala Leu Leu
                165                 170                 175

Ala Lys Arg Val Leu Asp Ala Glu Thr Ala Thr Val Pro Gly Leu Gly
            180                 185                 190

Leu Thr Leu Leu Pro Gly Pro Thr Gly Phe Lys Leu Ala Asn Gly Gln
        195                 200                 205

Trp Arg Leu Asn Pro Ser Tyr Ser Pro Pro Gln Val Ile Arg Gly Leu
    210                 215                 220

Gly Ala Arg Leu Pro Asp Asp Arg Ala Leu Gly Arg Ala Gly Val Gln
225                 230                 235                 240

His Cys Ser Arg Ala Ala Arg His Arg Ala Glu Arg Phe Ser Pro Asp
                245                 250                 255

Trp Ala Leu Tyr Arg Ala Gly Asn Gly Phe Gly Pro Asp Ser Gln Thr
            260                 265                 270

His Ala Glu Ser Ala Tyr Asn Ala Ile Arg Val Tyr Leu Trp Ala Gly
        275                 280                 285

Met Leu Asp Arg Ala Asp Pro Leu Ala Ala Pro Leu Leu Ala Lys Phe
    290                 295                 300

Ala Pro Phe Ala Asp His Ile Ala Val His Gly Ala Pro Pro Glu Lys
305                 310                 315                 320

Val Asp Thr Thr Thr Gly Val Ala Gly Pro Asn Asp Gly Asn Gly Gly
                325                 330                 335
```

Phe Ser Ala Ala Ala Val Pro Phe Leu Asp Ala Arg Gly Gln His Ala
                340                 345                 350

Leu Ala Asp Ala Gln Ala Thr Arg Val Asp Thr Leu Ala Arg Gln Ser
            355                 360                 365

Ala Pro Gly Tyr Tyr Thr Ser Val Leu Thr Leu Phe Gly Leu Gly Trp
        370                 375                 380

Arg Asp Gly Arg Tyr Arg Phe Gly Thr Asp Gly Thr Leu Asp Thr Arg
385                 390                 395                 400

Trp Gly Gly Arg Ser Cys Ala Ala Arg
                405

<210> SEQ ID NO 12
<211> LENGTH: 342
<212> TYPE: PRT
<213> ORGANISM: Streptococcus sanguinis

<400> SEQUENCE: 12

Met Gly Ser Thr Pro Asn Ile Lys Lys Ile Tyr Ser Gln Trp Ala
1               5                   10                  15

Lys Glu Tyr Val Val Thr Lys Asp Lys Leu Ser Tyr Ile Arg Thr Thr
                20                  25                  30

Asn Ser Lys Thr Glu Asp Val Val Leu Ser Glu Ala Gln Gly Tyr Gly
            35                  40                  45

Met Val Ile Ala Val Asp Ala Ala Lys Gln Gly Asp Ala Ser Ser Ala
        50                  55                  60

Asp Phe Glu Lys Leu Tyr Gln Tyr Tyr Leu Ala His Arg Leu Lys Asp
65                  70                  75                  80

Thr Gln Leu Met Ser Trp Lys Gln Thr Ile Lys Asp Gly Lys Ser Asn
                85                  90                  95

His Glu Asp Glu Asn Asn Ala Thr Asp Gly Asp Leu Tyr Ile Ala Tyr
            100                 105                 110

Ala Leu Ile Gln Ala Ala Lys Gln Trp Pro Asp Lys Ala Lys Glu Tyr
        115                 120                 125

Gln Asp Gln Ala Gln Ala Ile Leu Lys Asp Val Leu Ala Tyr Asn Tyr
    130                 135                 140

Asn Glu Ser Asn Gly Val Leu Thr Val Gly Asn Trp Ala Asn Ala Glu
145                 150                 155                 160

Ser Lys Phe Tyr Asn Leu Met Arg Thr Ser Asp Thr Leu Pro Gln Gln
                165                 170                 175

Phe Gln Ala Phe Tyr Glu Leu Thr Lys Asp Lys Gln Trp Leu Thr Ile
            180                 185                 190

Arg Asp Asn Met Leu Ser Lys Leu Glu Ala Ile Ser Ala Asp Asn Lys
        195                 200                 205

Thr Gly Leu Ile Pro Asp Phe Ile Trp Val Glu Gly Asp Lys Val Arg
    210                 215                 220

Ala Ala Asp Ala Asp Thr Val Glu Ser Ala Asn Asp Gly Tyr Tyr Ser
225                 230                 235                 240

Tyr Asn Ala Cys Arg Leu Pro Tyr Asn Leu Ala Gln Ser Lys Asp Glu
                245                 250                 255

Lys Ser Gln Lys Met Leu Lys Lys Met Leu Asn Phe Phe Leu Ser Gln
            260                 265                 270

Glu Lys Ile Tyr Ala Gly Tyr Thr Leu Lys Gly Lys Ala Leu Asn Ser
        275                 280                 285

Asn Gln Ala Gly Ser Phe Thr Ala Pro Val Phe Tyr Ala Ala Asn Asn

```
            290                 295                 300
Asn Met Glu Phe Arg Lys Leu Val Gln Gln Asn Lys Tyr Leu Phe Met
305                 310                 315                 320

Gln Gly Leu Pro Ser Asp Asn Tyr Tyr Asp Ala Ala Val Thr Thr Met
                325                 330                 335

Ile Ala Leu Glu Thr Leu
            340

<210> SEQ ID NO 13
<211> LENGTH: 366
<212> TYPE: PRT
<213> ORGANISM: Leptospirillum rubarum

<400> SEQUENCE: 13

Met Lys Pro Met Ile Leu Gly Val Met Ile Val Trp Phe Phe Val Trp
1               5                   10                  15

Gly Ser Gly Leu Ser Arg Ala Ser Glu Phe His Ala Val Trp Glu His
            20                  25                  30

Tyr Arg Ala Cys Cys Ile Gln Ser Asp Gly Arg Val Ile Asp Arg Gly
        35                  40                  45

Arg Gln Ser Val Thr Thr Ser Glu Gly Glu Ala Tyr Ala Leu Phe Phe
50                  55                  60

Ala Leu Val Asp Asn Asp Pro Leu Leu Tyr Ser Arg Leu Leu Arg Trp
65                  70                  75                  80

Thr Arg Asp Asn Leu Ser Arg Gly Asp Leu Ser Ala His Leu Pro Ala
                85                  90                  95

Trp Leu Trp Gly Glu Arg Lys Asn Gly Gln Trp Gly Val Leu Asp Gln
            100                 105                 110

Asn Ser Ala Thr Asp Ala Asp Leu Trp Ile Ser Phe Asp Leu Met Glu
        115                 120                 125

Ala Gly Arg Leu Trp His Arg Ser Glu Tyr Leu Arg Leu Gly Glu Arg
130                 135                 140

Leu Ala Phe Leu Ile Ser Leu Arg Asp Phe Ala Asn Leu Pro Gly Phe
145                 150                 155                 160

Gly Ala Phe Pro Leu Gly Gly Glu Arg Gly Phe His Pro Ala Gly Thr
                165                 170                 175

Val Trp Arg Thr Asn Pro Ser Tyr Phe Pro Pro Phe Leu Leu Arg Phe
            180                 185                 190

Met Glu His Arg Phe Gly Gly Arg Pro Trp Ser Gly Leu Pro Gly Arg
        195                 200                 205

Phe Leu Ala Phe Val Lys Ser Val Ser Ser Cys Gly Phe Val Pro Asp
210                 215                 220

Trp Val Thr Tyr Asp Thr Gly Lys Gly Trp Gln Pro Asp Pro Val Thr
225                 230                 235                 240

Gly Pro Leu Gly Ser Tyr Asp Ala Ile Arg Val Tyr Leu Trp Ala Gly
                245                 250                 255

Met Thr Ser Val Arg Asp Pro Gln Glu Gln Leu Leu Leu Lys Arg Leu
            260                 265                 270

Gln Gly Trp Ser Arg Lys Gly Arg Ser Ser Pro Thr Leu Phe Val Asn
        275                 280                 285

Thr Lys Thr Cys Ser Ala Tyr Gly Lys Pro Pro Gly Phe Arg Ala
290                 295                 300

Ala Tyr Leu Pro Phe Leu Arg Arg Glu Asn Val Ser Ser Phe Arg Glu
305                 310                 315                 320
```

Glu Phe Arg Arg Met Leu Ser Arg Asp Pro Met Lys Asn Asp Pro Gly
            325                 330                 335

Tyr Tyr Asp Thr Asn Leu Tyr Leu Phe Gly Thr Gly Phe Leu Glu Lys
            340                 345                 350

Arg Phe Ser Phe Asp Glu Arg Gly Arg Leu His Val Arg Trp
            355                 360             365

<210> SEQ ID NO 14
<211> LENGTH: 416
<212> TYPE: PRT
<213> ORGANISM: Sagittula stellata

<400> SEQUENCE: 14

Met Gly Asn Ile Arg Ser Arg Ser Gly Tyr Ala Ile Val Ala Phe Ser
1               5                   10                  15

Val Ser Ala Ala Trp Thr Thr Leu Ala Ala Asp Val Ala Ala Gly Pro
            20                  25                  30

Thr Leu Pro Val Ala Pro Glu Asp Ala Ser Val Ile Tyr Pro Ser Val
            35                  40                  45

Asp Lys Asp His Arg Arg Ala Val Leu Asp Arg Phe Trp Arg Glu Trp
    50                  55                  60

Lys Arg Val Tyr Leu His Gln Gly Cys Gly Gly Ala Tyr Val Asp Ile
65                  70                  75                  80

Ala Gly Asp Gly Lys Pro Thr Tyr Gly Asp Ser Val Pro Asn Thr Leu
            85                  90                  95

Thr Val Ser Glu Ala His Gly Tyr Gly Met Leu Ala Leu Val Arg Met
            100                 105                 110

Ala Gly Arg Asp Thr Gln Ala Lys Pro Leu Phe Asp Glu Met Leu Ala
            115                 120                 125

Tyr Phe Arg Leu His Pro Ala Glu Ser Gly Pro Gly Leu Met Ala Trp
            130                 135                 140

Asn Gln Thr Arg Asp Cys Lys Asp Ala Pro Asp Gly Glu Met Thr Ala
145                 150                 155                 160

Ser Asp Gly Asp Ile Asp Ile Ala Leu Ala Leu Gln Met Ala Glu Arg
            165                 170                 175

Val Trp Gly Gly Tyr Ala Glu Asp Ala Ala Glu Val Arg Glu Ala Val
            180                 185                 190

Leu Ser Arg Glu Ile Thr Arg His Asp Leu Val Lys Leu Gly Asp Trp
            195                 200                 205

Ala Ser Tyr Asp Val Tyr Ala Glu Ala Ser Arg Ser Ser Asp Phe Thr
            210                 215                 220

Pro Phe Asn Phe Phe Ala Phe Ala Asp Ala Pro Gly Gly Asp Ala Thr
225                 230                 235                 240

Arg Trp Thr Asp Ile Arg Asn Thr Gly Tyr Ala Val Trp Gly Gln Ile
            245                 250                 255

Ser Glu Thr Tyr Ala Pro Asp Thr Gly Leu Val Pro Asp Phe Met Val
            260                 265                 270

Gly Met Pro Asn Asp Pro Arg Pro Ala Pro Ala Glu Phe Leu Glu Gly
            275                 280                 285

Glu Tyr Asp Gly Phe Tyr Ser Trp Asn Ala Leu Arg Tyr Pro Tyr Arg
            290                 295                 300

Leu Ala Ala Asp Phe Arg Val Ser Gly Asp Pro Arg Ala Ala Glu Arg
305                 310                 315                 320

Leu Arg Arg Ile Asn Lys Trp Ile Arg Ala Ala Thr Asn Gly Glu Pro
            325                 330                 335

Ser Arg Ile Ala Ser Thr Tyr Gln Leu Asp Gly Ser Ile Pro Gln Asp
            340                 345                 350

Gly Arg Trp Thr Gly Glu Pro Gly Trp Ile Ser Met Phe Thr Ala Gly
        355                 360                 365

Ala Ile Ala Gly Ser Gly Asp Pro Thr Ala Asp Gln Ala Trp Met Asp
    370                 375                 380

Ser Leu Trp Ala Ala Met Val Ser Ile Pro Ile Glu Glu Gly Asp Tyr
385                 390                 395                 400

Phe Gly Asn Thr Leu Lys Leu Leu Ala Met Ile Asp Leu Ala Glu Met
                405                 410                 415

<210> SEQ ID NO 15
<211> LENGTH: 437
<212> TYPE: PRT
<213> ORGANISM: Burkholderia mallei

<400> SEQUENCE: 15

Met Ala Ser Phe Ser Val Met Ala Phe Ala Ala Ala Thr Leu Pro Val
1               5                   10                  15

Ser Trp Arg Val Ala Ala Ala Glu Arg Thr Arg Ser Gly Gly Glu
            20                  25                  30

Arg Ala Gly Gly Leu Arg Asp Thr Ala Gly Leu Ile Glu Ile Ser Ala
        35                  40                  45

Ala Ala Pro Ala Ser Thr Pro Ile Pro Ala Ala Pro Arg Arg Phe Ala
    50                  55                  60

Gln Pro Phe Ala Gln Pro Ala Arg Ala Phe Ala Val Ala Ser Ala Cys
65                  70                  75                  80

Ala Pro Ser Trp Pro Arg Trp Asp Arg Phe Lys Arg Asp Phe Val Ser
                85                  90                  95

Ala Asp Gly Arg Val Ile Asp Val Gly Ser Ala Asp Glu Arg Thr Val
            100                 105                 110

Ser Glu Gly Gln Ala Tyr Gly Leu Phe Phe Ala Leu Val Ala Asn Asp
        115                 120                 125

Arg Ala Ala Phe Asp Ala Leu Leu Arg Trp Thr Glu Asp Asn Leu Ala
    130                 135                 140

Gln Gly Asp Leu Ser Ala Arg Leu Pro Ala Trp Leu Trp Gly Arg Ala
145                 150                 155                 160

Ala Asp Gly Ala Trp Arg Val Leu Asp Ala Asn Ala Ala Ser Asp Ala
                165                 170                 175

Asp Leu Trp Leu Ala Tyr Ala Leu Leu Glu Ala Gly Arg Leu Trp Arg
            180                 185                 190

Glu Arg Ser Tyr Thr Ala Arg Gly Ala Leu Leu Ala Lys Arg Val Leu
        195                 200                 205

Asp Glu Glu Thr Ala Thr Leu Pro Gly Leu Gly Leu Val Leu Leu Pro
    210                 215                 220

Gly Pro Met Gly Phe Arg Pro Ala Arg Asp Ala Trp Arg Leu Asn Pro
225                 230                 235                 240

Ser Tyr Ser Pro Pro Gln Ala Ile Arg Gly Ile Gly Ala His Val Pro
                245                 250                 255

Asp Asp Ala Arg Trp Ala Arg Leu Ala Ala Gly Phe Gly Arg Val Leu
            260                 265                 270

Thr Asp Ser Ala Pro Arg Gly Phe Ala Pro Asp Trp Ala Leu Tyr Arg
        275                 280                 285

Ala Gly Arg Gly Phe Glu Pro Asp Ala Glu Thr His Ala Val Ser Ala

```
            290                 295                 300
Tyr Asn Ala Ile Arg Val Tyr Leu Trp Ala Gly Met Leu Asp Ala Gly
305                 310                 315                 320

Asp Pro Leu Ala Arg Pro Leu Val Ala His Phe Ala Pro Phe Ala Glu
                325                 330                 335

His Val Ala Ala His Gly Ala Pro Pro Glu Ala Val Asp Ala Thr Thr
            340                 345                 350

Gly Ala Ala Pro Arg Asp Gly Asn Ala Gly Phe Ser Ala Ala Ala
        355                 360                 365

Val Pro Phe Leu Glu Ala Arg Gly Glu Arg Ala Ser Ala Asp Ala Gln
370                 375                 380

Leu Ala Arg Val Ala Arg Leu Glu Arg Glu Thr Ala Ser Gly Tyr Tyr
385                 390                 395                 400

Ala Asn Val Leu Thr Leu Phe Gly Leu Gly Trp Arg Asp Gly Arg Tyr
                405                 410                 415

Arg Phe Ala Ala Asp Gly Thr Leu Arg Val Arg Trp Ser Glu Pro Cys
            420                 425                 430

Ser Thr Pro Ala Arg
        435

<210> SEQ ID NO 16
<211> LENGTH: 356
<212> TYPE: PRT
<213> ORGANISM: Rhodobacter sphaeroides

<400> SEQUENCE: 16

Met Arg Arg Arg Thr Ile Leu Thr Ser Ala Ala Ala Leu Met Leu
1               5                   10                  15

Ala Pro Ala Gly Arg Leu Phe Ala Gln Ser Gly Gly Glu Ala Leu Ser
                20                  25                  30

Ala Asp His Pro Leu Gln Ala Ala Trp Arg Ser Trp Lys Asp Ala Phe
            35                  40                  45

Leu Leu Pro Ala Gly Arg Ile Val Asp Gly Pro Gln Gln Asn Ala Ser
50                  55                  60

His Ser Glu Gly Gln Gly Tyr Gly Ala Thr Leu Ala Ala Ile Phe Gly
65                  70                  75                  80

Asp Glu Glu Ala Leu Arg Arg Ile Val Asp Trp Thr Glu Ala Asn Leu
                85                  90                  95

Ala Arg Arg Glu Asp Lys Leu Leu Ser Trp Arg Trp Leu Pro Gly Val
            100                 105                 110

Ala Leu Ala Val Pro Asp Glu Asn Asn Ala Thr Asp Gly Asp Leu Phe
        115                 120                 125

Tyr Ala Trp Gly Leu Ala Met Ala Ala Gln Arg Phe Gly Lys Ala Asp
130                 135                 140

Tyr Ala Gly Arg Ala Thr Glu Leu Ala Arg Ala Ile Ala Leu His Cys
145                 150                 155                 160

Val Arg Pro His Pro Asp Gly Ser Glu Gln Leu Val Leu Leu Pro Gly
                165                 170                 175

Ala Ser Gly Phe Glu Thr Pro Asp Gly Val Val Leu Asn Pro Ser Tyr
            180                 185                 190

Tyr Met Pro Arg Ala Leu Thr Glu Leu Ala Ala Phe Ser Gly Gln Asp
        195                 200                 205

Arg Leu Ala Arg Cys Ala Arg Asp Gly Ala Asp Trp Ile Ala Ser Leu
    210                 215                 220
```

```
Gly Leu Pro Pro Asp Trp Ala Leu Val Thr Pro Phe Gly Thr Gln Pro
225                 230                 235                 240

Ala Pro Gly Leu Ser His Asn Ser Gly Tyr Asp Ala Leu Arg Val Pro
            245                 250                 255

Leu Phe Leu Leu Trp Ser Gly Leu Thr Ala Asn Pro Ala Leu Arg Arg
            260                 265                 270

Ala Val Glu Ala Ala Gly Asp Ala Ala Gly Asp Thr Pro Val Arg
            275                 280                 285

Phe Asp Arg Asp Thr Gly Ala Val Leu Glu Arg Ser Ala Asp Pro Gly
            290                 295                 300

Phe Arg Ala Val Leu Ala Leu Gly Asp Cys Ala Leu Ser Gly Arg Pro
305                 310                 315                 320

Gly Ala Ala Ile Pro Pro Phe Asp Ala Arg Gln Pro Tyr Tyr Pro Ala
                325                 330                 335

Thr Leu His Leu Met Ala Leu Val Ala Gln Val Glu Gly Phe Ser Ala
                340                 345                 350

Cys Val Pro Ile
            355

<210> SEQ ID NO 17
<211> LENGTH: 342
<212> TYPE: PRT
<213> ORGANISM: Rhodobacterales bacterium

<400> SEQUENCE: 17

Met Lys Leu Thr Arg Arg Leu Ile Ala Thr Leu Thr Gly Tyr Ala
1               5                   10                  15

Leu Pro Met Ala Phe Leu Thr Ser Val Arg Ala Asp Glu Arg Ala Ala
            20                  25                  30

Trp Asp Val Trp Lys Ser Arg Phe Leu Ala Gly Asn Gly Arg Val Ile
            35                  40                  45

Asp His Leu Gln Asn Gly Val Ser His Ser Glu Gly Gln Gly Tyr Gly
        50                  55                  60

Leu Leu Leu Ala Gln Ala Phe Gly Asp Arg Glu Ala Phe Asp Ala Ile
65                  70                  75                  80

Glu Ser Trp Thr Arg Glu His Leu Leu Ile Arg Asp Asp Ala Leu Met
                85                  90                  95

Ala Trp Arg Trp Ser Pro Ser Gly Asn Arg Asp Asp Glu Leu Ala Gly
            100                 105                 110

Asn Asp Trp His Thr Ala Thr Asp Gly Asp Leu Phe Arg Ala Trp Ala
        115                 120                 125

Leu Met Arg Ser Glu Val Phe Ser Gly Trp Gly Asp Arg Arg Gly Thr
130                 135                 140

Val Glu Ala Ile Ser Asn Ala Leu Ala Ala Leu Cys Leu Glu Pro Asp
145                 150                 155                 160

Pro Arg Ala Pro Asp Glu Pro Ile Leu Thr Pro Gly Ala Glu Ala Met
                165                 170                 175

Ser Glu Pro Asp Arg Val Leu Phe Asn Pro Ser Tyr Ile Met Pro Arg
            180                 185                 190

Ala Leu Arg Glu Leu Gly Leu Tyr Thr Glu Arg Glu Thr Leu Ile Arg
        195                 200                 205

Ala Ala Asp His Gly Glu Thr Ile Leu Ala Glu Leu Ala Ala Thr Gly
    210                 215                 220

Leu Val Pro Asp Trp Val Leu Val Thr Arg Asp Gly Phe Arg Pro Ala
225                 230                 235                 240
```

Glu Gly Phe Gly Ala Asn His Gly Tyr Asp Ala Ile Arg Val Ala Leu
                245                 250                 255

Tyr Leu His Trp Ser Gly Asn Ala Ala His Pro Ala Arg Thr Gln Lys
            260                 265                 270

Gln Glu Ile Trp Thr Gly Glu Ala Arg Val Pro Val Val Leu Thr Pro
        275                 280                 285

Gln Gly Glu Val Leu Glu Arg Ser Thr Tyr Pro Gly Tyr Arg Ala Val
    290                 295                 300

Ala Asp Leu Ile Arg Cys Ser Pro Asn Asp Pro Val Glu Asp Ala Gly
305                 310                 315                 320

Glu Pro Tyr Tyr Pro Ala Thr Leu Gly Leu Met Ala Ser Val Ala Arg
                325                 330                 335

Arg Glu Ser Gly Leu Cys
            340

<210> SEQ ID NO 18
<211> LENGTH: 380
<212> TYPE: PRT
<213> ORGANISM: Paenibacillus sp. W-61

<400> SEQUENCE: 18

Met Asn Ile Thr Gly Gln Gly Ala Tyr Asp Thr Asn Thr Tyr Asn Asn
1               5                   10                  15

Leu Phe His Lys Phe Gly Tyr Asp Glu Gln Ile Asn Ala Arg Leu
            20                  25                  30

Glu Glu Ser Trp Asn Glu Leu Phe Asp Gly Glu Glu Asp Thr Arg Ile
        35                  40                  45

Tyr Tyr Pro Met Gly Glu Asp Lys Gly Tyr Leu Leu Asp Thr Gly Asn
    50                  55                  60

Asn Asp Val Arg Ser Glu Gly Met Ser Tyr Gly Met Met Met Ala Val
65                  70                  75                  80

Gln Met Asp Lys Lys Glu Glu Phe Asp Arg Leu Trp Asn Phe Ser His
                85                  90                  95

Ala Phe Met Gln His Ala Glu Gly Arg Tyr Lys Asp Tyr Phe Ala Trp
            100                 105                 110

His Cys Lys Pro Asp Gly Thr Arg Leu Ser Gln Gly Pro Ala Pro Asp
        115                 120                 125

Gly Glu Glu Phe Phe Ala Met Ala Leu Phe Phe Ala Ser Asn Arg Trp
    130                 135                 140

Gly Asp Gly Asp Ala Pro Leu Asn Tyr Lys Glu Gln Ala Arg Arg Ile
145                 150                 155                 160

Leu Arg Ala Cys Ile His Gln Gly Glu Asn Gly Glu Gly Asp Pro Met
                165                 170                 175

Trp Asp Pro Glu Thr Lys Leu Ile Lys Phe Val Pro Glu Ser Pro Phe
            180                 185                 190

Ser Asp Pro Ser Tyr His Leu Pro His Phe Tyr Glu Leu Phe Ala Leu
        195                 200                 205

Tyr Ala Asp Glu Asp Gln Ser Phe Trp Arg Asp Ala Ala Ala Ala
    210                 215                 220

Ser Arg Ala Tyr Leu His Thr Ala Cys His Pro Val Thr Gly Leu Ser
225                 230                 235                 240

Pro Glu Tyr Ala Asn Tyr Asp Gly Ser Pro Ala Pro Val Gln Pro His
                245                 250                 255

Gly Asp Phe Arg His Phe Tyr Ser Asp Ala Tyr Arg Val Ala Ala Asn

```
                    260                 265                 270
Ile Ala Leu Asp Trp Glu Trp Phe Gly Lys Asp Pro Trp Gln Val Glu
            275                 280                 285

Gln Ser Asn Arg Ile Gln Ser Phe Ser Ser Ile Asp Val Ala Glu
        290                 295                 300

Tyr Arg Arg Tyr Thr Ile Glu Gly Glu Pro Phe Asp Glu Pro Ser Leu
305                 310                 315                 320

His Pro Ile Gly Leu Leu Ala Thr Asn Ala Met Ala Ser Leu Ala Ala
            325                 330                 335

Asp Gly Pro His Val Glu His Phe Val Arg Leu Phe Trp Asn Thr Pro
            340                 345                 350

Leu Arg Gln Gly Glu Arg Arg Tyr Tyr Asp Asn Cys Leu Tyr Phe Phe
            355                 360                 365

Ser Leu Leu Ala Leu Ser Gly Lys Tyr Arg Ile Tyr
            370                 375                 380

<210> SEQ ID NO 19
<211> LENGTH: 371
<212> TYPE: PRT
<213> ORGANISM: Cronobacter sakazakii

<400> SEQUENCE: 19

Met Lys Asn Leu Cys Arg Trp Leu Ala Ala Gly Leu Leu Leu Ala Thr
1               5                   10                  15

Val Ser Ala His Ala Ala Cys Gly Trp Ala Asp Trp Asp Arg Phe Lys
            20                  25                  30

Gly Gly Tyr Ile Ser Glu Glu Gly Arg Val Ile Asp Pro Ser Asp Pro
        35                  40                  45

Arg Lys Ile Thr Thr Ser Glu Gly Gln Ser Tyr Ala Leu Phe Phe Ala
    50                  55                  60

Leu Ala Ala Asn Asp Arg Glu Ala Phe Asp Asn Ile Leu Gln Trp Thr
65                  70                  75                  80

Glu Asn Asn Leu Ala Gln Gly Ser Leu Lys Asn Thr Leu Pro Ala Trp
                85                  90                  95

Leu Trp Gly Met Lys Gly Pro Asp Glu Trp Thr Val Leu Asp Thr Asn
            100                 105                 110

Ser Ala Ser Asp Ala Asp Leu Trp Ile Ala Trp Ser Leu Leu Glu Ala
        115                 120                 125

Gly Arg Leu Trp Lys Glu Pro Arg Tyr Ser Asp Thr Gly Lys Ala Leu
    130                 135                 140

Leu Asp Arg Ile Ala Lys Glu Val Val Asn Val Pro Ala Leu Gly
145                 150                 155                 160

Asp Met Leu Leu Pro Gly Lys Val Ser Phe Ala Glu Pro Thr Leu Trp
                165                 170                 175

Arg Phe Asn Pro Ser Tyr Met Pro Pro Gln Leu Ala Arg Tyr Phe Thr
            180                 185                 190

Arg Tyr Gly Lys Pro Trp Thr Thr Ile Arg Asp Thr Asn Leu Arg Leu
        195                 200                 205

Leu Leu Glu Thr Ala Pro Gln Gly Phe Ser Pro Asp Trp Val Ser Tyr
    210                 215                 220

Glu Ala Lys Lys Gly Trp Val Met Lys Pro Ala Ala Pro Gln Lys Pro
225                 230                 235                 240

Leu Ile Gly Ser Tyr Asp Ala Ile Arg Val Tyr Leu Trp Val Gly Met
                245                 250                 255
```

```
Met Asn Pro Ala Asp Glu Gln Gln Ala Pro Leu Leu Lys Lys Leu Ser
            260                 265                 270

Pro Met Glu Thr Ala Thr Ile Lys Ala Gly Val Pro Pro Glu Lys Val
        275                 280                 285

Arg Val Ile Asp Gly Lys Thr Gln Gly Asn Gly Pro Val Gly Phe Ser
    290                 295                 300

Ala Ala Leu Leu Pro Phe Leu Gln Asn Arg Asp Ile Gln Ala Leu Gln
305                 310                 315                 320

Arg Gln Arg Val Ala Asp Asn Tyr Pro Gln Gln Asp Ala Tyr Phe Ser
                325                 330                 335

Tyr Val Leu Thr Leu Phe Gly Gln Gly Trp Asp Glu His Arg Phe Arg
            340                 345                 350

Phe Thr Val Asp Gly Glu Leu Gln Pro Ala Trp Gly Glu Ser Cys Thr
        355                 360                 365

Ser Ser Arg
    370

<210> SEQ ID NO 20
<211> LENGTH: 407
<212> TYPE: PRT
<213> ORGANISM: Burkholderia vietnamiensis

<400> SEQUENCE: 20

Met Val Trp Ala Tyr Ala Thr Arg Arg Ala Ala Arg Arg Ala Gly Ala
1               5                   10                  15

Ala Leu Ala Leu Ala Ala Ala Ala Ala Ala Gly Pro Leu His Ala Ala
            20                  25                  30

Gln Asp Gly Ala Gly Ala Ala Ala Gly Ser Ala Gly Ala Ala Gly Ala
        35                  40                  45

Gln Cys Gly Gly Ala Ala Trp Pro Arg Trp Asp Ala Phe Lys Arg Asp
    50                  55                  60

Phe Val Ser Ala Asp Gly Arg Val Ile Asp Val Gly Ser Asp Asp Ser
65                  70                  75                  80

Arg Thr Val Ser Glu Gly Gln Ala Tyr Gly Leu Phe Phe Ala Leu Val
                85                  90                  95

Ala Asn Asp Arg Arg Thr Phe Asp Thr Ile Leu Ala Trp Thr Glu Asn
            100                 105                 110

Asn Leu Ala Gln Gly Asp Leu Ser Ala His Leu Pro Ala Trp Leu Trp
        115                 120                 125

Gly Arg Ala Pro Asp Gly Ala Trp Arg Val Leu Asp Ala Asn Ala Ala
    130                 135                 140

Ser Asp Ala Asp Leu Trp Ile Ala Tyr Thr Leu Val Glu Ala Gly Arg
145                 150                 155                 160

Leu Trp His Glu Arg Ser Tyr Thr Ala Arg Gly Ala Leu Leu Ala Lys
                165                 170                 175

Arg Val Leu Asp Thr Glu Thr Ala Ser Val Pro Gly Leu Gly Leu Thr
            180                 185                 190

Leu Leu Pro Gly Pro Thr Gly Phe Lys Leu Ala Asn Gly Gln Trp Arg
        195                 200                 205

Val Asn Pro Ser Tyr Ser Pro Pro Gln Val Ile Arg Gly Leu Ala Ala
    210                 215                 220

Arg Leu Pro Asp Glu Arg Arg Trp Ala Ala Leu Met Thr Ser Thr Gly
225                 230                 235                 240

Arg Val Leu Leu Asp Thr Ala Pro Lys Gly Phe Ala Pro Asp Trp Ala
                245                 250                 255
```

```
Leu Tyr Arg Ala Gly Ala Gly Phe Gly Pro Asp Pro Gln Thr His Ala
            260                 265                 270

Glu Ser Ala Tyr Asn Ala Ile Arg Val Tyr Leu Trp Ala Gly Met Leu
        275                 280                 285

Asp Arg Ser Asp Pro Leu Ala Ala Pro Leu Leu Ala Arg Phe Ala Pro
    290                 295                 300

Phe Ala Asp His Ile Ala Ala His Gly Ala Pro Glu Arg Val Asp
305                 310                 315                 320

Thr Thr Thr Gly Val Ala Ala Pro Asn Asp Gly Asn Gly Gly Phe Ser
                325                 330                 335

Ala Ala Ala Val Pro Phe Leu Ala Ala Arg Gly Gln Gln Ala Leu Ala
            340                 345                 350

Asp Ala Gln Ala Ala Arg Val Asp Ala Leu Ala Arg Gln Ser Pro Pro
        355                 360                 365

Gly Tyr Tyr Thr Ser Val Leu Thr Leu Phe Gly Leu Gly Trp Arg Asp
    370                 375                 380

Gly Arg Tyr Arg Phe Gly Ala Asp Gly Thr Leu Asp Ala Arg Trp Glu
385                 390                 395                 400

Gly Arg Pro Cys Ala Ala Arg
                405

<210> SEQ ID NO 21
<211> LENGTH: 337
<212> TYPE: PRT
<213> ORGANISM: Polynucleobacter necessarius

<400> SEQUENCE: 21

Met Thr Phe Ser Pro Leu Leu Arg Ser Trp Leu Val Thr Ile Ala Leu
1               5                   10                  15

Gly Val Ile Ser Ser Asn Ala Ile Cys Ala Asp Gln Asp Trp Gln Gln
            20                  25                  30

Phe Lys Asn Ala Tyr Ile Gln Asn Gly Arg Val Ile Asp Ser Gly Gln
        35                  40                  45

Asp Gly Met Ser His Thr Glu Gly Gln Gly Val Ala Met Leu Leu Ala
    50                  55                  60

Val Lys Asn Asn Asp Pro Gln Thr Phe Glu Leu Val Trp Asn Trp Thr
65                  70                  75                  80

Gln His Asn Leu Gln Val Arg Glu Asp Lys Leu Leu Ala Trp Ser Trp
                85                  90                  95

Ser Pro Thr Gln Gly Val Met Asp Thr Asn Asn Ala Ser Asp Gly Asp
            100                 105                 110

Leu Phe Ile Ala Trp Ala Leu Ser Gln Ala Tyr Thr Arg Trp Gln Glu
        115                 120                 125

Pro Arg Tyr Leu Phe Tyr Ala Leu Gln Ile Ser Gln Ser Ile Arg Glu
    130                 135                 140

Lys Leu Ile Arg Lys Thr Asn Phe Gly Thr Val Ile Leu Pro Gly Ala
145                 150                 155                 160

Phe Gly Phe Glu Lys Pro Glu Gly Leu Lys Leu Asn Leu Ser Tyr Trp
                165                 170                 175

Val Phe Pro Ala Ile Thr Glu Leu Ala Val Leu Asp Pro Ala Pro Glu
            180                 185                 190

Trp Asn Glu Leu Gln Leu Thr Gly Leu Arg Leu Leu Glu Gln Ala Gln
        195                 200                 205

Tyr Gly Lys Trp Lys Leu Pro Pro Asp Trp Leu Met Tyr Lys Asp Gly
```

```
            210                 215                 220
Ile Ser Thr Pro Thr Asp Gly Asn Arg Phe Gly Tyr Asp Ala Val Arg
225                 230                 235                 240

Ile Pro Leu Tyr Leu Ile Trp Gly Asn Gln Ala Gly Asn Ser Asn Met
                245                 250                 255

Lys Pro Phe Gln Ser Phe Trp Ser Ser Phe Gln Gly Gln Glu Phe Leu
                260                 265                 270

Pro Ala Trp Val Asp Leu Lys Thr Gly Asp Ile Gly Thr Tyr Asn Ala
                275                 280                 285

Ser Leu Gly Phe His Ser Ile Ala Ala Leu Thr Leu Ser Tyr Pro Gln
            290                 295                 300

Ile Asp Leu Ala Gln Leu Pro Asn Phe Asp Pro Thr Glu Gly Tyr Tyr
305                 310                 315                 320

Ser Ser Met Leu Tyr Leu Phe Thr Lys Ser Ala Val Glu Asp Leu Lys
                325                 330                 335

Lys

<210> SEQ ID NO 22
<211> LENGTH: 360
<212> TYPE: PRT
<213> ORGANISM: Enterobacter sp. 638

<400> SEQUENCE: 22

Met Val Ala Leu Val Leu Ala Ala Ala Asn Ala Arg Ala Ala Cys Ser
1               5                   10                  15

Trp Pro Ala Trp Glu Gln Phe Lys Gln Asp Tyr Ile Ser Asp Gly Gly
                20                  25                  30

Arg Val Ile Asp Pro Ser Asp Ala Arg Lys Ile Ser Thr Ser Glu Gly
            35                  40                  45

Gln Ser Tyr Ala Leu Phe Phe Ala Leu Ala Ala Asn Asp Arg Lys Ala
    50                  55                  60

Phe Asp Leu Leu Leu Thr Trp Thr Ser Asp Asn Leu Ala Gln Gly Ser
65                  70                  75                  80

Leu Ser Gln His Leu Pro Ala Trp Leu Trp Gly Lys Lys Asp Ala Asp
                85                  90                  95

Thr Trp Ala Val Ile Asp Lys Asn Ser Ala Ser Asp Ala Asp Ile Trp
                100                 105                 110

Ile Ala Trp Ser Leu Leu Glu Ala Gly Arg Leu Trp Lys Ala Pro Gln
            115                 120                 125

Tyr Thr Ala Thr Gly Lys Ala Leu Leu Lys Arg Ile Ala Ser Glu Glu
    130                 135                 140

Val Ile Lys Val Pro Gly Leu Gly Leu Met Leu Leu Pro Gly Asn Val
145                 150                 155                 160

Gly Phe Thr Glu Glu Lys Ala Trp Arg Phe Asn Pro Ser Tyr Leu Pro
                165                 170                 175

Pro Gln Leu Ala Asn Tyr Phe Arg Phe Gly Ala Pro Trp Thr Thr
                180                 185                 190

Leu Arg Glu Thr Asn Leu Arg Leu Leu Glu Thr Ala Pro Lys Gly
            195                 200                 205

Phe Ala Pro Asn Trp Val Gln Tyr Gln Gln Lys Gly Trp Gln Leu
    210                 215                 220

Gln Pro Glu Lys Thr Phe Ile Gly Ser Tyr Asp Ala Ile Arg Val Tyr
225                 230                 235                 240

Leu Trp Thr Gly Met Met His Asp Arg Asp Pro Gln Lys Ala Arg Leu
```

```
                245                 250                 255
Leu Ala Arg Phe Lys Pro Met Ala Thr Leu Thr Thr Lys Asn Gly Val
            260                 265                 270

Pro Pro Glu Lys Val Asp Val Ala Ser Gly Lys Pro Thr Gly Asp Gly
            275                 280                 285

Pro Val Gly Phe Ser Ala Ser Leu Leu Pro Phe Leu Gln Asp Arg Asp
            290                 295                 300

Ala Gln Ala Val Gln Arg Gln Val Ala Asp His Phe Pro Gly Asn
305                 310                 315                 320

Asp Ala Tyr Tyr Ser Tyr Val Leu Thr Leu Phe Gly Gln Gly Trp Asp
                325                 330                 335

Gln His Arg Phe Arg Phe Thr Ala Lys Gly Glu Leu His Pro Asp Trp
            340                 345                 350

Gly Gln Glu Cys Ala Ser Ser His
            355                 360

<210> SEQ ID NO 23
<211> LENGTH: 330
<212> TYPE: PRT
<213> ORGANISM: Enterobacter sp. 638

<400> SEQUENCE: 23

Met Arg Lys Pro Ala Cys Ala Ala Leu Ala Val Met Met Thr Met Ile
1               5                   10                  15

Phe Ser Pro Phe Ser Gln Ala Gly Gln Ala Trp Glu Ser Tyr Lys Ala
            20                  25                  30

Arg Phe Leu Met Pro Asp Gly Arg Val Val Asp Thr Gly Asn Gly Asn
            35                  40                  45

Val Ser His Thr Glu Gly Gln Gly Phe Ala Met Leu Met Ala Val Ala
        50                  55                  60

Ser Asp Asp Lys Thr Ala Phe Asp Lys Leu Trp His Trp Thr Asp Ser
65                  70                  75                  80

Thr Leu Lys Asn Lys Ser Asn Gly Leu Phe Tyr Trp Arg Tyr Asn Pro
                85                  90                  95

Val Leu Pro Asp Pro Ile Pro Asp Lys Asn Ala Ser Asp Gly Asp
            100                 105                 110

Ala Leu Ile Ala Trp Ala Leu Leu Lys Ala Asp Ala Arg Trp His Asp
            115                 120                 125

Ala Arg Tyr Ser Gln Ala Ser Asp Ala Ile Thr Lys Ser Leu Val Ala
130                 135                 140

Arg Thr Val Ile Arg Tyr Ala Gly Tyr Arg Val Met Leu Pro Gly Ala
145                 150                 155                 160

Gln Gly Phe Asn Leu Asn Ser Glu Val Ile Leu Asn Pro Ser Tyr Phe
                165                 170                 175

Ile Phe Pro Ala Trp Gln Ala Phe Ala Asp Arg Ser His Leu Gln Val
            180                 185                 190

Trp Arg Glu Leu Ile Gln Asp Gly His Lys Val Leu Gly Lys Met Gly
            195                 200                 205

Thr Gly Thr Ala Asn Leu Pro Thr Asp Trp Met Ser Leu Ala Ala Gly
            210                 215                 220

Gly Lys Leu Thr Pro Ala Asn Ala Trp Pro Pro Arg Met Ser Tyr Asp
225                 230                 235                 240

Ala Ile Arg Ile Pro Leu Tyr Ile His Trp Ser Ser Pro Gln Ser Pro
                245                 250                 255
```

```
Ser Leu Thr Pro Trp Arg Ser Trp Phe Gly Gln Phe Ser Arg Glu Lys
                260                 265                 270

Thr Pro Ala Trp Val Asn Val Thr Asn Glu Tyr Ala Pro Tyr Met
            275                 280                 285

Met Glu Gly Gly Leu Leu Ala Val Arg Asp Leu Thr Met Gly Gln Ala
290                 295                 300

Ser Gly Glu Pro Asp Ile Thr Ala Lys Asp Tyr Tyr Ser Ala Ser
305                 310                 315                 320

Leu Lys Met Leu Val Trp Leu Ala Asp Gln
                325                 330

<210> SEQ ID NO 24
<211> LENGTH: 356
<212> TYPE: PRT
<213> ORGANISM: Rhodobacter sphaeroides

<400> SEQUENCE: 24

Met Arg Arg Arg Thr Leu Leu Arg Leu Ala Ala Thr Ala Leu Ala
1               5                   10                  15

Ser Pro Ala Gly Arg Leu Leu Ala Gln Glu Gly Gly Val Leu Pro Ser
                20                  25                  30

Asp His Pro Leu Gln Thr Ala Trp Glu Ser Trp Lys Ala Ala Phe Leu
            35                  40                  45

Leu Pro Ala Gly Arg Ile Val Asp Gly Pro Gln Gln Asn Ala Ser His
50                  55                  60

Ser Glu Gly Gln Gly Tyr Gly Ala Ala Leu Ala Ala Ile Phe Gly Asp
65                  70                  75                  80

Glu Ala Ala Leu Arg Arg Ile Val Asp Trp Thr Glu Thr Asn Leu Ala
                85                  90                  95

Arg Arg Asp Asp Asn Leu Leu Ser Trp Arg Trp Leu Pro Gly Val Pro
                100                 105                 110

Leu Ala Val Pro Asp Glu Asn Asn Ala Thr Asp Gly Asp Leu Phe Tyr
            115                 120                 125

Gly Trp Gly Leu Ala Leu Ala Ala Gln Arg Phe Gly Asn Ala Asp Leu
130                 135                 140

Ala Lys Arg Ala Thr Glu Ile Ala Arg Ala Ile Ala Leu His Cys Val
145                 150                 155                 160

Arg Pro His Pro Asp Gly Ser Glu Arg Leu Val Leu Leu Pro Gly Ala
                165                 170                 175

Thr Gly Phe Glu Thr Glu Glu Gly Leu Val Leu Asn Pro Ser Tyr Tyr
            180                 185                 190

Met Pro Arg Ala Met Thr Glu Leu Ala Ala Phe Ser Gly Gln Glu Arg
        195                 200                 205

Leu Ala Arg Cys Ala Gln Asp Gly Ala Leu Trp Ile Gly Gly Leu Gly
210                 215                 220

Leu Ala Pro Asp Trp Val Leu Val Thr Ser Thr Gly Asp Leu Pro Ala
225                 230                 235                 240

Lys Gly Leu Ser Ala His Ser Gly Tyr Asp Ala Met Arg Val Pro Leu
                245                 250                 255

Phe Leu Leu Trp Ser Gly Leu Thr Ala Asn Pro Ala Leu Arg Arg Phe
            260                 265                 270

Ile Glu Val Gln Arg Glu Ala Glu Pro Gly Thr Gly Thr Pro Val Val
        275                 280                 285

Phe Asp Arg Asp Thr Gly Ala Leu Leu Glu Arg Ser Ala Asp Pro Gly
290                 295                 300
```

Phe Ala Ser Val Pro Ala Leu Ala Asp Cys Ala Leu Ser Gly Arg Pro
305                 310                 315                 320

Gly Ala Ala Ile Pro Pro Phe Asp Ala Arg Gln Pro Tyr Tyr Pro Ala
                325                 330                 335

Thr Leu His Leu Met Thr Leu Val Ala Gln Val Glu Gly Phe Ser Ala
            340                 345                 350

Cys Ala Pro Ile
            355

<210> SEQ ID NO 25
<211> LENGTH: 362
<212> TYPE: PRT
<213> ORGANISM: Rhodobacter sphaeroides

<400> SEQUENCE: 25

Met Lys Arg Arg His Phe Met Ala Ser Leu Leu Gly Thr Leu Ala Ala
1               5                   10                  15

Gly Arg Ala Phe Gly Gly Phe Ala Gln Glu Gly Ala Ala Phe Val Leu
            20                  25                  30

Pro Ala Asp His Pro Leu Gln Pro Ala Trp Gln Ala Trp Lys Ser Leu
        35                  40                  45

Cys Leu Gln Glu Asp Gly Arg Ile Val Asp Ala Pro Gln Ser Gly Ala
50                  55                  60

Ser His Ser Glu Gly Gln Gly Tyr Gly Leu Arg Leu Ala Val Ala Phe
65                  70                  75                  80

Gly Asp Glu Glu Ala Phe Arg Arg Ile Phe Glu Trp Ser Glu Ser His
                85                  90                  95

Leu Ala Leu Arg Glu Asp Gly Leu Leu Ser Trp Arg Tyr Leu Pro Glu
            100                 105                 110

Ala Gly Asp Pro Val Pro Asp Arg Asn Asn Ala Ser Asp Gly Asp Leu
        115                 120                 125

Phe Tyr Gly Trp Ala Leu Ile Gln Gly Ala Met Ala Trp Asn Glu Pro
    130                 135                 140

Leu Phe Ala Asp Arg Ala Arg Met Ile Gly Thr Ala Leu Ala Arg Ser
145                 150                 155                 160

Cys Leu Ala Asp His Pro Asp Gly Ser Gly Arg Arg Tyr Leu Leu Pro
                165                 170                 175

Ala Ala Tyr Gly Phe Thr Ser Asp Arg Ala Ile Thr Leu Asn Leu Ser
            180                 185                 190

Tyr Cys Met Pro Arg Ala Met Arg Glu Leu Gly Ala Phe Ala Glu Ala
        195                 200                 205

Pro Ala Leu Val Thr Ala Ala Gln Asp Gly Leu Asp Leu Met Asn Gly
    210                 215                 220

Ile Ala Gly Ser Gly Leu Leu Pro Asp Trp Leu Gln Leu Thr Pro Glu
225                 230                 235                 240

Gly Arg Thr Pro Ala Pro Gly Leu Pro Asp Gln Ser Gly Tyr Glu Ala
                245                 250                 255

Leu Arg Ile Pro Leu Tyr Leu Cys Trp Ser Gly Met Thr Asp Thr Pro
            260                 265                 270

Ala Gln Gln Arg Phe Arg Glu Met His Arg Gln Ala Ala Arg Asp
        275                 280                 285

Arg Gly Thr Ala Thr Val Phe Asp Pro Glu Thr Gly Arg Ile Arg Glu
    290                 295                 300

Ser Ser Asp Glu Val Gly Tyr Arg Ala Leu Val Ala Leu Asn Asp Cys

```
             305                 310                 315                 320
Val Leu Ser Arg Thr Ala Gly Ser Ala Met Pro Asp Phe Asp Ala Ala
                 325                 330                 335

Gln Val Tyr Phe Pro Ala Thr Leu His Leu Met Ala Leu Val Ala Gln
                 340                 345                 350

Ala Glu Phe Phe Pro Lys Cys Leu Pro Val
                 355                 360

<210> SEQ ID NO 26
<211> LENGTH: 430
<212> TYPE: PRT
<213> ORGANISM: Flavobacterium johnsoniae

<400> SEQUENCE: 26

Met Thr Val His His Asn Ile Thr Asn Gly Tyr Leu Ser Lys Ile His
1               5                   10                  15

Leu Leu Leu Leu Ile Phe Ala Leu Ile Val Pro Ala Phe Val Ile Ser
                20                  25                  30

Gln Asn Lys Lys Lys Ile Asp Arg Glu Leu Lys Lys Pro Gln Tyr Arg
            35                  40                  45

Asn Leu Phe Lys Glu Ala Gly Tyr Ser Gln Asp Ile Asp Lys Lys
    50                  55                  60

Leu Thr Lys Ala Tyr Tyr Asp Val Phe Glu Gly Pro Asp Lys Val Tyr
65                  70                  75                  80

Phe Glu Glu Gly Asp Ser Leu Gly Tyr Val Ser Asp Val Lys Asn Lys
                85                  90                  95

Asp Ala Arg Thr Glu Gly Met Ser Tyr Gly Met Met Val Ala Val Gln
            100                 105                 110

Phe Asn Lys Lys Asp Val Phe Asp Arg Leu Trp Arg Trp Ser Val Lys
        115                 120                 125

Tyr Met Gln His Gln Asp Gly Pro Arg Glu Gly Tyr Phe Ala Trp Ser
130                 135                 140

Val Asn Pro Gln Thr Lys Lys Gln Asn Ser Ala Gly Ser Ala Ser Asp
145                 150                 155                 160

Gly Glu Leu Tyr Tyr Ile Thr Ser Leu Leu Phe Ala Ser Asn Lys Trp
                165                 170                 175

Gly Asn Asp Thr Gly Ile Asn Tyr Tyr Lys Glu Ala Arg Arg Ile Leu
            180                 185                 190

Asp Ala Met Trp Lys Lys Asp Gly Thr Gly Asn Ile Tyr Asn Ile Ile
        195                 200                 205

Asn Thr Glu His Lys Gln Ile Ser Phe Val Pro Glu Gly Gly Gly Tyr
210                 215                 220

Asn Trp Thr Asp Pro Ser Tyr His Val Pro Ala Phe Tyr Glu Ile Trp
225                 230                 235                 240

Ala Leu Tyr Ala Lys Asp Gly His Glu Gln Phe Tyr Lys Glu Cys Ala
                245                 250                 255

Glu Val Ser Arg Lys Phe Leu His Lys Ala Cys His Pro Val Thr Gly
            260                 265                 270

Leu Thr Ser Asp Tyr Thr Glu Phe Asn Gly Glu Pro His Pro Thr Pro
        275                 280                 285

Trp Leu Pro Pro Gly Phe Arg Tyr Asp Ser Trp Arg Val Pro Met Asn
        290                 295                 300

Ile Ala Met Asp Tyr Thr Trp Tyr Gly Lys Asp Lys Glu Trp Gln Glu
305                 310                 315                 320
```

```
Asp Tyr Ala Lys Arg Phe Gln Asn Phe Leu Arg Ser Lys Gly Leu Glu
            325                 330                 335

Thr Tyr Glu Asp Gln Phe Asn Leu Asp Gly Ser Thr Pro Glu Phe Ile
            340                 345                 350

Leu Gln Ala Gly Pro Val Lys Lys Leu Arg His Ser Ile Gly Leu Val
            355                 360                 365

Gly Thr Ala Ala Thr Ala Ser Leu Val Asn Lys Asp Lys Ala Ser Ile
370                 375                 380

Asp Phe Val His Ala Val Trp Asn Ala Lys Leu Glu Pro Tyr Glu Asp
385                 390                 395                 400

Gly Tyr Phe Asp Pro Tyr Tyr Asp Gly Leu Met Tyr Leu Phe Ser Leu
            405                 410                 415

Met His Leu Ser Gly Asn Tyr Gln Ile Ile Val Pro Lys Gly
            420                 425                 430

<210> SEQ ID NO 27
<211> LENGTH: 465
<212> TYPE: PRT
<213> ORGANISM: Flavobacterium johnsoniae

<400> SEQUENCE: 27

Met Lys Asn Leu Leu Ile Thr Val Ala Phe Leu Cys Leu Glu Ser
1               5                   10                  15

Asn Ala Gln Lys Gln Pro Phe Pro Ala Asn Val Val Phe Asn Asn Gly
                20                  25                  30

Leu Met Pro Ser Ala Lys Asn Ser Gln Asp Ala Lys Asn Asn Tyr Asp
            35                  40                  45

Thr Trp Lys Thr Asn Phe Val Glu Gly Cys Ser Asn Gly Arg Tyr Arg
    50                  55                  60

Val Lys Phe Asp Ser Ser Trp Glu Thr Val Ser Glu Gly Ile Gly Tyr
65                  70                  75                  80

Gly Met Leu Leu Ser Val Tyr Met Ala Asp Lys Thr Leu Phe Asp Gly
                85                  90                  95

Leu Trp Leu Tyr Tyr Lys Asp Asn Val Asn Asn Lys Val Met Asn
            100                 105                 110

Trp Lys Ile Asn Gly Cys Ser Gly Thr Ile Gly Gln Asn Gly Ala Thr
    115                 120                 125

Asp Ala Glu Leu Asp Ala Ala Phe Ala Leu Ile Val Ala Asp Tyr Gln
130                 135                 140

Trp Ala Ser Ala Gly Thr Ile His Tyr Lys Asn Asp Ala Thr Ala Leu
145                 150                 155                 160

Ile Ser Ala Ile Lys Asn His Glu Val Glu Ala Asn Thr Tyr Val Leu
                165                 170                 175

Lys Pro Gly Asp Gln Phe Gly Gly Ser Gln Ile Thr Asn Pro Ser Tyr
            180                 185                 190

Phe Ser Pro Ala Tyr Tyr Arg Val Phe Gly Thr Phe Thr Asn Asp Thr
    195                 200                 205

Ala Phe Trp Asn Gln Ile Ala Ala Lys Ser Tyr Thr Ile Ile Asn Asn
210                 215                 220

Asn Leu Thr Gln Asn Asn Ala Val Gly Gly Leu Val Ser Asp Trp Cys
225                 230                 235                 240

Glu Ala Ser Gly Ala Tyr Ser Ser Gln Ala Gly Gly Tyr Ala Asn Gly
                245                 250                 255

Gly Lys Met Tyr Thr Tyr Asp Ala Ala Arg Thr Pro Trp Arg Ile Ala
            260                 265                 270
```

```
Val Asp Tyr Leu Trp His Gly Asn Ala Asp Ala Lys Ala Tyr Ala Lys
        275                 280                 285

Lys Ser Ser Asp Phe Val Arg Val Asn Leu Gly Gly Ser Leu Asn Ile
    290                 295                 300

Lys Asp Gly Tyr Asn Gln Asn Gly Ser Val Ser Gly Gln Trp His Asn
305                 310                 315                 320

Ala Thr Phe Val Gly Ala Phe Ala Cys Ala Ala Met Ala Gly Glu Asn
                325                 330                 335

Gln Asn His Leu Asp Ala Ser Tyr Thr Asp Leu Lys Asn Leu Asn Glu
            340                 345                 350

Pro Asn Ser Tyr Phe Asn His Thr Leu Lys Thr Leu Tyr Ser Phe Leu
        355                 360                 365

Leu Thr Gly Asn Phe Tyr Leu Pro Leu Asn Ala Asn Leu Ser Asn Asp
    370                 375                 380

Thr Phe Asp Ile Glu Lys Ser Thr Val Thr Leu Tyr Pro Asn Pro Ser
385                 390                 395                 400

Pro Asp Arg Ile Thr Val Asn Ala Pro Gln Gln Ser Thr Ile Ser Val
                405                 410                 415

Ile Ser Pro Ser Gly Ser Val Ile Tyr Gln Lys Lys Thr Thr Ser Glu
            420                 425                 430

Asn Thr Glu Ile Asn Leu Gly Ser Gln Ser Ser Gly Ile Tyr Phe Val
        435                 440                 445

Lys Ile Ser Asn Asp Asp Phe Lys Ser Ile Thr Lys Lys Val Ile Leu
    450                 455                 460

Lys
465

<210> SEQ ID NO 28
<211> LENGTH: 376
<212> TYPE: PRT
<213> ORGANISM: Acidiphilium cryptum

<400> SEQUENCE: 28

Met Thr Asp Met Ala Arg Arg Asn Phe Leu Gly Leu Leu Gly Ala Ala
1               5                   10                  15

Ala Leu Thr Gly Gly Pro Val Met Met Ala Arg Glu Leu Trp Gln Ser
            20                  25                  30

Ser Trp Arg Gly Tyr Arg His Gly Phe Ile Asp Gly Gln Gly Arg Val
        35                  40                  45

Ile Asp Tyr Ser Ala Asn Lys Gly Phe Ser Thr Ser Glu Gly Gln Ser
    50                  55                  60

Tyr Gly Met Phe Leu Ser Leu Val Ala Gly Asp Arg Ala Thr Phe Arg
65                  70                  75                  80

Arg Ile Leu Asn Trp Thr Asn Thr Asn Met Ala Gly Gly Arg Leu Gly
                85                  90                  95

Glu Val Leu Ala Ala Trp Lys Trp Gly Leu His Gly Gly Lys Trp Gly
            100                 105                 110

Val Ile Gly Ala Asn Ser Ala Ala Asp Ala Asp Ala Trp Met Ala Tyr
        115                 120                 125

Ser Leu Leu Glu Ala Ala Arg Ile Trp Lys Asp His Asn Leu Gly Ala
    130                 135                 140

Glu Gly His Lys Leu Ala Thr Arg Ile Ala Asp Asp Glu Ser Val Ala
145                 150                 155                 160

Ile Asn Gly Phe Gly Arg Val Leu Ile Pro Gly Ala Ser Asp Phe Pro
```

```
            165                 170                 175
Asp Thr Pro Pro Val Ile Val Asp Pro Ser Tyr Thr Pro Leu Phe Leu
            180                 185                 190

Ala Arg Gly Ile Ala Arg Ala Thr Asn Leu Pro Lys Trp Gln Ala Ile
            195                 200                 205

Ala Ala Thr Leu Pro Arg Leu Met Thr Thr Ile Cys Arg Asn Gly Phe
            210                 215                 220

Ala Pro Asp Trp Ala Trp Ala Pro Gln Ala Pro Ala Ser Pro Pro Ala
225                 230                 235                 240

Gly Leu Pro Glu Thr Gly Thr Gly Ser Phe Asp Ala Ile Arg Cys Tyr
            245                 250                 255

Leu Trp Ala Gly Leu Thr Ala Pro Glu Thr Glu Gly Ser Ala Thr Val
            260                 265                 270

Leu Ala Ser Leu Lys Gly Met Ala Arg Tyr Leu Ala Thr His Arg Ala
            275                 280                 285

Pro Pro Gln Ser Val Asp Leu Ala Ser Gln Ala Thr His Gly Thr Gly
            290                 295                 300

Gly Ile Gly Phe Ser Ala Ala Leu Leu Pro Tyr Leu Ala Ala Leu Gly
305                 310                 315                 320

Arg His Arg Leu Leu His Gln Gln Leu Gly Arg Val Leu Ala Gln Arg
            325                 330                 335

Glu Thr Ser Gly Leu Phe Gly Gln Pro Ala Asp Tyr Tyr Ser Glu Asn
            340                 345                 350

Leu Ile Leu Phe Gly Leu Gly Gly Leu Ser Gly Ser Ile Arg Phe Asp
            355                 360                 365

Lys Gln Gly Gly Leu Ile Thr Ser
            370                 375

<210> SEQ ID NO 29
<211> LENGTH: 392
<212> TYPE: PRT
<213> ORGANISM: Vibrio fischeri

<400> SEQUENCE: 29

Met Lys Met Gln Leu Thr Val Leu Ser Leu Leu Ile Gly Thr Leu Thr
1               5                   10                  15

Cys Ser Ser Ser Ala Ile Ala Gln Asp Glu Asn Tyr Thr Thr Pro Ile
            20                  25                  30

Val Ser Ser Ala Ala Leu Thr Lys Glu Asn Gln Cys Glu Trp Gly Gln
            35                  40                  45

Trp Glu Ser Phe Lys Arg His Tyr Ile Glu Asn Gly Arg Val Val Asp
        50                  55                  60

Asn Ser Asp Pro Arg Leu Ile Thr Thr Ser Glu Gly Gln Ser Tyr Ala
65                  70                  75                  80

Leu Phe Phe Ala Leu Ile Ala Asn Asp Lys Lys Thr Phe Asp Glu Leu
                85                  90                  95

Leu Gly Trp Thr Glu Leu His Leu Ala Gly Gly Asp Leu Thr Ala Gln
            100                 105                 110

Leu Pro Ala Trp Leu Trp Gly Thr Gln Pro Asp Gly Ser Gln Gly Ile
            115                 120                 125

Leu Asp Ser Asn Ser Ala Ala Asp Ser Asp Leu Trp Ile Ala Tyr Ser
        130                 135                 140

Leu Leu Glu Ala Gly Arg Leu Trp Asp Asn His Tyr Tyr Gln Ser Leu
145                 150                 155                 160
```

```
Gly His Leu Leu Ala Ser Arg Ile Leu Arg Asp Glu Thr Ile Lys Val
            165                 170                 175

Ser Gly Leu Gly Thr Val Leu Leu Pro Gly Lys Val Gly Phe Val Leu
        180                 185                 190

Gly Lys Asn His Val Arg Leu Asn Pro Ser Tyr Val Pro Leu Gln Leu
        195                 200                 205

Leu Thr Arg Met Asn Thr Val Phe Pro Ser Tyr Gln Trp Glu Glu Ile
    210                 215                 220

Tyr Gln Ser Ser Ala Lys Leu Leu Lys Glu Thr Met Pro Lys Gly Tyr
225                 230                 235                 240

Ser Pro Asp Trp Val Glu Trp Asp Lys Thr Gln Phe Lys Lys Asp Ser
                245                 250                 255

Lys Ala Gln Ser Val Gly Ser Tyr Asn Ala Ile Arg Val Tyr Leu Trp
            260                 265                 270

Ala Gly Met Leu Pro Asp Ser Asp Pro Asn Lys Ala Leu Leu Leu Gly
            275                 280                 285

Lys Met Lys Pro Leu Leu Arg Val Ile Glu Arg Asn Lys Gly Met Pro
        290                 295                 300

Glu Thr Ile Asn Val Leu Thr Gly Lys Gly Lys Asn Gln Gly Gly Val
305                 310                 315                 320

Gly Met Asn Ala Ala Ile Leu Pro Leu Leu Ser Ser Leu Asp Ser Asn
                325                 330                 335

Thr Asn Val Ala Glu Tyr Glu Lys Lys Ile Gln Ala Glu Leu Pro Lys
            340                 345                 350

Ile Glu Ser Asp Tyr Tyr Asn Ser Val Leu Thr Leu Phe Gly Leu
        355                 360                 365

Gly Trp Tyr Gln Asp Leu Tyr Ser Phe Asn Asp Asp Gly Ser Val Thr
    370                 375                 380

Ser Lys Trp Val Asn Val Cys Gln
385                 390

<210> SEQ ID NO 30
<211> LENGTH: 369
<212> TYPE: PRT
<213> ORGANISM: Vibrionales bacterium SWAT-3

<400> SEQUENCE: 30

Met Lys Lys Leu Ile Leu Leu Ser Leu Leu Leu Ser Pro Gln Leu
1               5                   10                  15

Met Ala Ala Thr Cys Glu Trp Pro Leu Trp Ser Asn Phe Lys Ser Ile
            20                  25                  30

Tyr Ile Glu Asn Gly Arg Val Ile Asp Gly Ser Asp Glu Arg Leu Ile
        35                  40                  45

Thr Thr Ser Glu Gly Gln Ser Tyr Ala Leu Phe Phe Ala Leu Val Ala
    50                  55                  60

Asn Asp Gln Gln Ala Phe Asp Gln Val Leu Lys Trp Thr Gln Ala Asn
65                  70                  75                  80

Leu Ala Gly Gly Asp Leu Thr Ala Arg Leu Pro Ala Trp Leu Trp Gly
            85                  90                  95

Lys Arg Leu Asp Gly Gln Phe Gly Ile Leu Asp Thr Asn Pro Ala Ser
            100                 105                 110

Asp Ser Asp Leu Trp Ile Ala Tyr Ala Leu Gly Glu Ala Gly Arg Leu
            115                 120                 125

Trp Asn Asn Tyr Tyr Tyr Gln Ser Leu Gly His Leu Leu Ala Ala Arg
    130                 135                 140
```

```
Ile Leu Arg Glu Glu Ser Val His Ile Ala Gly Val Gly Thr Thr Leu
145                 150                 155                 160

Leu Pro Ala Pro Lys Gly Phe Asp Leu Gly Lys Gly Gly Tyr Arg Leu
                165                 170                 175

Asn Pro Ser Tyr Val Pro Leu Gln Leu Ile Ala Arg Met Lys Glu Leu
            180                 185                 190

Tyr Pro Gln Tyr Ser Trp Asp Ser Met Tyr Gln Ser Ser Thr Leu Ile
        195                 200                 205

Leu Ser Gln Thr Leu Thr Ala Gly Phe Ser Pro Asp Trp Val Thr Leu
210                 215                 220

Asn Gly Lys Arg Phe Asn Val Asp Lys Val Thr Gly Pro Ile Gly Ser
225                 230                 235                 240

Tyr Asn Ala Ile Arg Thr Tyr Leu Trp Val Gly Met Leu Asn Glu Lys
                245                 250                 255

Asn Lys Glu Lys Glu Gln Leu Val Lys Lys Met Glu Pro Phe Ala Thr
            260                 265                 270

Ala Ile Glu Arg Leu Gly Ala Pro Pro Arg Glu Val Asp Thr Glu Thr
        275                 280                 285

Gly Lys Tyr Ser Gln Ser Gly Ser Ala Gly Phe Ser Ala Ala Ala Leu
290                 295                 300

Pro Leu Leu Thr Ser Met Asp Tyr Ser Asn Leu Leu Glu Ala Gln Ala
305                 310                 315                 320

Thr Arg Ala Gln Asn Glu Leu Val Thr Ser Arg Asn Asp His Tyr Tyr
                325                 330                 335

Asp Asn Val Leu Ser Leu Phe Gly Leu Gly Trp His Asn Glu Arg Phe
            340                 345                 350

Arg Phe Gly Glu His Gly Glu Leu Gln Pro Thr Trp Gly Lys Gln Cys
        355                 360                 365

Gln

<210> SEQ ID NO 31
<211> LENGTH: 367
<212> TYPE: PRT
<213> ORGANISM: Pseudomonas putida

<400> SEQUENCE: 31

Met Leu Val Gly Leu Val Ala Leu Gly Leu Pro Val Phe Ala Asn Ala
1               5                   10                  15

Gly Ser Val Cys Pro Trp Pro Ala Trp Glu Arg Phe Lys Ala Glu Leu
            20                  25                  30

Val Ser Val Asp Gly Arg Val Ile Asp Pro Ser Asp Glu Arg Leu Ile
        35                  40                  45

Thr Thr Ser Glu Gly Gln Ser Tyr Ala Leu Phe Phe Ala Leu Val Gly
    50                  55                  60

Asn Asp Arg Gln Thr Phe Ala Gln Leu Leu Arg Trp Thr Ser Asn Asn
65                  70                  75                  80

Leu Ala Glu Gly Asp Leu Ala Arg His Leu Pro Ala Trp Leu Trp Gly
                85                  90                  95

Arg Asp Gly Gln Gln Gln Trp Gln Val Leu Asp Ala Asn Asn Ala Ser
            100                 105                 110

Asp Ala Asp Leu Trp Ile Ala Tyr Ser Leu Leu Glu Ala Gly Arg Leu
        115                 120                 125

Trp Asp Gln Pro Ala Tyr Thr Gln Leu Gly Gln His Leu Leu Trp Arg
    130                 135                 140
```

Ile Ala Ala Gln Thr Val Arg Lys Leu Pro Gly Leu Gly Val Met Leu
145                 150                 155                 160

Leu Pro Gly Asp Tyr Gly Phe Glu Asp Ala Gln Gly Thr Arg Leu Asn
            165                 170                 175

Pro Ser Tyr Leu Pro Leu Gln Leu Leu Asp Arg Phe Ser Glu Val Asp
            180                 185                 190

Pro Leu Trp Gly Glu Leu Ala Ala Asn Thr Arg Arg Leu Trp Leu Ala
            195                 200                 205

Ser Ser Pro Lys Gly Phe Ala Pro Asp Trp Leu Leu Trp Thr Pro Ala
210                 215                 220

Gly Lys Pro Ala Ala Asp Thr Lys His Gly Asn Ala Gly Asp Tyr Asp
225                 230                 235                 240

Ala Ile Arg Val Tyr Leu Trp Val Gly Met Leu Ala Glu Gly Ala Ala
            245                 250                 255

Gln Arg Arg Glu Leu Val Ala His Tyr Ala Pro Met Ala Ala Leu Thr
            260                 265                 270

Gln Arg Gln Gly Leu Pro Pro Glu His Leu Asp Ala Arg Ser Gly Glu
            275                 280                 285

Ala Arg Gly His Gly Pro Ala Gly Phe Ser Ala Ala Leu Leu Pro Leu
            290                 295                 300

Leu Ala Ala Ser Pro Glu His Val Ala Gly Leu Ala Ala Gln Arg Gln
305                 310                 315                 320

Arg Leu Arg Glu Gln Pro Val Glu Ala Lys Ala Tyr Tyr Ser Gln Val
            325                 330                 335

Leu Ala Leu Phe Gly Gln Gly Phe Asp Glu Ala Arg Tyr Arg Phe Asp
            340                 345                 350

Pro His Gly Arg Leu Leu Pro Ala Trp Ser Ala Pro Cys Ser Glu
            355                 360                 365

<210> SEQ ID NO 32
<211> LENGTH: 369
<212> TYPE: PRT
<213> ORGANISM: Vibrio harveyi

<400> SEQUENCE: 32

Met Lys Lys Leu Ile Ala Leu Met Ile Leu Met Ala Ser Pro Gln Leu
1               5                   10                  15

Trp Ala Asn Thr Cys Asp Trp Pro Gln Trp Asp Thr Phe Lys Ser Val
            20                  25                  30

Tyr Ile Glu Gln Gly Arg Val Val Asp Gly Ser Asp Glu Arg Met Ile
            35                  40                  45

Thr Thr Ser Glu Gly Gln Ser Tyr Ala Leu Phe Phe Ala Leu Val Ala
50                  55                  60

Asn Asp Arg Lys Ala Phe Ala Glu Val Leu Lys Trp Thr Gln Ile His
65                  70                  75                  80

Leu Ala Gly Gly Asp Leu Thr Ala Arg Leu Pro Ala Trp Leu Trp Gly
            85                  90                  95

Arg Lys Ala Asn Gly Ser Phe Gly Val Leu Asp Thr Asn Ala Ala Ser
            100                 105                 110

Asp Ser Asp Leu Trp Ile Ala Tyr Ala Leu Val Glu Ala Gly Arg Leu
            115                 120                 125

Trp Asp Asn Tyr Tyr Gln Ser Leu Gly His Leu Leu Ala Ser Arg
            130                 135                 140

Ile Leu Arg Glu Glu Thr Ala Ser Ile Asp Gly Val Gly Ser Val Leu

```
            145                 150                 155                 160
Leu Pro Ala Pro Thr Gly Phe Glu Phe Gly Asp Arg Tyr Arg Val Asn
                    165                 170                 175

Pro Ser Tyr Val Pro Leu Gln Leu Ile Ala Arg Met Glu Ala Leu Tyr
                180                 185                 190

Pro Gln Tyr Pro Trp Asp Gly Met Tyr Lys Ala Ser Ala Gln Met Leu
            195                 200                 205

Thr Gln Thr Met Pro Lys Gly Phe Ser Pro Asp Trp Ala Thr Leu Ser
        210                 215                 220

Gln Gly Gln Tyr Ser Ala Asp Ser Val Thr Gly Pro Ile Gly Ser Tyr
225                 230                 235                 240

Asn Ala Ile Arg Thr Tyr Leu Trp Ala Gly Met Leu Asp Asp Gln Val
                245                 250                 255

Ala Glu Lys Ala Ser Leu Ile Gln Gln Met Gln Pro Phe Val Ala Ala
                260                 265                 270

Thr Lys Ala Leu Gly Ala Pro Pro Arg Glu Val Asn Thr Glu Thr Gly
            275                 280                 285

Glu Tyr Thr Gln Val Gly Ser Ala Gly Phe Ser Ala Ala Ser Leu Pro
        290                 295                 300

Leu Leu Ala Ala Ser Gly Glu Ser Glu Leu Leu Lys Ala Gln Ala Ser
305                 310                 315                 320

Arg Ala Gln Gln Glu Leu Ile Ser Asp Arg Asn Asp His Tyr Tyr Asp
                325                 330                 335

Asn Val Leu Ser Leu Phe Gly Leu Gly Trp His Gln Ala Arg Tyr Arg
                340                 345                 350

Phe Gly Lys Gln Gly Glu Leu Leu Pro Ala Trp Ser Glu Gln Cys Gln
            355                 360                 365

Glu

<210> SEQ ID NO 33
<211> LENGTH: 452
<212> TYPE: PRT
<213> ORGANISM: Plesiocystis pacifica

<400> SEQUENCE: 33

Met Thr Ala Glu Asp Leu Glu Ala Gly Thr Glu Leu Gly Gly Ser Asp
1               5                   10                  15

Asp Val Gly Ser Thr Asp Gly Gly Ser Thr Asp Gly Gly Ser Thr Gly
                20                  25                  30

Gly Ser Thr Gly Thr Thr Gly Gly Gly Asp Thr Thr Ser Gly Gly
            35                  40                  45

Thr Glu Gly Ser Gly Asp Gly Ala Cys Ser Gly Ser Trp Asp Thr Ala
        50                  55                  60

Gln Pro Phe Gly Ser His Pro Phe Gly Tyr Ala Pro Gly Thr Ile Leu
65                  70                  75                  80

Pro Asn His Leu Glu Gln Gly Ala Leu Asp Gln Val Ala Gln Phe
                85                  90                  95

Tyr Ala Gly Trp Lys Gln Arg Tyr Leu Ser Gly Gly Cys Gly Thr Gly
            100                 105                 110

Arg Tyr Tyr Val Asp Ile Gln Thr Ala Asp Arg Leu Thr Val Ser Glu
        115                 120                 125

Ala His Gly Tyr Gly Met Leu Ile Ser Ala Tyr Met Ala Gly His Asp
    130                 135                 140

Pro Asp Ala Lys Ala Ile Phe Asp Gly Met Tyr Asp Tyr Phe Arg Asp
```

His Pro Ser Gln Gly Asn Ser Gln Leu Met Ala Trp Ala Gln Asp Gly
                145                 150                 155                 160

Val Cys Glu Asn Thr Asp Gly Ala Thr Ser Ala Thr Asp Gly Asp Leu
            165                 170                 175

Asp Ile Ala Tyr Ala Leu Leu Leu Ala Asn Lys Gln Trp Gly Ser Gly
        180                 185                 190

Gly Ala Ile Asp Tyr Ala Gly Glu Ala Ala Ile Leu Gly Ala Ile
    195                 200                 205

Asp Gln Ala Glu Val Asp Asp Ser Gly Ser Tyr Val Arg Leu Gly Asp
210                 215                 220

Trp Thr His Pro Ser Asn Ala Thr Tyr Tyr Asp Ala Thr Arg Ser Ser
225                 230                 235                 240

Asp Phe Met Pro Ala His Phe Ala Thr Phe Ala Thr Phe Ile Gly Gly
            245                 250                 255

Arg Trp Asp Gly Val Arg Asn Ala Thr Tyr Asp Leu Ile Ala Thr Val
        260                 265                 270

Gln Ala Thr Tyr Ser Gln Gly Ser Gly Leu Leu Pro Asp Phe Ile Gln
    275                 280                 285

His Pro Thr Ser Gly Ser Pro Ser Val Ser Pro Asn Trp Leu Glu
290                 295                 300

Gly Pro Tyr Asp Gly Glu Tyr Tyr Phe Asn Ala Cys Arg Asn Pro Trp
305                 310                 315                 320

Arg Ile Gly Val Asp Tyr Leu Leu Asn Gly Asp Pro Arg Ala Gln Ala
            325                 330                 335

Ala Val Thr Gln Met Asn Gly Trp Val Gln Ser Ala Thr Gly Gly Ser
        340                 345                 350

Pro Gly Asn Ile Arg Ala Gly Tyr Trp Leu Asp Gly Asp Ala Leu Pro
    355                 360                 365

Thr Gly Asp Tyr Phe Glu Leu Ala Phe Ala Ala Pro Phe Gly Val Ala
370                 375                 380

Ala Met Ala Asp Pro Gly Ser Gln Ala Trp Leu Asn Asn Leu Trp Asp
385                 390                 395                 400

Thr Leu Ile Ala Ala Asp Gly His Thr Tyr Tyr Gly Asp Ser Ile Thr
            405                 410                 415

Met Leu Ser Leu Leu Ala Met Ser Gly Asn Trp Trp Ala Pro Glu Asp
        420                 425                 430

Pro Pro Cys Gln
    450

<210> SEQ ID NO 34
<211> LENGTH: 383
<212> TYPE: PRT
<213> ORGANISM: Limnobacter

<400> SEQUENCE: 34

Met Ala Leu Trp Arg Asn Cys Val Gln Arg Leu Gly Gln Val Ala Val
1               5                   10                  15

Leu Leu Ala Ala Thr Ala Ala Cys Ser Ala Thr Pro Ala Gln Ala Trp
            20                  25                  30

Pro Ala Trp Asp Gly Phe Lys Ser Ala Phe Val Ser Asp Asp Gly Arg
        35                  40                  45

Val Ile Asp Arg Ser Gln Glu Asp Leu Arg Thr Val Ser Glu Gly Gln
    50                  55                  60

```
Ser Tyr Ala Leu Phe Phe Ala Leu Val Ala Gln Asp Lys Lys Ala Phe
 65                  70                  75                  80

Asp Ala Val Leu Gln Trp Thr Glu Asn Asn Leu Ser Ala Gly Asp Leu
                 85                  90                  95

Gly Lys Gln Leu Pro Ala Trp Ile Trp Gly Lys Lys Gly Glu Ser Trp
            100                 105                 110

Gly Val Ile Asp Ala Asn Ser Ala Ser Asp Ala Asp Leu Trp Ile Ala
        115                 120                 125

Tyr Ser Leu Leu Glu Ala Ser Arg Val Trp Cys Asn Pro Gly Tyr Ala
    130                 135                 140

Asp Lys Ala Arg Ala Leu Gly Asp Leu Ile Leu Asn Gln Glu Ser Met
145                 150                 155                 160

Glu Val Ser Gly Leu Gly Leu Ser Ile Leu Pro Gly His Thr Gly Phe
                165                 170                 175

Val Leu Asp Asn Gly Ala Val Lys Leu Asn Pro Ser Tyr Leu Pro Pro
            180                 185                 190

Phe Met Met Ala Arg Phe Ala Asn Ala Trp Ala Asp Asp Thr Arg Trp
        195                 200                 205

Ala Gln Val Tyr Leu Ala Ser Gln Lys Leu Leu Leu Asp Thr Gly Arg
    210                 215                 220

Thr Gly Gln Tyr Pro Asp Trp Val Leu Tyr Asn Asn Gly Glu Met Ser
225                 230                 235                 240

Leu Pro Glu Asp Glu Gln Arg Gly Asp Tyr Asp Ala Ile Arg Thr Tyr
                245                 250                 255

Leu Trp Ile Ala Met Ser Ser Glu Ser Asp Pro Thr Thr Ala Pro Leu
            260                 265                 270

Leu Arg Gln Leu Ser Pro Leu Thr Ala Leu Leu Lys Arg Gln Asn
        275                 280                 285

Met Pro Glu Trp Phe Glu Pro Gln Ser Gly Lys Phe Ser Ala Thr Arg
    290                 295                 300

Gly Pro Ala Gly Phe Gln Ala Ala Met Ala Pro Leu Leu Gln Thr Met
305                 310                 315                 320

Gly Met Pro Glu Leu Ala Lys Lys Phe His Ala Gln Ser Leu Lys Thr
                325                 330                 335

Gln Ser Lys Glu Ser Trp Leu Lys Tyr Gly Tyr Asn Gly Ala Leu
            340                 345                 350

Ser Leu Phe Ala Gln Gly Tyr Ile Asp Lys Phe Tyr Arg Phe Asn Ser
        355                 360                 365

Leu Gly Glu Leu Leu Pro Arg Gly Lys Glu Val Lys Ser Cys Gly
    370                 375                 380

<210> SEQ ID NO 35
<211> LENGTH: 380
<212> TYPE: PRT
<213> ORGANISM: Limnobacter

<400> SEQUENCE: 35

Met Ile Leu Gly Phe Leu Asn Val Leu Phe Val Ala Gly Phe Val Leu
 1               5                  10                  15

Ile Ala Asn Pro Gln Gln Ala Leu Ala Ser Ser Gln Cys Thr Lys Pro
                 20                  25                  30

Trp Pro Glu Leu Lys Leu Phe Glu Ser Lys His Val Gln Ala Asp Gly
            35                  40                  45

Arg Val Val Asp Phe Ser Thr Pro Glu Gln Ile Thr Ser Glu Gly
        50                  55                  60
```

```
Gln Ser Tyr Ala Met Phe Phe Ala Leu Val Asp Asn Asp Gln Val Arg
 65                  70                  75                  80

Phe Lys Gln Leu Leu Asp Trp Thr Glu Arg Asn Leu Ala Pro Gly Gly
                 85                  90                  95

Val Ala Gln Ser Leu Pro Ala Trp Lys Trp Gly Arg Val Arg Ala Asn
            100                 105                 110

Gln Phe Gly Met Leu Asp Ala Asn Ser Ala Ser Asp Ser Asp Leu Trp
        115                 120                 125

Ile Ala Tyr Asn Leu Leu Glu Ala Ala Arg Leu Trp Asn Met Pro Glu
130                 135                 140

Tyr Lys Glu Lys Gly Leu Ala Leu Met Gln Leu Ile Arg Asp Asn Glu
145                 150                 155                 160

Ala Gly Asp Val Pro Gly Tyr Gly Arg Met Val Leu Pro Gly Ala Val
                165                 170                 175

Gly Phe Asn Pro Ala Pro Gly Val Tyr Arg Met Asn Pro Ser Tyr Leu
            180                 185                 190

Pro Leu Phe Leu Met Arg Lys Leu Ser Glu Ala His Ser Asp Ser Phe
        195                 200                 205

Trp Lys Ser Gln Pro Glu Leu Ser Ala Gln Leu Ile Val Asn Ser Ala
210                 215                 220

Pro Lys Gly Tyr Val Pro Asp Trp Val Thr Val Lys Ala Asp Gly Ile
225                 230                 235                 240

Ser Ala Asp Ile Glu Lys Gly Asn Val Gly Ser Tyr Asp Ala Ile Arg
                245                 250                 255

Thr Tyr Leu Trp Ala Gly Leu Thr Ala Arg Asp Glu Pro Glu Arg Lys
            260                 265                 270

Ala Leu Met Gln Ala Val Tyr Ala Tyr Met Gln Leu Ser Asn Arg Leu
        275                 280                 285

Gly Glu Pro Leu Glu Arg Val Asp Thr Ser Ser Gly Ile Trp Tyr Gly
290                 295                 300

Thr Ala Ala Pro Gly Phe Tyr Tyr Ala Leu Glu Pro Leu Ala Gln Glu
305                 310                 315                 320

Leu Arg Leu Ser Arg Leu Leu Leu Ala Ile Lys Ala Lys His Gln Glu
                325                 330                 335

Val Lys Asn Gln Asn Tyr Ala Gln Leu Ser Tyr Tyr Asp Trp Val Leu
            340                 345                 350

Phe Leu Tyr Ala Lys Gly Trp Val Glu Gly Arg Tyr Arg Phe Asp Lys
        355                 360                 365

Arg Gly Ala Leu Gln Val Ser Trp Asn Lys Lys Cys
370                 375                 380

<210> SEQ ID NO 36
<211> LENGTH: 369
<212> TYPE: PRT
<213> ORGANISM: Klebsiella pneumoniae

<400> SEQUENCE: 36

Met Met Lys Val Leu Cys Gly Ala Val Leu Ser Ala Leu Leu Leu Ala
 1                5                  10                  15

Ala Gly Gln Val Gly Ala Ala Cys Gln Trp Pro Ala Trp Glu Gln Phe
                 20                  25                  30

Lys Gln Ala Tyr Val Ser Pro Glu Gly Arg Val Ile Asp Pro Ser Asp
             35                  40                  45

Ala Arg Lys Ile Ser Thr Ser Glu Gly Gln Ser Tyr Gly Leu Phe Phe
```

```
                50                  55                  60
Ala Leu Ala Ala Asn Asp Arg Ala Gly Phe Asp Lys Leu Leu Thr Trp
 65                  70                  75                  80

Thr Gln Asn Asn Leu Ala Glu Gly Asp Leu Lys Gln His Leu Pro Gly
                 85                  90                  95

Trp Leu Trp Gly Lys Lys Asp Asp Glu Gln Trp Thr Leu Leu Asp Ser
                100                 105                 110

Asn Ser Ala Ser Asp Ser Asp Leu Trp Ile Ala Trp Ala Leu Leu Glu
                115                 120                 125

Ala Gly Arg Leu Trp Gln Gln Pro Gln Tyr Thr Glu Thr Gly Lys Ala
                130                 135                 140

Leu Leu Ala Arg Ile Val Ala Glu Glu Thr Val Ala Val Pro Gly Leu
145                 150                 155                 160

Gly Thr Met Leu Leu Pro Gly Lys Val Gly Phe Ala Asp Asp Arg Gly
                165                 170                 175

Trp Arg Phe Asn Pro Ser Tyr Leu Pro Pro Gln Leu Ala Thr Tyr Phe
                180                 185                 190

Val Arg Phe Gly Ala Pro Trp Pro Ala Leu Arg Asp Ser Asn Leu Arg
                195                 200                 205

Leu Leu Leu Glu Thr Ala Pro Lys Gly Phe Thr Pro Asp Trp Val Arg
                210                 215                 220

Tyr Glu Lys Gly Lys Gly Trp Gln Leu Lys Thr Glu Lys Pro Pro Ile
225                 230                 235                 240

Gly Ser Tyr Asp Ala Ile Arg Val Tyr Leu Trp Val Gly Met Leu His
                245                 250                 255

Asp Gly Asp Lys Gln Lys Ala Arg Leu Leu Gln Arg Phe Ala Pro Met
                260                 265                 270

Ala Ala Gln Thr Thr Glu Gln Gly Val Pro Pro Glu Lys Val Asn Ile
                275                 280                 285

Ala Thr Gly Lys Thr Ser Gly Gln Gly Pro Val Gly Phe Ser Ala Ala
                290                 295                 300

Met Leu Pro Phe Leu Gln Asp Asp Glu Ala Arg Ser Val Gln Arg Gln
305                 310                 315                 320

Arg Val Ala Asp Asn Tyr Pro Gly Ala Asp Ala Tyr Tyr Ser Ala Val
                325                 330                 335

Leu Thr Leu Phe Gly Gln Gly Trp Asp Gln His Arg Phe Arg Phe Thr
                340                 345                 350

Ala Ser Gly Glu Leu Gln Pro Asp Trp Asn Gln Glu Cys Ala Ser Ser
                355                 360                 365

His

<210> SEQ ID NO 37
<211> LENGTH: 333
<212> TYPE: PRT
<213> ORGANISM: Klebsiella pneumoniae

<400> SEQUENCE: 37

Met Pro Leu Arg Ala Leu Val Ala Met Ile Val Thr Thr Val Val Met
 1               5                  10                  15

Leu Val Pro Arg Ala Trp Ala Asp Thr Ala Trp Glu Arg Tyr Lys Ala
                20                  25                  30

Arg Phe Met Met Pro Asp Gly Arg Ile Ile Asp Thr Ala Asn Gly Asn
                35                  40                  45

Val Ser His Thr Glu Gly Gln Gly Phe Ala Met Leu Leu Ala Val Ala
```

```
                    50                  55                  60
Asn Asn Asp Arg Pro Ala Phe Asp Lys Leu Trp Gln Trp Thr Asp Asn
 65                  70                  75                  80

Thr Leu Arg Asn Lys Ser Asn Gly Leu Phe Tyr Trp Arg Tyr Asn Pro
                     85                  90                  95

Val Ala Pro Asp Pro Ile Ala Asp Lys Asn Asn Ala Ser Asp Gly Asp
                100                 105                 110

Thr Leu Ile Ala Trp Ala Leu Leu Arg Ala Gln Lys Gln Trp Gln Asp
                115                 120                 125

Lys Arg Tyr Ala Ile Ala Ser Asp Ala Ile Thr Ala Ala Leu Leu Lys
130                 135                 140

Ser Thr Val Val Ser Phe Ala Gly Arg Gln Val Met Leu Pro Gly Val
145                 150                 155                 160

Lys Gly Phe Asn Leu Asn Asp His Leu Asn Leu Asn Pro Ser Tyr Phe
                165                 170                 175

Ile Phe Pro Ala Trp Arg Ala Phe Ala Glu Arg Thr His Leu Thr Ala
                180                 185                 190

Trp Arg Thr Leu Gln Ser Asp Gly Gln Ala Leu Leu Gly Gln Met Gly
                195                 200                 205

Trp Gly Lys Ser His Leu Pro Ser Asp Trp Val Ala Leu Arg Ala Asp
210                 215                 220

Gly Lys Met Leu Pro Ala Lys Glu Trp Pro Pro Arg Met Ser Phe Asp
225                 230                 235                 240

Ala Ile Arg Ile Pro Leu Tyr Leu Ser Trp Ala Asp Pro His Ser Ala
                245                 250                 255

Leu Leu Ala Pro Trp Lys Ala Trp Met Gln Ser Tyr Pro Arg Leu Gln
                260                 265                 270

Thr Pro Ala Trp Ile Asn Val Ser Thr Asn Glu Val Ala Pro Trp Tyr
                275                 280                 285

Met Ala Gly Gly Leu Leu Ala Val Arg Asp Leu Thr Leu Gly Glu Pro
                290                 295                 300

Gln Glu Ala Pro Gln Ile Asp Asp Lys Asp Asp Tyr Tyr Ser Ala Ser
305                 310                 315                 320

Leu Lys Leu Leu Val Trp Leu Ala Lys Gln Asp Gln Arg
                325                 330

<210> SEQ ID NO 38
<211> LENGTH: 344
<212> TYPE: PRT
<213> ORGANISM: Sinorhizobium medicae

<400> SEQUENCE: 38

Met Lys Pro Leu Val Val Leu Met Leu Leu Leu Leu Ala Tyr Pro Thr
  1                   5                  10                  15

His Ala Gln Glu Pro Ala Thr Val Glu Ala Thr Ala Trp Gln Lys Tyr
                 20                  25                  30

Lys Thr Arg Phe Leu Asp Pro Gly Gly Arg Ile Ile Asp Asp Ala Asn
             35                  40                  45

Gly Asp Ile Ser His Ser Glu Gly Gln Gly Tyr Gly Leu Leu Leu Ala
         50                  55                  60

Phe Leu Ala Gly Ser Arg Ala Asp Phe Glu Leu Ile Trp Ser Phe Thr
 65                  70                  75                  80

Arg Arg Glu Leu Leu Leu Arg Asp Asp Gly Leu Ala Ala Trp Lys Trp
                 85                  90                  95
```

-continued

```
Ser Pro Gly Glu Ala Pro His Val Ser Asp Thr Asn Asn Ala Thr Asp
            100                 105                 110

Gly Asp Ile Leu Ile Ala Tyr Ala Leu Ala Arg Ala Gly Val Ser Trp
        115                 120                 125

Asp Arg Lys Asp Tyr Thr Arg Ala Ala Thr Ala Leu Ala Glu Ala Ile
    130                 135                 140

Leu Glu Lys Thr Val Val Glu His Gly Gly Leu Thr Leu Leu Leu Pro
145                 150                 155                 160

Gly Ala Gln Gly Phe Ser Ala Ala Asp Arg Ala Asp Gly Pro Val Ile
                165                 170                 175

Asn Pro Ser Tyr Trp Val Phe Glu Ala Phe Pro Val Leu Glu Gln Leu
            180                 185                 190

Val Pro Ser Pro Ala Trp Lys Ala Leu Ala Ala Asp Gly Glu Ala Ile
        195                 200                 205

Leu Lys Arg Leu Glu Phe Gly Pro Lys Lys Leu Pro Ala Asp Trp Ile
    210                 215                 220

Ser Ala Arg Thr Val Phe Lys Pro Ala Glu Gly Phe Pro Ser Glu Tyr
225                 230                 235                 240

Gly Tyr Asn Ala Leu Arg Ile Pro Leu Tyr Leu Val Arg Ser Gly Arg
                245                 250                 255

Thr Asp Ser Glu Leu Leu Ser Arg Ile Tyr Arg Gly Met Ser Asp Ala
            260                 265                 270

Lys Gly Ala Val Leu Leu Ser Asp Val Glu Ser Gly Ala Val Glu Glu
        275                 280                 285

Thr Leu Thr Asp Pro Gly Tyr Arg Ile Ile Asn His Ile Leu Ala Cys
    290                 295                 300

Val Leu Gln Gly Thr Lys Leu Pro Asp Asp Met Lys Thr Phe Glu Pro
305                 310                 315                 320

Thr Gln Tyr Tyr Pro Ser Thr Met His Leu Leu Gly Leu Ser Phe Val
                325                 330                 335

Glu Glu Met Arg Pro Glu Cys Leu
            340

<210> SEQ ID NO 39
<211> LENGTH: 417
<212> TYPE: PRT
<213> ORGANISM: Marinomonas

<400> SEQUENCE: 39

Met Asn Tyr Phe Gln Lys Ala Leu Ile Lys Leu Leu Ala Tyr Ser Leu
1               5                   10                  15

Trp Ile Phe Ser Ser Ser Ile Gln Ala Thr Pro Ala Ser Val
            20                  25                  30

Ile Lys Pro Ser Gly Tyr Ser Gln Pro Glu Leu Asp Thr Ala Leu Leu
        35                  40                  45

Asn Phe Tyr Gln Asp Trp Lys Glu Thr Tyr Leu Arg Gln Gln Cys Gly
    50                  55                  60

Val Gly Arg Tyr Leu Val Asp Met Ala Ala Asp Gly Asn Thr Val Glu
65                  70                  75                  80

Gly Gly Thr Ala Ala Ser Thr Leu Thr Thr Ser Glu Ala His Gly Tyr
                85                  90                  95

Gly Met Leu Ile Thr Val Met Met Ala Asp Phe Asp Pro Gln Ala Arg
            100                 105                 110

Arg Ile Phe Asp Gly Met Val Asp Phe His Asp His Pro Ala Gln
        115                 120                 125
```

-continued

Ser Ala Pro Gly Leu Met Ala Trp Asn Gln Leu Arg Asn Cys Lys Asn
    130                 135                 140

Ala Gly Glu Asn Val Gly Gly Ser Asn Ser Ala Ser Asp Gly Asp Met
145                 150                 155                 160

Asp Ile Ala Tyr Ala Phe Leu Leu Ala Asp Lys Lys Trp Gly Ser Ser
                165                 170                 175

Gly Lys Ile Asn Tyr Lys His Glu Ala Val Asn Ala Ile Thr Ala Ile
                180                 185                 190

Lys Gln His Glu Val Asp Pro Lys Asn His Phe Ile Arg Leu Gly Asp
            195                 200                 205

Trp Val Asp Asp Ile Asp Asp Gly Gln Tyr Ala Asn Thr Thr Arg Ser
    210                 215                 220

Ser Asp Phe Met Val Ser His Leu Lys Ala Tyr Ala Asp Ala Thr Gly
225                 230                 235                 240

Asp Lys Ser Trp Asn Lys Val Arg Asp Thr Thr Tyr Ala Ile Met Ala
                245                 250                 255

Asn Ile Arg Gln Thr Asp Ser Pro Lys Thr Ala Leu Met Pro Asp Phe
                260                 265                 270

Ile Val Gly Leu Pro Asn His Pro Gln Pro Ala Lys Ala Met Phe Leu
            275                 280                 285

Glu Gly Glu Asp Asp Gly Ala Tyr Ser Trp Asn Ala Ala Arg Tyr Pro
    290                 295                 300

Trp Arg Val Ala Leu Asp Tyr Arg Leu Tyr Gly Asp Lys Arg Ala Leu
305                 310                 315                 320

Ser Ala Leu Ala Pro Ile Asn Gln Trp Ile Ile Asn Ile Thr His Gly
                325                 330                 335

Asp Pro Lys Lys Ile Ala Asp Thr Tyr Ala Leu Asp Gly His Tyr Ser
                340                 345                 350

Lys Asp Ser Gly Phe Asp Ser Met Ala Phe Ala Ser Met Phe Ala Val
            355                 360                 365

Ser Ala Thr Ile Asp Pro Ser Asn Gln Ala Trp Leu Asn Ala Leu Trp
    370                 375                 380

Glu Asn Ile Lys Asp Lys Pro Val Glu Ser Glu Asp Tyr Phe Gly Asn
385                 390                 395                 400

Thr Leu Lys Met Leu Ala Met Ile Thr Ile Thr Gly His Trp Asp Lys
                405                 410                 415

Pro

<210> SEQ ID NO 40
<211> LENGTH: 379
<212> TYPE: PRT
<213> ORGANISM: Bifidobacterium adolescentis

<400> SEQUENCE: 40

Met Thr Asn Ala Thr Asp Thr Asn Lys Thr Leu Gly Glu Ser Met Phe
1               5                   10                  15

Ala Gln Cys Gly Tyr Ala Gln Asp Ala Ile Asp Lys Arg Val Ser Gln
            20                  25                  30

Val Trp Tyr Glu Ile Phe Glu Gly Pro Asn Lys Phe Tyr Trp Glu Asn
        35                  40                  45

Asp Glu Gly Leu Ala Tyr Val Met Asp Thr Gly Asn Asn Asp Val Arg
    50                  55                  60

Thr Glu Gly Met Ser Tyr Ala Met Met Ile Ala Leu Gln Tyr Asp Arg
65                  70                  75                  80

Lys Asp Val Phe Asp Lys Leu Trp Gly Trp Val Met Arg His Met Tyr
                85                  90                  95

Met Lys Asp Gly His His Ala His Tyr Phe Ala Trp Ser Val Ala Pro
            100                 105                 110

Asp Gly Thr Pro Asn Ser Asn Gly Pro Ala Pro Asp Gly Glu Glu Tyr
        115                 120                 125

Phe Ala Met Asp Leu Phe Leu Ala Ser Arg Arg Trp Gly Asp Gly Glu
    130                 135                 140

Asp Ile Tyr Glu Tyr Ser Ala Trp Gly Arg Glu Ile Leu Arg Tyr Cys
145                 150                 155                 160

Val His Lys Gly Glu Arg Tyr Asp Gly Glu Pro Met Trp Asn Pro Asp
                165                 170                 175

Asn Lys Leu Ile Lys Phe Ile Pro Glu Thr Glu Trp Ser Asp Pro Ser
            180                 185                 190

Tyr His Leu Pro His Phe Tyr Glu Val Phe Ala Glu Glu Ala Asp Glu
        195                 200                 205

Glu Asp Arg Pro Phe Trp His Glu Ala Ala Ala Ser Arg Arg Tyr
    210                 215                 220

Leu Gln Ala Ala Cys Asp Glu Arg Thr Gly Met Asn Ala Glu Tyr Ala
225                 230                 235                 240

Asp Tyr Asp Gly Lys Pro His Val Asp Glu Ser Asn His Trp His Phe
                245                 250                 255

Tyr Ser Asp Ala Tyr Arg Thr Ala Ala Asn Ile Gly Leu Asp Ala Ala
            260                 265                 270

Trp Asn Gly Pro Gln Glu Val Leu Cys Asp Arg Val Ala Ala Leu Gln
        275                 280                 285

Arg Phe Phe Leu Thr His Asp Arg Thr Ser Val Tyr Ala Ile Asp Gly
    290                 295                 300

Thr Ala Val Asp Glu Val Val Leu His Pro Val Gly Phe Leu Ala Ala
305                 310                 315                 320

Thr Ala Gln Gly Ser Leu Ala Ala Val His Ser Ala Gln Pro Asp Ala
                325                 330                 335

Glu His Asn Ala Arg Glu Trp Val Arg Met Leu Trp Asn Thr Pro Met
            340                 345                 350

Arg Thr Gly Thr Arg Arg Tyr Tyr Asp Asn Phe Leu Tyr Ala Phe Ala
        355                 360                 365

Met Leu Ala Leu Ser Gly Lys Tyr Arg Tyr Glu
    370                 375

<210> SEQ ID NO 41
<211> LENGTH: 371
<212> TYPE: PRT
<213> ORGANISM: Yersinia pseudotuberculosis

<400> SEQUENCE: 41

Met Val Val Met Phe Lys His Leu Ala Ser Met Phe Leu Leu Leu Ala
1               5                   10                  15

Ser Phe Ser Leu Ala Ala Ala Ser Asn Trp Pro Ala Trp Gln Gln Phe
            20                  25                  30

Lys Gln Asp Tyr Ile Ser Glu Gly Gly Arg Ile Ile Asp Pro Gly Ser
        35                  40                  45

Pro Ser Lys Ile Thr Thr Ser Glu Gly Gln Ser Tyr Gly Leu Phe Phe
    50                  55                  60

Ala Leu Val Ala Asp Asp Gln Pro Met Phe Glu Arg Leu Leu Ala Trp

```
                 65                   70                   75                   80
        Thr Glu Asn Asn Leu Ala Ala Gly Asp Leu Thr Ser Arg Leu Pro Ala
                             85                   90                   95

Trp Leu Trp Gly Gln Asn Ser Gln Asn Asn Trp Asp Ile Leu Asp Pro
                            100                  105                  110

Asn Ser Ala Ser Asp Ala Asp Ile Leu Ile Ala Tyr Asn Leu Leu Glu
                            115                  120                  125

Ala Gly Arg Leu Trp Gly Asn Arg Arg Tyr Leu Ile Met Gly Thr Leu
                    130                  135                  140

Leu Leu Gln Arg Ile Ala Gln Glu Val Met Asp Ile Pro Gly Leu
        145                 150                  155                  160

Gly Gln Met Leu Leu Pro Gly Lys Ile Gly Phe Asn Asp Glu Asp Thr
                            165                  170                  175

Trp Arg Leu Asn Pro Ser Tyr Leu Pro Pro Gln Leu Leu Ala Arg Phe
                            180                  185                  190

Ser Ser Ile Asp Gly Pro Trp Glu Ala Met Val Glu Val Asn Gln Arg
                    195                  200                  205

Met Trp Leu Glu Thr Ala Pro Asn Gly Phe Ser Pro Asp Trp Val Val
        210                 215                  220

Trp Gln Lys Gly Lys Gly Trp Gln Pro Asp Thr Ile Lys Pro Asp Val
        225                 230                  235                  240

Gly Ser Asn Asp Ala Ile Leu Val Tyr Leu Trp Ala Gly Met Leu Ala
                    245                  250                  255

Met Asp Ser Pro Gln Lys Ala Glu Leu Ile Ala Arg Phe Gln Pro Met
                    260                  265                  270

Ala Val Ile Thr Gln Gln Gly Leu Pro Pro Phe Thr Thr Asn Ser
                    275                  280                  285

Asp Asn Gly Lys Thr Asn Gly Asp Gly Ser Val Gly Phe Ser Ala Ala
                    290                  295                  300

Leu Leu Pro Phe Leu Ala Ser Ser Pro Glu Pro Phe Asn Gln Gln Thr
        305                 310                  315                  320

Leu Asn Leu Gln Gln Arg Arg Val Gln Asn Ser Pro Pro Gly Ala Asp
                            325                  330                  335

Asp Tyr Tyr Ser Ala Ile Leu Thr Leu Phe Gly Gln Gly Trp Leu Gln
                    340                  345                  350

His Arg Tyr His Phe Thr His Gln Gly Glu Leu Gln Pro Ser Trp His
                    355                  360                  365

Arg Gln Arg
            370

<210> SEQ ID NO 42
<211> LENGTH: 345
<212> TYPE: PRT
<213> ORGANISM: Asaia bogorensis

<400> SEQUENCE: 42

Met Val Arg Arg Gln Phe Cys Arg Asp Ser Ile Leu Ala Ala Ala Ser
1               5                   10                  15

Phe Gly Ile Ala Gly Glu Ala Phe Ala Gln Thr Gln Gly Leu Gly Asp
                20                  25                  30

Pro Asp Trp Glu Leu Tyr Lys Lys Lys Tyr Leu Cys Pro Glu Gly Arg
            35                  40                  45

Ile Val Asp Thr Gly Asn Gln Asp Val Ser His Ser Glu Gly Gln Gly
        50                  55                  60
```

```
Tyr Gly Leu Leu Phe Ala Ser Thr Phe Asn Asp Gln Ala Ala Phe Asp
 65                  70                  75                  80

Gln Ile Trp Ala Trp Thr Arg Asp Asn Leu Lys His Lys Asp Gly Ser
                 85                  90                  95

Leu His Ser Trp Arg Trp Thr Pro Thr Ala Pro His Val Ser Asp Thr
            100                 105                 110

Asn Asn Ala Thr Asp Gly Asp Leu Met Ile Ala Trp Ala Leu Arg Arg
        115                 120                 125

Ala Ala Ile Leu Trp Arg Ser Glu Ala Tyr Leu Asp Gln Ala Lys Ala
    130                 135                 140

Ile Leu His Asp Leu Ala Glu Lys Cys Val Arg Lys Val Gly Ser Arg
145                 150                 155                 160

Leu Val Leu Leu Pro Gly Met Lys Gly Phe Asp Arg Pro Lys Ser Val
                165                 170                 175

Ile Ile Asn Leu Ser Tyr Tyr Leu Leu Pro Ala Leu Asp Arg Ala Val
            180                 185                 190

Leu Leu Asp Pro Ser Gly Pro Trp Lys Ser Val Ser Glu His Gly Gln
        195                 200                 205

Gln Leu Leu Gln Ser Cys Arg Phe Gly Leu Trp Gly Leu Pro Pro Asp
    210                 215                 220

Trp Leu Ala Ile Asp Arg Lys Ser Glu Arg Pro Val Pro Ala Pro Gly
225                 230                 235                 240

Tyr Pro Pro Arg Phe Ser Tyr Asp Ala Ile Arg Ile Pro Leu Tyr Phe
                245                 250                 255

Arg Trp Gly Lys Arg Leu Pro Ala Thr Leu Thr Gln Ser Leu Tyr Ala
            260                 265                 270

Val Ser Gln Asn Tyr Ser Met Thr Ala Leu Pro Ala Trp Val Asp Leu
        275                 280                 285

Met Thr Gly Glu Arg Ser Pro Tyr Asn Ala Pro Pro Gly Phe Arg Ala
    290                 295                 300

Val Tyr Leu Phe Ala Leu Asn Gly Ser Asp Ala Leu Ser Asp Leu Pro
305                 310                 315                 320

Asn Ile Lys Glu Ser Ser Asp Tyr Tyr Ser Ser Ser Leu Thr Leu Leu
                325                 330                 335

Ala Arg Ile Ala Pro Met Glu Met Val
            340                 345

<210> SEQ ID NO 43
<211> LENGTH: 365
<212> TYPE: PRT
<213> ORGANISM: Escherichia coli

<400> SEQUENCE: 43

Met Arg Ser Gly Ile Val Thr Met Leu Leu Leu Ala Ala Phe Ser Val
1               5                   10                  15

Gln Ala Ala Cys Thr Trp Pro Ala Trp Glu Gln Phe Lys Lys Asp Tyr
                20                  25                  30

Ile Ser Gln Glu Gly Arg Val Ile Asp Pro Ser Asp Ala Arg Lys Ile
            35                  40                  45

Thr Thr Ser Glu Gly Gln Ser Tyr Gly Met Phe Phe Ala Leu Ala Ala
        50                  55                  60

Asn Asp Arg Val Ala Phe Asp Asn Ile Leu Asp Trp Thr Gln Asn Asn
65                  70                  75                  80

Leu Ala Gln Gly Ser Leu Lys Glu Arg Leu Pro Ala Trp Leu Trp Gly
                85                  90                  95
```

```
Lys Lys Glu Asn Ser Lys Trp Glu Val Leu Asp Ser Asn Ser Ala Ser
                100                 105                 110

Asp Gly Asp Val Trp Met Ala Trp Ser Leu Leu Glu Ala Gly Arg Leu
            115                 120                 125

Trp Lys Glu Gln Arg Tyr Thr Asp Ile Gly Ser Ala Leu Leu Lys Arg
    130                 135                 140

Ile Ala Arg Glu Glu Val Val Thr Val Pro Gly Leu Gly Ser Met Leu
145                 150                 155                 160

Leu Pro Gly Lys Val Gly Phe Ala Glu Asp Asn Ser Trp Arg Phe Asn
                165                 170                 175

Pro Ser Tyr Leu Pro Pro Thr Leu Ala Gln Tyr Phe Thr Arg Phe Gly
            180                 185                 190

Ala Pro Trp Thr Thr Leu Arg Glu Thr Asn Gln Arg Leu Leu Leu Glu
        195                 200                 205

Thr Ala Pro Lys Gly Phe Ser Pro Asp Trp Val Arg Tyr Glu Lys Asp
    210                 215                 220

Lys Gly Trp Gln Leu Lys Ala Glu Lys Thr Leu Ile Ser Ser Tyr Asp
225                 230                 235                 240

Ala Ile Arg Val Tyr Met Trp Val Gly Met Met Pro Asp Ser Asp Pro
                245                 250                 255

Gln Lys Ala Arg Met Leu Asn Arg Phe Lys Pro Met Ala Thr Phe Thr
            260                 265                 270

Glu Lys Asn Gly Tyr Pro Pro Glu Lys Val Asp Val Ala Thr Gly Lys
        275                 280                 285

Ala Gln Gly Lys Gly Pro Val Gly Phe Ser Ala Ala Met Leu Pro Phe
    290                 295                 300

Leu Gln Asn Arg Asp Ala Gln Ala Val Gln Arg Gln Arg Val Ala Asp
305                 310                 315                 320

Asn Phe Pro Gly Ser Asp Ala Tyr Tyr Asn Tyr Val Leu Thr Leu Phe
                325                 330                 335

Gly Gln Gly Trp Asp Gln His Arg Phe Arg Phe Ser Thr Lys Gly Glu
            340                 345                 350

Leu Leu Pro Asp Trp Gly Gln Glu Cys Ala Asn Ser His
        355                 360                 365

<210> SEQ ID NO 44
<211> LENGTH: 369
<212> TYPE: PRT
<213> ORGANISM: Citrobacter koseri

<400> SEQUENCE: 44

Met Met Asn Ala Leu Arg Gly Trp Met Leu Thr Ala Leu Met Leu Ala
1               5                   10                  15

Thr Val Ser Val Gln Ala Ala Cys Thr Trp Pro Ala Trp Ile Gln Phe
                20                  25                  30

Lys Lys Asp Tyr Ile Ser Gln Glu Gly Arg Val Ile Asp Pro Ser Asp
            35                  40                  45

Ala Arg Lys Ile Thr Thr Ser Glu Gly Gln Ser Tyr Ala Leu Phe Phe
        50                  55                  60

Ala Leu Ala Ala Asn Asp Arg Pro Ala Phe Leu Ile Leu Asp Trp
65                  70                  75                  80

Thr Gln Asn Asn Leu Ala Gln Gly Ser Leu Gln Ser His Leu Pro Ala
                85                  90                  95

Trp Leu Trp Gly Gln Lys Asp Pro Ser Thr Trp Ala Val Leu Asp Ala
```

```
            100                 105                 110
Asn Ser Ala Ser Asp Gly Asp Ile Trp Met Ala Trp Ser Leu Leu Glu
        115                 120                 125

Ala Gly Arg Leu Trp Lys Thr Ser Arg Tyr Thr Asp Thr Gly Ala Ala
    130                 135                 140

Leu Leu Lys Arg Ile Ala Arg Glu Glu Val Val Thr Val Pro Gly Leu
145                 150                 155                 160

Gly Ser Met Leu Leu Pro Gly Asn Val Gly Phe Ala Glu Lys Thr Arg
                165                 170                 175

Trp Arg Phe Asn Pro Ser Tyr Leu Pro Pro Gln Leu Ala Gln Tyr Phe
            180                 185                 190

Thr Arg Phe Gly Ala Pro Trp Thr Thr Leu Arg Glu Thr Asn Met Arg
        195                 200                 205

Leu Leu Met Glu Thr Ala Pro Lys Gly Phe Ser Pro Asp Trp Val Arg
210                 215                 220

Tyr Glu Lys Asp Lys Gly Trp Gln Leu Lys Pro Glu Lys Thr Leu Val
225                 230                 235                 240

Ser Ser Tyr Asp Ala Ile Arg Val Tyr Leu Trp Ala Gly Met Met His
                245                 250                 255

Asp Gly Asp Pro Gln Lys Ala Arg Leu Leu Thr Arg Leu Lys Pro Met
            260                 265                 270

Ala Thr Leu Thr Thr Lys Asn Gly Val Pro Pro Glu Lys Val Asp Val
        275                 280                 285

Ala Ser Gly Lys Ala Gln Gly Asn Gly Pro Val Gly Phe Ser Ala Ser
        290                 295                 300

Leu Leu Pro Phe Leu Gln Asn Arg Asp Ala Gln Ala Val Gln Arg Gln
305                 310                 315                 320

Arg Val Ala Asp Asn Phe Pro Gly Ser Asp Ala Tyr Tyr Ser Tyr Val
                325                 330                 335

Leu Thr Leu Phe Gly Gln Gly Trp Asp Gln His Arg Phe Arg Phe Thr
            340                 345                 350

Ala Lys Gly Glu Leu Leu Pro Asp Trp Gly Gln Glu Cys Ala Ser Ser
        355                 360                 365

Asn

<210> SEQ ID NO 45
<211> LENGTH: 370
<212> TYPE: PRT
<213> ORGANISM: Serratia proteamaculans

<400> SEQUENCE: 45

Met Pro Ala Ala Leu Lys Arg Leu Thr Phe Gly Met Leu Leu Leu Cys
1               5                   10                  15

Ser Phe Ser Ala Val Ala Thr Cys Glu Trp Pro Ala Trp Gln Gln Tyr
                20                  25                  30

Lys Gln Phe Tyr Ile Ser Glu Gln Gly Arg Val Ile Asp Pro Ser Ser
            35                  40                  45

Pro Asn Arg Ile Thr Thr Ser Glu Gly Gln Ser Tyr Gly Leu Phe Phe
        50                  55                  60

Ala Leu Val Ala Asn Asp Arg Pro Ala Phe Asp Gln Leu Leu Thr Trp
65                  70                  75                  80

Thr Glu Asn Asn Leu Ala Ala Gly Asp Leu Ser Ala His Leu Pro Ala
                85                  90                  95

Trp Leu Trp Gly Glu Asp Asp Lys Lys Gln Trp Thr Val Leu Asp Ser
```

```
            100                 105                 110
Asn Ser Ala Ser Asp Ser Asp Leu Trp Ile Ala Tyr Asn Leu Leu Glu
            115                 120                 125

Ala Gly Arg Leu Trp Lys Ser Arg Arg Tyr Gln Thr Leu Gly Thr Leu
130                 135                 140

Leu Leu Gln Arg Ile Ala Arg Glu Glu Val Ala Asp Ile Pro Gly Leu
145                 150                 155                 160

Gly Leu Met Leu Leu Pro Gly Lys Val Gly Phe Val Ala Glu Asp Arg
                165                 170                 175

Trp Arg Leu Asn Pro Ser Tyr Leu Pro Pro Gln Leu Leu Ala Arg Phe
                180                 185                 190

Ala Ala Leu Asn Gly Pro Trp Arg Ala Met Gln Gln Thr Asn Gln Arg
                195                 200                 205

Leu Trp Leu Glu Thr Ala Pro Tyr Gly Phe Leu Pro Asp Trp Val Val
210                 215                 220

Trp Gln Val Gly Lys Gly Trp Gln Pro Asp Thr Val Lys Pro Asn Ile
225                 230                 235                 240

Gly Ser Tyr Asp Ala Ile Arg Ala Tyr Leu Trp Ala Gly Met Leu Ala
                245                 250                 255

Asp Asp Gln His Lys Ala Ala Leu Leu Lys Gln Leu Gln Pro Met
                260                 265                 270

Ala Gln Leu Thr Val Gln Gln Gly Val Pro Pro Glu Lys Thr Asp Thr
            275                 280                 285

Ala Ser Gly Lys Thr Met Gly Asn Gly Pro Val Gly Phe Ser Ala Ser
            290                 295                 300

Met Leu Pro Met Leu Ala Asn Gln Pro Glu Ala Leu Gln Val Gln Arg
305                 310                 315                 320

Gln Arg Ile Lys Gln Asn Pro Pro Gly Asp Asn Ala Tyr Phe Ser Ala
                325                 330                 335

Ser Leu Ala Leu Phe Gly Gln Gly Trp Asp Gln Gln Arg Tyr Arg Phe
                340                 345                 350

Asn Arg Gln Gly Glu Leu Gln Pro Ser Trp Gly Gly Gln Cys Val Thr
                355                 360                 365

Ser Glu
    370

<210> SEQ ID NO 46
<211> LENGTH: 369
<212> TYPE: PRT
<213> ORGANISM: Vibrio campbellii

<400> SEQUENCE: 46

Met Lys Lys Leu Leu Thr Leu Leu Ile Leu Ile Ala Ser Pro His Leu
1               5                   10                  15

Trp Ala Ser Asp Cys Gly Trp Pro Gln Trp Asp Thr Phe Lys Ala Val
                20                  25                  30

Tyr Ile Asp Gln Gly Arg Val Val Asp Gly Ser Asp Arg Ile Ile
            35                  40                  45

Thr Thr Ser Glu Gly Gln Ser Tyr Ala Leu Phe Phe Ala Leu Val Ala
        50                  55                  60

Asn Asp Gln Lys Thr Phe Ala Asp Val Leu Asn Trp Thr Gln Val His
65                  70                  75                  80

Leu Ala Asp Gly Asp Leu Thr Ala Arg Leu Pro Ala Trp Leu Trp Gly
                85                  90                  95
```

-continued

```
Arg Lys Glu Asn Gly Ser Phe Gly Val Leu Asp Thr Asn Ala Ala Ser
            100                 105                 110

Asp Ser Asp Leu Trp Ile Ala Tyr Ala Leu Val Glu Ala Gly Arg Leu
        115                 120                 125

Trp Asp Asn Tyr Tyr Tyr Gln Ser Leu Gly His Leu Leu Ala Ser Arg
    130                 135                 140

Ile Leu Arg Glu Glu Ser Val Ser Ile Asp Gly Thr Gly Thr Leu Leu
145                 150                 155                 160

Leu Pro Ala Pro Thr Gly Phe Glu Phe Ser Gln Arg Tyr Arg Val Asn
                165                 170                 175

Pro Ser Tyr Val Pro Leu Gln Leu Val Thr Arg Met Glu Ala Leu Tyr
            180                 185                 190

Pro Gln Tyr Ser Trp Asp Thr Met Tyr Gln Ala Ser Val Gln Met Leu
        195                 200                 205

Thr His Thr Met Pro Lys Gly Phe Ser Pro Asp Trp Ala Thr Leu Ser
    210                 215                 220

Gln Gly Glu Tyr Ser Val Asp Ser Val Thr Gly Pro Ser Gly Ser Tyr
225                 230                 235                 240

Asn Ala Ile Arg Thr Tyr Leu Trp Ala Gly Met Leu Asp Asp Gln Val
                245                 250                 255

Ala Glu Lys Ala Gln Leu Ile Gln Gln Met Gln Pro Phe Val Thr Ala
            260                 265                 270

Thr Lys Thr Leu Ser Ala Pro Pro Arg Asp Val Asn Thr Glu Thr Gly
        275                 280                 285

Gly Tyr Thr Gln Ala Gly Ser Ala Gly Phe Ser Ala Ala Val Leu Pro
    290                 295                 300

Leu Leu Ala Ser Ser Gly Glu Ser Glu Leu Leu Lys Ala Gln Ala Ser
305                 310                 315                 320

Arg Ala Gln Gln Met Leu Ile Ser Asp Arg Asn Asp His Tyr Tyr Asp
                325                 330                 335

Asn Val Leu Ser Leu Phe Gly Leu Gly Trp His Gln Ala Arg Phe Arg
            340                 345                 350

Phe Gly Lys His Gly Glu Leu Leu Pro Ala Trp Ser Glu Gln Cys Gln
        355                 360                 365

Glu
```

<210> SEQ ID NO 47
<211> LENGTH: 414
<212> TYPE: PRT
<213> ORGANISM: Burkholderia multivorans

<400> SEQUENCE: 47

```
Met Ala Gln Ala Ile Ala Thr Arg Cys Ala Asp Ser Ala Arg Arg Leu
1               5                   10                  15

Gly Ala Thr Phe Val Leu Ala Val Ala Ala Ala Cys Val Ala Gly Gly
            20                  25                  30

Thr Ala Ala Arg Ala Ala Thr Ala Pro Arg Thr Val Gly Gly Ala Ala
        35                  40                  45

Ser Ala Thr Asp Ala Ala Asp Ala Arg Cys Ala Ala Asp Trp Pro Arg
    50                  55                  60

Trp Asp Ala Phe Lys Arg Ala Phe Val Ser Ala Asp Gly Arg Val Ile
65                  70                  75                  80

Asp Val Gly Ser Ala Asp Ser Arg Thr Val Ser Glu Gly Gln Ala Tyr
                85                  90                  95
```

-continued

```
Gly Leu Phe Phe Ala Leu Val Ala Asn Asp Arg Arg Thr Phe Asp Thr
            100                 105                 110

Ile Leu Ala Trp Thr Glu Asn Asn Leu Ala Gln Gly Asp Leu Ser Ala
        115                 120                 125

Arg Leu Pro Ala Trp Leu Trp Gly Arg Ala Pro Asp Gly Thr Trp Arg
    130                 135                 140

Val Leu Asp Ala Asn Ala Ala Ser Asp Ala Asp Leu Trp Ile Ala Tyr
145                 150                 155                 160

Thr Leu Val Glu Ala Gly Arg Leu Trp Arg Glu Arg Ser Tyr Thr Ala
                165                 170                 175

Arg Gly Thr Leu Leu Ala Lys Arg Val Leu Asp Asp Glu Thr Ala Asn
            180                 185                 190

Val Pro Gly Leu Gly Leu Thr Leu Leu Pro Gly Pro Thr Gly Phe Ala
        195                 200                 205

Leu Ala Arg Asp Arg Trp Arg Val Asn Pro Ser Tyr Ser Pro Pro Gln
    210                 215                 220

Val Ile Arg Ala Leu Ala Val Arg Leu Pro Asp Asp Arg Arg Trp Ala
225                 230                 235                 240

Ala Leu Ala Ser Ser Thr Gly Arg Val Leu Leu Asp Thr Ala Pro Lys
                245                 250                 255

Gly Phe Ala Pro Asp Trp Ala Leu Tyr Arg Ala Gly Glu Gly Phe Gly
            260                 265                 270

Pro Asp Pro Gln Thr His Ala Glu Ser Ala Tyr Asn Ala Ile Arg Val
        275                 280                 285

Tyr Leu Trp Ala Gly Met Leu Asp Arg Ala Asp Pro Leu Ala Ala Pro
    290                 295                 300

Leu Leu Ala Arg Phe Ala Pro Phe Ala Asp Tyr Ile Ala Ala His Gly
305                 310                 315                 320

Ala Pro Pro Glu Lys Val Asp Thr Thr Thr Gly Val Ala Gly Pro Asn
                325                 330                 335

Asp Gly Asn Gly Gly Phe Ser Ala Ala Val Pro Phe Leu Asp Ala
            340                 345                 350

Arg Gly Gln His Ala Leu Ala Asp Ala Gln Ala Ala Arg Val Asp Ala
        355                 360                 365

Leu Ala Arg Glu Ser Ala Pro Gly Tyr Tyr Thr Ser Val Leu Thr Leu
    370                 375                 380

Phe Gly Leu Gly Trp Arg Glu Gly Arg Tyr Arg Phe Gly Ala Asp Gly
385                 390                 395                 400

Ser Leu Asp Val Arg Trp Gly Glu Arg Ser Cys Val Ala Arg
                405                 410

<210> SEQ ID NO 48
<211> LENGTH: 543
<212> TYPE: PRT
<213> ORGANISM: Herpetosiphon aurantiacus

<400> SEQUENCE: 48

Met Ala Glu Gln Pro Arg Ser Phe Phe Gly Ser Arg Leu Ile Gln Arg
1               5                   10                  15

Ala Ile Leu Ile Leu Ala Ile Cys Ala Val Ile Val Pro Leu Phe Ala
            20                  25                  30

Ser Lys Ser Ser Tyr Ala Ala Ala Thr Pro Arg Arg Pro Phe Pro Gln
        35                  40                  45

His Thr Gln Tyr Ala Ser Gly Thr Ile Lys Pro Asn His Arg Ser Gln
    50                  55                  60
```

```
Ala Gln Leu Asp Ser Asp Val Lys Ala Phe Tyr Asp Val Trp Lys Ser
 65                  70                  75                  80

Arg Tyr Val Val Arg Ala Gly Thr Ser Ser Ala Gly Asn Pro Tyr Tyr
                 85                  90                  95

Arg Ile Ser Phe Gly Ser Ser Ala Pro Asn Val Thr Val Ser Glu Gly
            100                 105                 110

Gln Gly Tyr Gly Met Val Ile Met Ala Leu Met Ala Gly Tyr Asp Pro
        115                 120                 125

Glu Ala Gln Thr Ile Phe Asp Gly Leu Trp Glu Phe Ser Arg Thr Asn
130                 135                 140

Pro Ser Asn Ile Asp Ser Arg Leu Met Gly Trp Arg Ile Pro Ser Asp
145                 150                 155                 160

Gly Ser Gly Asn Asp Ser Ala Phe Asp Gly Asp Ala Asp Ile Ala Tyr
                165                 170                 175

Gly Leu Ile Leu Ala Asp Ala Gln Trp Gly Ser Thr Gly Arg Ile Asn
            180                 185                 190

Tyr Ala Ser Ala Ala Asn Thr Val Leu Asp Gly Val Leu Ser Ser Thr
        195                 200                 205

Ile Gly Pro Asn Ser Arg Leu Pro Met Leu Gly Asp Trp Val Ser Pro
210                 215                 220

Asn Gly Ser Pro His Ser Gln Tyr Thr Pro Arg Pro Ser Asp Phe Met
225                 230                 235                 240

Pro Ser His Phe Arg Asp Tyr Arg Ala Phe Thr Gly Asn Ala Thr Trp
                245                 250                 255

Asp Thr Val Leu Ser Lys Thr Gln Gly Val Val Asp Ser Ile Gln Ala
            260                 265                 270

Gln Tyr Ser Pro Asn Thr Gly Leu Met Pro Asp Phe Val Val Gln Ala
        275                 280                 285

Asn Thr Thr Pro Lys Pro Ser Pro Ala Asn Phe Leu Glu Ser Glu Asn
290                 295                 300

Asp Gly Asn Tyr Tyr Tyr Asn Ser Gly Arg Val Pro Trp Arg Leu Gly
305                 310                 315                 320

Ala Asp Ala Val Ile Phe Gly Asp Ala Ala Ser Leu Arg Gln Ala Gln
                325                 330                 335

Lys Ile Ser Arg Trp Ile Glu Gln Ala Thr Gly Gly Thr Ala Ser Asn
            340                 345                 350

Ile Arg Ala Gly Tyr Ser Leu Asn Gly Thr Ala Leu Pro Asp Ser Gly
        355                 360                 365

Tyr Phe Ser Thr Phe Phe Ala Ala Pro Phe Gly Val Ala Ala Met Thr
370                 375                 380

Val Pro Ala Ser Gln Gln Trp Leu Asn Arg Val Tyr Asp Ala Val Arg
385                 390                 395                 400

Ser Asn His Gln Asp Tyr Phe Glu Asp Thr Val Thr Leu Gln Cys Leu
                405                 410                 415

Leu Leu Met Ser Gly Asn Tyr Trp Ser Pro Arg Ser Ser Thr Ser
            420                 425                 430

Pro Thr Ala Thr Pro Arg Pro Ala Thr Ala Thr Pro Arg Pro Ala Thr
                435                 440                 445

Ala Thr Pro Arg Pro Ala Thr Ala Thr Pro Arg Pro Ala Thr Ala Thr
            450                 455                 460

Pro Arg Pro Ala Thr Ala Thr Pro Arg Pro Ala Thr Ala Thr Pro Arg
465                 470                 475                 480
```

```
Pro Ala Thr Ala Thr Pro Gln Pro Ala Thr Ala Pro Asn Gly Val
                485                 490                 495

Ala Ala Trp Asp Gly Asn Met Arg Ala Tyr Lys Val Gly Asp Arg Val
        500                 505                 510

Ser Tyr Asn Gly Arg Ile Tyr Arg Cys Leu Gln Ala His Thr Ser Leu
            515                 520                 525

Ser Thr Trp Thr Pro Glu Ala Val Pro Ala Leu Trp Gln Ala Glu
    530                 535                 540

<210> SEQ ID NO 49
<211> LENGTH: 511
<212> TYPE: PRT
<213> ORGANISM: Herpetosiphon aurantiacus

<400> SEQUENCE: 49

Met Lys Gln Ala Leu His Ser Arg Trp Leu Ile Leu Val Met Leu Val
1               5                   10                  15

Gly Leu Gly Leu Ser Leu Pro Arg Gln Gln Ser Ala Ser Ala Asn Pro
            20                  25                  30

Gln Ala Phe Ser Phe Pro Tyr Asn Gln Ala Ser Gly Ile Asn Tyr Asn
        35                  40                  45

Val Thr Asp Leu Thr Gln Ala Trp Asn Glu Trp Lys Ser Ala Gln Ile
    50                  55                  60

Thr Ser Asn Asn Ala Gly Gly Gly Arg Leu Arg Val Leu Gly Gly
65                  70                  75                  80

Val Ser Asn Ser Thr Thr Val Ser Glu Gly Gln Gly Tyr Gly Leu Leu
                85                  90                  95

Phe Ala Ser Leu Phe Asp Asp Gln Ala Thr Phe Asp Gly Leu Trp Leu
            100                 105                 110

Phe Thr Arg Asp Tyr Phe Thr Ser Arg Gly Leu Met His Trp His Ile
        115                 120                 125

Gly Asn Pro Gly Gln Ile Asn Gly Ser Gly Ala Ala Thr Asp Gly Asp
    130                 135                 140

Glu Asp Ile Ala Met Gly Leu Val Asn Ala Cys Ile Lys Val Gln Gln
145                 150                 155                 160

Gly Val Trp Pro Ala Ser Ser Asn Gly Leu Asn Tyr Cys Thr Leu Ala
                165                 170                 175

Ser Thr Met Ile Asn Asn Ile Tyr Thr Tyr Glu Val Asp His Ala Gly
            180                 185                 190

Ser Asn Pro Pro Ala Gly Leu Pro Asn Asn Gln Gly Asn Glu Leu Leu
        195                 200                 205

Pro Gly Asp Ser Trp Ser Thr Ala Thr Glu Tyr Thr Gln Gly Ile Val
    210                 215                 220

Asn Leu Ser Tyr Phe Ser Pro Gly Tyr Ser Thr Val Phe Gly Lys Phe
225                 230                 235                 240

Thr Asn Lys Asn Thr Glu Trp Ala Ala Val Asn Thr Arg Asn Tyr Ala
                245                 250                 255

Ile Thr Asn Leu Val Gln Ala Lys Ala Gly Asn Cys Ser Lys Leu Val
            260                 265                 270

Pro Asn Trp Asn Gln Tyr Asp Gly Asp Val Gln Tyr Val Ser Trp Gln
        275                 280                 285

Pro Glu Glu Ser Ala Trp Trp Ser Tyr Asp Ala Ala Arg Phe Ala Trp
    290                 295                 300

Arg Ile Ala Ile Asp Lys Ala Trp Tyr Asn Thr Ser Asn Ser Arg Glu
305                 310                 315                 320
```

```
Thr Met Asn Glu Ile Gly Gly Phe Phe Ser Ser Val Gly Ile Asp Asn
                325                 330                 335

Ile Gln Ala Arg Tyr Arg Leu Asp Gly Thr Ser Val Asp Asn Tyr Arg
            340                 345                 350

Gly Val Phe Phe Val Ala Asn Ala Ala Ala Ile Trp Ala Ala Pro
        355                 360                 365

Ala Pro Gln Ala Val Asn Cys Gly Ala Ala Thr Ala Ser Leu Lys Thr
    370                 375                 380

Thr Pro Gln Gln Ala Tyr Asn Ala Val Leu Ala Thr Lys Asp Thr Pro
385                 390                 395                 400

Asn Ser Tyr Tyr Pro Asn Ala Trp Arg Leu Leu Ser Met Leu Leu Leu
                405                 410                 415

Thr Gly Asn Phe Pro Asn Leu Tyr Glu Met Ala Gln Ser Gly Thr Gly
                420                 425                 430

Gly Thr Ala Thr Pro Thr Ile Thr Pro Thr Ile Thr Arg Thr Pro Thr
            435                 440                 445

Ala Thr Ala Thr Arg Thr Ala Thr Ala Thr Pro Ser Asn Thr Pro Thr
    450                 455                 460

Arg Thr Ser Thr Gly Thr Pro Ala Thr Ile Thr Ile Thr Pro Ser Arg
465                 470                 475                 480

Thr Pro Thr Ala Thr Ile Thr Pro Ser Arg Thr Pro Thr Val Val Pro
                485                 490                 495

Asn Leu Asn Phe Arg Met Tyr Leu Pro Phe Ala Lys Ser Asn Ser
                500                 505                 510

<210> SEQ ID NO 50
<211> LENGTH: 609
<212> TYPE: PRT
<213> ORGANISM: Herpetosiphon aurantiacus

<400> SEQUENCE: 50

Met Leu Lys His Arg Lys Met Leu Leu Met Val Ala Leu Leu Thr Leu
1               5                   10                  15

Leu Thr Val Pro Trp Trp Gln Ser Lys Ala Ala Gln Gly Asn Ser Val
            20                  25                  30

Ser Pro Leu Leu Phe Pro Tyr Asn Gln Ala Ser Gly Ile Asn Tyr Asn
        35                  40                  45

Val Thr Asp Leu Thr Gln Ala Trp Asn Glu Trp Lys Ser Asn Met Ile
    50                  55                  60

Thr Ala Asn Asn Ala Gly Gly Asn Arg Leu Arg Val Met Gly Gly
65                  70                  75                  80

Val Asp Ser Ser Thr Val Ser Glu Gly Gln Gly Tyr Gly Ile Leu
                85                  90                  95

Phe Ala Ser Leu Phe Asp Asp Gln Thr Thr Leu Asp Gly Leu Trp Leu
            100                 105                 110

Phe Thr Arg Asp His Leu Asp Pro Asn Gly Leu Met His Trp His Ile
        115                 120                 125

Gly Asn Pro Gly Gln Leu Arg Gly Ser Tyr Ala Ala Thr Asp Gly Asp
    130                 135                 140

Glu Asp Ile Ala Leu Gly Leu Val Asn Ala Cys Val Lys Val Arg Lys
145                 150                 155                 160

Gly Val Trp Pro Asn Ser Ser Asn Gly Leu Asp Tyr Cys Ser Leu Ala
                165                 170                 175

Thr Thr Met Ile Asn Asn Ile Tyr Thr Tyr Glu Val Asp His Pro Gly
```

-continued

```
                180                 185                 190
Ser Ser Pro Val Ala Gly Leu Pro Ser Asn Pro Gly Asn Glu Leu Leu
        195                 200                 205
Pro Gly Asp Gly Trp Asn Leu Ala Arg Asp Tyr Pro Glu Gly Ile Val
        210                 215                 220
Asn Leu Ser Tyr Phe Ser Pro Gly Tyr Phe Thr Val Phe Gly Lys Phe
225                 230                 235                 240
Thr Gly Lys Thr Ser Glu Trp Glu Ala Val Asn Thr Arg Asn Tyr Glu
                245                 250                 255
Ile Thr Asn Leu Ala Gln Ser Arg Pro Gly Asn Cys Ser Lys Leu Val
                260                 265                 270
Pro Asn Trp Asn Gln Tyr Asp Gly Asp Ala Gln Leu Val Ser Trp Gln
                275                 280                 285
Pro Glu Glu Tyr Ala Trp Trp Ser Tyr Asp Ala Ala Arg Phe Ala Trp
                290                 295                 300
Arg Val Ala Val Asp Lys Ala Trp Tyr Asn Thr Ala Ser Ser Arg Glu
305                 310                 315                 320
Thr Met Asn Glu Val Gly Gly Phe Phe Ser Val Gly Ile Glu Asn
                325                 330                 335
Val Gln Ala Arg Tyr Arg Met Asn Gly Thr Ser Val Asp Asn Tyr Arg
                340                 345                 350
Gly Val Phe Phe Val Ala Asn Ala Ala Ala Ile Trp Ala Ala Pro
                355                 360                 365
Ala Pro Gln Ala Ile Asn Cys Gly Ala Ala Thr Gly Thr Leu Lys Thr
        370                 375                 380
Ser Pro Gln Gln Ala Tyr Asn Met Val Leu Thr Thr Lys Asp Ser Pro
385                 390                 395                 400
Asn Ser Tyr Tyr Val Asn Ala Trp Arg Leu Met Ser Met Leu Leu Leu
                405                 410                 415
Thr Gly Asn Phe Pro Asn Ile Tyr Glu Leu Ala Asn Gly Val Thr Pro
                420                 425                 430
Thr Asn Thr Pro Val Pro Thr Ser Val Pro Pro Thr Asn Thr Ala Val
                435                 440                 445
Pro Thr Asn Val Pro Pro Thr Asn Thr Thr Val Pro Pro Thr Ser Thr
        450                 455                 460
Pro Arg Pro Thr Asn Thr Pro Val Thr Ile Thr Pro Ile Leu Thr Pro
465                 470                 475                 480
Ile Pro Thr Leu Thr Pro Ile Pro Thr Thr Val Pro Thr Ser Val Pro
                485                 490                 495
Pro Thr Asn Thr Pro Ile Ala Gly Ala Cys Gln Ile Thr Tyr Ser Ile
        500                 505                 510
Ser Asn Asp Trp Gly Ser Gly Phe Thr Ala Asp Val Ser Ile Arg Asn
        515                 520                 525
Asn Gly Thr Ala Ile Asn Asn Trp Asn Val Arg Trp Asn Phe Ala Gly
        530                 535                 540
Asn Gln Gln Ile Asn Asn Leu Trp Asn Gly Thr Val Ser Gln Thr Gly
545                 550                 555                 560
Gln Ala Val Ser Val Asn Asn Val Gly Trp Asn Gly Tyr Ile Gly Ser
                565                 570                 575
Gly Gly Thr Ala Ser Phe Gly Phe Gln Ala Ser Tyr Asn Gly Ser Asn
                580                 585                 590
Pro Lys Pro Thr Ser Phe Ser Leu Asn Gly Thr Ala Cys Ser Val Ala
                595                 600                 605
```

Pro

<210> SEQ ID NO 51
<211> LENGTH: 351
<212> TYPE: PRT
<213> ORGANISM: Agrobacterium tumefaciens

<400> SEQUENCE: 51

Met Lys Ser Gly Ile Ser Lys Ile Ala Gly Ile Val Cys Leu Ser Ala
1               5                   10                  15

Met Met Leu Phe Ala Gly Leu Ser Leu Ser Arg Ala Ala Ser Ile Pro
                20                  25                  30

Thr Asp Ala Trp Ala Ala Tyr Lys Gly Ala Phe Leu Asp Pro Gly Gly
            35                  40                  45

Arg Ile Ile Asp Thr Gly Asn Ser Asn Ile Ser His Ser Glu Gly Gln
        50                  55                  60

Gly Tyr Gly Met Trp Leu Ala Val Leu Ala Asp Asn Leu Ser Asp Phe
65                  70                  75                  80

Glu Leu Ile Trp Ser Phe Thr Arg Thr Glu Leu Leu Val Arg Asp Asp
                85                  90                  95

Gly Leu Ser Ala Trp Lys Trp Asp Pro Arg Thr Arg Pro His Val Thr
            100                 105                 110

Asp Ile Asn Asn Ala Thr Asp Gly Asp Ile Leu Ile Ala Tyr Ala Leu
        115                 120                 125

Ala Leu Ala Ala Gly Gln Trp Asn Arg Gln Asp Tyr Ala Glu Ala Ser
130                 135                 140

Ala Ala Ile Ala Ser Val Ile Leu Lys Lys Thr Val Val Gln Arg Gly
145                 150                 155                 160

Gly Arg Thr Leu Leu Leu Pro Ala Ala Ser Gly Phe Gly Glu Gly Asp
                165                 170                 175

Arg Ala Asp Gly Pro Val Val Asn Pro Ser Tyr Leu Ile Phe Glu Ala
            180                 185                 190

Phe Pro Val Leu Asn Leu Val Ala Pro Ser Pro Leu Trp Lys Ala Val
        195                 200                 205

Ala Asp Asp Gly Val Ala Gln Ile Gly Ala Phe Ala Phe Ser Asp Arg
210                 215                 220

Lys Leu Pro Ala Asp Trp Val Ser Val Lys Thr Lys Pro Gln Pro Ala
225                 230                 235                 240

Ser Gly Phe Gln Pro Glu Phe Gly Tyr Asn Ala Val Arg Ile Pro Leu
                245                 250                 255

Tyr Leu Ala Arg Ala Asn Met Gly Ala Pro Glu Leu Leu Ser Arg Leu
            260                 265                 270

Lys Asp Gly Met Thr Leu Glu Ser Gly Ala Ala Gly Thr Phe Asp Leu
        275                 280                 285

Lys Ser Gly Ala Val Lys Asp Val Leu Ser Asp Ala Gly Tyr Arg Ile
290                 295                 300

Ile Pro Ala Leu Ala Ala Cys Ile Ala Gly Gly Pro Ala Val Ser Ala
305                 310                 315                 320

Glu Leu Lys Asn Phe Gln Pro Thr Leu Tyr Tyr Pro Ser Thr Leu His
                325                 330                 335

Leu Leu Ala Leu Ser Phe Leu Ala Arg Asn Asn Gly Glu Cys Arg
            340                 345                 350

<210> SEQ ID NO 52

<211> LENGTH: 383
<212> TYPE: PRT
<213> ORGANISM: Sorangium cellulosum

<400> SEQUENCE: 52

```
Met Ser Ser Asp Glu Leu Gly Pro Leu Thr Gly Pro Ser Glu Tyr Pro
1               5                   10                  15

Asn Ala Phe Arg Asp Val Leu Gly Lys Thr Asp Glu Glu Ile Ala Ala
            20                  25                  30

Lys Ile Glu Asp Ser Phe Glu Gln Leu Phe Tyr Gly Asp Arg Tyr Glu
        35                  40                  45

Glu Thr Val Tyr Tyr Pro Val Pro Gly Thr Gln Ala Tyr Ile Trp
    50                  55                  60

Asp Asp Tyr His Asn Ser Val Arg Ser Glu Gly Ile Gly Leu Gly Met
65                  70                  75                  80

Ile Ile Thr Val Glu Leu Asp Lys Arg Asp Glu Phe Asp Arg Ile Trp
                85                  90                  95

Arg Tyr Ala Lys Ser Thr Leu Gln Leu Lys Ser Gly Pro Gly Gln Gly
            100                 105                 110

Tyr Leu Met Ser Trp Cys Asp Val Pro Gly Gly Thr Ala Val Val Cys
        115                 120                 125

Phe Asp Pro Phe Gly Leu Gln Gln Val Ala Met Ala Leu Phe Phe Ala
130                 135                 140

His Gly Arg Trp Gly Ser Asp Thr Gly Thr Ile Asp Tyr Gly Met Asp
145                 150                 155                 160

Ala Ile Ser Leu Leu Glu Val Met Arg His Lys Glu Ala Leu Asn Gly
                165                 170                 175

Gly Val Ala Ser Gly Val Thr Asn Thr Phe Asp Pro Thr Thr Lys Leu
            180                 185                 190

Val Tyr Asp Tyr Pro His Val Ser Ala Ala Asp Val Thr Arg Pro Ser
        195                 200                 205

Ile Glu Met Pro Ala Tyr Tyr Glu Leu Trp Ala Gln Ala Met Arg Asp
    210                 215                 220

Pro Phe Trp Ser Glu Ala Ala Ala Ser Ala Arg Thr His Trp Gln Glu
225                 230                 235                 240

Ala Ala His Pro Ser Thr Gly Leu Ile Pro Val Arg Thr His Phe Asp
                245                 250                 255

Gly Thr Pro Val Leu Asn Trp Asp Tyr Phe Gly Ser Glu Ala Tyr Arg
            260                 265                 270

Thr Gln Leu Ser Ile Ala Leu Asp His Val Trp Phe Gly Val Asp Pro
        275                 280                 285

Trp Gln Val Glu Glu Ala Asp Arg Leu Leu Gly Phe Phe Ser Lys Leu
290                 295                 300

Gly Ile Asp Lys Tyr Gly Ala Val Phe Lys Ile Asn Gly Ala Met Leu
305                 310                 315                 320

Ser Ala Thr Pro Glu Ser Ala Leu Ile Phe Met Asn Gly Val Thr Gly
                325                 330                 335

Leu Ile Ala Thr Asn Asp Asp Arg Ala Ala Tyr Ile Glu Ala Val Trp
            340                 345                 350

Thr Thr Pro Pro Ala Thr Gly Glu Thr Arg Tyr Phe Ser Arg Leu Leu
        355                 360                 365

His Met Leu Ser Leu Leu Thr Leu Ser Gly Gln Phe Arg Val Tyr
    370                 375                 380
```

<210> SEQ ID NO 53
<211> LENGTH: 467
<212> TYPE: PRT
<213> ORGANISM: Sorangium cellulosum

<400> SEQUENCE: 53

| | | | | | | | | | | | | | | | |
|---|---|---|---|---|---|---|---|---|---|---|---|---|---|---|---|
| Met | Asn | Arg | Asn | Ser | Leu | Arg | Phe | Leu | Ser | Val | Gly | Leu | Leu | Leu | Ala |
| 1 | | | | 5 | | | | | 10 | | | | | 15 | |
| Ala | Val | Ala | Cys | Gly | Asp | Asp | Gly | Gly | Ser | Gly | Gly | Ala | Gly | Ser | |
| | | | 20 | | | | | 25 | | | | | 30 | | |
| Val | Ser | Ser | Gly | Thr | Gly | Gly | Ala | Gly | Gly | Thr | Gly | Gly | Ser | Ala | Asp |
| | | 35 | | | | | 40 | | | | | 45 | | | |
| Gly | Gly | Gly | Gly | Gly | Gly | Asp | Gly | Gly | Gly | Ala | Ser | Thr | Pro | Gly | |
| 50 | | | | | 55 | | | | | 60 | | | | | |
| Gly | Ser | Gly | Ala | Val | Asp | Thr | Gly | Val | Tyr | Arg | Asn | Leu | Phe | Val | Glu |
| 65 | | | | 70 | | | | | 75 | | | | | 80 | |
| Asn | Gly | Arg | Thr | Gln | Asp | Glu | Val | Asn | Ala | Lys | Ile | Thr | Ala | Ala | Trp |
| | | | | 85 | | | | | 90 | | | | | 95 | |
| Asp | His | Leu | Phe | Lys | Gly | Asp | Pro | Ala | Gln | Glu | Ala | Val | Tyr | Phe | Glu |
| | | | 100 | | | | | 105 | | | | | 110 | | |
| Gln | Glu | Glu | Asn | Asp | Asn | Gly | Pro | Leu | Ala | Gln | Ile | Arg | Asp | Ile | Ala |
| | | 115 | | | | | 120 | | | | | 125 | | | |
| Ser | Glu | Asp | Val | Arg | Ser | Glu | Gly | Met | Ser | Tyr | Gly | Met | Met | Ile | Ala |
| 130 | | | | | 135 | | | | | 140 | | | | | |
| Val | Gln | Thr | Asp | His | Gln | Ala | Glu | Phe | Asp | Ala | Leu | Trp | Asn | Trp | Ala |
| 145 | | | | 150 | | | | | 155 | | | | | 160 | |
| Lys | Thr | Tyr | Met | Phe | His | Ala | Asp | Glu | Thr | His | Pro | Ala | Tyr | Gly | Tyr |
| | | | | 165 | | | | | 170 | | | | | 175 | |
| Phe | Ser | Trp | Gln | Met | Asn | Phe | Asp | Gly | Thr | Pro | Leu | Asp | Glu | Met | Pro |
| | | | 180 | | | | | 185 | | | | | 190 | | |
| Ala | Pro | Asp | Gly | Glu | Glu | Tyr | Phe | Ala | Thr | Ala | Leu | Tyr | Phe | Ala | Ser |
| | | | 195 | | | | | 200 | | | | | 205 | | |
| Gly | Arg | Trp | Gly | Asn | Gly | Glu | Gly | Ile | Tyr | Asn | Tyr | Arg | Ala | Glu | Ala |
| | 210 | | | | | 215 | | | | | 220 | | | | |
| Asp | Arg | Leu | Leu | Asp | Leu | Met | Lys | Asn | Arg | Pro | Glu | Ile | Thr | Gly | Glu |
| 225 | | | | | 230 | | | | | 235 | | | | | 240 |
| Ser | Phe | Gly | Asn | Gly | Glu | Thr | Arg | Thr | Thr | Thr | Gly | Ser | Thr | Leu | Phe |
| | | | | 245 | | | | | 250 | | | | | 255 | |
| Asn | Thr | Glu | Asn | His | Gln | Ile | Arg | Phe | Thr | Pro | Asp | Thr | Gly | Asn | Phe |
| | | | 260 | | | | | 265 | | | | | 270 | | |
| Glu | Thr | Asn | Gly | Asp | His | Thr | Asp | Pro | Ser | Tyr | His | Leu | Pro | Ala | Phe |
| | | 275 | | | | | 280 | | | | | 285 | | | |
| Tyr | Glu | Ile | Trp | Ala | Lys | Tyr | Gly | Pro | Glu | Ala | Asp | Arg | Ala | Phe | Trp |
| | 290 | | | | | 295 | | | | | 300 | | | | |
| Ser | Glu | Ala | Ala | Glu | Val | Ser | Arg | Gly | Tyr | Phe | His | Leu | Ala | Ala | His |
| 305 | | | | | 310 | | | | | 315 | | | | | 320 |
| Pro | Glu | Thr | Gly | Leu | Thr | Pro | Asp | Tyr | Ala | Asn | Phe | Asp | Gly | Thr | Pro |
| | | | | 325 | | | | | 330 | | | | | 335 | |
| Lys | Ala | Ala | Ser | Trp | Lys | Pro | Glu | Ser | Val | Asp | Phe | Arg | Phe | Asp | Ala |
| | | | 340 | | | | | 345 | | | | | 350 | | |
| Trp | Arg | Thr | Ala | Met | Asn | Trp | Ser | Val | Asp | Trp | Ala | Trp | Ala | Lys | |
| | | 355 | | | | | 360 | | | | | 365 | | | |
| Asp | Glu | Arg | Gln | Gln | Glu | Leu | Ser | Asp | Arg | Ile | Gln | Ala | Phe | Phe | Glu |
| | 370 | | | | | 375 | | | | | 380 | | | | |

```
Ala Gln Gly Ala Glu Tyr Gly Asn Gln Phe Thr Leu Asp Gly Glu Ala
385                 390                 395                 400

Leu Ser Ala Asp His Ser Ser Gly Leu Val Ala Met Asn Ala Ala Ala
            405                 410                 415

Ser Leu Ala Ala Lys Asp Pro Arg Ser Ala Asp Phe Val Gln Ala Leu
            420                 425                 430

Trp Asp Leu Asp Pro Pro Ser Gly Gln Tyr Arg Tyr Tyr Asp Gly Met
        435                 440                 445

Leu Tyr Phe Met Ala Leu Leu His Val Gly Gly Gln Phe Gln Ala Tyr
    450                 455                 460

Ala Pro Gln
465

<210> SEQ ID NO 54
<211> LENGTH: 497
<212> TYPE: PRT
<213> ORGANISM: Sorangium cellulosum

<400> SEQUENCE: 54

Met Leu Thr Ser Pro Val Ala Ser Ala Trp Phe Ala Val Thr Val Ile
1               5                   10                  15

Ala Cys Ala Pro Ser Asn Gln Gly Thr Gln Val Gly Ser Pro Asp Pro
            20                  25                  30

Ala Ser Ser Ala Asn Pro Ala Gly Ser Ala Ala Pro Ala Ser Thr Ala
            35                  40                  45

Ser Pro Ser Ala Ala Gln Thr Pro Ala Pro Ala Glu Pro Ala Pro
    50                  55                  60

Leu Gly Pro Pro Leu Lys Pro Ala Ala Thr Gly Ala Phe Val Thr Gly
65              70                  75                  80

Glu Tyr Arg Asn Leu Phe Ala Glu Leu Gly His Lys Pro Ala Glu Ile
                85                  90                  95

Asp Ala Lys Ile Ala Lys Ala Tyr Glu Gln Leu Phe His Gly Asp Pro
            100                 105                 110

Lys Glu Gln Ala Val Leu Phe Pro Ala Gly Lys Asn Ala Asn Gly Pro
        115                 120                 125

Lys Ala Tyr Ile Met Asp Ile Gly Asn Asn Asp Val Arg Ser Glu Gly
    130                 135                 140

Met Ser Tyr Gly Met Met Ile Ala Val Gln Val Asp Arg Lys Asp Asp
145                 150                 155                 160

Phe Asp Ala Leu Trp Asn Trp Ala Lys Ser His Met Tyr Arg Ala Asp
                165                 170                 175

Pro Lys His Pro Gly Phe Gly Tyr Phe Ser Trp Gln Met Arg Pro Asp
            180                 185                 190

Gly Thr Ala Met Asp Glu Asn Pro Ala Pro Asp Ala Glu Glu Tyr Phe
        195                 200                 205

Ala Thr Ala Leu Leu Phe Ala Ser Asn Arg Trp Gly Asn Gly Lys Gly
    210                 215                 220

Ile Tyr Asp Tyr Lys Lys Glu Ala Phe Ala Ile Leu Asp Ala Met Lys
225                 230                 235                 240

Asn Arg Lys Pro Ile Thr Gly Pro Val Asn Lys Asp Lys Arg Lys Thr
                245                 250                 255

Thr Leu His Ser Leu Phe Asn Thr Glu His Lys Met Val Arg Phe Thr
            260                 265                 270

Pro Asp Ala Asp Asn Phe Ala Lys Asn Gly Asp His Thr Asp Pro Ser
        275                 280                 285
```

```
Tyr His Leu Pro Ala Phe Tyr Asp Leu Trp Ala Ala Trp Gly Pro Glu
        290                 295                 300

Ala Asp Arg Ala Phe Trp Ala Glu Ala Ala Lys Val Ser Arg Asp Tyr
305                 310                 315                 320

Phe Val Lys Val Thr His Pro Lys Thr Gly Leu Ala Pro Asp Tyr Ala
                325                 330                 335

Asn Phe Asp Gly Thr Pro Lys Ala Ala Ser Trp Asp Ala Gly Thr Ala
                340                 345                 350

Asn Phe Arg Gln Asp Ala Phe Arg Thr Ala Met Asn Trp Ser Val Asp
                355                 360                 365

Ala Ala Trp Trp Ala Lys Asp Pro Arg Gln Thr Glu Leu Ser Asp Arg
        370                 375                 380

Leu Leu Ala Phe Phe Glu Ala Gln Gly Pro Lys Tyr Lys Gly Asn Phe
385                 390                 395                 400

Thr Leu Glu Gly Lys Pro Ile Val Asp Tyr Asp Ser Leu Gly Leu Val
                405                 410                 415

Ala Ala Asn Ala Val Ala Ala Leu Ala Ala Thr His Pro Arg Ala Trp
                420                 425                 430

Arg Phe Val Glu Glu Leu Tyr Gln Arg Glu Ala Pro Thr Gly Lys Trp
        435                 440                 445

Arg Tyr Tyr Asp Gly Met Leu Tyr Thr Met Ser Leu Leu His Leu Ser
        450                 455                 460

Gly Lys Phe Arg Ile Ile Thr Pro Gln Ala Gln Ala Ala Pro Ala
465                 470                 475                 480

Ala Ala Ala Lys Ala Pro Ala Ala Pro Ala Ala Ala Ala Lys
                485                 490                 495

Lys

<210> SEQ ID NO 55
<211> LENGTH: 381
<212> TYPE: PRT
<213> ORGANISM: Clostridium phytofermentans

<400> SEQUENCE: 55

Met Asn Gly Ala Ile Lys Ser Gly Tyr Tyr Arg Asn Val Phe Thr Glu
1               5                   10                  15

Leu Gly Tyr Lys Glu Glu Asp Val Thr Lys Lys Val Glu Asp Ser Phe
                20                  25                  30

Gln Thr Leu Phe Tyr Gly Leu Pro Glu Glu Arg Ile Tyr Tyr Pro Val
            35                  40                  45

Gly Glu Asp Leu Gly Tyr Ile Val Asp Thr Gly Asn His Asp Val Arg
        50                  55                  60

Thr Glu Gly Met Ser Tyr Gly Met Met Met Cys Leu Gln Leu Asp Lys
65                  70                  75                  80

Lys Glu Glu Phe Asp Arg Leu Trp Lys Trp Ala Lys Thr Tyr Met Phe
                85                  90                  95

Met Asp Ser Gly Val Asn Lys Gly Tyr Phe Ala Trp Ser Cys Lys Thr
                100                 105                 110

Asp Gly Thr Lys Asn Ser Tyr Gly Pro Ala Pro Asp Gly Glu Glu Tyr
            115                 120                 125

Phe Ala Leu Ala Leu Phe Phe Ala Ser Asn Arg Trp Gly Asp Gly Asn
        130                 135                 140

Gly Ile Phe Glu Tyr Ser Lys Gln Ala Arg Glu Leu Leu His Glu Cys
145                 150                 155                 160
```

```
Ile His Lys Gly Glu Glu Asp Gly Ile Gly Glu Pro Met Trp Glu Pro
                165                 170                 175

Ser Asn Tyr Leu Ile Lys Phe Ile Pro Asn Cys Asn Phe Thr Asp Pro
            180                 185                 190

Ser Tyr His Leu Pro His Phe Tyr Gly Leu Phe Ala Leu Trp Ala Tyr
        195                 200                 205

Glu Glu Asp Arg Glu Phe Phe Lys Lys Ala Ala Glu Ala Ser Arg Ser
    210                 215                 220

Tyr Leu Lys Leu Ala Cys His Glu Lys Thr Gly Leu Cys Ala Glu Tyr
225                 230                 235                 240

Thr Glu Tyr Asp Gly Thr Ala His Ser Gly Asp Gln Glu Ile Phe Gly
                245                 250                 255

Arg His Asp Trp Tyr Tyr Ser Asp Ala Tyr Arg Thr Ile Ala Asn Ile
                260                 265                 270

Gly Leu Asp Tyr Leu Trp Phe Ala Ala Asp Glu Trp Gln Val Thr Cys
                275                 280                 285

Ala Asn His Leu Gln Gln Phe Phe Cys Glu Thr Val Lys Glu His Ala
            290                 295                 300

Ser Gly Ile Tyr Gln Val Asp Gly Thr Ile Ile Lys Gly Glu Ala Leu
305                 310                 315                 320

His Pro Val Ala Ile Ile Ala Thr Asn Ala Gln Ala Ser Leu Ala Ala
                325                 330                 335

Asn Gly Pro Phe Ala Lys Glu Cys Val Asp Lys Phe Tyr His Thr Glu
            340                 345                 350

Leu Arg Thr Gly Asp Arg Arg Tyr Tyr Asp Asn Cys Leu Tyr Met Phe
        355                 360                 365

Ala Leu Leu Ala Leu Ser Gly Lys Tyr Arg Met Trp Met
370                 375                 380

<210> SEQ ID NO 56
<211> LENGTH: 369
<212> TYPE: PRT
<213> ORGANISM: Salmonella arizonae

<400> SEQUENCE: 56

Met Met Thr Met Leu Arg Gly Trp Ile Thr Met Ile Val Met Leu Thr
1               5                   10                  15

Ala Ile Asn Ala Gln Ala Ala Cys Ser Trp Pro Ala Trp Glu Gln Phe
            20                  25                  30

Lys Lys Asp Tyr Ile Ser Gln Gln Gly Arg Val Ile Asp Pro Gly Asp
        35                  40                  45

Ala Arg Lys Ile Thr Thr Ser Glu Gly Gln Ser Tyr Ala Met Phe Phe
    50                  55                  60

Ala Leu Ala Ala Asn Asp Arg Pro Ala Phe Ala Gln Leu Phe Asn Trp
65                  70                  75                  80

Thr Gln Asn Asn Leu Ala Gln Gly Ser Leu Arg Glu His Leu Pro Ala
                85                  90                  95

Trp Leu Trp Gly Gln Lys Asp Pro Asp Thr Trp Ser Val Leu Asp Ser
            100                 105                 110

Asn Ser Ala Ser Asp Gly Asp Ile Trp Met Ala Trp Ser Leu Leu Glu
        115                 120                 125

Ala Gly Arg Leu Trp Lys Glu Thr Arg Tyr Thr Glu Val Gly Thr Ala
    130                 135                 140

Leu Leu Lys Arg Ile Ala Arg Glu Glu Val Val Asn Val Pro Gly Leu
```

```
                145                 150                 155                 160
Gly Ser Met Leu Leu Pro Gly Lys Ile Gly Phe Ala Glu Ala Asn Ser
                165                 170                 175

Trp Arg Phe Asn Pro Ser Tyr Leu Pro Pro Gln Leu Ala Gln Tyr Phe
                180                 185                 190

Ser Arg Phe Gly Ala Pro Trp Ser Thr Leu Arg Glu Thr Asn Leu Arg
                195                 200                 205

Leu Leu Leu Glu Thr Ala Pro Lys Gly Phe Ser Pro Asp Trp Val Arg
                210                 215                 220

Tyr Glu Arg Lys Gln Gly Trp Gln Leu Lys Ala Glu Lys Thr Leu Ile
225                 230                 235                 240

Ser Ser Tyr Asp Ala Ile Arg Val Tyr Leu Trp Ala Gly Met Met His
                245                 250                 255

Asp Gly Asp Pro Gln Lys Ala Arg Leu Leu Ala Lys Phe Lys Pro Met
                260                 265                 270

Ala Thr Leu Thr Met Lys Asn Gly Val Pro Pro Glu Lys Val Asp Val
                275                 280                 285

Ala Ser Gly Asn Ala Gln Gly Thr Gly Pro Val Gly Phe Ser Ala Ala
                290                 295                 300

Leu Leu Pro Phe Leu Gln Asn Arg Asp Ala Gln Ala Val Gln Arg Gln
305                 310                 315                 320

Arg Val Ala Asp His Phe Pro Gly Ser Asp Ala Tyr Tyr Asn Tyr Val
                325                 330                 335

Leu Thr Leu Phe Gly Gln Gly Trp Asp Gln His Arg Phe Arg Phe Thr
                340                 345                 350

Val Lys Gly Glu Leu Leu Pro Asp Trp Gly Gln Glu Cys Val Ser Ser
                355                 360                 365

Arg

<210> SEQ ID NO 57
<211> LENGTH: 368
<212> TYPE: PRT
<213> ORGANISM: Salmonella paratyphi

<400> SEQUENCE: 57

Met Thr Met Leu Arg Gly Trp Ile Thr Met Leu Val Met Leu Thr Ala
1               5                   10                  15

Ile Asn Ala Gln Ala Ala Cys Ser Trp Pro Ala Trp Glu Gln Phe Lys
                20                  25                  30

Lys Asp Tyr Ile Ser Gln Gln Gly Arg Val Ile Asp Pro Gly Asp Ala
                35                  40                  45

Arg Lys Ile Thr Thr Ser Glu Gly Gln Ser Tyr Ala Met Phe Phe Ala
                50                  55                  60

Leu Ala Ala Asn Asp Arg Pro Ala Phe Ala Gln Leu Phe Asn Trp Thr
65              70                  75                  80

Gln Asn Asn Leu Ala Gln Gly Ser Leu Arg Glu His Leu Pro Ala Trp
                85                  90                  95

Leu Trp Gly Gln Lys Asp Pro Asp Thr Trp Ser Val Leu Asp Ser Asn
                100                 105                 110

Ser Ala Ser Asp Gly Asp Ile Trp Met Ala Trp Ser Leu Leu Glu Ala
                115                 120                 125

Gly Arg Leu Trp Lys Glu Thr Arg Tyr Thr Glu Val Gly Thr Ala Leu
                130                 135                 140

Leu Lys Arg Ile Ala Arg Glu Glu Val Leu Asn Val Pro Gly Leu Gly
```

```
                145                 150                 155                 160
Ser Met Leu Leu Pro Gly Lys Ile Gly Phe Ala Glu Ala Asn Ser Trp
                165                 170                 175

Arg Phe Asn Pro Ser Tyr Leu Pro Pro Gln Leu Ala Gln Tyr Phe Ser
                180                 185                 190

Arg Phe Gly Ala Pro Trp Ser Thr Leu Arg Glu Thr Asn Leu Arg Leu
                195                 200                 205

Leu Leu Glu Thr Ala Pro Lys Gly Phe Ser Pro Asp Trp Val Arg Tyr
210                 215                 220

Glu Ser Lys Gln Gly Trp Gln Leu Lys Ala Glu Lys Thr Leu Ile Ser
225                 230                 235                 240

Ser Tyr Asp Ala Ile Arg Val Tyr Leu Trp Ala Gly Met Met His Asp
                245                 250                 255

Gly Asp Pro Gln Lys Ala Arg Leu Leu Ala Arg Phe Lys Pro Met Ala
                260                 265                 270

Thr Leu Thr Met Lys Asn Gly Val Pro Pro Glu Lys Val Asp Val Val
                275                 280                 285

Ser Gly Asn Ala Gln Gly Thr Gly Pro Val Gly Phe Ser Ala Ala Leu
290                 295                 300

Leu Pro Phe Leu Gln Asn Arg Asp Ala Gln Ala Val Gln Arg Gln Arg
305                 310                 315                 320

Val Ala Asp His Phe Pro Gly Ser Asp Ala Tyr Tyr Asn Tyr Val Leu
                325                 330                 335

Thr Leu Phe Gly Gln Gly Trp Asp Gln His Arg Phe Arg Phe Thr Val
                340                 345                 350

Lys Gly Glu Leu Leu Pro Asp Trp Gly Gln Glu Cys Val Ser Ser Arg
                355                 360                 365

<210> SEQ ID NO 58
<211> LENGTH: 453
<212> TYPE: PRT
<213> ORGANISM: Bacillus thuringiensis

<400> SEQUENCE: 58

Met Asn Gly Lys Arg Asn Ile Phe Thr Cys Ile Ser Ile Ile Gly Ile
1               5                   10                  15

Gly Leu Ala Ser Phe Ser Ser Phe Ser Phe Ala Ala Asn Val Thr Asp
                20                  25                  30

Asn Ser Val Gln Asn Ser Ile Pro Val Val Asn Gln Gln Val Ala Ala
                35                  40                  45

Ala Lys Glu Met Lys Pro Phe Pro Gln Gln Val Asn Tyr Ala Gly Val
                50                  55                  60

Ile Lys Pro Thr His Val Thr Gln Glu Ser Leu Asn Ala Ser Val Lys
65                  70                  75                  80

Ser Tyr Tyr Asp Asn Trp Lys Lys Tyr Leu Lys Asn Asp Leu Ser
                85                  90                  95

Ser Leu Pro Gly Gly Tyr Tyr Val Lys Gly Glu Ile Thr Gly Asp Ala
                100                 105                 110

Asp Gly Phe Lys Pro Leu Gly Thr Ser Glu Gly Gln Gly Tyr Gly Met
                115                 120                 125

Ile Ile Thr Val Leu Met Ala Gly Tyr Asp Ser Asn Ala Gln Lys Ile
                130                 135                 140

Tyr Asp Gly Leu Phe Lys Thr Ala Arg Thr Phe Lys Ser Ser Gln Asn
145                 150                 155                 160
```

Pro Asn Leu Met Gly Trp Val Val Ala Asp Ser Lys Lys Ala Gln Gly
                165                 170                 175

His Phe Asp Ser Ala Thr Asp Gly Asp Leu Asp Ile Ala Tyr Ser Leu
            180                 185                 190

Leu Leu Ala His Lys Gln Trp Gly Ser Asn Gly Thr Val Asn Tyr Leu
            195                 200                 205

Lys Glu Ala Gln Asp Met Ile Thr Lys Gly Ile Lys Ala Ser Asn Val
        210                 215                 220

Thr Asn Asn Ser Arg Leu Asn Leu Gly Asp Trp Asp Ser Lys Asn Ser
225                 230                 235                 240

Leu Asp Thr Arg Pro Ser Asp Trp Met Met Ser His Leu Arg Ala Phe
            245                 250                 255

Tyr Glu Phe Thr Gly Asp Lys Thr Trp Leu Thr Val Ile Asn Asn Leu
            260                 265                 270

Tyr Asp Val Tyr Thr Gln Phe Ser Asn Lys Tyr Ser Pro Asn Thr Gly
        275                 280                 285

Leu Ile Ser Asp Phe Val Val Lys Asn Pro Pro Gln Pro Ala Pro Lys
        290                 295                 300

Asp Phe Leu Glu Glu Ser Glu Tyr Thr Asn Ala Tyr Tyr Asn Ala
305                 310                 315                 320

Ser Arg Val Pro Leu Arg Ile Val Met Asp Tyr Ala Met Tyr Gly Glu
            325                 330                 335

Lys Arg Ser Lys Val Ile Ser Asp Lys Val Ser Ser Trp Ile Gln Asn
            340                 345                 350

Lys Thr Asn Gly Asn Pro Ser Lys Ile Val Asp Gly Tyr Gln Leu Asn
            355                 360                 365

Gly Ser Asn Ile Gly Ser Tyr Ser Thr Ala Val Phe Val Ser Pro Phe
        370                 375                 380

Ile Ala Ala Ser Ile Thr Ser Ser Asn Asn Gln Lys Trp Val Asn Ser
385                 390                 395                 400

Gly Trp Asp Trp Met Lys Asn Lys Arg Glu Ser Tyr Phe Ser Asp Ser
            405                 410                 415

Tyr Asn Leu Leu Thr Met Leu Phe Ile Thr Gly Asn Trp Trp Lys Pro
        420                 425                 430

Val Pro Asp Asp Lys Lys Ile Gln Asn Gln Ile Asn Asp Ala Ile Tyr
        435                 440                 445

Glu Gly Tyr Asp Asn
    450

<210> SEQ ID NO 59
<211> LENGTH: 377
<212> TYPE: PRT
<213> ORGANISM: Lactococcus lactis

<400> SEQUENCE: 59

Met Glu Asn Leu Leu Leu Lys Val Ala Pro Lys Glu Glu Ile Asp Lys
1               5                   10                  15

Lys Leu Glu Asn Val Phe Glu Thr Leu Phe Gly Gln Asp Ser Pro Glu
            20                  25                  30

Arg Ile Tyr Phe Glu Glu Asp Met Ala Tyr Ile Val Asp Thr Gly
        35                  40                  45

Asn Asp Asp Val Arg Thr Glu Gly Met Ser Tyr Gly Met Met Ile Ala
    50                  55                  60

Leu Gln Leu Asp Lys Pro Lys Ile Phe Ser Gln Leu Trp Lys Trp Val
65                  70                  75                  80

```
Lys Thr Tyr Met Thr Val Pro Lys Gly His Glu Asn Glu Gly Tyr Phe
                85                  90                  95

Ile Trp Ser Cys Ala Pro Asn Gly Gln Ala Asn Ser Asp Gly Pro Ala
            100                 105                 110

Pro Asp Gly Glu Glu Tyr Phe Ala Ala Ala Leu Leu Leu Ala Glu Lys
        115                 120                 125

Arg Trp Lys Ile Lys Glu Tyr Gly Asp Glu Ala Arg Ala Leu Leu His
    130                 135                 140

Ala Met Val His Lys Gly Glu Asn His Asp Gly Tyr Pro Met Phe Glu
145                 150                 155                 160

Pro Glu Asn Thr Tyr Ile Lys Phe Val Ala His Leu His Met Thr Asp
                165                 170                 175

Pro Ser Tyr His Leu Pro His Phe Tyr Gln Leu Tyr Ala Lys Tyr Gly
            180                 185                 190

Asn Pro Glu Asp Ser Ala Phe Phe Leu Lys Ser Glu Glu Ala Arg
        195                 200                 205

Lys Phe Trp Leu Lys Ser Ala Asn Ala Lys Thr Gly Leu Thr Pro Glu
    210                 215                 220

Tyr Ala Asp Tyr Glu Gly Lys Pro Tyr Asp Ile Asp Gly His Trp Thr
225                 230                 235                 240

Phe Phe Ser Asp Ala Tyr Arg Thr Val Ala Asn Ile Gly Leu Asp Trp
                245                 250                 255

Leu Trp Glu His Lys Glu Ile Gly Gln Ser Gln Ile Ala Leu Asn Ile
            260                 265                 270

Gln Lys Phe Phe Glu Pro Tyr Leu Glu Asn Asp Glu Glu Ile Pro Val
        275                 280                 285

Phe Lys Ile Asp Gly Gln Pro Leu Arg Lys Glu Glu Gln Thr Ala Glu
    290                 295                 300

Gly Phe Pro Pro Leu Lys Val His His Pro Ile Gly Leu Trp Ser Thr
305                 310                 315                 320

Leu Ala Gln Ala Ser Leu Val Thr Asn Glu Phe Asp Ser Thr Leu Ala
                325                 330                 335

Leu Lys Tyr Leu Lys Tyr Phe Trp Asn Leu Lys Leu Arg Arg Gly Lys
            340                 345                 350

Tyr Arg Tyr Tyr Asp Asn Leu Leu Tyr Leu Phe Ala Leu Leu Ala Leu
        355                 360                 365

Ser Arg Asn Tyr Gln Lys Glu Trp Ser
    370                 375

<210> SEQ ID NO 60
<211> LENGTH: 371
<212> TYPE: PRT
<213> ORGANISM: Lactococcus lactis

<400> SEQUENCE: 60

Met Ser Lys Arg Ile Leu Ser Phe Val Trp Phe Phe Ile Val Ile Leu
1               5                   10                  15

Leu Phe Ile Phe Ser Val Met Tyr Ile Lys Glu Glu Ser Ser Gln His
            20                  25                  30

Asn Lys Gln Gln Ile Tyr Asn Gln Trp Gln Tyr Lys Tyr Ile Val Lys
        35                  40                  45

Thr Ser Gln Gly Ser Tyr Val Asn Thr Ser Ala Asn Ser Lys Asn Arg
    50                  55                  60

Ile Ala Leu Ser Glu Ala Gln Gly Tyr Gly Met Leu Ile Ser Val Leu
```

```
                65                  70                  75                  80
Asn Asn Gln Asp Lys Ala Ser Glu Ser Gln Phe His Asp Phe Phe Thr
                85                  90                  95

Tyr Tyr Thr His His Arg Ile Lys Gly Thr Ser Leu Met Ser Trp Arg
            100                 105                 110

Tyr Ile Asn Gly Ser Lys Thr Gln Lys Gln Thr Asp Leu Asn Asn Asn
            115                 120                 125

Ala Thr Asp Gly Asp Leu Tyr Ile Ala Tyr Ala Leu Ile Leu Ala Ser
130                 135                 140

Glu Lys Trp Ser Gln His Lys Pro Leu Tyr Lys Thr Thr Ala Lys Gln
145                 150                 155                 160

Ile Leu Asn Asp Ile Leu Thr Tyr Asn Val Asn His Asn Asn Asn Ile
                165                 170                 175

Leu Thr Val Gly Asn Trp Ala Asn Ala Ser Ser Lys Tyr Gln Asn Leu
            180                 185                 190

Met Arg Thr Ser Asp Val Leu Pro Ser Phe Phe Asp Lys Phe Tyr Lys
            195                 200                 205

Phe Ser Asn Asn Ser Gln Trp Arg Leu Ile Lys Thr Lys Met Leu Asp
            210                 215                 220

Ser Leu Tyr Gln Ala Ser His Lys Ser Lys Val Gly Leu Val Pro Asp
225                 230                 235                 240

Phe Ile Gln Val Thr Asn Gly Asn Lys Val His Ser Leu Ser Gln Asp
                245                 250                 255

Lys Asn Leu Lys Leu Asn Lys His Asp Asp Tyr Tyr Tyr Asn Ala
            260                 265                 270

Phe Arg Val Pro Tyr Asn Leu Ala Ile Asn Lys Asn Lys Ser Ser Lys
            275                 280                 285

Glu Lys Gln Val Leu Thr Glu Met Met Lys Phe Phe Ser Ser Leu Gln
            290                 295                 300

Lys Ile Ser Gly Gly Tyr Thr Met Ser Gly Lys Pro Leu Asn Lys Phe
305                 310                 315                 320

Gln Ser Thr Ser Ile Ser Ala Pro Ile Phe Tyr Ala Ser Ser Ile Ser
                325                 330                 335

Gln Arg Trp Gln Thr Leu His Arg Glu Gln Ser Phe Val Leu Asp Tyr
            340                 345                 350

Gly Ser Leu Asn His Asn Tyr Tyr Asp Asp Thr Leu Leu Val Leu Val
            355                 360                 365

Leu Phe Ser
    370

<210> SEQ ID NO 61
<211> LENGTH: 419
<212> TYPE: PRT
<213> ORGANISM: Methylobacterium extorquens

<400> SEQUENCE: 61

Met Arg Pro Pro Arg Thr Pro Arg Arg Ile Gly Trp Ala Phe Ala Ser
1               5                   10                  15

Ala Leu Ala Leu Ala Ala Ala Gly Ser Ala Ala Ala Gln Thr Thr Pro
            20                  25                  30

Gln Pro Ala Ser Pro Gln Pro Ala Ser Pro Glu Thr Ser Ser Gln Met
            35                  40                  45

Pro Gln Pro Ala Pro Gln Pro Ala Pro Gln Gln Thr Glu Ala Thr Thr
50                  55                  60
```

-continued

Val Pro Pro Ala Thr Ala Leu Pro Gly Pro Pro Arg Ala Glu Thr Ser
 65                  70                  75                  80

Ala Arg Thr Asp Ser Gly Pro Leu Leu Ala Asn Thr Leu Gly Asp Asp
                 85                  90                  95

Ala Ala Trp Arg Ala Tyr Arg Ser Arg Phe Ile Thr Glu Gln Gly Arg
            100                 105                 110

Ile Val Asp Thr Ala Asn Gly Leu Ile Ser His Ser Glu Gly Gln Gly
        115                 120                 125

Tyr Gly Met Leu Leu Ala Val Ala Ala Gly Asp Arg Ser Thr Phe Glu
    130                 135                 140

Arg Ile Trp Gly Trp Thr Arg Ala Asn Leu Met Val Arg Ser Asp Glu
145                 150                 155                 160

Leu Leu Ala Trp Arg Trp Ala Pro Asp His Arg Pro Ala Val Ser Asp
                165                 170                 175

Met Asn Asn Ala Thr Asp Gly Asp Ile Leu Val Ala Trp Ala Leu Thr
            180                 185                 190

Glu Ala Ala Glu Ala Trp Gly Glu Pro Ser Tyr Arg Thr Ala Ala Arg
        195                 200                 205

Arg Ile Ala Val Glu Phe Gly Arg Lys Thr Ile Leu Phe Lys Asp Pro
    210                 215                 220

His Gly Pro Val Leu Leu Pro Ala Val Ser Gly Phe Ser Ala Arg Glu
225                 230                 235                 240

Arg Ala Asp Gly Pro Leu Ile Asn Leu Ser Tyr Trp Val Phe Pro Ala
                245                 250                 255

Phe Gln Arg Leu Pro Ile Val Ala Pro Glu Tyr Asp Trp Ala Ser Leu
            260                 265                 270

Ile Arg Ser Gly Val Asp Phe Leu Arg Gln Ser Arg Phe Gly Pro Ser
        275                 280                 285

Ser Leu Pro Thr Glu Trp Ile Ser Ala Lys Asp Ser Leu Arg Pro Ala
    290                 295                 300

Asp Gly Phe Pro Pro Leu Phe Ser Tyr Asn Ala Ile Arg Val Pro Leu
305                 310                 315                 320

Tyr Leu Ala Trp Ala Gly Val Gly Arg Pro Glu Asp Tyr Ala Pro Phe
                325                 330                 335

Lys Thr Leu Trp Gly Gly Ile Glu Arg Glu Arg Leu Pro Ile Val Asp
            340                 345                 350

Thr Arg Asp Gly Gln Pro Val Glu Trp Leu Ser Glu Pro Gly Tyr Met
        355                 360                 365

Ala Ile Ser Ala Ile Thr Ala Cys Ala Ala Asp Gly Thr Pro Phe Pro
    370                 375                 380

Glu Ala Leu Arg Thr Val Gln Asp Asn Gln Asn Tyr Tyr Pro Ala Thr
385                 390                 395                 400

Leu Gln Leu Leu Ser Leu Ile Ala Ala Arg Met Arg Tyr Pro Ser Cys
                405                 410                 415

Val Lys Ser

<210> SEQ ID NO 62
<211> LENGTH: 371
<212> TYPE: PRT
<213> ORGANISM: Pseudomonas putida

<400> SEQUENCE: 62

Met Met Arg Gln Met Leu Val Gly Leu Val Ala Leu Gly Leu Pro Val
1               5                   10                  15

Phe Ala Asn Ala Glu Ala Ala Cys Ser Trp Pro Ala Trp Glu Arg Phe
            20                  25                  30

Lys Ala Glu Leu Val Ser Ala Asp Gly Arg Val Ile Asp Pro Ser Asp
        35                  40                  45

Ala Arg Leu Ile Thr Thr Ser Glu Gly Gln Ser Tyr Gly Leu Phe Phe
    50                  55                  60

Ala Leu Val Gly Asn Asp Arg Asp Ala Phe Ala Gln Leu Leu Arg Trp
65                  70                  75                  80

Thr Gly Asn Asn Leu Ala Glu Gly Asp Leu Ala Arg His Leu Pro Ala
                85                  90                  95

Trp Leu Trp Gly Arg Asn Glu Gln Gln Gln Trp Gln Val Leu Asp Ala
            100                 105                 110

Asn Asn Ala Ser Asp Ala Asp Leu Trp Ile Ala Tyr Ser Leu Leu Glu
        115                 120                 125

Ala Gly Arg Leu Trp Gln Gln Pro Ala Tyr Thr Gln Leu Gly Gln Arg
    130                 135                 140

Leu Leu Trp Arg Ile Ala Ala Gln Thr Val Arg Lys Leu Pro Gly Leu
145                 150                 155                 160

Gly Val Met Leu Leu Pro Gly Asp Tyr Gly Phe Glu Asp Ala Gln Gly
                165                 170                 175

Thr Arg Leu Asn Pro Ser Tyr Leu Pro Leu Gln Leu Phe Asp Arg Phe
            180                 185                 190

Ser Glu Val Asp Pro Leu Trp Gly Glu Leu Ala Ala Asn Thr Arg Arg
        195                 200                 205

Leu Trp Leu Ala Ser Ser Pro Lys Gly Phe Ala Pro Asp Trp Leu Leu
    210                 215                 220

Trp Thr Pro Ala Gly Lys Pro Ala Ala Asp Pro Gln His Gly Ser Ala
225                 230                 235                 240

Gly Asp Tyr Asp Ala Ile Arg Val Tyr Leu Trp Val Gly Met Leu Ala
                245                 250                 255

Lys Asp Ala Val Gln Arg Asn Glu Leu Val Ala His Tyr Ala Pro Met
            260                 265                 270

Ala Ala Leu Thr Gln Arg Gln Gly Leu Pro Pro Glu Arg Ala Asp Ala
        275                 280                 285

Arg Ser Gly Glu Ala Ser Gly Gln Gly Pro Ala Gly Phe Ser Ala Ala
    290                 295                 300

Leu Leu Pro Leu Leu Ala Ala Ser Pro Ala His Val Ala Gly Leu Ala
305                 310                 315                 320

Ala Gln Arg Gln Arg Leu Arg Asp Gln Pro Val Glu Ala Lys Ala Tyr
                325                 330                 335

Tyr Ser Gln Val Leu Val Leu Phe Gly Gln Gly Trp Asp Glu Ala Arg
            340                 345                 350

Tyr Arg Phe Asp Pro His Gly Arg Leu Leu Pro Ala Trp Ser Ala Pro
        355                 360                 365

Cys Asn Glu
    370

<210> SEQ ID NO 63
<211> LENGTH: 393
<212> TYPE: PRT
<213> ORGANISM: Methylobacterium sp. 4-46

<400> SEQUENCE: 63

Met Arg Ser Phe Leu Arg Leu Ala Ala Thr Ile Leu Ile Leu Gly Ser
1               5                   10                  15

Ala Ala Leu Gly Gly Ala Arg Pro Gly Leu Ala Gln Gln Pro Gly Ala
            20                  25                  30

Ala Glu Pro Pro Arg Ala Arg Asp Ala Lys Asn Arg Asp Gly Glu
        35                  40                  45

Ser Arg Thr Gly Glu Asn Arg Thr Gly Glu Pro Ala Ser Leu His Asn
 50                  55                  60

Ala Leu Gly Asn Gly Ala Ala Trp Arg Ala Tyr Lys Ala Arg Phe Val
 65                  70                  75                  80

Thr Asp Gln Gly Arg Val Val Asp Thr Ala Asn Gly Arg Ile Ser His
                 85                  90                  95

Ser Glu Gly Gln Gly Tyr Gly Met Leu Leu Ala Val Ala Ala Gly Asp
            100                 105                 110

Arg Asp Ala Phe Gln Arg Ile Trp Asp Trp Thr Arg Ala Asn Leu Met
            115                 120                 125

Val Arg Asp Asp Ser Leu Leu Ala Trp Arg Trp Glu Pro Asp Lys Arg
130                 135                 140

Pro Gly Val Ala Asp Met Asn Asn Ala Thr Asp Gly Asp Leu Leu Val
145                 150                 155                 160

Ala Trp Ala Leu Ile Glu Ala Ala Asp Ala Trp Gln Asp Glu Gly Tyr
                165                 170                 175

Arg Leu Ala Ala Arg Arg Ile Ala Val Asp Ile Gly Arg Arg Thr Val
            180                 185                 190

Leu Phe Arg Ser Glu Gly Ala Ala Leu Leu Pro Gly Met Ala Gly
            195                 200                 205

Phe Ser Ala Glu Asp Arg Ala Asp Gly Pro Val Ile Asn Leu Ser Tyr
        210                 215                 220

Trp Ile Phe Pro Ala Leu Ala Arg Leu Pro Ala Val Ala Pro Glu Phe
225                 230                 235                 240

Asp Trp Ala Arg Leu Ser Ala Ala Gly Leu Asp Leu Ala Leu Arg Ala
                245                 250                 255

Arg Phe Gly Glu Ala Ala Leu Pro Val Glu Trp Thr Ser Leu Arg Gly
            260                 265                 270

Gly Glu Pro Lys Ala Ala Gly Phe Pro Val Phe Ser Tyr Asn
            275                 280                 285

Ala Val Arg Val Pro Leu Tyr Leu Ala Met Ala Gly Ile Ala Glu Arg
        290                 295                 300

Arg Tyr Tyr Ala Pro Phe Val Lys Ala Trp Ala Glu Val Gly Ala Ser
305                 310                 315                 320

Gly Leu Pro Val Val Asp Thr Ala Ser Asn Asp Val Val Gly Arg Met
                325                 330                 335

Gln Glu Pro Gly Tyr Leu Ala Val Ala Ala Leu Thr Ala Cys Ala Ala
            340                 345                 350

Gly Thr Ala Ser Leu Pro Pro Ala Leu Pro Asp Pro Thr Ser Pro Gln
            355                 360                 365

Asn Tyr Tyr Pro Ala Thr Leu Gln Leu Leu Ala Leu Ala Ala Val Asn
        370                 375                 380

Met Arg Tyr Ala Ser Cys Leu Gly Arg
385                 390

<210> SEQ ID NO 64
<211> LENGTH: 369
<212> TYPE: PRT
<213> ORGANISM: Escherichia albertii

<400> SEQUENCE: 64

| Met | Met | Asn | Val | Leu | Arg | Asn | Gly | Ile | Val | Thr | Met | Leu | Leu | Gln | Ala |
|---|---|---|---|---|---|---|---|---|---|---|---|---|---|---|---|
| 1 | | | | 5 | | | | | 10 | | | | | 15 | |

| Ala | Phe | Ser | Val | Gln | Ala | Ala | Cys | Asn | Trp | Pro | Ala | Trp | Glu | Gln | Phe |
|---|---|---|---|---|---|---|---|---|---|---|---|---|---|---|---|
| | | | 20 | | | | | 25 | | | | | 30 | | |

| Lys | Lys | Asp | Tyr | Ile | Ser | Gln | Glu | Gly | Arg | Val | Ile | Asp | Pro | Ser | Asp |
|---|---|---|---|---|---|---|---|---|---|---|---|---|---|---|---|
| | | | 35 | | | | | 40 | | | | | 45 | | |

| Ala | Arg | Lys | Ile | Thr | Thr | Ser | Glu | Gly | Gln | Ser | Tyr | Gly | Met | Phe | Phe |
|---|---|---|---|---|---|---|---|---|---|---|---|---|---|---|---|
| | 50 | | | | | 55 | | | | | 60 | | | | |

| Ala | Leu | Ala | Ala | Asn | Asp | Arg | Ala | Ala | Phe | Asp | Asn | Leu | Leu | Asp | Trp |
|---|---|---|---|---|---|---|---|---|---|---|---|---|---|---|---|
| 65 | | | | | 70 | | | | | 75 | | | | | 80 |

| Thr | Gln | Asn | Asn | Leu | Ala | Gln | Gly | Ser | Leu | Lys | Glu | His | Leu | Pro | Ala |
|---|---|---|---|---|---|---|---|---|---|---|---|---|---|---|---|
| | | | | 85 | | | | | 90 | | | | | 95 | |

| Trp | Leu | Trp | Gly | Lys | Lys | Glu | Asn | Thr | Lys | Trp | Glu | Val | Leu | Asp | Ser |
|---|---|---|---|---|---|---|---|---|---|---|---|---|---|---|---|
| | | | 100 | | | | | 105 | | | | | 110 | | |

| Asn | Ser | Ala | Ser | Asp | Gly | Asp | Ile | Trp | Met | Ala | Trp | Ser | Leu | Leu | Glu |
|---|---|---|---|---|---|---|---|---|---|---|---|---|---|---|---|
| | | | 115 | | | | | 120 | | | | | 125 | | |

| Ala | Gly | Arg | Leu | Trp | Lys | Glu | Gln | Arg | Tyr | Thr | Asp | Ile | Gly | Ser | Ala |
|---|---|---|---|---|---|---|---|---|---|---|---|---|---|---|---|
| | 130 | | | | | 135 | | | | | 140 | | | | |

| Leu | Leu | Lys | Arg | Ile | Ala | Gln | Glu | Glu | Val | Val | Thr | Val | Pro | Gly | Leu |
|---|---|---|---|---|---|---|---|---|---|---|---|---|---|---|---|
| 145 | | | | | 150 | | | | | 155 | | | | | 160 |

| Gly | Ser | Met | Leu | Leu | Pro | Gly | Lys | Val | Gly | Phe | Val | Glu | Asp | Asn | Thr |
|---|---|---|---|---|---|---|---|---|---|---|---|---|---|---|---|
| | | | | 165 | | | | | 170 | | | | | 175 | |

| Trp | Arg | Phe | Asn | Pro | Ser | Tyr | Leu | Pro | Pro | Thr | Leu | Ala | His | Tyr | Phe |
|---|---|---|---|---|---|---|---|---|---|---|---|---|---|---|---|
| | | | 180 | | | | | 185 | | | | | 190 | | |

| Thr | Arg | Phe | Gly | Ala | Pro | Trp | Thr | Thr | Leu | Arg | Glu | Thr | Asn | Gln | Arg |
|---|---|---|---|---|---|---|---|---|---|---|---|---|---|---|---|
| | | | 195 | | | | | 200 | | | | | 205 | | |

| Leu | Leu | Leu | Glu | Thr | Ala | Pro | Lys | Gly | Phe | Ser | Pro | Asp | Trp | Val | Arg |
|---|---|---|---|---|---|---|---|---|---|---|---|---|---|---|---|
| | 210 | | | | | 215 | | | | | 220 | | | | |

| Tyr | Glu | Lys | Asp | Lys | Gly | Trp | Gln | Leu | Lys | Ala | Glu | Lys | Thr | Leu | Ile |
|---|---|---|---|---|---|---|---|---|---|---|---|---|---|---|---|
| 225 | | | | | 230 | | | | | 235 | | | | | 240 |

| Ser | Ser | Tyr | Asp | Ala | Ile | Arg | Val | Tyr | Met | Trp | Val | Gly | Met | Met | Pro |
|---|---|---|---|---|---|---|---|---|---|---|---|---|---|---|---|
| | | | | 245 | | | | | 250 | | | | | 255 | |

| Asp | Ser | Asp | Pro | Gln | Lys | Ala | Arg | Leu | Leu | Ser | Arg | Phe | Lys | Pro | Met |
|---|---|---|---|---|---|---|---|---|---|---|---|---|---|---|---|
| | | | 260 | | | | | 265 | | | | | 270 | | |

| Ala | Thr | Phe | Thr | Glu | Lys | Asn | Gly | Tyr | Pro | Pro | Glu | Lys | Val | Asp | Val |
|---|---|---|---|---|---|---|---|---|---|---|---|---|---|---|---|
| | | | 275 | | | | | 280 | | | | | 285 | | |

| Ala | Met | Gly | Lys | Ala | Gln | Gly | Thr | Gly | Pro | Glu | Gly | Phe | Ser | Ala | Ala |
|---|---|---|---|---|---|---|---|---|---|---|---|---|---|---|---|
| | 290 | | | | | 295 | | | | | 300 | | | | |

| Met | Leu | Pro | Phe | Leu | Gln | Asn | Arg | Asp | Ala | Gln | Ala | Val | Gln | Arg | Gln |
|---|---|---|---|---|---|---|---|---|---|---|---|---|---|---|---|
| 305 | | | | | 310 | | | | | 315 | | | | | 320 |

| Arg | Val | Ala | Asp | Asn | Leu | Pro | Gly | Ser | Asp | Ala | Tyr | Tyr | Asn | Ser | Val |
|---|---|---|---|---|---|---|---|---|---|---|---|---|---|---|---|
| | | | | 325 | | | | | 330 | | | | | 335 | |

| Leu | Thr | Leu | Phe | Gly | Gln | Gly | Trp | Asp | Gln | His | Arg | Phe | Arg | Phe | Ser |
|---|---|---|---|---|---|---|---|---|---|---|---|---|---|---|---|
| | | | 340 | | | | | 345 | | | | | 350 | | |

| Thr | Lys | Gly | Glu | Leu | Leu | Pro | Asp | Trp | Gly | Gln | Glu | Cys | Ala | Asn | Ser |
|---|---|---|---|---|---|---|---|---|---|---|---|---|---|---|---|
| | | | 355 | | | | | 360 | | | | | 365 | | |

His

<210> SEQ ID NO 65
<211> LENGTH: 476
<212> TYPE: PRT
<213> ORGANISM: Burkholderia graminis

<400> SEQUENCE: 65

```
Met Val Lys Arg Thr Val Gln Val Arg Ala Asn Gly Val Gln Ser Pro
1               5                   10                  15
Ser Val Gly Val Ala Arg Ala Ala Cys Ala Arg Asn Ala Arg Arg Val
            20                  25                  30
Ala Ser Gly Val Cys Gly Ala Val Leu Ala Trp Leu Ala Ala Gly Val
        35                  40                  45
Ala Leu Ala Pro Ala Ser Val Ala Ala Ala Ser Ala Ala Ser Ser
    50                  55                  60
Ala Ala Asn Ser Ala Ala Ser Ser Ala Ala Ala Ser Ala Gly Thr Ser
65                  70                  75                  80
Ala Thr Ser Ser Ala Ala Thr Ser Ala Thr Gly Ala Thr Gly Thr Ala
                85                  90                  95
Ala Cys Pro Ala Gln Ala Phe Arg Ala Phe Asp Asn Ala Gly Gly Ala
            100                 105                 110
Gln Ser Thr Ala Leu Ala Val Ser Ala Asp Trp Pro Ala Trp Glu Gln
        115                 120                 125
Phe Arg Arg Lys Phe Val Ser Pro Asp Gly Arg Val Ile Asp Val Gly
    130                 135                 140
Ser Asp Asp Arg Thr Val Ser Glu Gly Gln Ser Tyr Gly Leu Phe
145                 150                 155                 160
Phe Ala Leu Val Ala Asn Asp Arg Ala Ser Phe Asp Arg Leu Leu His
                165                 170                 175
Trp Thr Glu Asn Asn Leu Ala Ala Gly Asp Leu Thr Ala His Leu Pro
            180                 185                 190
Ala Trp Leu Trp Gly Arg Gly Pro Asp Gly Lys Trp Gly Val Leu Asp
        195                 200                 205
Ser Asn Ala Ala Ser Asp Ala Asp Leu Trp Ile Ala Tyr Ala Leu Leu
    210                 215                 220
Glu Ala Gly Arg Val Trp Asn Glu Arg Ser Tyr Thr Ala Arg Gly Ala
225                 230                 235                 240
Ala Leu Ala Arg Arg Val Leu Asp Glu Glu Thr Ala Arg Val Pro Thr
                245                 250                 255
Leu Gly Leu Thr Leu Leu Pro Gly Pro Thr Gly Phe His Pro Glu Ala
            260                 265                 270
Asp Leu Trp Arg Val Asn Pro Ser Tyr Ala Pro Val Gln Val Leu Arg
        275                 280                 285
Gly Leu Ala Ser Ala Leu Pro Ser Asp Arg Arg Trp Gln Ala Leu Val
    290                 295                 300
Asp Ser Ser Ala Arg Met Leu Val Asp Ser Ala Pro Gln Gly Phe Ser
305                 310                 315                 320
Pro Asp Trp Ser Leu Tyr Arg Ala Gly Lys Gly Phe Leu Pro Asp Pro
                325                 330                 335
Ala Thr His Ala Glu Ser Ala Tyr Asn Ala Ile Arg Val Tyr Leu Trp
            340                 345                 350
Ile Gly Met Leu Asn Gly Ser Asp Pro Leu Lys Ser Arg Leu Leu Asn
        355                 360                 365
His Phe Thr Pro Phe Ala Arg Tyr Ile Ala Glu His Gly Ala Pro Pro
    370                 375                 380
Glu Arg Ile Asp Thr Thr Asp Ala Lys Pro Gly Ala Asn Asp Gly Asn
385                 390                 395                 400
Ala Gly Phe Ser Ala Ala Ile Pro Phe Leu Ile Ala Arg Gly Glu
                405                 410                 415
```

```
Thr Ser Ile Ala Asp Arg Gln Ser Ala Arg Val Asp Gln Leu Asp Ala
            420                 425                 430

Gln Thr Ala Pro Gly Tyr Tyr Thr Ser Val Leu Thr Leu Phe Gly Leu
        435                 440                 445

Gly Trp Arg Asp Gly Arg Tyr Arg Phe Ala Ala Asp Gly Ser Leu Asp
    450                 455                 460

Leu Pro Trp Ser Ser Val Cys Arg Pro Ala Lys Arg
465                 470                 475

<210> SEQ ID NO 66
<211> LENGTH: 513
<212> TYPE: PRT
<213> ORGANISM: Burkholderia pseudomallei

<400> SEQUENCE: 66

Met Ala Arg Gln Ala Gly Arg Asp Glu Gly Val Gly Arg Ile Gly Arg
1               5                   10                  15

Ile Gly Arg Glu Ala Gly Asp Ala Arg Glu Ala Ala Gly Ala Gly Glu
            20                  25                  30

Ala Cys Gly Arg Arg His Ala Arg Ala Asp Thr Trp Ala Arg Arg Ala
        35                  40                  45

Ser Arg Ala Ser Arg Gly Trp Arg Thr Phe Trp Arg Gly Arg Gly Gly
    50                  55                  60

Val Arg Ala Val Val Ala Ser Val Val Ala Ser Phe Ser Val Met Ala
65                  70                  75                  80

Phe Ala Ala Ala Thr Leu Pro Val Ser Trp Arg Val Ala Ala Ala Ala
                85                  90                  95

Glu Arg Thr Arg Ser Gly Gly Glu Arg Ala Gly Gly Leu Arg Asp Thr
            100                 105                 110

Ala Gly Leu Ile Glu Ile Ser Ala Ala Pro Ala Ser Thr Pro Ile
        115                 120                 125

Pro Ala Ala Pro Arg Arg Phe Ala Gln Pro Phe Ala Gln Thr Phe Ala
    130                 135                 140

Gln Pro Ala Arg Ala Phe Ala Val Ala Ser Ala Cys Ala Pro Ser Trp
145                 150                 155                 160

Pro Arg Trp Asp Arg Phe Lys Arg Asp Phe Val Ser Ala Asp Gly Arg
                165                 170                 175

Val Ile Asp Val Gly Ser Ala Asp Glu Arg Thr Val Ser Glu Gly Gln
            180                 185                 190

Ala Tyr Gly Leu Phe Phe Ala Leu Val Ala Asn Asp Arg Ala Ala Phe
        195                 200                 205

Asp Ala Leu Leu Arg Trp Thr Glu Asp Asn Leu Ala Gln Gly Asp Leu
    210                 215                 220

Ser Ala Arg Leu Pro Ala Trp Leu Trp Gly Arg Ala Ala Asp Gly Ala
225                 230                 235                 240

Trp Arg Val Leu Asp Ala Asn Ala Ala Ser Asp Ala Asp Leu Trp Leu
                245                 250                 255

Ala Tyr Ala Leu Leu Glu Ala Gly Arg Leu Trp Arg Glu Arg Ser Tyr
            260                 265                 270

Thr Ala Arg Gly Ala Leu Leu Ala Lys Arg Val Leu Asp Glu Glu Thr
        275                 280                 285

Ala Thr Leu Pro Gly Leu Gly Leu Val Leu Leu Pro Gly Pro Thr Gly
    290                 295                 300

Phe Arg Pro Ala Arg Asp Ala Trp Arg Leu Asn Pro Ser Tyr Ser Pro
```

```
                305                 310                 315                 320
        Pro Gln Ala Ile Arg Gly Ile Gly Ala His Val Pro Asp Asp Ala Arg
                        325                 330                 335

Trp Ala Arg Leu Ala Ala Gly Val Gly Arg Val Leu Thr Asp Ser Ala
                        340                 345                 350

Pro Arg Gly Phe Ala Pro Asp Trp Ala Leu Tyr Arg Ala Gly Arg Gly
                        355                 360                 365

Phe Glu Pro Asp Ala Glu Thr His Ala Val Ser Ala Tyr Asn Ala Ile
                370                 375                 380

Arg Val Tyr Leu Trp Ala Gly Met Leu Asp Ala Gly Asp Pro Leu Ala
        385                 390                 395                 400

Arg Pro Leu Val Ala His Phe Ala Pro Phe Ala Glu His Val Ala Ala
                        405                 410                 415

His Gly Ala Pro Pro Glu Ala Val Asp Ala Thr Thr Gly Ala Ala Ala
                        420                 425                 430

Pro Arg Asp Gly Asn Ala Gly Phe Ser Ala Ala Val Pro Phe Leu
                        435                 440                 445

Glu Ala Arg Gly Glu Arg Ala Ser Ala Asp Ala Gln Leu Ala Arg Val
                450                 455                 460

Ala Arg Leu Glu Arg Glu Thr Ala Ser Gly Tyr Tyr Ala Asn Val Leu
        465                 470                 475                 480

Thr Leu Phe Gly Leu Gly Trp Arg Asp Gly Arg Tyr Arg Phe Ala Ala
                        485                 490                 495

Asp Gly Thr Leu Arg Val Arg Trp Ser Glu Pro Cys Ser Thr Pro Ala
                        500                 505                 510

Arg

<210> SEQ ID NO 67
<211> LENGTH: 371
<212> TYPE: PRT
<213> ORGANISM: Yersinia pseudotuberculosis

<400> SEQUENCE: 67

Met Val Val Met Phe Lys His Leu Ala Ser Met Phe Leu Leu Leu Ala
        1               5                   10                  15

Ser Phe Ser Leu Ala Ala Thr Ser Asn Trp Pro Ala Trp Gln Gln Phe
                        20                  25                  30

Lys Gln Asp Tyr Ile Ser Glu Gly Gly Arg Ile Ile Asp Pro Gly Ser
                    35                  40                  45

Pro Ser Lys Ile Thr Thr Ser Glu Gly Gln Ser Tyr Gly Leu Phe Phe
                50                  55                  60

Ala Leu Val Ala Asp Asp Gln Pro Met Phe Glu Arg Leu Leu Ala Trp
        65                  70                  75                  80

Thr Glu Asn Asn Leu Ala Ala Gly Asp Leu Thr Ser Arg Leu Pro Ala
                        85                  90                  95

Trp Leu Trp Gly Gln Asn Ser Gly Asn Asn Trp Asp Ile Leu Asp Pro
                        100                 105                 110

Asn Ser Ala Ser Asp Ala Asp Ile Leu Ile Ala Tyr Asn Leu Leu Glu
                        115                 120                 125

Ala Gly Arg Leu Trp Gly Asn Arg Arg Tyr Leu Ile Met Gly Thr Leu
                    130                 135                 140

Leu Leu Gln Arg Ile Ala Gln Glu Glu Val Met Asp Ile Pro Gly Leu
        145                 150                 155                 160

Gly Gln Met Leu Leu Pro Gly Lys Ile Gly Phe Asn Asp Glu Asp Thr
```

```
                     165                 170                 175
Trp Arg Leu Asn Pro Ser Tyr Leu Pro Pro Gln Leu Leu Ala Arg Phe
                180                 185                 190

Ser Ser Ile Asp Gly Pro Trp Glu Ala Met Val Glu Val Asn Gln Arg
            195                 200                 205

Met Trp Leu Glu Thr Ala Pro Asn Gly Phe Ser Pro Asp Trp Val Val
        210                 215                 220

Trp Gln Lys Gly Lys Gly Trp Gln Pro Asp Thr Ile Lys Pro Asp Val
225                 230                 235                 240

Gly Ser Asn Asp Ala Ile Leu Val Tyr Leu Trp Ala Gly Met Leu Ala
                245                 250                 255

Met Asp Ser Pro Gln Lys Ala Glu Leu Ile Ala Arg Phe Gln Pro Met
            260                 265                 270

Ala Val Ile Thr Gln Gln Gln Gly Leu Pro Pro Phe Thr Thr Asn Ser
        275                 280                 285

Asp Asn Gly Lys Thr Asn Gly Asp Gly Ser Val Gly Phe Ser Ala Ala
    290                 295                 300

Leu Leu Pro Phe Leu Ala Ser Ser Pro Glu Pro Phe Asn Gln Gln Thr
305                 310                 315                 320

Leu Asn Leu Gln Gln Arg Arg Val Gln Asn Ser Pro Pro Gly Ala Asp
                325                 330                 335

Asp Tyr Tyr Ser Ala Ile Leu Thr Leu Phe Gly Gln Gly Trp Leu Gln
            340                 345                 350

His Arg Tyr His Phe Thr His Gln Gly Glu Leu Gln Pro Ser Trp His
        355                 360                 365

Arg Gln Arg
    370

<210> SEQ ID NO 68
<211> LENGTH: 409
<212> TYPE: PRT
<213> ORGANISM: Burkholderia cenocepacia

<400> SEQUENCE: 68

Met Ala Arg Ala Met Thr Lys Arg Arg Ala Met Gln Pro Ala Arg Arg
1               5                   10                  15

Val Gly Ala Thr Leu Ala Leu Ala Val Ala Val Thr Cys Ala Ala Ala
            20                  25                  30

Gly Met Ala Thr Arg Ala His Ala Ala Ala Gly Ala Ala Asp Ala
        35                  40                  45

Ala Ser Ala Gly Cys Ser Ala Ala Trp Pro Arg Trp Asp Ala Phe Lys
50                  55                  60

Arg Asp Phe Ile Ser Ala Asp Gly Arg Val Ile Asp Val Gly Ser Ala
65                  70                  75                  80

Asp Ser Arg Thr Val Ser Glu Gly Gln Ala Tyr Gly Leu Phe Phe Ala
                85                  90                  95

Leu Val Ala Asn Asp Arg Arg Met Phe Asp Thr Ile Leu Ala Trp Thr
            100                 105                 110

Glu Asn Asn Leu Ala Gln Gly Asp Leu Ser Ala His Leu Pro Ala Trp
        115                 120                 125

Leu Trp Gly Arg Ala Pro Asp Gly Ala Trp Arg Val Leu Asp Ala Asn
    130                 135                 140

Pro Ala Ser Asp Ala Asp Leu Trp Ile Ala Tyr Ala Leu Val Glu Ala
145                 150                 155                 160
```

```
Gly Arg Leu Trp His Glu Arg Ser Tyr Thr Ala Arg Gly Ala Leu Leu
            165                 170                 175

Ala Lys Arg Val Leu Asp Ala Glu Thr Ala Thr Val Pro Gly Leu Gly
        180                 185                 190

Leu Thr Leu Leu Pro Gly Pro Thr Gly Phe Lys Leu Ala Asn Gly Gln
    195                 200                 205

Trp Arg Val Asn Pro Ser Tyr Ser Pro Pro Gln Val Ile Arg Ala Leu
210                 215                 220

Gly Ala Arg Leu Pro Asp Asp Arg Arg Trp Ala Leu Ala Ser Ser
225                 230                 235                 240

Thr Ala Arg Val Leu Leu Asp Thr Ala Pro Lys Gly Phe Ser Pro Asp
                245                 250                 255

Trp Ala Leu Tyr Arg Ala Gly Asn Gly Phe Gly Pro Asp Pro Gln Thr
                260                 265                 270

His Ala Glu Ser Ala Tyr Asn Ala Ile Arg Val Tyr Leu Trp Ala Gly
            275                 280                 285

Met Leu Asp Arg Ala Asp Pro Leu Ala Ala Pro Leu Leu Ala Lys Phe
        290                 295                 300

Ala Pro Phe Ala Asp His Val Ala Ala His Gly Ala Pro Pro Glu Lys
305                 310                 315                 320

Val Asp Thr Thr Thr Gly Val Ala Gly Pro Asn Asp Gly Asn Gly Gly
                325                 330                 335

Phe Ser Ala Ala Ala Val Pro Phe Leu Asp Ala Arg Gly Gln His Ala
                340                 345                 350

Leu Ala Asp Ala Gln Ala Ala Arg Val Asp Thr Leu Ala Arg Gln Ser
            355                 360                 365

Ala Pro Gly Tyr Tyr Thr Ser Val Leu Thr Leu Phe Gly Leu Gly Trp
        370                 375                 380

Arg Asp Gly Arg Tyr Arg Phe Gly Ala Asp Gly Thr Leu Asp Thr Arg
385                 390                 395                 400

Trp Gly Gly Arg Ser Cys Ala Ala Arg
                405

<210> SEQ ID NO 69
<211> LENGTH: 370
<212> TYPE: PRT
<213> ORGANISM: Escherichia coli

<400> SEQUENCE: 69

Met Lys Met Asn Val Leu Arg Ser Gly Leu Val Thr Met Leu Leu Leu
1               5                   10                  15

Ala Ala Phe Ser Val Gln Ala Ala Cys Asn Trp Pro Ala Trp Glu Gln
            20                  25                  30

Phe Lys Lys Asp Tyr Ile Ser Gln Glu Gly Arg Val Ile Asp Pro Ser
        35                  40                  45

Asp Ala Arg Lys Ile Thr Thr Ser Glu Gly Gln Ser Tyr Gly Met Phe
    50                  55                  60

Phe Ala Leu Ala Ala Asn Asp Arg Ala Ala Phe Asp Asn Ile Leu Asp
65                  70                  75                  80

Trp Thr Gln Asn Asn Leu Ala Gln Gly Ser Leu Lys Glu Arg Leu Pro
                85                  90                  95

Ala Trp Leu Trp Gly Lys Lys Glu Asn Ser Lys Trp Glu Val Leu Asp
            100                 105                 110

Ser Asn Ser Ala Ser Asp Gly Asp Val Trp Met Ala Trp Ser Leu Leu
        115                 120                 125
```

Glu Ala Gly Arg Leu Trp Lys Glu Gln Arg Tyr Thr Asp Ile Gly Ser
        130                 135                 140

Ala Leu Leu Lys Arg Ile Ala Arg Glu Glu Val Val Thr Val Pro Gly
145                 150                 155                 160

Leu Gly Ser Met Leu Leu Pro Gly Lys Val Gly Phe Ala Glu Asp Asn
                165                 170                 175

Ser Trp Arg Phe Asn Pro Ser Tyr Leu Pro Pro Thr Leu Ala Gln Tyr
            180                 185                 190

Phe Thr Arg Phe Gly Ala Pro Trp Thr Thr Leu Arg Glu Thr Asn Gln
        195                 200                 205

Arg Leu Leu Leu Glu Thr Ala Pro Lys Gly Phe Ser Pro Asp Trp Val
    210                 215                 220

Arg Tyr Glu Lys Asp Lys Gly Trp Gln Leu Lys Ala Glu Lys Thr Leu
225                 230                 235                 240

Ile Ser Ser Tyr Asp Ala Ile Arg Val Tyr Met Trp Val Gly Met Met
                245                 250                 255

Pro Asp Ser Asp Pro Gln Lys Ala Arg Met Leu Asn Arg Phe Lys Pro
            260                 265                 270

Met Ala Thr Phe Thr Glu Lys Asn Gly Tyr Pro Pro Glu Lys Val Asp
        275                 280                 285

Val Ala Thr Gly Lys Ala Gln Gly Lys Gly Pro Val Gly Phe Ser Ala
    290                 295                 300

Ala Met Leu Pro Phe Leu Gln Asn Arg Asp Ala Gln Ala Val Gln Arg
305                 310                 315                 320

Gln Arg Val Ala Asp Asn Phe Pro Gly Ser Asp Ala Tyr Tyr Asn Tyr
                325                 330                 335

Val Leu Thr Leu Phe Gly Gln Gly Trp Asp Gln His Arg Phe Arg Phe
            340                 345                 350

Ser Thr Lys Gly Glu Leu Leu Pro Asp Trp Gly Gln Glu Cys Ala Asn
        355                 360                 365

Ser His
    370

<210> SEQ ID NO 70
<211> LENGTH: 384
<212> TYPE: PRT
<213> ORGANISM: Methylobacterium radiotolerans

<400> SEQUENCE: 70

Met Ser Arg Arg Asp Arg Ala Pro Leu Ala Ala Phe Leu Val Ala
1               5                   10                  15

Ala Met Leu Pro Ala Ala Ala Ser Thr Gln Asp Glu Pro Ala Val
            20                  25                  30

Pro Pro Ser Thr Ala Gln Pro Gly Thr Gln Pro Ala Gln Thr Ala Arg
        35                  40                  45

Ala Ala Ser Pro Gly Leu Ala Gly Lys Leu Gly Asn Asp Ala Ala Trp
    50                  55                  60

Arg Ala Tyr Arg Ser Arg Phe Ile Thr Asp Gln Gly Arg Val Val Asp
65                  70                  75                  80

Thr Ala Asn Gly Leu Ile Ser His Ser Glu Gly Gln Gly Tyr Gly Met
                85                  90                  95

Leu Leu Ala Val Ala Ala Gly Asp Arg Val Ser Phe Glu Arg Ile Trp
            100                 105                 110

Gly Trp Thr Arg Ala Asn Leu Met Val Arg Gly Asp Glu Leu Leu Ala

```
                115                 120                 125
Trp Arg Trp Ser Pro Asp Lys Arg Pro Ala Val Ser Asp Met Asn Asn
    130                 135                 140

Ala Thr Asp Gly Asp Ile Leu Val Ala Trp Ala Leu Thr Glu Ala Ala
145                 150                 155                 160

Glu Ala Trp Asn Glu Pro Ser Tyr Arg Thr Ala Ala Arg Arg Ile Ala
                165                 170                 175

Ile Glu Phe Gly Arg Lys Thr Ile Leu Phe Arg Asp Pro His Gly Ala
            180                 185                 190

Leu Leu Leu Pro Ala Val Ser Gly Phe Ser Ala Arg Glu Arg Pro Asp
        195                 200                 205

Gly Pro Leu Val Asn Leu Ser Tyr Trp Ile Phe Pro Ala Phe Pro Arg
    210                 215                 220

Leu Ala Leu Val Ala Pro Glu Tyr Asp Trp Ala Ala Leu Thr Arg Ser
225                 230                 235                 240

Gly Leu Ser Leu Leu Arg Gln Ser Arg Phe Gly Pro Ser Asn Leu Pro
                245                 250                 255

Thr Glu Trp Ile Ser Ala Lys Asp Ala Pro His Pro Ala Thr Gly Phe
            260                 265                 270

Pro Pro Leu Phe Ser Tyr Asn Ala Ile Arg Val Pro Leu Tyr Leu Ala
        275                 280                 285

Trp Ala Gly Leu Val Arg Pro Asp Asp Leu Ala Pro Phe Gln Ala Leu
    290                 295                 300

Trp Ser Ser Ser Asp Arg Glu Arg Leu Pro Ile Val Asp Thr Gly Asp
305                 310                 315                 320

Gly Arg Lys Val Glu Trp Leu Thr Glu Ala Gly Tyr Met Gly Ile Pro
                325                 330                 335

Ala Leu Val Ala Cys Ala Leu Asp Gly Thr Pro Phe Pro Glu Asp Ala
            340                 345                 350

Arg Gly Asp Ile Gly Asn Gln Asn Tyr Tyr Pro Ala Thr Leu Ser Leu
        355                 360                 365

Leu Ala Leu Thr Ala Ala Arg Met Arg Tyr Pro Ser Cys Leu Lys Ser
    370                 375                 380

<210> SEQ ID NO 71
<211> LENGTH: 367
<212> TYPE: PRT
<213> ORGANISM: Methylobacterium radiotolerans

<400> SEQUENCE: 71

Met Ser Val Leu Ile Ser Val Leu Leu Arg Gly Leu Ala Gly Leu Cys
1               5                   10                  15

Val Leu Thr Leu Leu Ala Ala Arg Pro Ala Leu Ala Ala Thr Ala Ser
            20                  25                  30

Ala Pro Pro Leu Ala Gly Thr Leu Arg Asn Ala Glu Ala Trp Arg Ala
        35                  40                  45

Tyr Lys Ala Arg Phe Val Ser Glu Gln Gly Arg Val Val Asp Thr Ala
    50                  55                  60

Asn Gly Gly Ile Ser His Ser Glu Gly Gln Gly Tyr Gly Met Leu Leu
65                  70                  75                  80

Ala Val Ala Ala Gly Asp Arg Glu Thr Phe Glu Arg Ile Trp Thr Trp
                85                  90                  95

Thr Arg Ala Asn Leu Met Val Arg Asp Asp Gln Leu Ile Ala Trp Arg
            100                 105                 110
```

```
Trp Glu Pro Asp Lys Arg Pro Ala Val Ala Asp Met Asn Asp Ala Ser
            115                 120                 125

Asp Gly Asp Leu Leu Val Ala Trp Ala Leu Thr Glu Ala Ala Glu Ala
130                 135                 140

Trp His Glu Pro Glu His Gln Val Ala Gly Arg Arg Ile Ala Val Glu
145                 150                 155                 160

Leu Gly Arg Lys Leu Leu Pro Arg Ala Pro Gln Gly Pro Leu Ile
                165                 170                 175

Leu Pro Ala Val Ala Gly Phe Ser Glu Asp Arg Ala Asp Gly Pro
                180                 185                 190

Val Val Asn Leu Ser Tyr Trp Val Phe Pro Ala Leu Asp Arg Val Gly
                195                 200                 205

Leu Leu Ala Pro Glu Phe Asp Trp Arg Ala Leu Ala Arg Ser Gly Arg
            210                 215                 220

Arg Leu Ile Ala Ala Ala Arg Phe Gly Ser Gln Arg Leu Pro Val Glu
225                 230                 235                 240

Trp Ile Ser Leu Ser Gly Ala Ala Pro Arg Pro Ala Glu Gly Phe Pro
                245                 250                 255

Ala Glu Phe Gly Tyr Asn Ala Leu Arg Ile Pro Leu Tyr Leu Ala Met
                260                 265                 270

Ala Gly Ile Thr Glu Pro Asp Leu Tyr Ala Pro Phe Leu Ala Leu Trp
            275                 280                 285

Gln Lys Pro Glu Ala Gly Leu Ala Leu Val Glu Thr Gly Thr Gly Arg
    290                 295                 300

Val Ala Ala Arg Leu Thr Glu Thr Gly Tyr Ala Ala Ile Pro Ala Leu
305                 310                 315                 320

Ala Ala Cys Ala Ser Arg Gly Ala Pro Phe Pro Ala Ala Leu Thr Arg
                325                 330                 335

Val Arg Ala Glu Ser Glu Asn Tyr Tyr Pro Val Thr Leu Gln Leu Leu
                340                 345                 350

Ala Leu Ala Ala Leu Asn Ala Arg Tyr Pro Ala Cys Ala Pro Arg
            355                 360                 365

<210> SEQ ID NO 72
<211> LENGTH: 359
<212> TYPE: PRT
<213> ORGANISM: Burkholderia ambifaria

<400> SEQUENCE: 72

Met Gln Cys Gly Ala Ala Trp Pro Arg Trp Asp Ala Phe Lys Arg Asp
1               5                   10                  15

Phe Val Ser Ala Asp Gly Arg Val Ile Asp Val Gly Ser Ala Asp Ser
                20                  25                  30

Arg Thr Val Ser Glu Gly Gln Ala Tyr Gly Leu Phe Phe Ala Leu Val
            35                  40                  45

Ala Asn Asp Arg Arg Thr Phe Asp Thr Ile Leu Ala Trp Thr Glu Asn
        50                  55                  60

Asn Leu Ala Gln Gly Asp Leu Ser Ala Arg Leu Pro Ala Trp Leu Trp
65                  70                  75                  80

Gly Arg Ala Pro Asp Gly Ala Trp Arg Val Leu Asp Ala Asn Ala Ala
                85                  90                  95

Ser Asp Ala Asp Leu Trp Ile Ala Tyr Thr Leu Val Glu Ala Gly Arg
            100                 105                 110

Leu Trp Arg Glu Arg Ser Tyr Thr Ala Arg Gly Ala Leu Leu Ala Lys
        115                 120                 125
```

```
Arg Val Leu Asp Asp Glu Thr Ala Ser Val Pro Gly Leu Gly Leu Thr
            130                 135                 140

Leu Leu Pro Gly Pro Thr Gly Phe Lys Arg Ala Asn Gly Gln Trp Arg
145                 150                 155                 160

Val Asn Pro Ser Tyr Ser Pro Pro Gln Val Ile Arg Gly Leu Ala Ala
                165                 170                 175

Arg Leu Pro Asp Asp Arg Arg Trp Ala Ala Leu Ala Ala Ser Thr Gly
            180                 185                 190

Arg Val Leu Leu Asp Thr Ala Pro Lys Gly Phe Ser Pro Asp Trp Ala
            195                 200                 205

Leu Tyr Arg Ala Gly Ala Gly Phe Gly Pro Asp Pro Gln Thr Arg Ala
            210                 215                 220

Glu Ser Ala Tyr Asn Ala Ile Arg Val Tyr Leu Trp Ala Gly Met Leu
225                 230                 235                 240

Asp Arg Ala Asp Pro Leu Ala Ala Pro Leu Leu Ala Arg Phe Ala Pro
                245                 250                 255

Phe Ala Asp Tyr Ile Ala Ala His Gly Ala Pro Pro Glu Lys Val Asp
            260                 265                 270

Thr Thr Thr Gly Val Ala Gly Pro Asn Asp Gly Asn Gly Gly Phe Ser
            275                 280                 285

Ala Ala Ala Val Pro Phe Leu Asp Ala Arg Gly Gln His Ala Leu Ala
290                 295                 300

Asp Ala Gln Ala Ala Arg Val Asp Thr Leu Ala Arg Gln Ser Ala Pro
305                 310                 315                 320

Gly Tyr Tyr Thr Ser Val Leu Thr Leu Phe Gly Leu Gly Trp Arg Asp
                325                 330                 335

Gly Arg Tyr Arg Phe Gly Ala Asp Gly Ala Leu Asp Ala Arg Trp Glu
            340                 345                 350

Gly Arg Pro Cys Ala Ala Arg
            355
```

<210> SEQ ID NO 73
<211> LENGTH: 379
<212> TYPE: PRT
<213> ORGANISM: Leptothrix cholodnii

<400> SEQUENCE: 73

```
Met Ala Thr Arg Ala Gln Ser Ala Asn Pro Cys Ser Ala Val Glu Gly
1               5                   10                  15

Pro Thr Gly Trp Pro Ala Trp Gln Thr Leu Arg Arg Thr Leu Met Ser
                20                  25                  30

Arg Asp Gly Arg Val Ile Asp Arg Tyr Ala Ser Asp Ala Thr Thr Ser
            35                  40                  45

Glu Gly Gln Ala Tyr Gly Leu Phe Phe Ala Leu Val Asp Asn Asp Arg
    50                  55                  60

Ala Ala Phe Glu Leu Leu Leu Arg Trp Thr Glu Asp Asn Leu Ala Ala
65                  70                  75                  80

Gly Asp Leu Ala Ala Arg Leu Pro Ala Trp Arg Trp Gly Arg Arg Ala
                85                  90                  95

Asp Gly Ser Trp Asn Val Ile Asp Ala Asn Ser Ala Ala Asp Ala Asp
                100                 105                 110

Leu Trp Leu Ser Tyr Val Leu Ser Glu Ala Gly Arg Leu Trp Lys Asn
            115                 120                 125

Arg Arg Tyr Asp Ala Leu Gly Arg Val Leu Ala Arg Arg Ile Ala Ala
```

```
                130               135                140
        Glu Val Ile Glu Leu Pro Gly Leu Gly Thr Thr Leu Leu Pro Gly
        145                 150                 155                 160

Pro Gln Gly Phe Arg Arg Gly Glu Arg Gly Ala Lys Leu Asn Pro Ser
                        165                 170                 175

Tyr Leu Pro Pro Gln Leu Leu Arg Trp Phe Ala Arg Asn Arg Thr Glu
                    180                 185                 190

Ser Val Trp Val Pro Leu Arg Asp Ala Ser Leu Arg Leu Leu His Asp
                195                 200                 205

Ser Ala Pro His Gly Leu Ala Pro Asp Trp Thr Val Phe Asp Ala Asp
            210                 215                 220

Arg Gly Trp Ser Leu Ala Glu Leu Ala Asp Asp Glu Arg Ser Gly Ser
        225                 230                 235                 240

Tyr Asn Ala Ile Arg Val Tyr Leu Trp Leu Gly Leu Thr Asp Pro Gly
                        245                 250                 255

Asp Pro Ala Arg Gly Arg Leu Leu Ala Arg Tyr Ala Pro Met Ala Arg
                    260                 265                 270

Leu Ser Glu Leu Leu Gly Gly Val Pro Glu Lys Val Asp Pro Ala Arg
                275                 280                 285

Pro Ala Leu Glu Gln Ser Ala Gly Ala Gln Ala Asn Gly Pro Val Gly
            290                 295                 300

Phe Gln Ala Ala Met Leu Pro Phe Ala Asp Ala Leu Gly Gln Thr Ala
        305                 310                 315                 320

Leu Ser Glu Arg Leu Ala Asp Arg Val Ala Thr Gln Gly Val Gln Pro
                        325                 330                 335

Asp Ala Tyr Tyr Asp Gln Val Leu Ser Leu Phe Ala Leu Gly Phe Arg
                    340                 345                 350

Glu Arg Arg Tyr Arg Phe Ala Ala Asp Gly Ser Leu Gln Pro Gly Trp
                355                 360                 365

Ala Ser Cys Asp Ala Pro Pro Gly Ser Ser Arg
            370                 375

<210> SEQ ID NO 74
<211> LENGTH: 406
<212> TYPE: PRT
<213> ORGANISM: Burkholderia ambifaria

<400> SEQUENCE: 74

Met Ala Trp Ala Phe Ala Arg Arg Ala Thr Arg Pro Ala Arg Arg
        1               5                   10                  15

Val Gly Thr Thr Leu Val Leu Ala Val Ala Ala Cys Ala Ser Ala
                        20                  25                  30

Ala Thr Ala Gly Arg Ala Gln Ala Ala Gln Ser Gly Ala Ala Asp Ala
                    35                  40                  45

Gln Cys Gly Ala Ala Trp Pro Arg Trp Asp Ala Phe Lys Arg Asp Phe
        50                  55                  60

Val Ser Ala Asp Gly Arg Val Ile Asp Val Gly Ser Ala Asp Ser Arg
        65                  70                  75                  80

Thr Val Ser Glu Gly Gln Ala Tyr Gly Leu Phe Phe Ala Leu Val Ala
                        85                  90                  95

Asn Asp Arg Arg Thr Phe Asp Thr Ile Leu Ala Trp Thr Glu Asn Asn
                    100                 105                 110

Leu Ala Gln Gly Asp Leu Ser Ala Arg Leu Pro Ala Trp Leu Trp Gly
                115                 120                 125
```

-continued

```
Arg Ala Pro Asp Gly Ala Trp Arg Val Leu Asp Ala Asn Ala Ala Ser
    130                 135                 140

Asp Ala Asp Leu Trp Ile Ala Tyr Thr Leu Val Glu Ala Gly Arg Leu
145                 150                 155                 160

Trp Arg Glu Arg Ser Tyr Thr Ala Arg Gly Ala Leu Leu Ala Lys Arg
                165                 170                 175

Val Leu Asp Asp Glu Thr Ala Ser Val Pro Gly Leu Gly Leu Thr Leu
            180                 185                 190

Leu Pro Gly Pro Thr Gly Phe Lys Leu Ala Asn Gly Gln Trp Arg Val
        195                 200                 205

Asn Pro Ser Tyr Ser Pro Pro Gln Leu Ile Arg Gly Leu Ala Ala Arg
210                 215                 220

Leu Pro Asp Asp Arg Arg Trp Ala Ala Leu Ser Ala Ser Thr Gly Arg
225                 230                 235                 240

Val Leu Leu Asp Thr Ala Pro Lys Gly Phe Ser Pro Asp Trp Ala Leu
                245                 250                 255

Tyr Arg Ala Gly Ala Gly Phe Gly Pro Asp Pro Gln Thr Arg Ala Glu
            260                 265                 270

Ser Ala Tyr Asn Ala Ile Arg Val Tyr Leu Trp Ala Gly Met Leu Asp
        275                 280                 285

Arg Ala Asp Pro Leu Ala Ala Pro Leu Leu Ala Arg Phe Ala Pro Phe
290                 295                 300

Ala Asp Tyr Ile Ala Ala His Gly Ala Pro Pro Glu Lys Val Asp Thr
305                 310                 315                 320

Thr Thr Gly Val Ala Gly Pro Asn Asp Gly Asn Gly Gly Phe Ser Ala
                325                 330                 335

Ala Ala Val Pro Phe Leu Asp Ala Arg Gly Gln Arg Ala Leu Ala Asp
            340                 345                 350

Ala Gln Ala Ala Arg Val Asp Thr Leu Ala Arg Gln Ser Ala Pro Gly
        355                 360                 365

Tyr Tyr Thr Ser Val Leu Thr Leu Phe Gly Leu Gly Trp Arg Glu Gly
370                 375                 380

Arg Tyr Arg Phe Gly Ala Asp Gly Ser Leu Asp Ala Arg Trp Glu Gly
385                 390                 395                 400

Arg Pro Cys Val Ala Arg
                405

<210> SEQ ID NO 75
<211> LENGTH: 421
<212> TYPE: PRT
<213> ORGANISM: Methylobacterium populi

<400> SEQUENCE: 75

Met Arg Pro Pro Arg Thr Pro Cys Arg Ser Arg Leu Gly Gly Thr Leu
1               5                   10                  15

Arg Arg Ala Gly Trp Ala Leu Ala Leu Ala Ala Ser Pro Ala Ala
            20                  25                  30

Ala Gln Pro Thr Pro Gln Pro Ala Pro Gln Pro Ala Ser Pro Gln
        35                  40                  45

Gln Thr Ser Pro Gln Met Ala Gln Pro Ala Pro Gln Gln Thr Glu Thr
    50                  55                  60

Ser Thr Val Pro Pro Ala Thr Ala Leu Pro Gly Leu Pro Arg Ser Glu
65                  70                  75                  80

Thr Pro Ala Arg Thr Asp Ser Gly Pro Ser Leu Ala Asn Thr Leu Asp
                85                  90                  95
```

```
Asp Asp Ala Ala Trp Arg Ala Tyr Arg Ala Arg Phe Ile Thr Glu Gln
            100                 105                 110

Gly Arg Ile Val Asp Thr Ala Asn Gly Met Ile Ser His Ser Glu Gly
        115                 120                 125

Gln Gly Tyr Gly Met Leu Ile Ala Val Ala Ala Gly Asp Arg Ala Ala
    130                 135                 140

Phe Glu Arg Ile Trp Gly Trp Thr Arg Ala Asn Leu Met Val Arg Ser
145                 150                 155                 160

Asp Glu Leu Leu Ala Trp Arg Ala Pro Asp His Arg Pro Ala Val
                165                 170                 175

Ala Asp Met Asn Asn Ala Thr Asp Gly Asp Ile Leu Val Ala Trp Ala
            180                 185                 190

Leu Thr Glu Ala Ala Glu Ala Trp Gly Glu Pro Ser Tyr Arg Thr Ala
        195                 200                 205

Ala Arg Arg Ile Ala Val Glu Phe Gly Arg Lys Thr Ile Leu Phe Lys
    210                 215                 220

Asp Pro His Gly Pro Leu Leu Pro Ala Val Ser Gly Phe Ser Ala
225                 230                 235                 240

Arg Glu Arg Ala Asp Gly Pro Leu Ile Asn Leu Ser Tyr Trp Val Phe
                245                 250                 255

Pro Ala Phe Gln Arg Leu Pro Ile Val Ala Pro Glu Tyr Asp Trp Ala
            260                 265                 270

Ser Leu Ile Arg Ser Gly Leu Asp Phe Leu Arg Gln Ser Arg Phe Gly
        275                 280                 285

Pro Ser Ser Leu Pro Thr Glu Trp Ile Ser Ala Lys Asp Ser Leu Arg
    290                 295                 300

Pro Ala Asp Gly Phe Pro Pro Leu Phe Ser Tyr Asn Ala Ile Arg Val
305                 310                 315                 320

Pro Leu Tyr Leu Ala Trp Ala Gly Val Gly Arg Pro Glu Asp Tyr Thr
                325                 330                 335

Pro Phe Lys Thr Leu Trp Gly Gly Ile Glu Arg Glu Arg Leu Pro Ile
            340                 345                 350

Val Asp Thr Arg Asp Gly Gln Pro Val Glu Trp Leu Ser Glu Val Gly
        355                 360                 365

Tyr Thr Ala Ile Pro Ala Leu Thr Ala Cys Ala Ala Asp Gly Thr Pro
    370                 375                 380

Phe Pro Glu Ser Leu Arg Thr Val Gln Glu Asn Gln Asn Tyr Tyr Pro
385                 390                 395                 400

Met Thr Leu His Leu Leu Ala Leu Ile Ala Ala Arg Met Arg Tyr Pro
                405                 410                 415

Ser Cys Val Lys Ser
            420

<210> SEQ ID NO 76
<211> LENGTH: 412
<212> TYPE: PRT
<213> ORGANISM: Opitutus terrae

<400> SEQUENCE: 76

Met Arg Phe Pro Phe Leu Pro Leu Val Leu Gly Leu Ala Leu Gly Ser
1               5                   10                  15

Leu Ser Ala Val Ala Ala Thr Ala Ala Gln Gly Ala Ala Glu Thr Gly
            20                  25                  30

Arg Tyr Arg Asn Pro Phe Lys Glu Leu Leu Gly Lys Ser Asp Ala Glu
```

```
              35                  40                  45
Ile Asn Ala Lys Leu Gln Ala Ala Trp Gln Gln Leu Phe Tyr Gly Asp
 50                  55                  60

Glu Asn Ser Gln Arg Leu Phe Tyr Pro Ile Ala Gly Asp Met Ala Tyr
 65                  70                  75                  80

Val Pro Asp Ile Asn Asn Asp Val Arg Ser Glu Gly Leu Ser Tyr
                 85                  90                  95

Gly Met Met Ile Ala Val Gln Met Asp Arg Gln Lys Glu Phe Asn Gln
                100                 105                 110

Ile Trp Lys Phe Ala Lys His Tyr Met Tyr Asp Ala Gly Pro Phe
            115                 120                 125

Arg Gly Tyr Phe Ala Trp His Thr Ala Phe Asp Gly Arg Arg Leu Ser
        130                 135                 140

Pro Gly Pro Ala Pro Asp Gly Glu Glu Trp Trp Val Met Ala Leu Phe
145                 150                 155                 160

Phe Ala Ser His Arg Trp Gly Asp Gly Glu Gly Ile Phe Asn Tyr Arg
                165                 170                 175

Lys Glu Ala Gln Asp Leu Leu Arg Thr Met Leu His Lys Asn Glu Glu
            180                 185                 190

Pro Asp Arg Gly Pro Ile Thr Ala Met Phe Asp Pro Val His Lys Gln
        195                 200                 205

Ile Val Phe Val Pro Gln Gly Pro Gly Ala Gln Phe Thr Asp Pro Ser
210                 215                 220

Tyr His Leu Pro Ala Tyr Tyr Glu Leu Trp Ala Arg Trp Ala Ala Asp
225                 230                 235                 240

Pro Ala Asp Arg Ala Phe Met Ala Glu Ala Lys Ile Ser Arg Glu
                245                 250                 255

His Phe Arg Thr Ala Ala His Pro Lys Thr Gly Leu Met Pro Asp Tyr
            260                 265                 270

Ser Asn Phe Asp Gly Thr Pro Tyr Thr Ala Arg Trp Gly Asn His Gln
        275                 280                 285

Asp Phe Leu Tyr Asp Ala Trp Arg Thr Leu Asn Asn Pro Ala Leu Asp
    290                 295                 300

Tyr Ser Trp Trp Ala Ala Asp Pro Trp Val Val Glu Gln Ser Asn Arg
305                 310                 315                 320

Val Leu Thr Phe Leu Ser Ser Phe Gly Ser Glu Val Pro Asp Arg Phe
                325                 330                 335

Lys Leu Asp Gly Thr Pro Val Ser Thr Asp Thr Asn Thr Ala Gly Leu
            340                 345                 350

Thr Ala Met Ala Ala Cys Ala Gly Leu Ala Ala Asp Ser Val Ile Ala
        355                 360                 365

Lys Pro Trp Val Gln Gln Leu Trp Asp Met Pro Ile Pro Thr Gly Arg
    370                 375                 380

His Arg Tyr Tyr Gly Gly Leu Leu Thr Met Ile Ala Leu Leu Glu Cys
385                 390                 395                 400

Ser Gly Asn Phe Lys Ile Tyr Gly Pro Val Ala Lys
                405                 410

<210> SEQ ID NO 77
<211> LENGTH: 445
<212> TYPE: PRT
<213> ORGANISM: Opitutus terrae

<400> SEQUENCE: 77
```

```
Met Thr Phe Val Leu Arg Lys Pro Ala Asn Asp Cys Cys Gly Ala Arg
1               5                   10                  15

His Arg Ala Asp Val Ala Gly Val Gly Asp Pro Gly Pro Gly Ser Ala
            20                  25                  30

Ser Pro Ala Thr Asn Val Ser Pro Pro Arg Phe Val Ala Trp Ala Ala
            35                  40                  45

Ala Phe Ala Ala Leu Leu Val Ser Ser Leu Ala Ala Ala Pro Ala Pro
        50                  55                  60

Arg Asn Leu Phe Ala Glu Leu Leu Gly Arg Ser Asp Ala Glu Ile Thr
65                  70                  75                  80

Ala Lys Ile Asp Ala Gly Trp Gln Gln Leu Phe Tyr Gly Ser Asp Thr
                85                  90                  95

Glu Glu Arg Leu Tyr Tyr Pro Val Asp Pro Asp Leu Ala Tyr Leu Ala
            100                 105                 110

Asp Ile Asn Asn Gly Asp Val Arg Ser Glu Gly Met Ser Tyr Gly Met
            115                 120                 125

Met Leu Ala Val Gln Ile Asp Arg Arg Ala Glu Phe Asp Arg Leu Tyr
        130                 135                 140

Arg Trp Ala Arg Lys Tyr Met Leu His Thr Asp Ser Pro Arg Arg Gly
145                 150                 155                 160

Tyr Phe Ala Trp Gln Val Ser Phe Asp Gly Arg Gln Ile Asp Pro Gly
                165                 170                 175

Ser Ala Ser Asp Gly Glu Glu Trp Ile Ala Thr Ala Leu Leu Leu Ala
            180                 185                 190

Ala Glu Arg Trp Gly Ser Ser Asp Ala Gly Ser Phe Asn Tyr Leu Ala
        195                 200                 205

Asp Ala Gln Ala Leu Leu His Glu Met Leu His Lys Pro Thr Glu Gly
        210                 215                 220

Asn Ile Thr Ala Ile Phe Ser Arg Glu Glu Lys Gln Val Val Phe Ala
225                 230                 235                 240

Pro Thr Leu Ala Gly Ser Gln Phe Thr Asp Pro Ser Tyr His Leu Pro
                245                 250                 255

Ala Phe Tyr Glu Val Trp Ala Arg His Ala Asp Ser Pro Glu Asp Arg
            260                 265                 270

Ala Phe Trp Arg Asp Ala Thr Gln Thr Ser Arg Ala Phe Phe His Arg
        275                 280                 285

Ala Ala His Pro Gln Thr Gly Leu Met Pro Glu Tyr Ala His Phe Asp
        290                 295                 300

Gly Arg Pro Tyr Thr Gly Phe Gly Ala Glu Arg Gly Asp Phe Arg Tyr
305                 310                 315                 320

Asp Ala Trp Arg Ile Leu Ala Asn Val Ala Phe Asp His Ala His Phe
                325                 330                 335

Ala Ala Asp Pro Trp Gln Val Glu Gln Ser Asn Arg Ile Leu Arg Phe
            340                 345                 350

Leu Ser Ser His Gln Pro Ala Ile Pro Asn Phe Thr Leu Asp Gly
        355                 360                 365

Arg Pro Leu Ser Thr Asp Val Asn Ser Thr Gly Leu Met Ala Met Ala
        370                 375                 380

Ala Val Ala Gly Leu Ala Glu Pro Glu Leu Ala Arg Pro Phe Val
385                 390                 395                 400

Gln Phe Leu Trp Asp Ala Pro Ile Pro Arg Gly Gln Tyr Arg Tyr Tyr
                405                 410                 415

Asp Gly Val Leu Tyr Gln Leu Ala Leu Leu Gln Val Ser Gly Arg Phe
```

```
                420               425               430
Gln Leu Ser Phe His Leu Thr Ala Pro Thr Thr Ser Lys
            435               440               445

<210> SEQ ID NO 78
<211> LENGTH: 393
<212> TYPE: PRT
<213> ORGANISM: Cupriavidus taiwanensis

<400> SEQUENCE: 78

Met Thr Asp Gln Thr Arg Arg Tyr Val Thr Tyr Ala Cys Ala Leu
1               5                   10                  15

Gly Ala Ser Ala Leu Thr Ala Ala Trp Pro Thr Glu Thr Arg Ala His
            20                  25                  30

Ala Pro Pro Ala Thr Arg Arg Ala Ser Arg Trp Pro Leu Tyr Arg Gln
        35                  40                  45

Phe Leu Glu Arg Phe Val Gln Ala Asp Gly Arg Val Ile Asp Tyr Ser
    50                  55                  60

Thr Pro Thr Leu Gln Ser Thr Ser Glu Gly Gln Ser Tyr Gly Met Val
65                  70                  75                  80

Phe Ala Leu Val Ala Asp Asp Arg Asp Ala Phe Asp Arg Leu Trp Arg
                85                  90                  95

Trp Ser Val Ala His Leu Gly Asn Gly Arg Leu Asp Asp Lys Leu Pro
            100                 105                 110

Ala Trp Gln Trp Gly Arg Arg Ala Asp Gly Thr Trp Gly Val Leu Asp
        115                 120                 125

Arg Asn Pro Ala Ala Asp Ala Asp Leu Trp Phe Phe Ala Leu Ala
    130                 135                 140

Glu Ala Ala Arg Leu Trp Gln Ala Pro Ser Tyr Ala Asp Ala Ala Arg
145                 150                 155                 160

Ala Leu Leu Arg Arg Val Ala Ala Gln Glu Val Val Thr Leu Pro Gly
                165                 170                 175

Phe Gly Pro Met Leu Leu Pro Gly Pro Gln Gly Phe Ile Asp Asp Gly
            180                 185                 190

Pro Asp Gly Ser Arg Arg Trp Arg Leu Asn Ala Ser Tyr Leu Pro Val
        195                 200                 205

Pro Leu Leu Arg Arg Leu Ala Ala Phe Asp Pro Ser Gly Pro Trp Asp
    210                 215                 220

Lys Leu Ala Ala Gln Val Ala Arg Leu Ile Gly Ala Val Ser His Ala
225                 230                 235                 240

Gly Ile Val Pro Asp Trp Ser Ala Tyr Arg Val Gly Arg Gln
                245                 250                 255

Gly Phe Val Arg Asp Pro Val Lys Gly Asp Val Ser Ser Tyr Asp Ala
        260                 265                 270

Val Arg Val Tyr Leu Trp Ala Gly Met Thr Pro Asp Gln Asp Ser Thr
    275                 280                 285

Trp Gly Ala Ile Met Gln Ala Leu Leu Pro Asn Ala Ala Arg Leu Ala
            290                 295                 300

Gly Arg Ala Ala Pro Pro Glu Lys Met Tyr Ala Glu Ser Gly Lys Val
305                 310                 315                 320

Glu Gly Ile Gly Pro Pro Ala Phe Ser Ala Leu Leu Pro Phe Leu
                325                 330                 335

Gln Ala Ala Gly Ser Pro Ala Leu Ala Thr Gln Met Ala Arg Ala Gln
            340                 345                 350
```

```
Lys Ile Val Gly Ala Pro Pro Gly Gly Pro Thr Tyr Tyr Asp
            355                 360             365

Thr Val Leu Gly Leu Phe Gly Leu Gly Phe Met Glu Gly Arg Tyr Arg
    370                 375                 380

Phe Ser Ala Ser Gly Gln Leu Asp Arg
385                 390

<210> SEQ ID NO 79
<211> LENGTH: 388
<212> TYPE: PRT
<213> ORGANISM: Burkholderia phymatum

<400> SEQUENCE: 79

Met Arg Arg Lys Arg Leu Leu Thr Gln Arg Phe Ala Arg Ile Pro Lys
1               5                   10                  15

Cys Gly Ala Val Arg Arg Leu Val Gly Leu Ala Val Ala Cys Leu Gln
            20                  25                  30

Val Ser Val Ala Ala His Ala Asp Cys Arg Trp Pro Leu Trp Glu Arg
        35                  40                  45

Tyr Ala Gln Gln Gln Ile Ser Lys Asp Gly Arg Ile Val Glu Pro Gly
    50                  55                  60

Lys Gly Asp Arg Thr Thr Ser Glu Ala Gln Ala Tyr Ala Met Phe Phe
65                  70                  75                  80

Ala Val Val Gly Asp Asp Arg Val Arg Phe Asp Ser Leu Leu Asn Trp
                85                  90                  95

Ala Leu Ala His Thr Trp Ala Thr Thr Gly His Pro Pro Ala Trp Leu
            100                 105                 110

Trp Ala Lys Arg Ala Asp Gly Thr Phe Asp Val Leu Asp Asp Asn Ser
        115                 120                 125

Ala Thr Asp Ala Asp Leu Trp Met Ala Tyr Ala Met Leu Glu Ala Ala
    130                 135                 140

Arg Arg Trp Ser Glu Pro Arg Tyr Arg Ala Leu Gly Leu Arg Leu Leu
145                 150                 155                 160

Asp Gln Ile Thr Ala Thr Glu Val Val Trp Gln Asp Glu Thr Ser Ala
                165                 170                 175

Phe Leu Ile Pro Gly Arg Leu Gly Phe Arg Leu Ser Glu His Ala Tyr
            180                 185                 190

Leu Val Asn Pro Ser Tyr Ala Pro Ile Gln Leu Leu Arg Arg Phe Ile
        195                 200                 205

Lys Glu Gln Pro His Gly Pro Trp Val Ser Val Leu Asn His Gln Val
    210                 215                 220

Asp Leu Leu Val Ala Ser Ala Pro Gln Gly Phe Val Pro Asp Trp Tyr
225                 230                 235                 240

Arg Phe Asp Thr Phe Lys Gly Tyr Met Leu Glu Pro Ser Lys Gly Pro
                245                 250                 255

Thr Gly Gly Phe Asp Ala Val Arg Thr Tyr Met Trp Ala Gly Met Leu
            260                 265                 270

Asp Pro Thr Asp Pro Ala Arg Gly Glu Val Ile Pro Ala Leu Ser Gly
        275                 280                 285

Met Ala Asp Leu Val Ala Gln Thr Gly Arg Met Pro Leu Tyr Val Asn
    290                 295                 300

Ile Glu Ser Gly Glu Thr Phe Asp Glu Gly Ser Ala Gly Phe Arg Ala
305                 310                 315                 320

Ala Val Ile Pro Leu Leu Phe Val Thr Gly His Pro Ser Ala Ala Ser
                325                 330                 335
```

```
Arg Leu Ala Gln Glu Thr Lys Val Met Gln Gln Ala Arg Glu Trp Asp
            340                 345                 350

Gly Leu His Tyr Tyr Asp Arg Asn Leu Leu Phe Ala Ala Gly Trp
        355                 360                 365

Leu Glu Gly Arg Tyr Arg Phe Asp His Glu Gly Thr Leu Gln Leu Lys
370                 375                 380

Pro Cys Arg Pro
385

<210> SEQ ID NO 80
<211> LENGTH: 410
<212> TYPE: PRT
<213> ORGANISM: Burkholderia phymatum

<400> SEQUENCE: 80

Met Arg Glu Ala Phe Ile Phe Ser Ser Trp Arg Phe Arg Leu Arg Ala
1               5                   10                  15

Pro Leu Ala Arg Pro Leu Val Cys Ala Gly Leu Val Gly Ser Leu Val
                20                  25                  30

Ala Ser Met Thr Gly His Ala Gln Ala Ala Thr Cys Asp Asp Trp Pro
            35                  40                  45

Ala Tyr Arg Ala Phe Val Ser Arg Phe Val Gln Gln Asp Gly Arg Val
        50                  55                  60

Val Asp Phe Ser Thr Pro Thr Gln Gln Thr Thr Ser Glu Gly Gln Ser
65                  70                  75                  80

Tyr Gly Met Phe Phe Ala Leu Val Ala Asn Asp Arg Ala Thr Phe Glu
                85                  90                  95

Arg Leu Leu Arg Trp Thr Arg Ala Asn Leu Ser Ala Gly Arg Phe Asp
            100                 105                 110

Gly Gly Asp Val Lys Leu Pro Ala Trp Gln Trp Gly Lys Lys Pro Asp
        115                 120                 125

Gly Ala Tyr Gly Val Ile Asp Pro Asn Ser Ala Ala Asp Ser Asp Leu
    130                 135                 140

Trp Ile Ala Tyr Asp Leu Phe Glu Ala Gly Arg Leu Trp Arg Glu Pro
145                 150                 155                 160

Ala Tyr Thr Gln Leu Ala Tyr Ala Leu Val Thr Gln Val Glu Lys Gln
                165                 170                 175

Glu Val Ala Asp Leu Arg Gly Leu Gly Pro Met Leu Leu Pro Gly Ser
            180                 185                 190

Gln Gly Phe Arg Asn Gly Ala Thr Thr Arg Leu Asn Pro Ser Tyr Leu
        195                 200                 205

Pro Leu Pro Leu Ile Arg Ala Leu Ala Ala Gln Ser Pro Asn Gly Pro
    210                 215                 220

Trp Ser Arg Ile Ala Asp Asn Ala Phe Lys Leu Val Lys Thr Thr Ala
225                 230                 235                 240

Pro Leu Gly Phe Ala Pro Asp Trp Ala Ala Tyr Arg Asp Gly Gln Phe
                245                 250                 255

Val Val Asp Pro Gln Thr Gly Asp Ala Gly Ser Tyr Asp Ala Ile Arg
            260                 265                 270

Val Tyr Leu Trp Ala Gly Leu Ala Ala Ser Ala Asp Pro Leu Ala Lys
        275                 280                 285

Pro Trp Leu Ala Ala Leu His Gly Met Arg Asp Arg Ile Ala Gln Thr
    290                 295                 300

Gly Val Pro Pro Glu Lys Val Ala Thr Thr Gly Asn Ala Ala Gly
```

```
                305                 310                 315                 320
Glu Gly Pro Ile Gly Phe Trp Gly Ala Leu Leu Pro Tyr Phe Arg Ala
                    325                 330                 335

Leu Gly Asp Thr Arg Ala Ala Gly Leu Ala Gln Thr His Leu Ala Ser
                340                 345                 350

Leu Ala Thr Pro Ala Pro Gly Ala Ala Gln Ala Ala Arg Asn Gln Pro
                355                 360                 365

Val Tyr Tyr Asp Glu Val Leu Met Leu Phe Gly Thr Ala Ser Ala Asp
                370                 375                 380

Gly Arg Tyr Arg Phe Asp Glu Asn Gly Arg Leu Val Pro Arg Trp Glu
385                 390                 395                 400

Asn Thr Cys Gln Ser Ala Asn Ala Arg Leu
                    405                 410

<210> SEQ ID NO 81
<211> LENGTH: 365
<212> TYPE: PRT
<213> ORGANISM: Escherichia coli

<400> SEQUENCE: 81

Met Arg Ser Gly Ile Val Thr Met Leu Leu Leu Ala Ala Phe Ser Val
1               5                   10                  15

Gln Ala Ala Cys Thr Trp Pro Ala Trp Glu Gln Phe Lys Lys Asp Tyr
                20                  25                  30

Ile Ser Gln Glu Gly Arg Val Ile Asp Pro Ser Asp Ala Arg Lys Ile
            35                  40                  45

Thr Thr Ser Glu Gly Gln Ser Tyr Gly Met Phe Phe Ala Leu Ala Ala
        50                  55                  60

Asn Asp Arg Ala Ala Phe Asp Asn Ile Leu Asp Trp Thr Gln Asn Asn
65                  70                  75                  80

Leu Ala Gln Gly Ser Leu Lys Glu Arg Leu Pro Ala Trp Leu Trp Gly
                85                  90                  95

Lys Lys Glu Asn Ser Lys Trp Glu Val Leu Asp Ser Asn Ser Ala Ser
                100                 105                 110

Asp Gly Asp Val Trp Met Ala Trp Ser Leu Leu Glu Ala Gly Arg Leu
            115                 120                 125

Trp Lys Glu Gln Arg Tyr Thr Asp Ile Gly Ser Ala Leu Leu Lys Arg
        130                 135                 140

Ile Ala Arg Glu Glu Val Val Thr Val Pro Gly Leu Gly Ser Met Leu
145                 150                 155                 160

Leu Pro Gly Lys Val Gly Phe Ala Glu Asp Asn Ser Trp Arg Phe Asn
                165                 170                 175

Pro Ser Tyr Leu Pro Pro Thr Leu Ala Gln Tyr Phe Thr Arg Phe Gly
                180                 185                 190

Ala Pro Trp Thr Thr Leu Arg Glu Thr Asn Gln Arg Leu Leu Leu Glu
            195                 200                 205

Thr Ala Pro Lys Gly Phe Ser Pro Asp Trp Val Arg Tyr Glu Lys Asp
        210                 215                 220

Lys Gly Trp Gln Leu Lys Ala Glu Lys Thr Leu Ile Ser Ser Tyr Asp
225                 230                 235                 240

Ala Ile Arg Val Tyr Met Trp Val Gly Met Met Pro Asp Ser Asp Pro
                245                 250                 255

Gln Lys Ala Arg Met Leu Asn Arg Phe Lys Pro Met Ala Thr Phe Thr
                260                 265                 270
```

```
Glu Lys Asn Gly Tyr Pro Pro Glu Lys Val Asp Val Ala Thr Gly Lys
            275                 280                 285

Ala Gln Gly Lys Gly Pro Val Gly Phe Ser Ala Ala Met Leu Pro Phe
        290                 295                 300

Leu Gln Asn Arg Asp Ala Gln Ala Val Gln Arg Gln Arg Val Ala Asp
305                 310                 315                 320

Asn Phe Pro Gly Ser Asp Ala Tyr Tyr Asn Tyr Val Leu Thr Leu Phe
                325                 330                 335

Gly Gln Gly Trp Asp Gln His Arg Phe Arg Phe Ser Thr Lys Gly Glu
                    340                 345                 350

Leu Leu Pro Asp Trp Gly Gln Glu Cys Ala Asn Ser His
                355                 360                 365

<210> SEQ ID NO 82
<211> LENGTH: 393
<212> TYPE: PRT
<213> ORGANISM: Burkholderia phytofirmans

<400> SEQUENCE: 82

Met Arg Val Arg Ile Asn Lys Lys Ile Gly Val Ala Leu Ala Leu Gly
1               5                   10                  15

Leu Ala Ala Ser Val Ser Phe Ala Asn Leu Val Lys Val Ala Gln Thr
                20                  25                  30

Thr Ala Ala Pro Gly Ala Cys Gly Asp Trp Ser Gly Tyr Arg Ala Phe
            35                  40                  45

Val Glu Arg Phe Val Gln Ala Asp Gly Arg Val Ile Asp Tyr Ser Thr
        50                  55                  60

Pro Ala Gln Gln Thr Thr Ser Glu Gly Gln Ser Tyr Ala Leu Phe Phe
65                  70                  75                  80

Ala Leu Val Ala Asn Asp Arg Ala Thr Phe Asp Arg Leu Leu Gly Trp
                85                  90                  95

Thr Arg Thr Asn Leu Ala Gly Asn Gln Phe Asp Ala Gln Asn Met Arg
            100                 105                 110

Leu Pro Ser Trp Gln Trp Gly Arg Lys Ala Asp Gly Ser Tyr Gly Val
        115                 120                 125

Leu Asp Pro Asn Ser Ala Ser Asp Ser Asp Leu Trp Ile Ala Tyr Asp
    130                 135                 140

Leu Leu Gln Ala Gly Arg Leu Trp His Glu Ala Ala Tyr Thr Gln Leu
145                 150                 155                 160

Gly Glu Ala Leu Ala Ala Gln Ile Ala Arg Gln Glu Met Thr Thr Leu
                165                 170                 175

Pro Gly Val Gly Pro Met Leu Leu Pro Gly Pro Gln Gly Phe Lys Ser
            180                 185                 190

Gly Gly Val Thr Arg Leu Asn Pro Ser Tyr Leu Pro Leu Pro Val Leu
        195                 200                 205

Arg Ser Leu Ala His Asp Met Pro Asn Gly Pro Trp Gly Lys Leu Ala
    210                 215                 220

Asp Ser Ala Tyr Lys Leu Ile Lys Thr Thr Ala Pro Gln Gly Phe Ala
225                 230                 235                 240

Pro Asp Trp Ala Ala Trp Gln Asn Gly Gln Phe Val Val Asp Pro Lys
                245                 250                 255

Asn Gly Asp Thr Gly Ser Tyr Asp Ala Ile Arg Val Tyr Leu Trp Ala
            260                 265                 270

Gly Leu Ala Ser Pro Ala Asp Pro Leu Ala Lys Pro Trp Leu Ala Ala
        275                 280                 285
```

```
Leu Gly Gly Met Arg Ala Arg Val Ala Gln Thr Gly Phe Pro Pro Glu
    290                 295                 300

Lys Val Ser Ser Thr Ser Gly Thr Ala Ser Gly Glu Gly Pro Leu Ser
305                 310                 315                 320

Tyr Trp Ala Ala Leu Ala Pro Tyr Phe Lys Ala Leu Gly Asp Glu Arg
                325                 330                 335

Gly Leu Gly Leu Ala Arg Thr His Leu Ala Ala Leu Asp Thr Asn Val
            340                 345                 350

Pro Gly Arg Glu Pro Val Tyr Tyr Asp Arg Val Leu Gly Leu Phe Gly
        355                 360                 365

Thr Gly Phe Ile Asp Gly Arg Tyr Arg Phe Asp Glu Ala Gly Arg Leu
    370                 375                 380

Val Pro Ser Trp Arg Lys Glu Cys Asp
385                 390
```

<210> SEQ ID NO 83
<211> LENGTH: 365
<212> TYPE: PRT
<213> ORGANISM: Shigella boydii

<400> SEQUENCE: 83

```
Met Arg Ser Gly Ile Val Thr Met Leu Leu Leu Ala Ala Phe Ser Val
1               5                   10                  15

Gln Ala Ala Cys Thr Trp Pro Ala Trp Glu Gln Phe Lys Lys Asp Tyr
                20                  25                  30

Ile Ser Gln Glu Gly Arg Val Ile Asp Pro Ser Asp Ala Arg Lys Ile
            35                  40                  45

Thr Thr Ser Glu Gly Gln Ser Tyr Gly Met Phe Phe Ala Leu Ala Ala
        50                  55                  60

Asn Asp Arg Ala Ala Phe Asp Asn Ile Leu Asp Trp Thr Gln Asn Asn
65                  70                  75                  80

Leu Ala Gln Gly Ser Leu Lys Glu Arg Leu Pro Ala Trp Leu Trp Gly
                85                  90                  95

Lys Lys Glu Asn Ser Lys Trp Glu Val Leu Asp Ser Asn Ser Ala Ser
                100                 105                 110

Asp Gly Asp Val Trp Met Ala Trp Ser Leu Leu Glu Ala Gly Arg Leu
            115                 120                 125

Trp Lys Glu Gln Arg Tyr Thr Asp Ile Gly Ser Ala Leu Leu Lys Arg
        130                 135                 140

Ile Ala Arg Glu Glu Val Val Thr Val Pro Gly Leu Gly Ser Met Leu
145                 150                 155                 160

Leu Pro Gly Lys Val Gly Phe Ala Glu Asp Asn Ser Trp Arg Phe Asn
                165                 170                 175

Pro Ser Tyr Leu Pro Pro Thr Leu Ala Gln Tyr Phe Thr Arg Phe Gly
                180                 185                 190

Ala Pro Trp Thr Thr Leu Arg Glu Thr Asn Gln Arg Leu Leu Leu Glu
            195                 200                 205

Thr Ala Pro Lys Gly Phe Ser Pro Asp Trp Val Arg Tyr Glu Lys Asp
        210                 215                 220

Lys Gly Trp Gln Leu Lys Ala Glu Lys Thr Leu Ile Ser Ser Tyr Asp
225                 230                 235                 240

Ala Ile Arg Val Tyr Met Trp Val Gly Met Met Pro Asp Ser Asp Pro
                245                 250                 255

Gln Lys Ala Arg Met Leu Asn Arg Phe Lys Pro Met Ala Thr Phe Thr
```

```
                260                 265                 270
Glu Lys Asn Gly Tyr Pro Pro Glu Lys Val Asp Val Ala Thr Gly Lys
            275                 280                 285

Ala Gln Gly Lys Gly Pro Val Gly Phe Ser Ala Ala Met Leu Pro Phe
        290                 295                 300

Leu Gln Asn Arg Asp Ala Gln Val Val Gln Arg Gln Arg Val Ala Asp
305                 310                 315                 320

Asn Phe Pro Gly Ser Asp Ala Tyr Tyr Asn Tyr Val Leu Thr Leu Phe
                325                 330                 335

Gly Gln Gly Trp Asp Gln His Arg Phe Arg Phe Ser Thr Lys Gly Glu
            340                 345                 350

Leu Leu Pro Asp Trp Gly Gln Glu Cys Ala Asn Ser His
        355                 360                 365

<210> SEQ ID NO 84
<211> LENGTH: 333
<212> TYPE: PRT
<213> ORGANISM: Erwinia tasmaniensis

<400> SEQUENCE: 84

Met Met Ala Met Phe Arg Thr Gly Leu Leu Leu Ala Leu Met Leu
1               5                   10                  15

Gly Met Ala Gln Ala Ala Ala Asp Gly Trp Ser Ser Phe Lys Leu
            20                  25                  30

Arg Phe Met Thr Ser Asp Gly Arg Ile Gln Asp Thr Gly Asn Gln Asn
        35                  40                  45

Val Ser His Thr Glu Gly Gln Gly Tyr Ala Met Leu Met Ala Val Tyr
    50                  55                  60

Tyr Asp Asp Arg Ser Ser Phe Asp Lys Leu Trp Arg Trp Thr Gln Asn
65                  70                  75                  80

Asn Leu Ser Asn Pro Lys Asn Gly Leu Phe Tyr Trp Lys Tyr Asn Pro
                85                  90                  95

Ala Ala Arg Asp Pro Val Ser Asp Lys Asn Asn Ala Ala Asp Gly Asp
            100                 105                 110

Val Leu Ile Ala Trp Ala Leu Leu Gln Ala Gly Glu Lys Trp Gln Val
        115                 120                 125

Ala Gly Trp Leu Gln Gln Ser Asp Arg Ile Gln Arg Ala Ile Val Ala
    130                 135                 140

His Asn Val Ile Val Phe Gly Gly Arg Thr Leu Met Leu Pro Gly Ala
145                 150                 155                 160

Glu Gly Phe Asn Lys Thr Ser Tyr Val Val Leu Asn Pro Ser Tyr Phe
                165                 170                 175

Val Phe Pro Ala Trp Arg Asp Phe Ala Arg Arg Ser His Leu Lys Leu
            180                 185                 190

Trp Asp Lys Leu Ile Lys Asp Gly Leu Asp Leu Leu Thr Glu Met Arg
        195                 200                 205

Phe Gly Asp Thr Ala Leu Pro Leu Asp Trp Val Ala Met Asn Val Asp
    210                 215                 220

Gly Ser Leu Ala Pro Ala Thr Ala Trp Pro Ala Arg Phe Ser Tyr Asp
225                 230                 235                 240

Ala Ile Arg Ile Pro Leu Tyr Leu His Trp Tyr Asp Ala Ala Ser Leu
                245                 250                 255

Arg Leu Val Pro Phe Gln Arg Phe Trp Met Gly Phe Pro Arg Leu Gln
            260                 265                 270
```

```
Thr Pro Ala Trp Ile Asp Val Leu Thr Asn Glu Lys Ala Pro Tyr Asn
            275                 280                 285

Met Ala Gly Gly Leu Leu Ala Val Arg Asp Leu Thr Leu Asp Asp Ala
        290                 295                 300

Gly Tyr Leu Asn Asp Ser Pro Gly Ala Ser Glu Asp Tyr Tyr Ser Ser
305                 310                 315                 320

Ser Leu Gln Leu Leu Ala Trp Leu Ala Phe Lys Ser Arg
                325                 330

<210> SEQ ID NO 85
<211> LENGTH: 419
<212> TYPE: PRT
<213> ORGANISM: Bacteroides intestinalis

<400> SEQUENCE: 85

Met Lys Asn Leu Phe Tyr Leu Leu Leu Cys Leu Ile Ala Gly Thr Ser
1               5                   10                  15

Cys Ser Gln Ala Asp Pro Thr Lys Pro Trp Asp Lys Gly Ala Phe Glu
            20                  25                  30

Thr Gln Lys Tyr Arg Asn Leu Leu Ala Glu Met Gly Tyr Lys Gln Ala
        35                  40                  45

Asp Ile Asp Ala Lys Leu Lys Ser Val Phe Asp Gly Val Phe Tyr Gly
    50                  55                  60

Pro Asp Lys Val Tyr Phe Glu Val Gly Asp Ser Met Ala Tyr Ile Ser
65                  70                  75                  80

Asp Ile Lys Asn His Asp Val Arg Thr Glu Gly Met Ser Tyr Gly Leu
                85                  90                  95

Met Ile Ala Val Gln Phe Asp Arg Lys Asp Ile Phe Asp Arg Leu Trp
            100                 105                 110

Arg Trp Gly Thr Lys Tyr Met Gln His Gln Asp Gly Pro Leu Lys Gly
        115                 120                 125

Tyr Phe Ala Trp Ser Cys Glu Thr Asp Gly Thr Arg Asn Ser Gln Gly
    130                 135                 140

Pro Ala Ser Asp Gly Glu Leu Tyr Tyr Val Thr Ala Leu Ile Phe Ala
145                 150                 155                 160

Ser Asn Arg Trp Gly Asn Asp Thr Gly Ile Asn Tyr Leu Ala Glu Ala
                165                 170                 175

Arg Asn Ile Leu Asn Cys Ser Met Glu Lys Asp Gly Thr Asp Arg Val
            180                 185                 190

Met Pro Phe Ile Asn Val Glu His Lys Leu Ile Thr Phe Val Pro Asp
        195                 200                 205

Ile Arg Gly Gly Leu Phe Thr Asp Pro Ser Tyr His Val Pro Ala Phe
    210                 215                 220

Tyr Glu Val Trp Ala Arg Trp Ala Asp Gly Arg Ala Asp Phe Trp
225                 230                 235                 240

Arg Glu Cys Ala Glu Cys Ser Arg Glu Tyr Leu His Lys Ser Ile His
                245                 250                 255

Pro Val Thr Gly Leu Asn Pro Asp Tyr Asn Asn Tyr Asp Gly Ser Leu
            260                 265                 270

Leu Gly Asn Asn Arg Ile Ile Gly Asp Ala Phe Arg Phe Asp Ser Trp
        275                 280                 285

Arg Val Pro Met Asn Ile Ala Leu Asp Tyr Ser Trp Ala Cys Ala Asp
    290                 295                 300

Lys Glu Trp Gln Gln Glu Tyr Gly Asn Lys Ile Gln Asn Phe Leu Tyr
305                 310                 315                 320
```

```
Ser Gln Gly Ile Asp Thr Phe Val Asp Gln Tyr Asn Ile Asp Gly Thr
                325                 330                 335

Gln Val Lys Asp Thr Leu Arg Ala Gly Glu His Lys Ala Leu Arg His
            340                 345                 350

Ser Leu Gly Leu Val Ala Thr Ser Ala Val Ala Ser Leu Met Cys Thr
        355                 360                 365

His Glu Lys Ser Arg Glu Phe Val Asp Lys Leu Trp Asn Ala Lys His
    370                 375                 380

Glu Pro Tyr Glu Asp Gly Tyr Phe Asp Ala Tyr Tyr Asp Gly Leu Leu
385                 390                 395                 400

Arg Leu Phe Ala Phe Met His Leu Ser Gly Asn Tyr Arg Ile Ile Phe
                405                 410                 415

Pro Glu Lys

<210> SEQ ID NO 86
<211> LENGTH: 418
<212> TYPE: PRT
<213> ORGANISM: Bacteroides intestinalis

<400> SEQUENCE: 86

Met Met Lys Leu Thr Thr Leu Phe Ala Val Ser Val Ser Leu Ile Leu
1               5                   10                  15

Ser Gly Phe Cys Ser Leu Gly Val Gln Ala His Pro Val Gln Glu Asp
            20                  25                  30

Ser Ser Gly Gly Pro Val Pro Ala Gly Ala Tyr Tyr Thr Asp Asn Tyr
        35                  40                  45

Arg Asn Leu Phe Asn Glu Tyr Leu Gly Ile Ser Gln Gln Gln Thr Asp
    50                  55                  60

Gln Lys Met Glu Gln Ile Trp Asn His Phe Phe Val Asn Glu Lys Thr
65                  70                  75                  80

Lys Val Tyr Tyr Glu Ser Asp Asp Asn Thr Ala Tyr Ile Tyr Asp Thr
                85                  90                  95

Gly Asn Gln Asp Val Arg Thr Glu Gly Met Ser Tyr Gly Met Met Ile
            100                 105                 110

Cys Val Gln Leu Asp Lys Gln Ala Glu Phe Asp Lys Leu Trp Arg Trp
        115                 120                 125

Ala Lys Lys Tyr Met Leu Tyr Thr Ser Gly Lys Trp Ser Gly Tyr Tyr
    130                 135                 140

Ala Trp His Cys Thr Pro Arg Gly Val Lys Ile Gly Lys Glu Pro Ser
145                 150                 155                 160

Cys Ala Ser Asp Gly Glu Ile Tyr Phe Ile Thr Ser Leu Phe Phe Ala
                165                 170                 175

Ser His Arg Trp Gly Asn Asp Gly Ala Tyr Asp Tyr Asn Gln Glu Ala
            180                 185                 190

Gln Lys Ile Leu Lys Asp Val Met Ser Lys Asp Gly Ser Gln Gly Val
        195                 200                 205

Tyr Asn Leu Phe Asn Thr Glu Ser Lys Leu Val Thr Phe Val Pro Glu
    210                 215                 220

Lys Val Tyr Tyr Asn Tyr Thr Asp Pro Ser Tyr Asn Leu Pro Ala Phe
225                 230                 235                 240

Phe Glu Leu Trp Ala Leu Trp Ser Asp Thr Asn Lys Glu Phe Trp Lys
                245                 250                 255

Gln Thr Pro Asp Ala Ala Arg Arg Leu Leu Ala Asp Ala Ser His Lys
            260                 265                 270
```

```
Lys Thr Gly Leu Phe Pro Asp Tyr Ser Ala Phe Asp Gly Thr Pro Trp
            275                 280                 285

Lys Pro Lys Asn Trp Gly Tyr Asp Thr Arg Arg Tyr Gln Phe Asp Ala
290                 295                 300

Leu Arg Cys Ala Met Asn Val Gly Met Asp Tyr Tyr Trp Phe Gly Lys
305                 310                 315                 320

Asp Ala Thr Asn Gln Ala Glu Met Met Ser Arg Leu Leu Asn Phe Phe
                325                 330                 335

Lys Gln Asp Asn Phe Thr His Glu Tyr Phe Asn Val Asp Gly Ser Ala
            340                 345                 350

Pro Ala Gly Asn Tyr Ser Thr Gly Met Ile Gly Ala Asn Ala Val Gly
            355                 360                 365

Ala Phe Ala Leu Asn Asp Lys Asn Leu Ala Lys Glu Cys Ile Gln Lys
        370                 375                 380

Leu Trp Asn Glu Pro Leu Pro Thr Gly Lys Phe Arg Tyr Tyr Ser Gly
385                 390                 395                 400

Met Val Tyr Met Met Ser Met Leu His Val Ser Gly Asn Phe Arg Ile
                405                 410                 415

Ile Lys

<210> SEQ ID NO 87
<211> LENGTH: 407
<212> TYPE: PRT
<213> ORGANISM: Geobacillus

<400> SEQUENCE: 87

Met Lys Val Phe Arg Asn Ser Ile Ile Arg Lys Ser Ala Ala Leu Val
1               5                   10                  15

Cys Ala Val Leu Leu Ile Leu Pro Ala Gly Leu Ser Leu Ala Ala Asn
            20                  25                  30

Lys Pro Phe Pro Gln His Thr Ser Tyr Thr Ser Gly Ser Ile Lys Pro
        35                  40                  45

Asn Asn Val Thr Gln Thr Ala Met Asp Asn Ala Val Lys Ser Lys Trp
50                  55                  60

Asn Ser Trp Lys Gly Ser Phe Leu Lys Pro Ala Ala Thr Gly Gln Tyr
65                  70                  75                  80

Tyr Val Lys Tyr Asn Ser Ala Gly Glu Thr Val Ser Glu Ala His Gly
                85                  90                  95

Tyr Gly Met Ile Phe Thr Val Leu Met Ala Gly Tyr Asp Ser Asn Ala
            100                 105                 110

Gln Ser Tyr Phe Asp Gly Leu Tyr Arg Tyr Tyr Lys Ala His Pro Ser
        115                 120                 125

Asp Asn Asn Pro Tyr Leu Met Ala Trp Lys Gln Asn Ser Ser Phe Gln
    130                 135                 140

Asn Ile Glu Gly Ala Asn Ser Ala Thr Asp Gly Asp Met Asp Ile Ala
145                 150                 155                 160

Tyr Ala Leu Leu Leu Ala Asp Lys Gln Trp Gly Ser Ser Gly Ser Ile
                165                 170                 175

Asn Tyr Leu Gln Ala Ala Lys Asp Ile Ile Asn Ala Ile Met Ser Asn
            180                 185                 190

Asp Val Asn Gln Ser Gln Trp Thr Leu Arg Leu Gly Asp Trp Ala Thr
        195                 200                 205

Ser Gly Asn Tyr Asn Thr Ala Thr Arg Pro Ser Asp Phe Met Leu Asn
    210                 215                 220
```

```
His Met Lys Ala Phe Arg Ala Thr Gly Asp Ala Arg Trp Asp Asn
225                 230                 235                 240

Val Ile Asn Lys Thr Tyr Thr Ile Ile Asn Ser Ile Tyr Asn Gly Tyr
            245                 250                 255

Ser Ser Asn Thr Gly Leu Leu Pro Asp Phe Val Val Met Ser Gly Gly
            260                 265                 270

Asn Tyr Gln Pro Ala Ala Ala Gly Phe Leu Glu Gly Ala Asn Asp Gly
            275                 280                 285

Lys Tyr Tyr Tyr Asn Ser Ala Arg Thr Pro Trp Arg Ile Thr Thr Asp
            290                 295                 300

Tyr Leu Met Thr Gly Asp Thr Arg Ala Leu Asn Gln Leu Asn Lys Met
305                 310                 315                 320

Asn Thr Phe Ile Lys Ser Ala Ala Asn Ser Asn Pro Ala Asn Ile Lys
                325                 330                 335

Ala Gly Tyr Asn Leu Asn Gly Thr Ala Leu Val Thr Tyr Asn Ser Gly
                340                 345                 350

Ala Phe Tyr Ala Pro Phe Gly Val Ser Ala Met Thr Ser Ser Ser His
            355                 360                 365

Gln Ser Trp Leu Asn Ser Val Trp Asn Tyr Thr Ala Asn Ala Ser Ala
370                 375                 380

Glu Gly Tyr Tyr Glu Glu Ser Ile Lys Leu Phe Ser Met Met Val Met
385                 390                 395                 400

Ser Gly Asn Trp Trp Thr Tyr
                405

<210> SEQ ID NO 88
<211> LENGTH: 348
<212> TYPE: PRT
<213> ORGANISM: Rhizobium etli

<400> SEQUENCE: 88

Met Arg Leu Trp Arg Ala Leu Leu Val Ala Ala Thr Ala Met Leu Ala
1               5                   10                  15

Pro Ala Ile Pro Pro Ala Val Ala Gln Gln Ala Met Ile Asn Ala Asp
            20                  25                  30

Ala Trp Ser Ala Tyr Lys Ser Lys Phe Leu Asp Pro Ser Gly Arg Ile
        35                  40                  45

Ile Asp Asn Gly Asn Gly Asn Ile Ser His Ser Glu Gly Gln Gly Tyr
    50                  55                  60

Gly Met Leu Leu Ala Tyr Leu Ser Ala Ser Pro Ala Asp Phe Glu Gln
65                  70                  75                  80

Ile Trp Tyr Phe Thr Arg Thr Glu Leu Leu Leu Arg Asp Asp Gly Leu
                85                  90                  95

Ala Val Trp Lys Trp Asp Pro Asn Val Lys Pro His Val Thr Asp Thr
            100                 105                 110

Asn Asn Ala Thr Asp Gly Asp Met Leu Ile Ala Tyr Ala Leu Ala Leu
        115                 120                 125

Ala Gly Thr Gln Trp Asn Arg Asn Asp Tyr Ile Leu Ala Ala Ser Arg
    130                 135                 140

Met Ala Glu Ala Leu Leu Ala Lys Thr Val Ala Arg Ser Ala Gly Gln
145                 150                 155                 160

Met Leu Leu Leu Pro Gly Ser Glu Gly Phe Thr Ala Ala Asp Arg Lys
                165                 170                 175

Asp Gly Pro Val Val Asn Pro Ser Tyr Trp Ile Tyr Glu Ala Ile Pro
```

```
            180                 185                 190
Val Met Ala Ala Leu Ala Pro Ser Asp Ala Trp Lys Glu Leu Ser Asp
            195                 200                 205

Asp Gly Val Ala Leu Leu Lys Thr Met Gln Phe Gly Pro Arg Lys Leu
            210                 215                 220

Pro Ala Glu Trp Val Ser Leu Ser Gly Pro Pro Arg Pro Ala Glu Gly
225                 230                 235                 240

Phe Asp Ala Glu Phe Ala Tyr Asn Ala Leu Arg Ile Pro Leu Tyr Leu
                245                 250                 255

Ala Arg Gly Gly Ile Thr Asp Lys Ala Leu Leu Thr Arg Leu Arg Lys
            260                 265                 270

Gly Met Ser Gln Asp Gly Ile Pro Ala Thr Ile Asp Leu Thr Thr Gly
            275                 280                 285

Arg Pro Lys Thr Val Leu Ser Asp Pro Gly Tyr Arg Ile Val Asn Asp
            290                 295                 300

Val Val Ala Cys Val Val Asp Gly Thr Lys Leu Pro Ser Ser Ala Leu
305                 310                 315                 320

Gln Phe Ala Pro Thr Leu Tyr Tyr Pro Ser Thr Leu Gln Leu Leu Gly
                325                 330                 335

Leu Ala Tyr Ile Gly Glu Lys His Pro Glu Cys Leu
                340                 345

<210> SEQ ID NO 89
<211> LENGTH: 370
<212> TYPE: PRT
<213> ORGANISM: Escherichia coli

<400> SEQUENCE: 89

Met Lys Met Asn Val Leu Arg Ser Gly Ile Val Thr Met Leu Leu Leu
1               5                   10                  15

Ala Ala Phe Ser Val Gln Ala Ala Cys Thr Trp Pro Ala Trp Glu Gln
                20                  25                  30

Phe Lys Lys Asp Tyr Ile Ser Gln Glu Gly Arg Val Ile Asp Pro Ser
            35                  40                  45

Asp Ala Arg Lys Ile Thr Thr Ser Glu Gly Gln Ser Tyr Gly Met Phe
        50                  55                  60

Phe Ala Leu Ala Ala Asn Asp Arg Val Ala Phe Asp Asn Ile Leu Asp
65                  70                  75                  80

Trp Thr Gln Asn Asn Leu Ala Gln Gly Ser Leu Lys Glu Arg Leu Pro
                85                  90                  95

Ala Trp Leu Trp Gly Lys Lys Glu Asn Ser Lys Trp Glu Val Leu Asp
            100                 105                 110

Ser Asn Ser Ala Ser Asp Gly Asp Val Trp Met Ala Trp Ser Leu Leu
        115                 120                 125

Glu Ala Gly Arg Leu Trp Lys Glu Gln Arg Tyr Thr Asp Ile Gly Ser
130                 135                 140

Ala Leu Leu Lys Arg Ile Ala Arg Glu Glu Val Thr Val Pro Gly
145                 150                 155                 160

Leu Gly Ser Met Leu Leu Pro Gly Lys Val Gly Phe Ala Glu Asp Asn
                165                 170                 175

Ser Trp Arg Phe Asn Pro Ser Tyr Leu Pro Pro Thr Leu Ala Gln Tyr
            180                 185                 190

Phe Thr Arg Phe Gly Ala Pro Trp Thr Thr Leu Arg Glu Thr Asn Gln
            195                 200                 205
```

```
Arg Leu Leu Glu Thr Ala Pro Lys Gly Phe Ser Pro Asp Trp Val
210                 215                 220

Arg Tyr Glu Lys Asp Lys Gly Trp Gln Leu Lys Ala Glu Lys Thr Leu
225                 230                 235                 240

Ile Ser Ser Tyr Asp Ala Ile Arg Val Tyr Met Trp Val Gly Met Met
                245                 250                 255

Pro Asp Ser Asp Pro Gln Lys Ala Arg Met Leu Asn Arg Phe Lys Pro
            260                 265                 270

Met Ala Thr Phe Thr Glu Lys Asn Gly Tyr Pro Pro Glu Lys Val Asp
            275                 280                 285

Val Ala Thr Gly Lys Ala Gln Gly Lys Gly Pro Val Gly Phe Ser Ala
290                 295                 300

Ala Met Leu Pro Phe Leu Gln Asn Arg Asp Ala Gln Ala Val Gln Arg
305                 310                 315                 320

Gln Arg Val Ala Asp Asn Phe Pro Gly Ser Asp Ala Tyr Tyr Asn Tyr
                325                 330                 335

Val Leu Thr Leu Phe Gly Gln Gly Trp Asp Gln His Arg Phe Arg Phe
                340                 345                 350

Ser Thr Lys Gly Glu Leu Leu Pro Asp Trp Gly Gln Glu Cys Ala Asn
                355                 360                 365

Ser His
    370

<210> SEQ ID NO 90
<211> LENGTH: 380
<212> TYPE: PRT
<213> ORGANISM: Lactobacillus reuteri

<400> SEQUENCE: 90

Met Lys Arg Pro Val Tyr Ile Trp Leu Leu Thr Leu Val Val Ala Val
1               5                   10                  15

Ile Tyr Ile Ala Thr Leu Ala Phe Val Arg Ile Lys Asn Pro Glu His
                20                  25                  30

Ile Gln Tyr Glu Ala Tyr Arg Arg Trp Gln Ala Ala Tyr Leu Val Arg
            35                  40                  45

Lys Asn Ser Lys Gln Thr Tyr Val Asn Thr Ser Asn Asp Gln Lys His
50                  55                  60

Pro Val Ala Leu Ser Glu Gly Gln Gly Tyr Gly Leu Gln Val Val Ser
65                  70                  75                  80

Arg Ala Ala Glu Lys Gly Trp Ala Ser Glu Asn Asp Phe Asp Lys Leu
                85                  90                  95

Leu Asn Tyr Tyr Leu Ala His Arg Asn Tyr Val Gly Glu His His Asp
            100                 105                 110

His Leu Thr Tyr Leu Met Ala Trp Arg Gln Ser Tyr Asn Lys Lys Gly
        115                 120                 125

Gln Trp Val Asp Asp His Asn Ser Ala Thr Asp Gly Asp Leu Tyr Ile
    130                 135                 140

Ala Ala Ala Leu His Arg Ala Ala Lys Val Trp Pro Gln Lys Ala Pro
145                 150                 155                 160

Tyr Tyr His Lys Leu Glu Gln Gln Ile Ala Thr Asp Ile Leu Lys Tyr
                165                 170                 175

Glu Tyr Asn Pro Thr Thr His Met Leu Thr Val Gly Asp Trp Val Thr
            180                 185                 190

Lys Asp Ser Lys Phe Tyr Tyr Leu Leu Arg Thr Ser Asp Val Met Pro
        195                 200                 205
```

```
Thr Val Phe Asp His Leu Tyr Asp Cys Thr His Asp Ser Arg Trp Gln
    210                 215                 220
Met Ile Lys Asn Asn Met Leu Asp Arg Leu Ala Ala Leu Ser Lys Leu
225                 230                 235                 240
His Gln Thr Gly Leu Val Pro Asp Phe Ala Trp Ala Arg Pro Gly Ser
                245                 250                 255
Thr Lys Pro Val Gly Pro Asn Thr Val Ala Gly Lys Tyr Asp Gly Asp
                260                 265                 270
Tyr Ser Ala Asn Ala Cys Arg Val Pro Met Met Leu Ala Lys Ser Asn
                275                 280                 285
Asp Pro Arg Ala Gln Lys Val Leu Asn Lys Met Met Arg Phe Phe Ser
            290                 295                 300
Glu Gln Tyr Tyr Ile Thr Ala Gly Tyr Ser Leu Asn Gly His Arg Leu
305                 310                 315                 320
Val Lys Tyr Gln Ser Asn Ser Phe Ser Ala Pro Ile Phe Tyr Ala Val
                325                 330                 335
Ser Cys Asn Arg Asn Glu Gly Tyr Asp Asn Leu Phe Ala Ser Gln Lys
                340                 345                 350
His Ile Phe Ser Lys Pro Leu Thr Glu Lys Asn Tyr Tyr Asp Ala Thr
            355                 360                 365
Leu Thr Thr Leu Ala Ala Leu Glu Gly Met Asn Asn
    370                 375                 380

<210> SEQ ID NO 91
<211> LENGTH: 369
<212> TYPE: PRT
<213> ORGANISM: Salmonella enterica

<400> SEQUENCE: 91

Met Met Thr Met Leu Arg Gly Trp Ile Thr Met Ile Val Met Leu Thr
1               5                   10                  15
Ala Ile Asn Ala Gln Ala Ala Cys Ser Trp Pro Ala Trp Glu Gln Phe
                20                  25                  30
Lys Lys Asp Tyr Ile Ser Gln Gln Gly Arg Val Ile Asp Pro Gly Asp
            35                  40                  45
Ala Arg Lys Ile Thr Thr Ser Glu Gly Gln Ser Tyr Ala Met Phe Phe
    50                  55                  60
Ala Leu Ala Ala Asn Asp Arg Pro Ala Phe Ala Gln Leu Phe Asn Trp
65                  70                  75                  80
Thr Gln Asn Asn Leu Ala Gln Gly Ser Leu Arg Glu His Leu Pro Ala
                85                  90                  95
Trp Leu Trp Gly Gln Lys Asn Pro Asp Thr Trp Ser Val Leu Asp Ser
            100                 105                 110
Asn Ser Ala Ser Asp Gly Asp Ile Trp Met Ala Trp Ser Leu Leu Glu
        115                 120                 125
Ala Gly Arg Leu Trp Lys Glu Thr Arg Tyr Thr Glu Val Gly Thr Ala
    130                 135                 140
Leu Leu Lys Arg Ile Ala Arg Glu Val Val Asn Val Pro Gly Leu
145                 150                 155                 160
Gly Ser Met Leu Leu Pro Gly Lys Ile Gly Phe Ala Glu Ala Asn Ser
                165                 170                 175
Trp Arg Phe Asn Pro Ser Tyr Leu Pro Pro Gln Leu Ala Gln Tyr Phe
            180                 185                 190
Ser Arg Phe Gly Ala Pro Trp Ser Thr Leu Arg Glu Thr Asn Leu Arg
```

```
        195                 200                 205

Leu Leu Leu Glu Thr Ala Pro Lys Gly Phe Ser Pro Asp Trp Val Arg
    210                 215                 220

Tyr Glu Ser Lys Gln Gly Trp Gln Leu Lys Ala Glu Lys Thr Leu Ile
225                 230                 235                 240

Ser Ser Tyr Asp Ala Ile Arg Val Tyr Leu Trp Ala Gly Met Met His
                245                 250                 255

Asp Gly Asp Pro Gln Lys Ala Arg Leu Leu Ala Arg Phe Lys Pro Met
            260                 265                 270

Ala Thr Leu Thr Met Lys Asn Gly Val Pro Pro Glu Lys Val Asp Val
        275                 280                 285

Val Ser Gly Asn Ala Gln Gly Thr Gly Pro Val Gly Phe Ser Ala Ala
    290                 295                 300

Leu Leu Pro Phe Leu Gln Asn Arg Asp Ala Gln Ala Val Gln Arg Gln
305                 310                 315                 320

Arg Val Ala Asp His Phe Pro Gly Ser Asp Ala Tyr Tyr Asn Tyr Val
                325                 330                 335

Leu Thr Leu Phe Gly Gln Gly Trp Asp Gln His Arg Phe Arg Phe Thr
            340                 345                 350

Val Lys Gly Glu Leu Leu Pro Asp Trp Gly Gln Glu Cys Val Ser Ser
        355                 360                 365

Arg

<210> SEQ ID NO 92
<211> LENGTH: 453
<212> TYPE: PRT
<213> ORGANISM: Bacillus cereus

<400> SEQUENCE: 92

Met Asn Gly Lys Arg Asn Ile Phe Thr Cys Ile Ser Ile Val Gly Ile
1               5                   10                  15

Gly Leu Ala Ser Phe Ser Asn Ser Ser Phe Ala Ala Ser Val Thr Asp
            20                  25                  30

Asn Ser Ile Gln Asn Ser Ile Pro Val Val Asn Gln Gln Val Ala Ala
        35                  40                  45

Ala Lys Glu Met Lys Pro Phe Pro Gln Gln Val Asn Tyr Ala Gly Val
    50                  55                  60

Ile Lys Pro Asn His Val Thr Gln Glu Ser Leu Asn Ala Ser Val Arg
65                  70                  75                  80

Ser Tyr Tyr Asp Asn Trp Lys Lys Lys Tyr Leu Lys Asn Asp Leu Ser
                85                  90                  95

Ser Leu Pro Gly Gly Tyr Tyr Val Lys Gly Glu Ile Thr Gly Asp Ala
            100                 105                 110

Asp Gly Phe Lys Pro Leu Gly Thr Ser Glu Gly Gln Gly Tyr Gly Met
        115                 120                 125

Ile Ile Thr Val Leu Met Ala Gly Tyr Asp Ser Asn Ala Gln Lys Ile
    130                 135                 140

Tyr Asp Gly Leu Phe Lys Thr Ala Arg Thr Phe Lys Ser Ser Gln Asn
145                 150                 155                 160

Pro Asn Leu Met Gly Trp Val Val Ala Asp Ser Lys Lys Ala Gln Gly
                165                 170                 175

His Phe Asp Ser Ala Thr Asp Gly Asp Leu Asp Ile Ala Tyr Ser Leu
            180                 185                 190

Leu Leu Ala His Lys Gln Trp Gly Ser Asn Gly Ala Val Asn Tyr Leu
```

```
                195                 200                 205
Lys Glu Ala Gln Asp Met Ile Thr Lys Gly Ile Lys Ala Ser Asn Val
210                 215                 220

Thr Asn Asn Ser Arg Leu Asn Leu Gly Asp Trp Asp Ser Lys Ser Ser
225                 230                 235                 240

Leu Asp Thr Arg Pro Ser Asp Trp Met Met Ser His Leu Arg Ala Phe
                245                 250                 255

Tyr Glu Phe Thr Gly Asp Lys Thr Trp Leu Thr Val Ile Asn Asn Leu
            260                 265                 270

Tyr Asp Val Tyr Thr Gln Phe Ser Asn Lys Tyr Ser Pro Asn Thr Gly
        275                 280                 285

Leu Ile Ser Asp Phe Val Val Lys Asn Pro Pro Gln Pro Ala Pro Lys
    290                 295                 300

Asp Phe Leu Asn Glu Ser Glu Tyr Thr Asn Ala Tyr Tyr Asn Ala
305                 310                 315                 320

Ser Arg Val Pro Leu Arg Ile Val Met Asp Tyr Ala Met Tyr Gly Glu
                325                 330                 335

Lys Arg Ser Lys Val Ile Ser Asp Lys Val Ser Ser Trp Ile Gln Asn
            340                 345                 350

Lys Thr Asn Gly Asn Pro Ser Lys Ile Val Asp Gly Tyr Gln Leu Asn
        355                 360                 365

Gly Ser Asn Ile Gly Ser Tyr Pro Thr Ala Val Phe Val Ser Pro Phe
    370                 375                 380

Ile Ala Ala Ser Ile Thr Asn Ser Asn Asn Gln Lys Trp Val Asn Ser
385                 390                 395                 400

Gly Trp Asp Trp Met Lys Asn Lys Arg Glu Ser Tyr Phe Ser Asp Ser
                405                 410                 415

Tyr Asn Leu Leu Thr Met Leu Phe Ile Thr Gly Asn Trp Trp Lys Pro
            420                 425                 430

Ile Pro Asp Asn Lys Lys Ala Gln Asn Gln Ile Asn Asp Ala Ile Tyr
        435                 440                 445

Glu Gly Tyr Asp Asn
    450

<210> SEQ ID NO 93
<211> LENGTH: 412
<212> TYPE: PRT
<213> ORGANISM: Bacillus cereus

<400> SEQUENCE: 93

Met Arg Arg Asn His Asp Phe Asn Asp Ser Gly Lys Lys Arg Leu Glu
1               5                   10                  15

Lys Val Glu Ser Ile Phe Thr Ile His Lys Pro Phe Pro Gln Gln Val
            20                  25                  30

Thr Tyr Pro Gly Val Val Lys Pro Asn His Ile Ser Gln Glu Glu Leu
        35                  40                  45

Asn Glu Ser Val Lys Ser Tyr Tyr Asn His Trp Lys Met Asn Tyr Leu
    50                  55                  60

Lys Asn Asp Leu Ser Ser Leu Pro Gly Gly Tyr Tyr Val Lys Gly Glu
65                  70                  75                  80

Ile Thr Gly Asn Pro Glu Gly Phe Thr Pro Leu Gly Thr Ser Glu Gly
                85                  90                  95

Gln Gly Tyr Gly Met Val Ile Thr Val Leu Met Ala Gly Tyr Asp Ser
            100                 105                 110
```

```
Ala Ala Gln Ser Ile Tyr Asn Gly Leu Phe Lys Thr Val Lys Thr Phe
            115                 120                 125

Lys Ser Ser Lys Asn Ser Asn Leu Met Gly Trp Ile Val Thr Asp Asp
    130                 135                 140

Lys Lys Ala Phe Gly Tyr Phe Pro Ser Ala Thr Asp Gly Asp Leu Asp
145                 150                 155                 160

Ile Ala Tyr Ser Leu Leu Ala His Thr Gln Trp Gly Ser Thr Gly
                165                 170                 175

Ala Ile Asn Tyr Leu Lys Glu Ala Gln Met Ile Thr Glu Gly Ile
                180                 185                 190

Lys Lys Ser Leu Val Thr Ile Asn Lys Arg Leu Asn Leu Gly Asp Trp
    195                 200                 205

Asp Lys Asp Thr Thr Leu Asn Thr Arg Ser Ser Asp Trp Met Met Ser
    210                 215                 220

Asn Phe Arg Ala Phe Tyr Glu Phe Thr Asn Asp Gln Ile Trp Leu Asn
225                 230                 235                 240

Thr Ile Asp Asn Leu Tyr Asn Ile Tyr Glu Glu Phe Ser Thr Lys Tyr
                245                 250                 255

Ser Pro Asn Thr Gly Leu Val Ser Asp Phe Val Val Asp Ser Pro Pro
                260                 265                 270

Gln Pro Ala Ser Glu Asn Phe Leu Asn Glu Ser Glu Tyr Thr Gly Ala
                275                 280                 285

Tyr Tyr Tyr Asn Ala Ser Arg Val Pro Leu Arg Ile Val Met Asp Tyr
                290                 295                 300

Ala Met Tyr Gly Glu Lys Arg Ser Lys Ile Ile Ser Asp Lys Ile Ser
305                 310                 315                 320

Thr Trp Ile Arg Asn Gln Thr Ser Glu Asn Pro Ser Asn Ile Val Asp
                325                 330                 335

Gly Tyr His Leu Asn Gly Ser Val Ile Gly Ser Tyr Ala Thr Ala Val
                340                 345                 350

Phe Val Ser Pro Phe Ile Ala Ala Ser Ile Thr Asn Thr Ser Asn Gln
                355                 360                 365

Asn Trp Ile Asn Ser Gly Trp Asp Trp Met Glu Asn Lys Lys Glu Ser
    370                 375                 380

Tyr Tyr Ser Asp Ser Tyr Asn Leu Leu Thr Met Leu Phe Ile Ser Gly
385                 390                 395                 400

Asn Trp Trp Lys Pro Val Pro Glu Asn Arg Gln Ile
                405                 410

<210> SEQ ID NO 94
<211> LENGTH: 477
<212> TYPE: PRT
<213> ORGANISM: Clostridium thermocellum

<400> SEQUENCE: 94

Met Lys Asn Val Lys Lys Arg Val Gly Val Val Leu Ile Leu Ala
1               5                   10                  15

Val Leu Gly Val Tyr Met Leu Ala Met Pro Ala Asn Thr Val Ser Ala
                20                  25                  30

Ala Gly Val Pro Phe Asn Thr Lys Tyr Pro Tyr Gly Pro Thr Ser Ile
                35                  40                  45

Ala Asp Asn Gln Ser Glu Val Thr Ala Met Leu Lys Ala Glu Trp Glu
                50                  55                  60

Asp Trp Lys Ser Lys Arg Ile Thr Ser Asn Gly Ala Gly Gly Tyr Lys
65                  70                  75                  80
```

-continued

Arg Val Gln Arg Asp Ala Ser Thr Asn Tyr Asp Thr Val Ser Glu Gly
            85                  90                  95

Met Gly Tyr Gly Leu Leu Leu Ala Val Cys Phe Asn Glu Gln Ala Leu
                100                 105                 110

Phe Asp Asp Leu Tyr Arg Tyr Val Lys Ser His Phe Asn Gly Asn Gly
            115                 120                 125

Leu Met His Trp His Ile Asp Ala Asn Asn Val Thr Ser His Asp
130                 135                 140

Gly Gly Asp Gly Ala Ala Thr Asp Ala Asp Glu Asp Ile Ala Leu Ala
145                 150                 155                 160

Leu Ile Phe Ala Asp Lys Leu Trp Gly Ser Gly Ala Ile Asn Tyr
                165                 170                 175

Gly Gln Glu Ala Arg Thr Leu Ile Asn Asn Leu Tyr Asn His Cys Val
            180                 185                 190

Glu His Gly Ser Tyr Val Leu Lys Pro Gly Asp Arg Trp Gly Gly Ser
            195                 200                 205

Ser Val Thr Asn Pro Ser Tyr Phe Ala Pro Ala Trp Tyr Lys Val Tyr
            210                 215                 220

Ala Gln Tyr Thr Gly Asp Thr Arg Trp Asn Gln Val Ala Asp Lys Cys
225                 230                 235                 240

Tyr Gln Ile Val Glu Glu Val Lys Lys Tyr Asn Asn Gly Thr Gly Leu
                245                 250                 255

Val Pro Asp Trp Cys Thr Ala Ser Gly Thr Pro Ala Ser Gly Gln Ser
                260                 265                 270

Tyr Asp Tyr Lys Tyr Asp Ala Thr Arg Tyr Gly Trp Arg Thr Ala Val
                275                 280                 285

Asp Tyr Ser Trp Phe Gly Asp Gln Arg Ala Lys Ala Asn Cys Asp Met
            290                 295                 300

Leu Thr Lys Phe Phe Ala Arg Asp Gly Ala Lys Gly Ile Val Asp Gly
305                 310                 315                 320

Tyr Thr Ile Gln Gly Ser Lys Ile Ser Asn Asn His Asn Ala Ser Phe
                325                 330                 335

Ile Gly Pro Val Ala Ala Ala Ser Met Thr Gly Tyr Asp Leu Asn Phe
                340                 345                 350

Ala Lys Glu Leu Tyr Arg Glu Thr Val Ala Val Lys Asp Ser Glu Tyr
                355                 360                 365

Tyr Gly Tyr Tyr Gly Asn Ser Leu Arg Leu Leu Thr Leu Leu Tyr Ile
            370                 375                 380

Thr Gly Asn Phe Pro Asn Pro Leu Ser Asp Leu Ser Gly Gln Pro Thr
385                 390                 395                 400

Pro Pro Ser Asn Pro Thr Pro Ser Leu Pro Pro Gln Val Val Tyr Gly
                405                 410                 415

Asp Val Asn Gly Asp Gly Asn Val Asn Ser Thr Asp Leu Thr Met Leu
            420                 425                 430

Lys Arg Tyr Leu Leu Lys Ser Val Thr Asn Ile Asn Arg Glu Ala Ala
                435                 440                 445

Asp Val Asn Arg Asp Gly Ala Ile Asn Ser Ser Asp Met Thr Ile Leu
450                 455                 460

Lys Arg Tyr Leu Ile Lys Ser Ile Pro His Leu Pro Tyr
465                 470                 475

<210> SEQ ID NO 95
<211> LENGTH: 383

<212> TYPE: PRT
<213> ORGANISM: Burkholderia cenocepacia

<400> SEQUENCE: 95

```
Met Thr Cys Ala Ala Ala Gly Met Ala Thr Arg Ala His Ala Ala Gly
1               5                   10                  15

Thr Gly Ala Ala Asp Ala Ala Gly Ala Gly Cys Ser Val Ala Trp Pro
            20                  25                  30

Arg Trp Asp Ala Phe Lys Arg Asp Phe Ile Ser Ala Asp Gly Arg Val
        35                  40                  45

Ile Asp Val Gly Ser Ala Asp Ser Arg Thr Val Ser Glu Gly Gln Ala
    50                  55                  60

Tyr Gly Leu Phe Phe Ala Leu Val Ala Asn Asp Arg Arg Met Phe Asp
65                  70                  75                  80

Thr Ile Leu Ala Trp Thr Glu Asn Asn Leu Ala Gln Gly Asp Leu Ser
                85                  90                  95

Ala His Leu Pro Ala Trp Leu Trp Gly Arg Ala Pro Asp Gly Ala Trp
            100                 105                 110

Arg Val Leu Asp Ala Asn Pro Ala Ser Asp Ala Asp Leu Trp Ile Ala
        115                 120                 125

Tyr Ala Leu Val Glu Ala Gly Arg Leu Trp Arg Glu Arg Ser Tyr Thr
    130                 135                 140

Ala Arg Gly Ala Leu Leu Ala Lys Arg Val Leu Asp Ala Glu Thr Ala
145                 150                 155                 160

Thr Val Pro Gly Leu Gly Leu Thr Leu Leu Pro Gly Pro Thr Gly Phe
                165                 170                 175

Lys Leu Ala Asp Gly Gln Trp Arg Val Asn Pro Ser Tyr Ser Pro Pro
            180                 185                 190

Gln Val Ile Arg Ala Leu Gly Ala Arg Leu Pro Asp Asp Arg Arg Trp
        195                 200                 205

Ala Ala Leu Ala Ser Ser Thr Gly Arg Val Leu Leu Asp Thr Ala Pro
    210                 215                 220

Lys Gly Phe Ser Pro Asp Trp Ala Leu Tyr Arg Ala Gly Lys Gly Phe
225                 230                 235                 240

Gly Pro Asp Pro Asp Thr His Ala Gln Ser Ala Tyr Asn Ala Ile Arg
                245                 250                 255

Val Tyr Leu Trp Ala Gly Met Leu Asp Arg Ala Asp Pro Leu Ala Ala
            260                 265                 270

Pro Leu Leu Ala Lys Phe Ala Pro Phe Ala Asp Ala Ile Ala Ala His
        275                 280                 285

Gly Ala Pro Pro Glu Arg Val Asp Thr Thr Thr Gly Val Ala Gly Pro
    290                 295                 300

Asn Asp Gly Asn Gly Gly Phe Ser Ala Ala Ala Val Pro Phe Leu Asp
305                 310                 315                 320

Ala Arg Gly Gln His Ala Leu Ala Asp Ala Gln Ala Ala Arg Val Asp
                325                 330                 335

Thr Leu Ala Arg Gln Ser Ala Pro Gly Tyr Tyr Thr Ser Val Leu Thr
            340                 345                 350

Leu Phe Gly Leu Gly Trp Arg Asp Gly Arg Tyr Arg Phe Gly Ala Asp
        355                 360                 365

Gly Thr Leu Asp Thr Arg Trp Gly Asp Arg Ser Cys Ala Ala Arg
    370                 375                 380
```

<210> SEQ ID NO 96

```
<211> LENGTH: 345
<212> TYPE: PRT
<213> ORGANISM: Proteus mirabilis

<400> SEQUENCE: 96

Met Ser Ile Arg Gln Leu Ser Arg Leu Thr His Arg Leu Gly Ile Leu
1               5                   10                  15

Leu Thr Leu Ser Val Met Leu Met Ile Ser Pro Met Thr Gln Ala Thr
            20                  25                  30

Glu Thr Gln Ala Gly Trp Gln Gln Phe Lys Ala Arg Tyr Ile Thr Pro
        35                  40                  45

Glu Gly Arg Val Ile Asp Ser Ala Asn Gln Asn Ile Ser His Ser Glu
50                  55                  60

Gly Gln Gly Tyr Gly Met Leu Met Ala Val Met Ser Asp Asp Arg Gln
65                  70                  75                  80

Thr Phe Ala Gln Leu Trp His Trp Thr Ala Met Ser Leu Tyr Arg Gly
                85                  90                  95

Asp Leu Gly Leu Phe Lys Trp Arg Tyr Glu Pro Glu Asn Asn Gln His
            100                 105                 110

Thr Pro Asp Pro Asn Asn Ala Thr Asp Gly Asp Ile Leu Ile Ala Trp
        115                 120                 125

Ala Leu Leu Lys Ala Gly Glu Lys Trp His Asp Glu Ser Tyr Leu Ser
130                 135                 140

Ala Ser Asp Ser Ile Gln His Ala Ile Leu Glu His Thr Leu Val Lys
145                 150                 155                 160

Thr Glu Asn Tyr Ser Val Leu Leu Pro Gly Ile Asn Gly Phe Lys Thr
                165                 170                 175

Pro Glu Glu Ile Ile Ile Asn Pro Ser Tyr Phe Ile Phe Pro Ala Trp
            180                 185                 190

Lys Asp Phe Tyr Arg Val Ser His Asp Ser Arg Trp Lys Asn Leu Ile
        195                 200                 205

Asn Asp Ser Gln Ser Leu Leu Arg Lys Met Arg Phe Gly Lys Tyr Lys
210                 215                 220

Leu Pro Ser Asp Trp Val Ser Leu Tyr Pro Asp Gly His Leu Ala Pro
225                 230                 235                 240

Ser Glu Lys Trp Pro Ala Arg Phe Ser Phe Asp Ala Ile Arg Ile Pro
                245                 250                 255

Leu Tyr Leu Ala Trp Ala Gln Asp Lys Leu Ala Leu Gln Pro Phe Val
            260                 265                 270

Asn Tyr Trp Gln Gln Phe Asp Arg Asp Lys Thr Pro Ala Trp Ile Ser
        275                 280                 285

Ile Asp Gly Lys Glu Arg Ala Asp Tyr Asn Leu Thr Pro Gly Met Met
290                 295                 300

Ala Val Arg Asp Leu Thr Met Lys Thr Val Ile Glu Asn Val Asp Leu
305                 310                 315                 320

Thr Lys Asp Thr Asp Tyr Ser Ser Ala Leu His Leu Leu Ala Ala
                325                 330                 335

Phe Ala Gln Asn Asn His Asn Asp Tyr
            340                 345

<210> SEQ ID NO 97
<211> LENGTH: 366
<212> TYPE: PRT
<213> ORGANISM: Alteromonas macleodii

<400> SEQUENCE: 97
```

```
Met Val Thr Gly Phe Lys Ala Thr Lys Thr Leu Leu Ala Ile Ala Leu
 1               5                  10                  15

Thr Leu Leu Val Ser Cys Ser Thr Lys Glu Asp Asn Ala Phe Lys
            20                  25                  30

Ser Gln Phe Met Ala Tyr Lys Ala Leu Phe Ile Asp Gly Gly Arg Val
            35                  40                  45

Val Asp Thr Gly Asn Asp Glu Val Ser His Ser Glu Gly Gln Gly Tyr
 50                  55                  60

Gly Met Leu Phe Ala Val Ala Ala Asp Asp Lys Asp Thr Phe Asp Ala
 65                  70                  75                  80

Leu Trp His Trp Thr Gln Arg Thr Leu Leu Arg Ser Asp Gly Leu Phe
                 85                  90                  95

Ser Trp Arg Tyr Arg Pro Cys Ala Asp Asn Ser Glu Ser Cys Ile Asp
            100                 105                 110

Asp Pro Asn Asn Ala Ser Asp Gly Glu Ile Leu Ile Ala Trp Ala Leu
            115                 120                 125

Leu Arg Ala Ser Glu Lys Trp Gly Ile Lys Gly Tyr Gln Asp Glu Ala
130                 135                 140

Gly Lys Ile Val Gln Ala Val Glu Gln Lys Leu Leu Val Glu His Gln
145                 150                 155                 160

Gly Ser Val Met Leu Leu Pro Gly Glu Tyr Gly Phe Thr Ser Gln Ser
                165                 170                 175

Glu Gly Gln Lys Ser Leu Gln Leu Asn Leu Ser Tyr Trp Val Phe Pro
            180                 185                 190

Ala Leu Thr Asp Leu Ser Ala Leu Ser Asn Thr Pro Ser Arg Trp Gln
            195                 200                 205

Lys Leu His Gln Thr Gly Leu Thr Leu Leu Ser Asn Met Gln Phe Ser
210                 215                 220

Ser Tyr Gln Leu Pro Ser Asp Trp Val Arg Phe Glu Pro Arg Asn Ser
225                 230                 235                 240

Gly Ser Ala Lys Ser Gly Leu Ser Gly Glu Leu Thr Leu Thr Asn Val
                245                 250                 255

Val Ser Ala Glu Phe Gly Phe Asn Ala Ile Arg Ile Pro Leu Gln Leu
            260                 265                 270

Ala Trp Ser Val Gln Val Arg Asp Asn Ala Ala Leu Ala Glu Glu Leu
            275                 280                 285

Phe Ala Pro Tyr Tyr Gln Trp Trp Ala Lys Thr Pro Thr Pro Ala Thr
            290                 295                 300

Val Asn Leu Leu Thr Glu Gln Thr Ala Glu Tyr Glu Met Thr Pro Gly
305                 310                 315                 320

Met Gln Ser Val Lys Leu Ala Val Lys Tyr Leu Met Lys Ser Glu Glu
                325                 330                 335

Pro Val Trp Pro Thr Val Asn Arg Lys Met Asp Tyr Tyr Ser Ala Ser
            340                 345                 350

Leu Thr Leu Leu Ser Met Leu Ala Val Ser Asp Asn Ala Ser
            355                 360                 365

<210> SEQ ID NO 98
<211> LENGTH: 1140
<212> TYPE: PRT
<213> ORGANISM: Anaeromyxobacter

<400> SEQUENCE: 98

Met Arg Pro Thr Ala Arg Asn Leu Ala Pro Leu Leu Ala Val Leu Cys
```

-continued

```
1               5                   10                  15
Ala Pro Pro Ala Leu Gly Gly Cys Gly His Ala Glu Ala Arg Pro
             20                  25                  30

Arg Ala Ala Gln Asp Arg Asp Gly Leu Ser Ala Leu Trp Ser Tyr
             35                  40                  45

Tyr Arg Tyr Thr His Val Gln Gly Arg Val Ala Ala Leu Asp Glu
 50                  55                  60

Gly Gly Val Thr Thr Ser Glu Gly Gln Gly Tyr Ala Met Leu Arg Ala
 65                  70                  75                  80

Val Trp Met Asp Asp Arg Ala Thr Leu Asp Ala Val Trp Arg Trp Thr
                 85                  90                  95

Arg Glu Asn Leu Ala Val Arg Glu Asp Arg Leu Leu Ala Trp Arg Trp
                100                 105                 110

Leu Gly Gly Lys Val Gln Asp Arg Asn Ala Ala Thr Asp Ala Asp Gln
                115                 120                 125

Asp Val Ala Leu Ala Leu Val Leu Ala Ser Arg Arg Phe Gly Asp Pro
130                 135                 140

Arg Tyr Leu Glu Ala Ala Arg Pro Leu Leu Ala Asp Ile Trp Ala Arg
145                 150                 155                 160

Glu Val Ile Arg Ala Gly Gly Arg Trp Leu Pro Thr Gly Gly Asn Trp
                165                 170                 175

Ala Pro Ala Glu Arg Tyr Pro Thr Ile His Val Ala Tyr Leu Ala Pro
                180                 185                 190

Tyr Ala Tyr Gln Val Phe Ala Asp Val Asp Pro Glu Arg Pro Trp Ala
            195                 200                 205

Glu Leu Val Glu Ser Ser Tyr Gln Val Leu Arg Phe Leu Met Ile Glu
210                 215                 220

Lys Gly Leu Ala Leu Pro Pro Glu Arg Ile Trp Val Asp Pro Arg Thr
225                 230                 235                 240

Gly Glu Leu Leu Leu Ala Arg Pro Gly Gly Ala Pro Asp Ala Phe Gly
                245                 250                 255

Tyr Asp Ala Val Pro Ile Tyr Trp Arg Val Ala Leu Asp Ala Arg Trp
                260                 265                 270

Phe Gly Arg Arg Gly Glu Ala Glu Leu Arg Ala Arg Leu Leu Arg Phe
            275                 280                 285

Pro Ala Glu Ala Phe Arg Asp Glu Gly Arg Leu Arg Glu Arg Tyr Thr
290                 295                 300

Thr Ser Gly Arg Pro Leu Ser Gly Leu Asp Gly Leu Pro His Leu Ala
305                 310                 315                 320

Ala Val Gln Ala Leu Ala Gln Val Glu Asp Pro Glu Leu Ala Arg Ala
                325                 330                 335

Met Arg Ala Ala Ser Leu Asp Ala Leu Phe Asp Arg Ala Leu Ser Gly
            340                 345                 350

Glu Ala Thr Pro Tyr Tyr Leu His Asn Trp Leu Trp Phe Gly Arg Ala
            355                 360                 365

Leu Glu Ala Gly Leu Leu Arg Arg Phe Asp Glu Pro Leu Ala Phe Leu
370                 375                 380

Ser Ser Leu Asp Trp Gly Ala Phe Arg Asp Arg Phe Pro Leu Leu Ala
385                 390                 395                 400

Val Gly Leu Ala Leu Leu Leu Ala Pro Leu Ala Arg Arg Leu Trp Pro
                405                 410                 415

Ala Arg Ala Ala Leu Val Ala Leu Ala Leu Gly Leu Ser Val Arg Tyr
            420                 425                 430
```

```
Leu Ala Trp Arg Ala Gly Ala Thr Leu Asn Phe Val Glu Pro Leu Gly
            435                 440                 445

Pro Leu Leu Ser Leu Ser Leu Leu Ala Ala Glu Ala Tyr Ala Leu Ser
    450                 455                 460

Thr Val Ala Leu Leu Ala Val Gln Val Gly Leu Arg His Arg Ala Arg
465                 470                 475                 480

Pro Pro Glu Pro Pro Leu Gly Pro Glu Pro His Pro Ser Val Asp
                485                 490                 495

Val Met Val Pro Ile Tyr Ser Glu Pro Leu Asp Ile Leu Asp Lys Thr
                500                 505                 510

Leu Ala Ala Cys Ala Ala Met Arg Tyr Pro Arg Lys Thr Val Val
                515                 520                 525

Cys Asp Asp Ser His Arg Asp Glu Val Ala Arg Leu Ala Ala Glu His
            530                 535                 540

Gly Ala Arg Tyr Leu Ala Gly Pro Arg Arg His Ala Lys Ala Gly Asn
545                 550                 555                 560

Leu Asn Ala Ala Leu Ala Arg Thr Asp Gly Glu Leu Val Val Val Phe
                565                 570                 575

Asp Thr Asp His Val Pro Thr Ala Ala Phe Leu Glu Arg Thr Val Pro
            580                 585                 590

Cys Phe Arg Asp Pro Arg Leu Gly Val Val Gln Thr Pro His His Phe
            595                 600                 605

Tyr Asn Pro Asp Val Phe Gln Arg Ala Leu Gly Ala Pro Ala Ala Val
            610                 615                 620

Pro Asn Glu Ala Asp Leu Phe Asn His Ala Ile Gln Gly Gly Arg Asp
625                 630                 635                 640

Arg Trp Gly Gly Ala Phe Phe Val Gly Ser Gly Ala Val Phe Arg Arg
                645                 650                 655

Glu Ala Leu Ala Ser Val Gly Gly Phe His Leu Leu Ser Ile Thr Glu
            660                 665                 670

Asp Ile His Thr Ser Gln Lys Leu His Ala Arg Gly Trp Arg Thr Arg
            675                 680                 685

Phe Val Asp Glu Asp Leu Ala Ala Gly Leu Ser Ala Glu Asp Leu Ala
            690                 695                 700

Ser Tyr Val Val Gln Arg Arg Trp Met Leu Gly Cys Leu Gln Ile
705                 710                 715                 720

Phe Phe Arg Asp Asn Pro Leu Leu Gln Arg Gly Leu Pro Leu Arg His
                725                 730                 735

Arg Val Gly Tyr Leu Ala Ser Leu Trp Tyr Phe Phe Pro Leu Ala
                740                 745                 750

Arg Leu Val Phe Phe Ala Thr Pro Leu Ala Tyr Leu Leu Phe His Leu
                755                 760                 765

His Pro Leu Phe Ala Glu Leu Pro Val Leu Leu Ala Tyr Leu Val Pro
    770                 775                 780

His Leu Val Ala Ala Pro Leu Ala Ala Ser Ala Leu Val Pro Gly Trp
785                 790                 795                 800

Pro Arg Ala Leu Trp Gly Ser Leu Tyr Glu Gly Ala Val Ala Phe Pro
                805                 810                 815

Leu Ala Arg Ala Thr Leu Asp Leu Leu Leu Pro Arg Arg Leu Gly Phe
                820                 825                 830

Lys Val Thr Pro Lys Gly Val Arg Ser Glu Arg Arg Phe Asp Leu
                835                 840                 845
```

```
Arg Thr Ser Ala Phe Thr Leu Ala Ala Ala Gly Val Gly Leu Leu Ala
    850                 855                 860

Ile Ala Lys Gly Ala Ala Glu Leu Trp Ala Phe Gly Ile Glu Val Glu
865                 870                 875                 880

Ala Tyr Ala Phe Asn Leu Ala Trp Ala Ala Asn Leu Val Ser Val
                885                 890                 895

Leu Leu Ala Leu Val Val Ala Trp Glu Arg Pro Gln Arg Arg Glu Asp
            900                 905                 910

Glu Arg Ile Arg Arg Val Pro Val Arg Leu Glu Ala Pro Gly Leu
                915                 920                 925

Ser Leu Asp Ala Thr Thr Leu Asp Leu Ala Arg Gly Gly Ala Ala Val
    930                 935                 940

Ala Leu Pro Pro Gly Ala Ala Leu Pro Ala Glu Val Glu Val Ala Phe
945                 950                 955                 960

Gly Ala Pro Glu Pro Leu Arg Leu Arg Ala Arg Val Ala Tyr Leu Glu
                965                 970                 975

Ala Val Gly Gly Thr Pro Arg Ala Gly Leu Ala Phe Gln Gly Val Ser
            980                 985                 990

Ala Ala Asp Ala Arg Ala Leu Val  Arg Ile Ala Phe Ser  Ala Asp Gly
                995                 1000                1005

Ala His  Ala Gly Ala His  Ala  Gly Arg Ser Arg Trp  Gln Val Ala
    1010                1015                1020

Met Ala  Trp His Leu Leu Ala  Gly Leu Trp Arg Ala  Val Arg Pro
    1025                1030                1035

Leu Arg  Ala Arg Arg Arg Leu  Gly Ser Arg Arg Arg  Thr Leu Arg
    1040                1045                1050

Pro Leu  Arg Leu Cys Gly Ala  Gly Arg Ala Cys Arg  Ala Val Ala
    1055                1060                1065

Val Asp  Ala Ser Pro Gly Gly  Leu Gly Leu Val Ala  Ala Gly Pro
    1070                1075                1080

Gly Asp  Ala Met Pro Ala Pro  Gly Thr Ser Leu Ala  Leu Leu Ala
    1085                1090                1095

Pro Glu  Gly Ile Ala Trp Ala  Arg Val Ala His Ala  His Arg Ile
    1100                1105                1110

Leu Pro  Gly Leu Trp Arg Leu  Gly Leu Thr Leu Gln  Ala Glu Pro
    1115                1120                1125

Val Pro  Gly Ala Glu Pro His  Ala Tyr Leu Ala Ala
    1130                1135                1140

<210> SEQ ID NO 99
<211> LENGTH: 454
<212> TYPE: PRT
<213> ORGANISM: Microcoleus chthonoplastes

<400> SEQUENCE: 99

Met Thr Asn Asp Lys Gly Gln Arg Thr Asn His Trp Val Arg Ser Arg
1               5                   10                  15

His Phe Ser Ala Arg Ser Ala Lys Ala Leu Thr Thr Ser Met Thr Ile
            20                  25                  30

Ser Ala Met Leu Leu Leu Leu Asn Leu Thr Ser Cys Val Ser Ile Lys
        35                  40                  45

Phe Ser Glu Pro Glu Pro Pro Glu Ala Ser Val Ser Pro Ser Pro Ser
    50                  55                  60

Pro Val Thr Ala Ser Pro Val Ala Asp Phe Pro Val Leu Ser Pro Ser
65                  70                  75                  80
```

Pro Pro Ile Gln Asp Ile Leu Glu Gln Ser Trp Val Ile Tyr Arg Gln
            85                  90                  95

Gln Phe Ile Gln Glu Asp Gly Arg Val Ile Asp Tyr Glu Ala Ser Asp
            100                 105                 110

Arg Ser Thr Ser Glu Gly Gln Ala Tyr Ala Met Leu Arg Ala Val Leu
            115                 120                 125

Ile Asn Asp Pro Thr Thr Phe Ala Leu Thr Leu Glu Trp Ala Glu Asp
130                 135                 140

Asn Leu His Arg Leu Thr Glu Thr Gly Glu Pro Glu Asp Asn Leu Trp
145                 150                 155                 160

Val Trp Leu Trp Gly Gln Asp Glu Gly Asn Trp Gly Ala Ile Asp
            165                 170                 175

Arg Asn Phe Ala Ser Asp Ala Asp Ile Asp Ala Ile Thr Ala Leu Ile
            180                 185                 190

Trp Ala Tyr Arg Arg Trp Asp Arg Pro Glu Tyr Leu Glu Leu Ala Arg
            195                 200                 205

Ile Lys Leu Arg Asp Leu Trp Asp Tyr Ser Thr Ile Ala Gly Pro Asp
            210                 215                 220

Gly Lys Arg Tyr Leu Leu Pro Gly Pro Lys Gln Ala Phe Val Pro Ser
225                 230                 235                 240

Pro Ser Thr Ile Tyr Leu Asn Pro Ser Tyr Leu Ala Pro Tyr Ala Phe
            245                 250                 255

Arg Leu Phe Ala Gln Val Asp Pro Glu Arg Asp Trp Leu Ser Leu Ile
            260                 265                 270

Asp Ser Tyr Tyr Val Leu Glu Asn Ser Ser Lys Val Ser Ala Val
            275                 280                 285

Gly Leu Pro Ser Asp Trp Ile Ala Leu Asp Leu Gln Thr Asn Gln Phe
            290                 295                 300

Gln Ser Ile Pro Pro Gln Ser Lys Leu Lys Ser Val Tyr Ser Phe Asp
305                 310                 315                 320

Ala Tyr Arg Val Trp Trp Arg Ile Ala Trp Asp Ala Glu Trp Phe Gln
            325                 330                 335

Ser Thr Glu Ala Leu Asn Tyr Leu Glu Thr Ala Thr Gln Tyr Leu Glu
            340                 345                 350

Asp Gln Trp Gln Ser Ser Ser Arg Leu Pro Ala Arg Ile Asn Leu Asp
            355                 360                 365

Gly Glu Ser Leu Val Lys Tyr Asp Ala Thr Ser Gln Tyr Ala Met Leu
            370                 375                 380

Tyr Pro Ala Met Arg Leu Ile Asn Pro Ala Ile Ala Glu Gln Leu Leu
385                 390                 395                 400

Glu Arg Lys Leu Leu Pro Gln Tyr Asn Gln Gly Ile Trp Asp Asp Glu
            405                 410                 415

Ser Ala Tyr Tyr Thr Gln Asn Leu Ala Trp Ile Ala Leu Val Ser Pro
            420                 425                 430

Asp Leu Val Lys Asn Ser Gln Phe Phe Gln Ser Gln Gln Gln Phe Ser
            435                 440                 445

Arg Asn Ala Ile Arg Glu
        450

<210> SEQ ID NO 100
<211> LENGTH: 326
<212> TYPE: PRT
<213> ORGANISM: Microbacteriaceae

<400> SEQUENCE: 100

```
Met Leu Ala Leu Ala Leu Leu Pro Val Ala Gly His Ala Gly Asp
1               5                   10                  15

Ala Arg Trp Asp Asp Phe Val Ser Arg Phe Val Ala Ala Asp Gly Arg
            20                  25                  30

Val Ile Asp Thr Gly Asn Gly Ile Ser His Ser Glu Gly Gln Gly
        35                  40                  45

Tyr Thr Leu Leu Leu Ala Val Ala Gln Asn Asp Arg Ala Thr Phe Gly
    50                  55                  60

Arg Val Trp Ala Trp Thr Arg Ser Arg Leu Gln Thr Arg Gly Asp Ala
65                  70                  75                  80

Leu Phe Ser Trp Gln Trp Lys Pro Asp Ala Asp Gly Gly Lys Ile Gly
                85                  90                  95

Asp Arg Asn Asn Ala Ser Asp Gly Asp Leu Leu Ile Ala Trp Ala Leu
                100                 105                 110

Leu Arg Gly Ala Gln Arg Trp Gln Gln Pro Ala Tyr Arg Ala Glu Ala
            115                 120                 125

Leu Lys Ile Leu Ala Asp Val Arg Gly Lys Leu Ile Lys Pro Ser Arg
130                 135                 140

Phe Gly Pro Leu Leu Met Pro Ala Glu Lys Gly Phe Asp Lys Pro Ala
145                 150                 155                 160

Gly Pro Ile Val Asn Pro Ser Tyr Trp Leu Phe Pro Ala Phe Ala Glu
                165                 170                 175

Phe Ala Arg Ala Asp Arg Ala Pro Val Trp Ala Glu Leu Arg Gln Ser
            180                 185                 190

Gly Leu Ala Leu Leu Ala Gly Arg Phe Gly Gln Trp Gln Leu Pro
        195                 200                 205

Pro Asp Trp Leu Gln Val Gly Asp Thr Leu Ala Pro Ala Met Ser His
210                 215                 220

Gln Tyr Gly Tyr Asn Ala Leu Arg Val Pro Leu Tyr Leu Ala Trp Ala
225                 230                 235                 240

Gly Leu Asp Thr Pro Glu Arg Ile Ala Pro Phe Leu Ala Tyr Trp Asp
                245                 250                 255

Thr Asn Pro Glu Arg Leu Pro Ala Trp Thr Asp Leu Ala Thr Asn Ala
            260                 265                 270

Ile Asp Pro Asp Ser Ala Gln Pro Gly Leu Tyr Thr Ile Val Ala Leu
        275                 280                 285

Val Arg Gln Arg Gln Ala Gly Gly Thr Val Arg Phe Gly Asp Gly Asp
290                 295                 300

Asn Arg Asp Tyr Tyr Pro Ala Val Leu Asp Leu Leu Ser Arg Gln Ala
305                 310                 315                 320

Ala Arg Glu Ala Arg Arg
                325
```

<210> SEQ ID NO 101
<211> LENGTH: 387
<212> TYPE: PRT
<213> ORGANISM: Verrucomicrobiae

<400> SEQUENCE: 101

```
Met Leu Leu Leu Thr Ser Cys Ala Pro Glu Pro Gln Ile Lys Pro Gln
1               5                   10                  15

Thr Asp Gln Arg Asn Leu Phe Ala Glu Tyr Leu Gly Lys Ser Gln Gln
            20                  25                  30
```

Glu Thr Asp Ala Lys Val Glu Asp Ala Phe Gln Gln Leu Phe Tyr Gly
            35                  40                  45

Asp Asp Glu Ser Glu Arg Ile Tyr Tyr Pro Val Gly Asp Asp Met Ala
 50                  55                  60

Tyr Ile Trp Asp Val Gly Ser Asp Val Arg Ser Glu Gly Met Ser
 65                  70                  75                  80

Tyr Gly Met Met Ile Ala Val Gln Leu Asp Lys Lys Asp Glu Phe Asp
                 85                  90                  95

Arg Leu Trp Lys Trp Ser His Thr Tyr Met Arg Leu His Glu Gly Pro
            100                 105                 110

Phe Glu Gly Tyr Phe Asn Trp Gln Asn Ala Thr Ser Gly Glu Lys Ile
        115                 120                 125

Ser Pro Gly Ser Ala Ser Asp Gly Glu Glu Trp Phe Ala Met Ala Leu
130                 135                 140

Phe Phe Ala Ser Asn Leu Trp Gly Asp Gly Glu Gly Ile Phe Asn Tyr
145                 150                 155                 160

Arg Ala Glu Ala Asn Asn Ile Leu Arg Glu Met Leu His Lys Gln Pro
                165                 170                 175

Ser Asp Pro Lys Met Val Ser Ile Phe Asp Tyr Glu Arg His Met Val
            180                 185                 190

Arg Phe Val Pro Trp Thr Asp Trp Asp Gly Val Thr Asp Ala Ser Tyr
        195                 200                 205

His Leu Pro Ala Phe Tyr Glu Leu Trp Ala Lys Trp Ala Asp Ser Asp
    210                 215                 220

Asn Asp Tyr Trp Ala Lys Thr Ala Asp Val Ser Arg Glu Phe Lys
225                 230                 235                 240

Thr Ala Ala His Pro Glu Thr Gly Leu Met Pro Asp Tyr Ser Tyr Tyr
                245                 250                 255

Lys Glu Thr Glu Arg Gln Ile Gly Ser His Ala Asp Phe Arg Phe Asp
            260                 265                 270

Ala Trp Arg Val Met Pro Asn Val Ala Leu Asp His Asp Trp Trp Gly
        275                 280                 285

Lys Asp Ala Gln Trp Gln Thr Met Gln Ser Asp Arg Ile Leu Lys Phe
290                 295                 300

Leu Gly Ser His Leu Pro Asp Ile Pro Asn Gln Phe Ala Val Asp Gly
305                 310                 315                 320

Thr Pro Leu Asp Thr Gln Ser Ser Pro Gly Leu Tyr Ala Met Ala Ala
                325                 330                 335

Thr Ala Gly Leu Ala Ala Asn Arg Asp Val Ala Glu Pro Phe Val Gln
            340                 345                 350

Arg Leu Trp Asp Gln Pro Val Pro Thr Gly His Trp Arg Tyr Tyr Asp
        355                 360                 365

Gly Val Ile His Met Leu Gly Leu Leu Gln Thr Ser Gly His Phe Lys
370                 375                 380

Ile Ile Glu
385

<210> SEQ ID NO 102
<211> LENGTH: 431
<212> TYPE: PRT
<213> ORGANISM: Verrucomicrobiae

<400> SEQUENCE: 102

Met Lys Thr Ile Gly Ile Leu Ala Val Leu Leu Trp Val Ser Ala Val
 1               5                  10                  15

```
Thr Ala Ala Pro Pro Gly Ala Ala Leu Thr Gly Glu Tyr Pro
         20              25              30

Asn Leu Phe Lys Thr Tyr Leu Gly Lys Thr Asp Ala Glu Ile Glu Ala
         35              40              45

Lys Val Glu Ala Ala Phe Asn Gln Leu Phe Tyr Gly Asp Pro Phe Thr
 50              55              60

Glu Arg Val Tyr Tyr Thr Ala Ser Glu Asp Thr Ala Tyr Leu Ala Asp
 65              70              75              80

Val Gly Ser Arg Asp Val Arg Ser Glu Gly Ile Ser Tyr Gly Met Met
             85              90              95

Ile Thr Val Gln Met Asp Lys Gln Lys Glu Phe Asn Ala Leu Trp Lys
             100             105             110

Trp Ala Lys Val His Met Gln Tyr Thr Glu Gly Pro Leu Arg Gly Tyr
         115             120             125

Phe Ala Trp His Arg Asp Tyr Asp Gly Asp Met Thr Arg Ala Asp Gly
 130             135             140

Ser Glu Ile Arg Gly Gly Gly Pro Ala Pro Asp Gly Glu Asn Trp Met
145             150             155             160

Val Met Ala Leu Phe Phe Ala Ser His Arg Trp Gly Asp Gly Glu Gly
             165             170             175

Ile Phe Asn Tyr Gly Gln Glu Ala Gln Glu Leu Leu Arg Met Met Ile
             180             185             190

His Lys Asp Asp Glu Pro Asp Arg Gly Asp Ile Val Ser Met Phe His
         195             200             205

Pro Glu Glu Lys Gln Ile Arg Phe Thr Pro Asp Gly Trp Gly Pro
 210             215             220

Lys Phe Thr Asp Pro Ser Tyr His Thr Pro His Phe Thr Glu Leu Met
225             230             235             240

Ala Arg Trp Ala Glu Asn Pro Ala Asp Arg Ala Phe Leu Ala Glu Val
             245             250             255

Thr Gln Thr Ser Arg Gln Leu Phe Arg Asn Ala Ala His Pro Glu Thr
         260             265             270

Gly Ile Met Ala Asn Tyr Thr Glu Phe Asp Gly Thr Pro Ile Val Arg
         275             280             285

Trp Asp Arg Ala Phe Ala Ala Asp Ala Trp Arg Thr Leu Gly Trp Pro
290             295             300

Ala Met Asp Trp Ser Trp Trp Gly Glu Asp Glu Trp Met Val Glu Gln
305             310             315             320

Ser Asn Arg Ile Leu Gly Phe Tyr Ala Ala Gln Pro Glu Asp Asp Trp
             325             330             335

Pro Asp His Met Glu Leu Asp Gly Thr Val Gln Arg Arg Asn Gly Trp
         340             345             350

Ala His Gly Leu Ser Gly Met Ala Ala Thr Ala Ala Leu Ala Ala Asp
         355             360             365

Pro Glu Leu Gly Lys Pro Met Val Glu Arg Leu Trp Asn Leu Glu Leu
         370             375             380

Pro Asn Asp Val Gly Arg Asp Thr Asp Gly Leu Met Ala Glu Gly Glu
385             390             395             400

Leu Arg Ser His Arg Tyr Tyr Ser Gly Leu Leu Met Met Phe Gly Leu
             405             410             415

Leu His Ala Ser Gly Asn Phe Gln Val Tyr Gly Pro Val Glu Pro
             420             425             430
```

<210> SEQ ID NO 103
<211> LENGTH: 385
<212> TYPE: PRT
<213> ORGANISM: Methylobacterium chloromethanicum

<400> SEQUENCE: 103

Met Met Phe Gly Arg Pro Arg Ala Ile Ala Ala Ser Leu Leu Leu Gly
1               5                   10                  15

Leu Thr Leu Ala Pro Leu Gln Ala Met Ala Glu Pro Ala Pro Ile Glu
            20                  25                  30

Ala Lys Pro Ala Ala Gly Ala Thr Val Gly Lys Ala Ala Ser Val Thr
        35                  40                  45

Ala Glu Thr Leu Pro Met Leu Asn Ser Leu Gly Gln Ala Gly Ala Trp
    50                  55                  60

Arg Ser Tyr Lys Ala Arg Phe Val Thr Asp Gln Gly Arg Val Val Asp
65                  70                  75                  80

Thr Ala Asn Gly Arg Ile Ser His Ser Glu Ser Gln Gly Tyr Gly Leu
                85                  90                  95

Leu Leu Ala Val Ala Ala Gly Asp Arg Asp Thr Phe Gln Arg Ile Trp
            100                 105                 110

Asn Trp Thr Arg Ala Asn Leu Met Val Arg Asp Asp Ala Leu Leu Ala
        115                 120                 125

Trp Arg Trp Glu Pro Asp Lys Arg Pro Ala Val Ala Asp Met Asn Asp
    130                 135                 140

Ala Thr Asp Gly Asp Ile Leu Val Ala Trp Ala Leu Val Glu Ala Gly
145                 150                 155                 160

Glu Gly Trp Ala Asp Asp Ser Tyr Arg Leu Ala Ala Arg Arg Ile Ala
                165                 170                 175

Val Asp Ile Ala Arg Arg Thr Val Leu Phe Arg Thr Glu Gly Pro Pro
            180                 185                 190

Leu Leu Leu Pro Ala Met Ser Gly Phe Ser Ala Glu Asp Arg Pro Asp
        195                 200                 205

Gly Pro Val Ile Asn Leu Ser Tyr Trp Ile Phe Pro Ala Phe Pro Arg
    210                 215                 220

Leu Ala Ala Val Ala Pro Glu Phe Asp Trp Asp Arg Leu Gly Ala Thr
225                 230                 235                 240

Gly Arg Asp Leu Val Leu Arg Ala Arg Phe Gly Asp Ala Lys Leu Pro
                245                 250                 255

Thr Glu Trp Ile Ser Met Arg Gly Gly Gln Pro Gln Pro Ala Ser Gly
            260                 265                 270

Phe Pro Pro His Phe Ser Tyr Asn Ala Leu Arg Val Pro Leu Tyr Leu
        275                 280                 285

Ala Met Ala Gly Ile Ser Glu Arg Tyr Tyr Glu Pro Leu Leu Ala
    290                 295                 300

Leu Trp Gly Glu Pro Asp Pro Ala Gly Leu Pro Ile Ile Asp Thr Glu
305                 310                 315                 320

Gly Gly Ser Val Ala Gly Arg Met Ala Glu Pro Gly Tyr Ala Ile Ile
                325                 330                 335

Pro Ala Leu Ala Ala Cys Ala Val Thr Gly Ala Pro Leu Pro Ala Gly
            340                 345                 350

Leu Gln Asp Pro Ala Thr Asp Glu Asn Tyr Tyr Pro Ala Thr Leu His
        355                 360                 365

Leu Leu Ala Leu Thr Ala Ala Asn Met Arg Tyr Arg Pro Cys Leu Gly
370                 375                 380

Arg
385

<210> SEQ ID NO 104
<211> LENGTH: 376
<212> TYPE: PRT
<213> ORGANISM: Clostridium cellulolyticum

<400> SEQUENCE: 104

Met Ser Lys Gly Ala Tyr Phe Thr Lys Gln Tyr Pro Asn Leu Phe Ala
1               5                   10                  15

Glu Leu Gly Ile Ser Asp Glu Gln Ile Asn Lys Lys Val Asn Asp Thr
            20                  25                  30

Phe Asn Thr Met Phe Phe Asp Pro Glu Glu Lys Ile Tyr Phe Glu Ile
        35                  40                  45

Gly Lys Asp Met Gly Tyr Met Met Asp Thr Gly Asn Asn Asp Ala Arg
    50                  55                  60

Thr Glu Gly Met Ser Tyr Gly Met Met Met Thr Leu Gln Met Asp Arg
65                  70                  75                  80

Lys Asp Ile Phe Asp Arg Leu Trp Leu Phe Ser Lys Thr Tyr Met Tyr
                85                  90                  95

Gln Asn Glu Gly Lys Tyr Gln Gly Tyr Phe Ala Trp Ser Val Ser Thr
            100                 105                 110

Asp Gly Lys Lys Asn Ala Glu Gly Pro Ala Pro Asp Gly Glu Glu Tyr
        115                 120                 125

Phe Ala Met Ala Leu Phe Phe Ala Gly Lys Arg Trp Gly Asp Gly Lys
    130                 135                 140

Pro Pro Phe Asp Tyr Ser Ile Gln Ala Arg Asp Ile Leu Lys His Cys
145                 150                 155                 160

Ile His Gln Ser Glu Ile Val Glu Gly Gly Glu Pro Met Trp Asp Ser
                165                 170                 175

Thr Asn His Tyr Ile Lys Phe Val Pro Glu Thr Pro Phe Ser Asp Pro
            180                 185                 190

Ser Tyr His Leu Pro His Phe Tyr Glu Leu Phe Ala Leu Leu Ala Asn
        195                 200                 205

Glu Glu Asp Lys Asp Phe Trp Lys Lys Ala Glu Ala Ser Arg Asn
    210                 215                 220

Tyr Leu His Ile Ser Cys Asp Arg Asp Thr Gly Met Ala Ser Glu Tyr
225                 230                 235                 240

Ala Glu Phe Asp Gly Thr Pro Lys Lys Leu Phe Arg Asp Phe Gln Phe
                245                 250                 255

Tyr Ser Asp Ser Tyr Arg Val Ala Met Asn Ile Gly Leu Asp Ala Ala
            260                 265                 270

Trp Phe Ser Lys Asp Glu Ser Leu Gly Asp Ile Val Asp Lys Leu Gln
        275                 280                 285

Ser Phe Phe Ser Glu Asn Thr Val Leu Gly Glu Tyr Lys Ala Tyr Thr
    290                 295                 300

Val Lys Gly Glu Pro Phe Asp Ala Pro Ala Met His Pro Val Ala Ile
305                 310                 315                 320

Ile Ala Thr Asn Ala Ala Gly Ser Leu Ala Ala Lys Gly Lys Tyr Arg
                325                 330                 335

Asp Gln Trp Val Lys Asp Phe Trp Glu Leu Pro Leu Arg Lys Gly Val
            340                 345                 350

His Arg Tyr Tyr Asp Asn Cys Leu Tyr Phe Phe Ser Leu Leu Met Leu

```
                355                 360                 365
Ala Gly Lys Tyr Lys Ile Tyr Ile
    370                 375

<210> SEQ ID NO 105
<211> LENGTH: 477
<212> TYPE: PRT
<213> ORGANISM: Clostridium cellulolyticum

<400> SEQUENCE: 105

Met Lys Lys Phe Phe Ala Cys Leu Leu Val Leu Ala Ile Ile Val Thr
1               5                   10                  15

Ile Val Pro Ile Asn Ile Ala Ser Ala Glu Thr Gly Gly Tyr Tyr Ala
            20                  25                  30

Thr Gly Asn Tyr Arg Asn Val Phe Val Glu Thr Gly Arg Thr Glu Ala
        35                  40                  45

Gln Val Gln Asp Lys Met Asn Thr Met Phe Asp Lys Phe Lys Gly
    50                  55                  60

Asp Thr Asn Asn Gln Arg Leu Phe Tyr Glu Thr Gly Thr Asp Glu Ala
65              70                  75                  80

Tyr Ile Arg Asp Thr Gly Asn Gly Asp Val Arg Ser Glu Gly Met Ser
                85                  90                  95

Tyr Gly Met Met Val Cys Val Gln Met Asp Lys Lys Lys Glu Phe Asp
            100                 105                 110

Met Leu Trp Lys Trp Ala Arg Asn His Met Tyr Gln Thr Ser Gly Gln
        115                 120                 125

Phe Lys Gly Phe Phe Ala Trp Gln Cys Asn Tyr Asp Gly Gly Ile Ile
    130                 135                 140

Asp Ser Thr Pro Ala Ser Asp Gly Asp Glu Tyr Phe Ala Met Ala Leu
145             150                 155                 160

Leu Phe Ala Ala Arg Arg Trp Gly Asn Gly Thr Gly Ile Tyr Asn Tyr
                165                 170                 175

Glu Ala Glu Ala Gln Thr Ile Leu Asp Ala Met Leu His Gln Ser Asp
            180                 185                 190

Asp Gly Val Gly Tyr Asn Met Ile Asn Lys Asn Ala Asn Gln Val Val
        195                 200                 205

Phe Cys Pro Ser Ala Gly Asn Tyr Asp Phe Thr Asp Pro Ser Tyr His
    210                 215                 220

Leu Pro Ala Phe Tyr Glu Leu Trp Ala Met Trp Gly Pro Glu Arg Asp
225             230                 235                 240

Arg Ala Thr Trp Ser Lys Val Ala Ala Thr Ser Arg Glu Phe Leu Lys
                245                 250                 255

Lys Ser Thr His Pro Thr Thr Gly Leu Asn Pro Asp Tyr Ala Asn Phe
            260                 265                 270

Asp Gly Ser Ala Lys Glu Val Ser Trp Ser Ser Gly His Gly Asp Phe
        275                 280                 285

Arg Phe Asp Ala Trp Arg Val Ile Gln Asn Ser Cys Val Asp Tyr Ala
    290                 295                 300

Trp Trp Gln Lys Asp Ser Trp Pro Ala Thr Thr Phe Ala Pro Lys Ile
305             310                 315                 320

Gln Ala Phe Phe Lys Asn Gln Gly Leu Ser Thr Tyr Gly Asn Gln Tyr
                325                 330                 335

Thr Leu Ser Gly Ser Lys Leu Ser Ser Asp His Ser Pro Gly Leu Val
            340                 345                 350
```

```
Ala Met Asn Ala Val Ser Ala Leu Ala Ser Asp Ala Thr Ala Lys
        355                 360                 365

Pro Phe Val Asp Glu Leu Trp Asn Thr Ala Val Pro Ser Gly Gln Tyr
370                 375                 380

Arg Tyr Tyr Asp Gly Met Leu Tyr Met Leu Gly Met Leu Asn Val Ser
385                 390                 395                 400

Gly Asn Phe Lys Ile Trp Gly Ala Pro Thr Glu Pro Ser Val Thr Arg
                405                 410                 415

Gly Asp Ile Asn Asp Asp Gly Thr Ile Asp Ser Val Asp Phe Ala Leu
            420                 425                 430

Leu Lys Ser Tyr Leu Leu Gly Arg Thr Thr Thr Leu Pro Asn Met Lys
        435                 440                 445

Ala Ala Asp Leu Asn Gly Asp Gly Val Val Asp Ala Met Asp Trp Ala
    450                 455                 460

Val Leu Arg Gln Tyr Leu Leu Gly Ile Ile Lys Thr Leu
465                 470                 475

<210> SEQ ID NO 106
<211> LENGTH: 380
<212> TYPE: PRT
<213> ORGANISM: Stenotrophomonas

<400> SEQUENCE: 106

Met Ala Asn Ser Ala Asp Leu His Arg Arg Leu Leu Gln Ala Ala
1               5                   10                  15

Ala Ala Val Pro Leu Leu Gly Trp Gly Ala Gln Ala Gln Pro Ala
            20                  25                  30

Pro Ser Ala Ser Arg Trp Pro Ala Trp Gln Val Leu Leu Asp Ser Ser
        35                  40                  45

Leu Ser Arg Asp Gly Arg Met Ile Asp Arg Ser Gln Asp Gln Arg
50                  55                  60

Ser Thr Ser Glu Gly Gln Ser Tyr Ala Leu Phe Phe Ala Leu Val Ala
65                  70                  75                  80

Asn Asp Gln Thr Leu Phe Asp Arg Ile Leu Ala Trp Thr Gln Asp Asn
                85                  90                  95

Leu Ala Gly Gly Asp Met Arg Gln His Leu Pro Ala Trp Leu Trp Gly
            100                 105                 110

Arg Asp Ala Lys Gly Gly Trp Gln Val Leu Asp Ser Asn Pro Ala Ser
        115                 120                 125

Asp Ser Asp Leu Trp Leu Ala Tyr Ala Leu Leu Glu Gly Ala Arg Leu
    130                 135                 140

Trp Arg Arg Pro Ala Leu Gln Ala Ile Ala Glu Gly Met Leu Gln Gln
145                 150                 155                 160

Val Arg Glu Arg Glu Ile Val Gln Leu Pro Gly Leu Gly Pro Met Leu
                165                 170                 175

Leu Pro Gly Pro Gln Gly Phe Val Glu Gly Asp Ala Thr Arg Ile Asn
            180                 185                 190

Pro Ser Tyr Leu Pro Leu Pro Leu Leu Arg Arg Phe Ala Ser Val Asp
        195                 200                 205

Arg Lys Gly Pro Trp Pro Ala Leu Ala Ala Asn Thr Val Arg Met Leu
    210                 215                 220

Gln Gln Ser Ser Pro His Gly Phe Ala Pro Asp Trp Thr Ala Trp Gln
225                 230                 235                 240

Ala Gly Gly Phe Val Ala Asp Pro Val Lys Gly Ala Val Gly Ser Tyr
                245                 250                 255
```

Asp Ala Ile Arg Cys Tyr Ala Trp Ala Gly Met Thr Ala Pro Arg Asp
            260                 265                 270

Pro Leu Phe Arg Pro Gln Leu Ala Ala Leu Ser Gly Pro Leu Gln Arg
        275                 280                 285

Leu Arg Ser Gly Ala Ala Met Trp Glu Lys Ile Asp Thr Arg Ser Gly
    290                 295                 300

Gln Gly Gln Gly Glu Gly Asn Tyr Gly Phe Arg Ala Ala Leu Leu Pro
305                 310                 315                 320

Tyr Leu Leu Ala Gln Gly Glu Asn Glu Arg Ala Arg Ala Leu Gln Ala
                325                 330                 335

Ser Leu Pro Ser Ala Glu Gln Gln Arg Ala Asp Ala Pro Ala Tyr Tyr
            340                 345                 350

Ser Gln Met Leu Ser Leu Phe Gly Leu Gly Trp Ala Glu Gly Arg Trp
        355                 360                 365

Arg Phe Asn Ala Asp Gly Arg Leu Gln Pro Arg Trp
    370                 375                 380

<210> SEQ ID NO 107
<211> LENGTH: 356
<212> TYPE: PRT
<213> ORGANISM: Rhodobacter sphaeroides

<400> SEQUENCE: 107

Met Arg Arg Arg Thr Ile Leu Thr Ser Ala Ala Ala Leu Met Leu
1               5                   10                  15

Ala Pro Ala Gly Arg Leu Leu Ala Gln Ser Gly Gly Glu Ala Leu Pro
            20                  25                  30

Ala Asp His Pro Leu Gln Ala Ala Trp Arg Ser Trp Lys Asp Ala Phe
        35                  40                  45

Leu Leu Pro Ala Gly Arg Ile Val Asp Gly Pro Gln Gln Asn Ala Ser
    50                  55                  60

His Ser Glu Gly Gln Gly Tyr Gly Ala Thr Leu Ala Ala Ile Phe Gly
65                  70                  75                  80

Asp Glu Glu Ala Leu Arg Arg Ile Val Asp Trp Thr Glu Ala Asn Leu
                85                  90                  95

Ala Arg Arg Glu Asp Lys Leu Leu Ser Trp Arg Trp Leu Pro Gly Val
            100                 105                 110

Ala Leu Ala Val Pro Asp Glu Asn Asn Ala Thr Asp Gly Asp Leu Phe
        115                 120                 125

Tyr Ala Trp Gly Leu Ala Met Ala Ala Gln Arg Phe Gly Lys Ala Asp
    130                 135                 140

Tyr Ala Gly Arg Ala Thr Glu Leu Ala Arg Ala Ile Ala Leu His Cys
145                 150                 155                 160

Val Arg Pro His Pro Asp Gly Ser Glu Gln Leu Val Leu Leu Pro Gly
                165                 170                 175

Ala Ser Gly Phe Glu Thr Pro Asp Gly Val Val Leu Asn Pro Ser Tyr
            180                 185                 190

Tyr Met Pro Arg Ala Leu Thr Glu Leu Ala Ala Phe Ser Gly Gln Asp
        195                 200                 205

Arg Leu Ala Arg Cys Ala Arg Asp Gly Ala Asp Trp Ile Ala Ser Leu
    210                 215                 220

Gly Leu Pro Pro Asp Trp Ala Leu Val Thr Pro Phe Gly Thr Gln Pro
225                 230                 235                 240

Ala Pro Gly Leu Ser His Asn Ser Gly Tyr Asp Ala Leu Arg Val Pro

```
                    245                 250                 255
Leu Phe Leu Leu Trp Ser Gly Leu Thr Ala Asn Pro Ala Leu Arg Arg
        260                 265                 270

Ala Val Glu Ala Ala Gly Asp Ala Ala Gly Asp Thr Pro Val Thr
        275                 280                 285

Phe Asp Arg Asp Thr Gly Ala Val Leu Glu Arg Ser Ala Asp Pro Gly
        290                 295                 300

Phe Arg Ala Val Leu Ala Leu Gly Asp Cys Ala Leu Ser Gly Arg Pro
305                 310                 315                 320

Gly Ala Ala Ile Pro Pro Phe Asp Ala Arg Gln Pro Tyr Tyr Pro Ala
                325                 330                 335

Thr Leu His Leu Met Ala Leu Val Ala Gln Val Glu Gly Phe Ser Ala
                340                 345                 350

Cys Val Pro Ile
        355

<210> SEQ ID NO 108
<211> LENGTH: 384
<212> TYPE: PRT
<213> ORGANISM: Bifidobacterium pseudocatenulatum

<400> SEQUENCE: 108

Met Met Arg Lys Asp Glu Thr Met Gly Ala Gly Ala Met Gly His Met
1               5                   10                  15

Glu Thr Ser Met Phe Glu Gln Cys Gly Tyr Gly Arg Glu Ala Ile Gln
            20                  25                  30

Ala Arg Leu Glu Arg Asn Trp Thr Glu Met Phe Glu Gly Pro Asp Lys
        35                  40                  45

Ile Tyr Trp Glu Asn Asp Glu Gly Leu Gly Tyr Val Met Asp Thr Gly
    50                  55                  60

Asn His Asp Val Arg Thr Glu Gly Met Ser Tyr Ala Met Met Ile Ala
65                  70                  75                  80

Val Gln Tyr Asp Arg Lys Asp Val Phe Asp Lys Leu Trp Gly Trp Val
                85                  90                  95

Met Lys Tyr Met Phe Met Thr Glu Gly Leu His Lys Gly Tyr Phe Ala
            100                 105                 110

Trp Ser Val Asp Leu Ser Gly Val Pro Asn Ala Asp Gly Pro Ala Pro
        115                 120                 125

Asp Gly Glu Glu Tyr Phe Ala Met Ala Leu Phe Leu Ala Ser Gly Arg
    130                 135                 140

Trp Gly Asp Gly Glu Gly Val Tyr Glu Tyr Ser Arg His Ala Arg Ser
145                 150                 155                 160

Ile Leu His Thr Cys Val His Arg Gly Glu Asp Gly Glu Gly Tyr Pro
                165                 170                 175

Met Trp Asn Pro Glu Asn His Leu Ile Lys Phe Ile Pro Glu Thr Glu
            180                 185                 190

Trp Thr Asp Pro Ser Tyr His Leu Pro His Phe Tyr Glu Val Phe Ala
        195                 200                 205

Gln Arg Ala Asp Glu Ala Asp Arg Pro Phe Trp Arg Glu Ala Ala Ala
    210                 215                 220

Ala Ser Arg Arg Tyr Leu Val Thr Ala Cys His Pro Glu Thr Gly Met
225                 230                 235                 240

Asn Pro Glu Tyr Ser Asn Tyr Asp Gly Thr Pro His Val Asp Glu Arg
                245                 250                 255
```

Asp His Trp His Phe Tyr Ser Asp Ala Tyr Arg Thr Ala Gly Asn Ile
            260                 265                 270

Gly Leu Asp Cys Leu Trp Asn Gly Val Val Pro Glu Leu Cys Asp Ala
        275                 280                 285

Asn Ala Arg Leu Gln Arg Phe Phe Leu Glu His Asp Arg Thr Cys Val
    290                 295                 300

Tyr Ala Val Asp Gly Thr Pro Val Asp Glu Thr Val Leu His Pro Val
305                 310                 315                 320

Gly Phe Ile Ala Ala Thr Ala Glu Gly Ser Leu Ala Ala Met His Ser
                325                 330                 335

Gln Glu Pro Asp Ala Leu Asp Asn Ala Ile Arg Trp Val Arg Leu Leu
            340                 345                 350

Trp Asp Thr Pro Ile Arg Thr Gly Thr Arg Arg Tyr Tyr Asp Asn Phe
        355                 360                 365

Leu Tyr Ala Phe Ala Phe Leu Ala Leu Ala Gly Glu Tyr Arg Val Trp
    370                 375                 380

<210> SEQ ID NO 109
<211> LENGTH: 388
<212> TYPE: PRT
<213> ORGANISM: Subdoligranulum variabile

<400> SEQUENCE: 109

Met Ile Met Glu Gly Ala Tyr Tyr Asn Gly Gln Tyr Leu Asn Arg Leu
1               5                   10                  15

Glu Arg Leu Gly Tyr Ser Gln Ala Glu Ile Asp Asn Lys Leu Glu Ser
            20                  25                  30

Thr Phe Glu Glu Met Phe Tyr Gly Pro Gln Gly Val Arg Leu Cys His
        35                  40                  45

Phe Ala Gly Pro Asp Met Met Tyr Ile Glu Asp Thr Gly Asn His Asp
    50                  55                  60

Val Arg Thr Glu Gly Met Ser Tyr Ala Met Met Phe Cys Val Gln Met
65                  70                  75                  80

Asn Arg Gln Lys Glu Phe Asp Cys Leu Trp Arg Trp Val Val Thr His
                85                  90                  95

Met Tyr Leu Thr Glu Gly Glu Asn Ala Gly Tyr Phe Ala Trp Ser Cys
            100                 105                 110

His Thr Asp Gly Ser Lys Asn Ser Asp Gly Pro Ala Pro Asp Gly Glu
        115                 120                 125

Glu Phe Phe Ala Met Ser Leu Phe Phe Ala Ala Asn Arg Trp Gly Ser
    130                 135                 140

Gly Glu Gly Val Leu Asp Tyr Ala Ser Trp Ala Arg Arg Ile Leu His
145                 150                 155                 160

Thr Cys Val His Lys Gly Glu Glu Ala Gly Ser Gly Phe Pro Met Trp
                165                 170                 175

Asn Pro Glu Asn His Leu Ile Lys Phe Val Pro Asn Cys Glu Phe Thr
            180                 185                 190

Asp Pro Ser Tyr His Leu Pro His Phe Tyr Glu Leu Phe Ala Leu Trp
        195                 200                 205

Ser Asp Glu Cys Asp Arg Pro Phe Trp His Ala Ala Ala Ala Ala Ser
    210                 215                 220

Arg Gln Tyr Leu Arg Lys Ala Cys His Ala Thr Gly Leu Ser Ala
225                 230                 235                 240

Glu Tyr Ala Glu Tyr Asp Gly Arg Pro His Arg Gly Asp Gln Pro Asp
                245                 250                 255

```
Arg His Asp Trp Phe Ser Asp Ala Tyr Arg Thr Leu Gly Asn Ile
            260                 265                 270

Ala Leu Asp Ala Gln Trp Phe Gly Asp Lys Asp Gly Trp Ala Gln Glu
        275                 280                 285

Thr Ala Ala His Ile Gln Gln Phe Phe Glu Lys Glu His Gly Gln
    290                 295                 300

Thr Asn Gly Ile Tyr Leu Ile Asp Gly Thr Pro Val Glu Gly Asn Ala
305                 310                 315                 320

Leu His Pro Val Gly Leu Leu Ala Thr Ile Ala Gln Gly Ser Leu Ile
                325                 330                 335

Leu Asp Asp Ala Cys Ala Asp Glu Trp Leu Arg Arg Phe Phe Ser Thr
            340                 345                 350

Pro Leu Arg Ser Gly Pro Arg Arg Tyr Tyr Asp Asn Cys Leu Tyr Leu
        355                 360                 365

Phe Ala Leu Leu Ala Leu Ser Gly His Tyr Arg Ile Trp Phe Pro Gln
370                 375                 380

Glu Ala Lys Val
385

<210> SEQ ID NO 110
<211> LENGTH: 350
<212> TYPE: PRT
<213> ORGANISM: Halomonas

<400> SEQUENCE: 110

Met Asn Gly Lys Ser Val Lys Ala Ala Val Ile Tyr Leu Leu Gly Gly
1               5                   10                  15

Leu Leu Val Leu Leu Gly Leu Ala Ser Met Pro Ala Ser Ala Asn Ala
            20                  25                  30

Asn Phe Ala Val Gly Asp Pro Gly Trp Glu Ala Tyr Lys Lys Arg Phe
        35                  40                  45

Leu Leu Pro Glu Gly Arg Ile Val Asp Thr Ala Asn Asn Asn Ile Ser
    50                  55                  60

His Thr Glu Gly Gln Gly Trp Gly Met Phe Leu Ala Val Gln Phe Asn
65                  70                  75                  80

Asp Arg Gln Ala Phe Asp Arg Ile Trp Gln Trp Thr Glu Ala His Leu
                85                  90                  95

Ala Arg Gln Asp Ile Ala Leu Tyr Ala Trp Arg Tyr Asp Pro Asn Ala
            100                 105                 110

Gln Pro Pro Val Ala Asp Asn Asn Ala Thr Asp Gly Asp Leu Phe
        115                 120                 125

Ala Ala Trp Ser Leu Gln Leu Ala Ala Asp Arg Trp Gly Asp Glu Arg
130                 135                 140

Tyr Ala Gln Arg Ser Glu Ala Ile Arg Gly Ala Ile Arg Asp His Leu
145                 150                 155                 160

Ile Ala Asp Val Gly Gly Tyr Gln Val Leu Leu Pro Gly Leu Asp Gly
                165                 170                 175

Phe Arg His Lys Thr Phe Thr Asp Ile Asn Leu Ser Tyr Trp Val Ile
            180                 185                 190

Pro Ala Leu Arg Asp Phe Ala Ala Arg His Pro Asp Glu Pro Trp Leu
        195                 200                 205

Ala Val Ile Asp Ser Gly Arg Gln Leu Leu Glu Arg Ala Gln Phe Gly
    210                 215                 220

Ser Ser Gln Leu Pro Ala Asp Trp Leu Arg Leu Gln Thr Ser Gly Glu
```

```
                 225                 230                 235                 240

Leu Arg Pro Ala Glu Gly Trp Pro Arg Phe Gly Phe Glu Asn Ile
                245                 250                 255

Arg Thr Pro Leu Tyr Phe Thr Trp Gly Gly Leu Arg Asp Ile Asp Thr
                260                 265                 270

Leu Glu Asp Ile Ala Arg Phe Trp Asp Gln Ser Ala Pro Ala Trp
                275                 280                 285

Val Asp Val Glu Ser Gly Asp Thr Ala Glu Tyr Pro Ile Ser Gln Gly
290                 295                 300

Gly Lys Ala Ile Ser Ala Leu Leu Ser Gly Arg Pro Trp Ala Ile Asp
305                 310                 315                 320

Ile Thr Pro Ala Ala Gly Glu Asn Tyr Tyr Ser Ala Thr Leu Leu Leu
                325                 330                 335

Leu Thr Arg Val Ala Ala Ala Gln Ile Ser Leu Ser Ala Gly
                340                 345                 350

<210> SEQ ID NO 111
<211> LENGTH: 390
<212> TYPE: PRT
<213> ORGANISM: Geodermatophilus obscurus

<400> SEQUENCE: 111

Met Ser Pro Arg Gly Ile Thr Val Gly Ala Leu Gly Val Leu Ala Leu
1               5                   10                  15

Leu Val Val Leu Ala Ala Val Gly Thr Arg Gly Gly Gly Thr
                20                  25                  30

Thr Gly Ala Pro Leu Pro Ser Pro Thr Gly Pro Ser Thr Val Ala Pro
                35                  40                  45

Ala Pro Pro Ala Glu Leu Arg Thr Tyr Thr Ala Ala Glu Ala Gly Arg
50                  55                  60

Ala Phe Leu Asp Gly Tyr Val Asp Glu Asp Gly Gln Val Val Arg Pro
65                  70                  75                  80

Asp Gln Gly Gly Asp Thr Val Ser Glu Gly Gln Ala Tyr Ala Met Leu
                85                  90                  95

Val Ala Val Gly Leu Gly Asp Ala Lys Thr Phe Ala Arg Ala Trp Asn
                100                 105                 110

Trp Thr Arg Glu Asn Leu Gln Arg Pro Asp Gly Leu Leu Ser Trp Arg
                115                 120                 125

Trp Glu Glu Gly Gly Val Val Asp Ala Ser Ser Ala Ser Asp Ala Asp
130                 135                 140

Leu Asp Ala Ala Arg Ala Leu Val Leu Ala Gly Glu Gln Phe Gly Arg
145                 150                 155                 160

Pro Glu Tyr Thr Ala Ala Gly Leu Asp Leu Gly Arg Ala Val Leu Asp
                165                 170                 175

Leu Glu Thr Val Pro Thr Ala Ala Gly Arg Ile Leu Thr Ala Gly Gln
                180                 185                 190

Trp Ala Thr Thr Glu Pro Tyr Ala Tyr Asn Pro Ser Tyr Ala Ser Pro
                195                 200                 205

Gly Ala Thr Ala Val Leu Ala Ala Ser Gly Asp Pro Arg Trp Thr
210                 215                 220

Glu Leu Ala Glu Gly Ser Arg Ala Val Thr Ala Ala Leu Leu Ser Gln
225                 230                 235                 240

Ala Pro Leu Pro Pro Asp Trp Ala Gln Val Arg Ala Asp Gly Thr Val
                245                 250                 255
```

```
Glu Ala Met Pro Gly Ala Met Gly Arg Gly Gln Ser Val Arg Tyr Gly
                260                 265                 270

Tyr Asp Ala Thr Arg Thr Pro Ile Arg Phe Ala Glu Ser Cys Asp Pro
            275                 280                 285

Ala Asp Arg Ala Leu Ala Ala Val Val Glu Pro Leu Asp Arg Gly
        290                 295                 300

Gly Asp Ser Ala Glu Leu Asp Leu Gly Gly Ser Pro Val Ala Pro Gly
305                 310                 315                 320

Glu Ser Val Val Ala Ala Gly Gln Ala Ala Val Ala Ala Ala
                325                 330                 335

Gly Asp Ala Gly Arg Ala Val Glu Glu Leu Val Asp Ala Asp His Leu
            340                 345                 350

Ala Gln Ser Ala Pro Ser Tyr Tyr Gly Ala Ala Trp Ala Ala Leu Gly
        355                 360                 365

Arg Phe Met Leu Thr Asp Asp Val Leu Gly Gly Cys Pro Pro Val Pro
        370                 375                 380

Ala Thr Ser Gly Thr Ala
385                 390

<210> SEQ ID NO 112
<211> LENGTH: 372
<212> TYPE: PRT
<213> ORGANISM: Lactobacillus gasseri

<400> SEQUENCE: 112

Met Lys Val Lys Asn Leu Ile Leu Ile Leu Gly Thr Ile Ala Tyr
1               5                   10                  15

Leu Gly Ile Ile Gly Tyr Val Arg Met Ser Asn Asp Arg Thr Leu Glu
            20                  25                  30

Lys Arg Tyr Tyr His Glu Trp Arg Glu Asp Tyr Ile Lys Asn Lys Asn
        35                  40                  45

Gln Asn Glu Gln Tyr Val Asn Ala Ala Gly Gly Lys Gly Pro Ser Phe
    50                  55                  60

Ala Leu Ser Glu Ala Gln Gly Tyr Gly Met Leu Leu Ala Ala Lys Ala
65                  70                  75                  80

Gly Glu Lys His Leu Gly Ser Arg Ile Asp Phe Gln Lys Leu Asp Asn
                85                  90                  95

Tyr Tyr Leu Ala His Arg Leu Ile Asn Ser Asn Leu Met Ser Trp Arg
            100                 105                 110

Gln Lys Asp Arg Lys Asn Ile Trp Arg Asp Asn Pro Val Ser Ala Ser
        115                 120                 125

Asp Gly Asp Ile Met Ile Ala Gln Ala Leu Leu His Ala Asn Arg Val
    130                 135                 140

Trp Pro Gly His Gly Tyr Lys Ser Gln Ala Val Asn Leu Ile Asn Asp
145                 150                 155                 160

Ile Lys Arg Leu Glu Ile Asn Gln Lys Ala Lys Met Val Thr Val Gly
                165                 170                 175

Asn Trp Ala Asn Lys Asp Ser Arg Phe Tyr Asn Val Leu Arg Thr Ser
            180                 185                 190

Asp Val Met Pro Lys Ala Phe Glu Glu Phe Tyr Gln Ala Thr Gly Asp
        195                 200                 205

Arg Glu Trp Leu Thr Ile Lys Ser Lys Met Leu Asn Tyr Leu Gln Lys
    210                 215                 220

Leu Ser Lys Lys His Asp Thr Gly Leu Val Pro Asp Phe Ala Trp Val
225                 230                 235                 240
```

```
Ser Asn Asn Tyr Val Lys Pro Ala Lys Ala Asn Glu Val Ala Thr Asn
                245                 250                 255

Asp Asp Gly His Tyr Ser Ala Asn Ala Cys Arg Val Pro Met Leu Leu
            260                 265                 270

Ala Glu Ser Asn Asp Lys Asn Ala Ala Gln Val Val Lys Lys Met Leu
        275                 280                 285

Lys Phe Phe Lys Lys Gly Thr Ser Ala Gly Phe Thr Leu Lys Gly
    290                 295                 300

Lys Lys Leu His Tyr Tyr Gln Ser Ala Ser Phe Ser Ala Pro Ile Phe
305                 310                 315                 320

Val Ala Ala Asn Lys Tyr Arg Asn Gln Gly Tyr Asp Thr Leu Val Glu
                325                 330                 335

Gln Glu Lys Tyr Ile Phe Ser Arg Ser Leu Pro Lys Asp Asn Tyr Tyr
            340                 345                 350

Asp Ala Thr Leu Thr Thr Leu Ala Ala Leu Asn Thr Asn Glu Leu Thr
            355                 360                 365

Gly Leu Glu Lys
    370

<210> SEQ ID NO 113
<211> LENGTH: 337
<212> TYPE: PRT
<213> ORGANISM: Azotobacter vinelandii

<400> SEQUENCE: 113

Met Ala Ala Arg Lys Ala Gly Pro Leu Gly Ala Leu Ile Ala Leu Leu
1               5                   10                  15

Leu Phe Cys Leu Pro Ala Ser Ala Gly Glu Asp Glu Tyr Trp Arg Leu
                20                  25                  30

Tyr Gln Thr Arg Tyr Ile Asp Gly Gly Arg Val Leu Asp Thr Gly Asn
            35                  40                  45

Lys Gly Val Ser His Ser Glu Gln Gly Trp Gly Met Leu Leu Ala
    50                  55                  60

Glu Ala Asn Gly Asp Arg Arg Thr Phe Asp Arg Leu Trp Ser Trp Thr
65                  70                  75                  80

Arg Arg His Leu Gln Arg Arg Asp Leu Ala Leu Phe Ser Trp Arg Tyr
                85                  90                  95

Asp Pro Ala Ala Ser Pro Val Gln Asp Leu Asn Asn Ala Thr Asp
            100                 105                 110

Gly Asp Leu Leu Ile Ala Trp Ala Leu Leu Arg Ala Ala Gln Arg Trp
        115                 120                 125

Asp Ala Ala Asp Tyr Arg Asn Ala Ser Ala Lys Ile Arg Gln Ala Ile
    130                 135                 140

Ala Gly Arg Leu Ile Lys Glu His Ala Gly Leu Thr Val Leu Leu Pro
145                 150                 155                 160

Gly Leu Gln Gly Phe Glu Gln Asn Gly Gln Leu Ile Leu Asn Pro Ser
                165                 170                 175

Tyr Leu Val Met Pro Ala Ile Arg Ala Phe Ala Arg Ala Asp Pro Gly
            180                 185                 190

Gly Gly Trp Gln Arg Leu Leu Asp Asp Ser Arg Ser Leu Asp Arg
        195                 200                 205

Ala Arg Phe Gly Thr Tyr Arg Leu Pro Pro Asp Trp Leu Ala Leu Gly
    210                 215                 220

Ala Asp Gly Thr Leu Glu Pro Ala Ala Ala Trp Pro Ala Arg Phe Gly
```

```
225                 230                 235                 240
Phe Asp Ala Val Arg Val Pro Leu Tyr Leu Ala Trp Asp Gly Glu Pro
                245                 250                 255
Leu Ser Ser Pro Arg Leu Ala Pro Phe Ala Asp Phe Trp Ser Cys Cys
                260                 265                 270
Glu Pro Leu His Ala Trp Val Asp Leu Asn Ser Gly Lys Leu Ser Pro
                275                 280                 285
Tyr Pro Gly Ser Val Gly Val Lys Ala Ile Ala Ala Leu Leu Arg Gly
                290                 295                 300
Glu Glu Pro Val Ala Thr Pro Glu Gln Leu Ala Lys Glu Asp Tyr Tyr
305                 310                 315                 320
Ser Met Ser Leu Leu Met Leu Ala Arg Leu Ala Arg Lys Glu Gly Ala
                325                 330                 335
Pro

<210> SEQ ID NO 114
<211> LENGTH: 320
<212> TYPE: PRT
<213> ORGANISM: Sulfurihydrogenibium azorense

<400> SEQUENCE: 114

Met Lys Arg Leu Leu Ile Ile Phe Ser Val Leu Gly Phe Leu Gly Phe
1                   5                   10                  15
Ser Asn Gly Gln Glu Ile Leu Thr Trp Gln Asn Tyr Lys Asn Lys Tyr
                20                  25                  30
Ile Pro Asn Gly Ser Tyr Val Ile Asp Pro Tyr Asn Glu Asn Arg Val
                35                  40                  45
Thr Ser Glu Ser Gln Gly Tyr Gly Met Ile Leu Ala Ile Leu Asn Asp
                50                  55                  60
Asp Lys Thr Thr Phe Asp Asn Leu Trp Gln Trp Thr Arg Lys Asn Leu
65                  70                  75                  80
Gln Arg Glu Asp Tyr Leu Phe Ser Trp Leu Trp Asn Asp Glu Val Lys
                85                  90                  95
Asp Lys Asn Asn Ala Thr Asp Gly Asp Phe Leu Ile Ala Tyr Ala Leu
                100                 105                 110
Leu Lys Ala Tyr Glu Lys Trp Gly Asp Lys Ala Tyr Lys Asp Glu Gly
                115                 120                 125
Glu Lys Ile Phe Asn Ser Leu Lys Asn Leu Ile Val Ile Val Lys Asp
                130                 135                 140
Asn Lys Leu Lys Asp Asn Tyr Leu Leu Leu Pro Ala Thr Tyr Gly Phe
145                 150                 155                 160
Ser Asn Glu Lys Tyr Asp Ile Val Ile Phe Pro Ser Tyr Tyr Ile Thr
                165                 170                 175
Phe Ile Leu Lys Glu Leu Ser Tyr Lys Asp Asn Leu Trp Lys Gly Val
                180                 185                 190
Tyr Asn Tyr Thr Lys Asn Ile Leu Phe Lys Thr Ile Leu Ser Thr Asn
                195                 200                 205
Leu Lys Phe Asn Leu Ile Glu Lys Lys Leu Ile Pro Ile Ser Pro Val
                210                 215                 220
Asn Leu Asp Val Tyr Arg Val Ile Pro Tyr Thr Tyr Met Ala Lys Glu
225                 230                 235                 240
Ser Leu Glu Asp Leu Lys Thr Ser Phe Ser Glu Val Asp Ser Phe Phe
                245                 250                 255
Lys Ala Lys Gly Tyr Ile Pro Phe Asn Tyr Asn Leu Gly Ser Leu Gln
```

```
                260                 265                 270
Gln Glu Val Ser Glu Ser Pro Phe Cys Val Tyr Arg Phe Phe Tyr Leu
            275                 280                 285

Leu Tyr Asn Asp Glu Lys Tyr Leu Glu Arg Tyr Lys Val Leu Lys Asn
        290                 295                 300

Asn Asp Lys Asn Asn Tyr Phe Cys Asp Thr Phe Glu Leu Phe Leu Asp
305                 310                 315                 320

<210> SEQ ID NO 115
<211> LENGTH: 388
<212> TYPE: PRT
<213> ORGANISM: Acidobacterium capsulatum

<400> SEQUENCE: 115

Met Met Arg Met Arg Met Lys Leu Leu Arg His Val Leu Ser Val Ala
1               5                   10                  15

Ser Leu Ser Ala Leu Ile Phe Ala Thr Gly Cys Arg Ala Gln Ser Trp
            20                  25                  30

Pro Leu Trp Gln Ala Tyr Gln Gly Lys Phe Leu Asn Ser Asp Gly Arg
        35                  40                  45

Val Val Asp Tyr Asn Ala Gln Ala Arg Thr Thr Ser Glu Gly Gln Ser
50                  55                  60

Tyr Ala Leu Phe Phe Ala Leu Val Ala Asn Asp Arg Pro Ala Phe Asp
65                  70                  75                  80

Lys Val Leu Ala Trp Thr Gln Asn Asn Leu Ala Gln Gly Asp Leu Thr
                85                  90                  95

Ala His Leu Pro Ala Trp Glu Trp Gly Lys Ala Lys Asp Gly Gln Trp
            100                 105                 110

Lys Thr Ile Asp Pro Asn Pro Ala Ser Asp Ala Asp Leu Trp Ile Ser
        115                 120                 125

Tyr Thr Leu Leu Gln Ala Gly Arg Leu Trp His Asp Pro His Tyr Thr
130                 135                 140

Ala Leu Gly Thr Val Met Ala Lys Arg Ile Ala Asn Glu Glu Val Ala
145                 150                 155                 160

Asn Leu Pro Gly Leu Gly Ser Met Leu Leu Pro Gly Pro Thr Gly Phe
                165                 170                 175

His Pro Asn Ala Ala Thr Trp Leu Leu Asn Pro Ser Tyr Met Pro Leu
            180                 185                 190

Pro Val Val Glu Gly Met Ala His Ala Asp Pro Ser Gly Pro Trp Ala
        195                 200                 205

Gly Met Ala Ala Ala Val Pro Asp Leu Val Lys Gly Ala Ser Pro Ala
210                 215                 220

Gly Phe Val Met Asp Trp Val Ser Tyr Ser Gln Ala Gly Gly Phe Gln
225                 230                 235                 240

Pro Ala Val Leu Pro Thr Ala Pro Lys Gly Thr Val Pro Met Gly Ser
                245                 250                 255

Tyr Asp Ala Ile Arg Val Tyr Leu Trp Thr Gly Met Ala Asn Pro Ala
            260                 265                 270

Thr Pro Gly Ala Lys Leu Thr Leu Arg Ala Leu Tyr Gly Met Ala Ala
        275                 280                 285

Tyr Leu Lys Ser His Thr Leu Pro Pro Glu Lys Val Asp Pro Gln Gly
290                 295                 300

Lys Val Leu Ser Thr Ser Ala Pro Val Gly Phe Ser Ala Ala Val Glu
305                 310                 315                 320
```

```
Pro Phe Leu Ser Ala Leu Gly Asp Lys Gly Asp Leu Asn Thr Gln Gln
            325                 330                 335

Ala Arg Leu Asp Ala Met Val Asn Pro Asn Thr Lys Leu Tyr Gly Glu
        340                 345                 350

Pro Pro Ala Tyr Phe Asp Gln Asn Leu Ala Met Phe Gly Glu Gly Trp
            355                 360                 365

Gln Gln His Arg Phe Gly Phe Ala Ser Asp Gly Asp Leu Trp Val Lys
370                 375                 380

Trp Lys Gly Arg
385

<210> SEQ ID NO 116
<211> LENGTH: 381
<212> TYPE: PRT
<213> ORGANISM: Lactobacillus jensenii

<400> SEQUENCE: 116

Met Glu Asp Ile Met Lys Gln Lys Ile Met Trp Val Ile Leu Pro Ile
1               5                   10                  15

Ile Ile Ala Asn Tyr Ile Ala Thr Phe Tyr Phe Ile Arg Thr Lys Asn
            20                  25                  30

Pro Glu Gln Ile Gln Ile Lys Thr Tyr Gln Asp Trp Lys Lys Asn Tyr
        35                  40                  45

Leu Val Thr Lys Asn Ser Asn Gln Val Phe Val Asn Ala Gly Thr Asn
50                  55                  60

Lys His Pro Val Ala Leu Ser Glu Ala Gln Gly Phe Gly Leu Ile Ile
65                  70                  75                  80

Thr Ala Lys Ala Gly Lys Arg Gly Trp Ala Ser Glu Thr Glu Phe Asp
            85                  90                  95

Lys Leu Leu Asn Tyr Tyr Leu Ala His Gln Asp Tyr Val Gly Asp His
        100                 105                 110

His Thr Gln Lys Val Ser Leu Met Gln Trp Lys Gln Tyr Tyr Asn His
    115                 120                 125

His Gly Lys Trp Val Ser Glu Tyr Asn Ser Ala Thr Asp Gly Asp Leu
130                 135                 140

Tyr Ile Ala Thr Ala Leu Asn Thr Ala Ala Lys Val Trp Pro Gln Lys
145                 150                 155                 160

Ala Asn Tyr Tyr His Ser Leu Glu Ala Lys Leu Ala Asn Asp Ile Leu
            165                 170                 175

Arg Tyr Glu Tyr Asn Pro Gln Thr Gly Ala Leu Thr Thr Gly Asp Trp
        180                 185                 190

Val Arg Leu Asp Ser Tyr Tyr Ala Asn Leu Met Arg Thr Ser Asp Val
    195                 200                 205

Leu Pro Phe Val Phe Thr Asn Leu Ala Lys Thr Thr Gly Asn Lys Gln
210                 215                 220

Trp Tyr Ala Val Gln Asp Ser Met Leu Glu Lys Leu Val Lys Leu Ser
225                 230                 235                 240

Lys Gln His Lys Ala Gly Leu Val Pro Asp Phe Ala Trp Val Gly Arg
            245                 250                 255

Asn Tyr Ala Lys Pro Val Ala Pro Lys Thr Ile Ala Gly Lys Asn Asp
        260                 265                 270

Gly Tyr Tyr Ala Tyr Asn Ala Cys Arg Val Pro Ile Met Leu Ala Lys
    275                 280                 285

Ser Glu Ser Pro Lys Ala Lys Phe Val Glu Lys Arg Ile Leu His Tyr
290                 295                 300
```

Phe Ser Lys Gln Tyr Asn Val Phe Gly Gly Tyr Lys Leu Asn Gly Glu
305                 310                 315                 320

Arg Leu Val Lys Asn Gln Ser Pro Ser Phe Ser Ala Pro Ile Phe Tyr
            325                 330                 335

Ala Val Asn Gln Tyr Arg Gly Gln Gly Tyr Asp Asn Leu Phe Val Ser
        340                 345                 350

Gln Lys Tyr Ile Phe Ser Lys Ala Leu Pro Lys Asn Asp Tyr Tyr Gly
    355                 360                 365

Ala Thr Leu Thr Thr Leu Val Ala Val Glu Gly Trp Glu
370                 375                 380

<210> SEQ ID NO 117
<211> LENGTH: 432
<212> TYPE: PRT
<213> ORGANISM: Spirosoma linguale

<400> SEQUENCE: 117

Met Asn Leu Ile Asn Asn Leu Pro Glu Asn Arg Trp Leu Leu Pro
1               5                   10                  15

Val Leu Ile Gly Ile Phe Leu Ile Val Thr Pro Met Ala Val Ala Gln
            20                  25                  30

Lys Lys Met Lys Asp Lys Pro Lys Ala Glu Ala Gln Val Gly Asn Tyr
        35                  40                  45

Arg Asn Leu Phe Arg Glu Ala Gly Tyr Lys Gln Ala Asp Ile Asp Ala
    50                  55                  60

Lys Leu Ala Lys Ala Tyr His Asp Val Phe Glu Gly Pro Asn Lys Val
65                  70                  75                  80

Tyr Phe Glu Val Gly Asp Thr Met Ala Tyr Val Ser Asp Val Lys Asn
                85                  90                  95

Lys Asp Ala Arg Thr Glu Gly Leu Ser Tyr Gly Met Met Ile Ala Val
            100                 105                 110

Gln Leu Asp Lys Lys Asp Val Phe Asp Arg Ile Trp Arg Trp Ser Lys
        115                 120                 125

Lys Tyr Leu Gln His Gln Ser Gly Pro Arg Glu Gly Tyr Phe Ala Trp
    130                 135                 140

Ser Ile Asn Pro Gln Thr Met Lys Lys Asn Ser Glu Gly Ser Ala Ser
145                 150                 155                 160

Asp Gly Glu Leu Tyr Tyr Ile Thr Ser Leu Leu Ala Ala Asn Lys
                165                 170                 175

Trp Gly Asn Asn Thr Gly Ile Asn Tyr Tyr Gly Glu Ala Arg Arg Ile
            180                 185                 190

Leu Asp Ala Ile Trp Lys Lys Asp Gly Thr Gly Asn Ile Tyr Asn Leu
        195                 200                 205

Ile Asn Thr Asp Thr Lys Gln Ile Ser Phe Val Pro Glu Gly Gly Met
    210                 215                 220

Tyr Asn Trp Thr Asp Pro Ser Tyr His Leu Pro Ala Phe Tyr Glu Val
225                 230                 235                 240

Trp Gly Thr Tyr Ala Lys Asp Gly His Glu Gln Phe Tyr Arg Glu Cys
                245                 250                 255

Ala Asp Thr Ser Arg Ala Phe Leu His Arg Ala Cys His Pro Val Thr
            260                 265                 270

Gly Leu Asn Ala Asp Tyr Thr Glu Phe Ser Gly Lys Pro His Asp Thr
        275                 280                 285

Arg Trp Ser Pro Ser Ala Phe Arg Tyr Asp Ser Trp Arg Val Pro Met

```
                290                 295                 300
Asn Ile Ala Met Asp Tyr Thr Trp Ser Gly Lys Asp Lys Ala Trp Gln
305                 310                 315                 320

Glu Asp Tyr Ala Lys Arg Phe Gln Gly Phe Leu Arg Ser Lys Gly Met
                325                 330                 335

Asp Thr Tyr Asp Asp Gln Phe Asn Leu Asp Gly Ser Arg Pro Glu Phe
                340                 345                 350

Ile Leu Gln Ala Gly Pro Val Lys Lys Leu Arg His Ser Leu Gly Leu
                355                 360                 365

Val Ser Thr Ser Ala Thr Leu Ser Leu Val Asn Lys Glu Pro Asn Ser
                370                 375                 380

Lys Asp Phe Val Arg Ala Val Trp Asn Ala Lys Leu Glu Pro Phe Asp
385                 390                 395                 400

Asp Gly Tyr Phe Asp Pro Tyr Tyr Asp Gly Leu Leu Tyr Val Phe Ser
                405                 410                 415

Leu Met His Leu Ser Gly Lys Tyr Arg Ile Ile Thr Pro Gln Ala Arg
                420                 425                 430

<210> SEQ ID NO 118
<211> LENGTH: 373
<212> TYPE: PRT
<213> ORGANISM: Edwardsiella ictaluri

<400> SEQUENCE: 118

Met Lys Glu Ser Val Tyr Arg Thr Leu Met Ala Ala Leu Leu Cys
1               5                   10                  15

Val Ser Val Ala Thr Val Gly Ala Pro Cys Glu Trp His Glu Trp Glu
                20                  25                  30

Gln Phe Arg Gln Gly Tyr Ile Ser Pro Asp Gly Arg Val Ile Asp Pro
                35                  40                  45

Ser Ser Pro Arg Gln Val Thr Thr Ser Glu Gly Gln Ser Tyr Ala Leu
                50                  55                  60

Phe Phe Ala Leu Val Asn Asn Asp Arg Ala Leu Phe Gly Lys Leu Leu
65                  70                  75                  80

Ala Trp Thr Gln Asn Asn Leu Ser Gln Gly Ser Leu Ser Gln Arg Leu
                85                  90                  95

Pro Ala Trp Lys Trp Gly Arg His Asp Asp Gly Arg Trp Arg Ile Leu
                100                 105                 110

Asp Asp Asn Ser Ala Ser Asp Ala Asp Leu Trp Ile Ala Tyr Thr Leu
                115                 120                 125

Leu Glu Ala Gly Arg Leu Trp Gln Asp Ser Asp Tyr Gln His Leu Ser
                130                 135                 140

Ile Gln Leu Leu Ala Arg Ile Ala Arg Glu Glu Val Val Ser Leu Pro
145                 150                 155                 160

Gly Phe Gly Met Met Leu Leu Pro Gly Arg Gln Gly Phe Arg Ser Gly
                165                 170                 175

Ala Leu Trp Thr Ile Asn Pro Ser Tyr Leu Pro Gln Ile Leu Ala
                180                 185                 190

Arg Ile Ala Pro Leu His Gly Pro Trp Asn Arg Leu Gln Tyr Ser Ala
                195                 200                 205

Leu Arg Met Leu Glu Ala Ser Ser Pro His Gly Ile Val Pro Asp Trp
                210                 215                 220

Thr Asn Trp Gln Arg Asn Lys Gly Trp Leu Pro Thr Pro Gly Arg Ala
225                 230                 235                 240
```

```
Tyr Ile Ser Gly Tyr Asp Ala Ile Arg Ala Tyr Leu Trp Ala Gly Met
            245                 250                 255

Leu Ala Asp Gly Ala Pro Ala Lys Ser Ala Leu Val Lys His Trp Gln
        260                 265                 270

Pro Met Val Ala Leu Ser Glu Arg Leu Gly Tyr Ile Pro Glu Lys Val
            275                 280                 285

Gly Val Leu Gly Val Glu Pro Gln Gly Glu Gly Asn Val Gly Phe Ser
        290                 295                 300

Ala Ala Met Leu Pro Phe Leu Asp Ala Ser Asn Ser Pro Leu Leu Ala
305                 310                 315                 320

Ala Gln Arg Gln Arg Val Lys Asp Asn Leu Pro Gly Asn Asn Asn Tyr
                325                 330                 335

Tyr Ser Ser Val Leu Thr Leu Phe Gly Leu Gly Trp Asp Gln Arg Arg
            340                 345                 350

Tyr Arg Phe Asn Leu Gln Gly Glu Leu Val Pro Asn Trp Gly Ser Val
        355                 360                 365

Cys Asp Val Ser Asp
        370

<210> SEQ ID NO 119
<211> LENGTH: 436
<212> TYPE: PRT
<213> ORGANISM: Teredinibacter turnerae

<400> SEQUENCE: 119

Met Phe Pro Arg Leu Ser Pro Ser Arg Phe Arg Gln Val Thr Leu Thr
1               5                   10                  15

Leu Leu Thr Leu Gly Leu Val Ser Leu Thr Gly Cys Ala Gly Asn Ser
            20                  25                  30

Lys Pro Asp Ala Asp Thr Ser Thr Ala Gly Ala Val Ala Thr Gly Glu
        35                  40                  45

Tyr Arg Asn Leu Phe Ala Glu Ile Gly Lys Ser Glu Ile Asp Ile Gln
    50                  55                  60

Arg Lys Ile Asp Glu Ala Phe Gln His Leu Phe Tyr Gly Asp Ala Lys
65                  70                  75                  80

Asp Ala Ala Val Tyr Tyr Gln Ala Gly Gly Asn Glu Asn Gly Pro Leu
                85                  90                  95

Ala Tyr Val Tyr Asp Val Asn Ser Asn Asp Val Arg Ser Glu Gly Met
            100                 105                 110

Ser Tyr Gly Met Met Ile Thr Val Gln Met Asp Lys Lys Ala Glu Phe
        115                 120                 125

Asp Ala Ile Trp Asn Trp Ala Lys Thr Tyr Met Tyr Gln Asp Ser Pro
130                 135                 140

Thr His Pro Ala Phe Gly Tyr Phe Ala Trp Ser Met Arg Arg Asp Gly
145                 150                 155                 160

Val Ala Asn Asp Asp Met Pro Ala Pro Asp Gly Glu Glu Tyr Phe Val
                165                 170                 175

Thr Ala Leu Tyr Phe Ala Ala Ala Arg Trp Gly Asn Gly Glu Gly Ile
            180                 185                 190

Phe Asn Tyr Gln Gln Glu Ala Asp Thr Ile Leu Ser Arg Met Arg His
        195                 200                 205

Arg Gln Val Ile Thr Gly Pro Thr Asn Arg Gly Val Met Thr Ala Thr
    210                 215                 220

Asn Leu Phe His Pro Glu Glu Ala Gln Val Arg Phe Thr Pro Asp Ile
225                 230                 235                 240
```

-continued

```
Asn Asn Ala Asp His Thr Asp Ala Ser Tyr His Leu Pro Ser Phe Tyr
            245                 250                 255

Glu Ile Trp Ala Arg Val Ala Pro Gln Glu Asp Arg Ala Phe Trp Ala
            260                 265                 270

Lys Ala Ala Asp Val Ser Arg Asp Tyr Phe Ala Lys Ala Ala His Pro
            275                 280                 285

Val Thr Ala Leu Thr Pro Asp Tyr Gly Asn Phe Asp Gly Thr Pro Trp
            290                 295                 300

Ala Ala Ser Trp Arg Pro Glu Ser Val Asp Phe Arg Tyr Asp Ala Trp
305                 310                 315                 320

Arg Ser Val Met Asn Trp Ser Met Asp Tyr Ala Trp Trp Gly Lys Asp
            325                 330                 335

Ser Gly Ala Pro Ala Arg Ser Asp Lys Leu Leu Ala Phe Phe Glu Thr
            340                 345                 350

Gln Glu Gly Lys Met Asn His Leu Tyr Ser Leu Asp Gly Lys Pro Leu
            355                 360                 365

Gly Gly Gly Pro Thr Leu Gly Leu Ile Ser Met Asn Ala Thr Ala Ala
            370                 375                 380

Met Ala Ala Thr Asp Pro Arg Trp His Asn Phe Val Glu Lys Leu Trp
385                 390                 395                 400

Gln Gln Gln Pro Pro Thr Gly Gln Tyr Arg Tyr Tyr Asp Gly Val Leu
            405                 410                 415

Tyr Leu Met Ala Leu Leu His Cys Ala Gly Glu Tyr Lys Ala Trp Ile
            420                 425                 430

Pro Asp Gly Glu
            435

<210> SEQ ID NO 120
<211> LENGTH: 325
<212> TYPE: PRT
<213> ORGANISM: Aquifex aeolicus

<400> SEQUENCE: 120

Met Lys Phe Phe Thr Val Leu Leu Phe Leu Ser Phe Val Phe Ser
1               5                   10                  15

Ala Ser Ile Asp Val Trp Lys Leu Trp Glu His Tyr Lys Lys Thr Phe
            20                  25                  30

Ile Ser Lys Glu Gly Tyr Val Val Asp Pro Tyr Asn Asn Tyr Arg Val
            35                  40                  45

Thr Ser Glu Ala Gln Gly Tyr Thr Leu Leu Ile Ser Ala Leu Ile Gly
            50                  55                  60

Asp Lys Glu Thr Phe Tyr Arg Val Trp Asn Trp Thr Lys Glu Asn Leu
65                  70                  75                  80

Lys Arg Lys Asp Asn Leu Phe Ser Trp Leu Trp Ile Asn Gly His Val
            85                  90                  95

Val Asp Arg Asn Asn Ala Thr Asp Ala Asp Leu Phe Ile Ala Tyr Ala
            100                 105                 110

Leu Leu Ile Ala Ser Gln Lys Trp Lys Asp Tyr Thr Leu Leu Ser Glu
            115                 120                 125

Ala Lys Arg Ile Lys Asp Ser Val Lys Glu Leu Val Pro Val Cys
            130                 135                 140

Asn Gly Arg Arg Asp Tyr Leu Phe Ile Pro Ala Lys Glu Gly Tyr Ile
145                 150                 155                 160

Lys Asn Asn Ile Val Ser Leu Asn Val Val Tyr Tyr Val Pro Phe Ile
```

```
                165                 170                 175
Phe Arg Lys Phe Tyr Glu Ser Phe Gly Glu Asp Val Trp Lys Asn Leu
            180                 185                 190

Tyr Arg Tyr Thr Tyr Asp Ile Tyr Thr Ile Arg Asn Ile Ser Thr His
            195                 200                 205

Leu Thr Tyr Asp Leu Phe Lys Lys Glu Leu Arg Lys Gly Asn Phe Ile
            210                 215                 220

Asp Ile Asp Gly Met Arg Phe Leu Ile Tyr Ala Tyr Val Asp Asp Lys
225                 230                 235                 240

Arg Ser Leu Leu Tyr Met Arg Asn Ala Val Glu Gly Ile Leu Lys Phe
            245                 250                 255

Tyr Arg Glu Lys Gly Tyr Ile Pro Leu Lys Tyr Asn Tyr Val Thr Gly
            260                 265                 270

Gly Ala Ser Lys Leu Lys Ala Pro Phe Cys Phe Tyr Tyr Val Phe Ser
            275                 280                 285

Lys Leu Leu Pro Ser Asp Lys Asn Leu Glu Lys Glu Phe Arg Asn Gly
            290                 295                 300

Leu Glu Tyr Asp Lys Lys Asn Tyr Tyr Cys Tyr Ala Leu Leu Leu Ile
305                 310                 315                 320

Ala Leu Leu His Asp
            325

<210> SEQ ID NO 121
<211> LENGTH: 341
<212> TYPE: PRT
<213> ORGANISM: Gluconacetobacter xylinus

<400> SEQUENCE: 121

Met Ala Val Ala Gly Ser Phe Pro Met Leu Ser Ser Gly Ala Glu Ala
1               5                   10                  15

Asp Asp Ala Ile Gly Ile Asn Pro Gln Ile Ala Gln Trp Ala Ile
            20                  25                  30

Phe Arg Asp Lys Tyr Phe His Pro Asn Gly Arg Ile Ile Asp Thr Gly
            35                  40                  45

Asn Ser Gly Glu Ser His Ser Glu Gly Gln Gly Tyr Gly Met Leu Phe
        50                  55                  60

Ser Ala Ala Ala Gly Asp Gln Ala Ala Phe Glu Val Ile Trp Val Trp
65                  70                  75                  80

Ala Arg Thr Asn Leu Gln His Lys Asp Asp Ala Leu Phe Ser Trp Arg
                85                  90                  95

Tyr Leu Asp Gly His Lys Pro Pro Val Ala Asp Lys Asn Asn Ala Thr
            100                 105                 110

Asp Gly Asp Leu Leu Ile Ala Leu Ala Leu Ala Trp Ala Gly Lys Arg
            115                 120                 125

Trp Lys Arg Ala Asp Tyr Ile Gln Asp Ala Met Asn Ile Tyr Gly Asp
            130                 135                 140

Val Leu Lys Leu Met Thr Lys Ser Val Gly Pro Tyr Thr Val Leu Leu
145                 150                 155                 160

Pro Gly Ala Val Gly Phe Leu Thr Lys Asp Thr Val Thr Leu Asn Leu
            165                 170                 175

Ser Tyr Tyr Val Met Pro Ser Leu Met Gln Ala Phe Ala Leu Thr Gly
            180                 185                 190

Asp Ala Lys Trp Thr Lys Val Met Gly Asp Gly Leu Gln Ile Ile Ala
            195                 200                 205
```

```
Lys Gly Arg Phe Gly Glu Trp Lys Leu Pro Pro Asp Trp Leu Ser Ile
210                 215                 220

Asn Leu His Thr Asn Ala Phe Ser Ile Ala Lys Gly Trp Pro Pro Arg
225                 230                 235                 240

Phe Ser Tyr Asp Ala Ile Arg Val Pro Leu Tyr Leu Ser Trp Ala His
                245                 250                 255

Met Leu Thr Pro Glu Leu Leu Ala Asp Phe Ser Arg Phe Trp Asn His
                260                 265                 270

Tyr Gly Ala Ser Ala Leu Pro Gly Trp Val Asp Leu Thr Asn Gly Ala
                275                 280                 285

Arg Ser Pro Tyr Asn Ala Pro Pro Gly Tyr Leu Ala Val Ala Ser Cys
290                 295                 300

Thr Gly Leu Ala Ser Ala Gly Glu Leu Pro Thr Leu Asp His Ala Pro
305                 310                 315                 320

Asp Tyr Tyr Ser Ala Ala Leu Thr Met Leu Ala Tyr Ile Ala Arg Asn
                325                 330                 335

Gln Gly Asp Gly Met
                340

<210> SEQ ID NO 122
<211> LENGTH: 359
<212> TYPE: PRT
<213> ORGANISM: Cellulomonas uda

<400> SEQUENCE: 122

Met Pro Leu Arg Ala Leu Val Ala Val Ile Val Thr Thr Ala Val Met
1               5                   10                  15

Leu Val Pro Arg Ala Trp Ala Gln Thr Ala Trp Glu Arg Tyr Lys Ala
                20                  25                  30

Arg Phe Met Met Pro Asp Ala Arg Ile Ile Asp Thr Ala Asn Gly Asn
                35                  40                  45

Val Ser His Thr Glu Gly Gln Gly Phe Ala Met Leu Leu Ala Val Ala
            50                  55                  60

Asn Asn Asp Arg Pro Ala Phe Asp Lys Leu Trp Gln Trp Thr Asp Ser
65                  70                  75                  80

Thr Leu Arg Asp Lys Ser Asn Gly Leu Phe Tyr Trp Arg Tyr Asn Pro
                85                  90                  95

Val Ala Pro Asp Pro Ile Ala Asp Lys Asn Asn Ala Thr Asp Gly Asp
                100                 105                 110

Thr Leu Ile Ala Trp Ala Leu Leu Arg Ala Gln Lys Gln Trp Gln Asp
            115                 120                 125

Lys Arg Tyr Ala Thr Ala Ser Asp Ala Ile Thr Ala Ser Leu Leu Lys
130                 135                 140

Tyr Thr Val Val Thr Phe Ala Gly Arg Gln Val Met Leu Pro Gly Val
145                 150                 155                 160

Lys Gly Phe Asn Arg Asn Asp His Leu Asn Leu Asn Pro Ser Tyr Phe
                165                 170                 175

Ile Phe Pro Ala Trp Arg Ala Phe Ala Glu Arg Thr His Leu Thr Ala
                180                 185                 190

Trp Arg Thr Leu Gln Ser Asp Gly Gln Ala Leu Leu Gly Gln Met Gly
            195                 200                 205

Trp Gly Lys Ser His Leu Pro Ser Asp Trp Val Ala Leu Arg Ala Asp
210                 215                 220

Gly Lys Met Leu Pro Ala Lys Glu Trp Pro Pro Arg Met Ser Phe Asp
225                 230                 235                 240
```

```
Ala Ile Arg Ile Pro Leu Tyr Ile Ser Trp Val Asp Pro His Ser Ala
                245                 250                 255

Leu Leu Ala Pro Trp Lys Ala Trp Met Gln Ser Tyr Pro Arg Leu Gln
            260                 265                 270

Thr Pro Ala Trp Ile Asn Val Ser Thr Asn Glu Val Ala Pro Trp Asn
        275                 280                 285

Met Ala Gly Gly Leu Leu Ala Val Arg Asp Leu Thr Leu Gly Glu Pro
    290                 295                 300

Leu Glu Arg Arg Arg Leu Thr Thr Arg Met Ile Ile Thr Pro Pro Ala
305                 310                 315                 320

Ser Ser Cys Trp Ser Gly Trp Arg Asn Arg Ile Ser Ala Ser Ala Val
                325                 330                 335

Met Ala Leu Gln Val Ser Gln Pro Val Cys Leu Arg Ala Glu Arg Lys
            340                 345                 350

Glu Gln Glu Arg Leu Thr Met
            355

<210> SEQ ID NO 123
<211> LENGTH: 332
<212> TYPE: PRT
<213> ORGANISM: Erwinia chrysanthemi

<400> SEQUENCE: 123

Met Gly Lys Pro Met Trp Arg Cys Trp Ala Leu Met Leu Met Val Trp
1               5                   10                  15

Phe Ser Ala Ser Ala Thr Ala Ala Asn Gly Trp Glu Ile Tyr Lys Ser
            20                  25                  30

Arg Phe Met Thr Thr Asp Gly Arg Ile Gln Asp Thr Gly Asn Lys Asn
        35                  40                  45

Val Ser His Thr Glu Gly Gln Gly Phe Ala Met Leu Met Ala Val His
    50                  55                  60

Tyr Asp Asp Arg Ile Ala Phe Asp Asn Leu Trp Asn Trp Thr Gln Ser
65                  70                  75                  80

His Leu Arg Asn Thr Thr Ser Gly Leu Phe Tyr Trp Arg Tyr Asp Pro
                85                  90                  95

Ser Ala Ala Asn Pro Val Val Asp Lys Asn Asn Ala Ser Asp Gly Asp
            100                 105                 110

Val Leu Ile Ala Trp Ala Leu Leu Lys Ala Gly Asn Lys Trp Gln Asp
        115                 120                 125

Asn Arg Tyr Leu Gln Ala Ser Asp Ser Ile Gln Lys Ala Ile Ile Ala
    130                 135                 140

Ser Asn Ile Ile Gln Phe Ala Gly Arg Thr Val Met Leu Pro Gly Ala
145                 150                 155                 160

Tyr Gly Phe Asn Lys Asn Ser Tyr Val Ile Leu Asn Pro Ser Tyr Phe
                165                 170                 175

Leu Phe Pro Ala Trp Arg Asp Phe Ala Asn Arg Ser His Leu Gln Val
            180                 185                 190

Trp Arg Gln Leu Ile Asp Asp Ser Leu Ser Leu Val Gly Glu Met Arg
        195                 200                 205

Phe Gly Gln Val Gly Leu Pro Thr Asp Trp Ala Ala Leu Asn Ala Asp
    210                 215                 220

Gly Ser Met Ala Pro Ala Thr Ala Trp Pro Ser Arg Phe Ser Tyr Asp
225                 230                 235                 240

Ala Ile Arg Ile Pro Leu Tyr Leu Tyr Trp Tyr Asp Ala Lys Thr Thr
```

```
                        245                 250                 255
Ala Leu Val Pro Phe Gln Leu Tyr Trp Arg Asn Tyr Pro Arg Leu Thr
                260                 265                 270

Thr Pro Ala Trp Val Asp Val Leu Ser Ser Asn Thr Ala Thr Tyr Asn
            275                 280                 285

Met Gln Gly Gly Leu Leu Ala Val Arg Asp Leu Thr Met Gly Asn Leu
        290                 295                 300

Asp Gly Leu Ser Asp Leu Pro Gly Ala Ser Glu Asp Tyr Tyr Ser Ser
305                 310                 315                 320

Ser Leu Arg Leu Leu Val Met Leu Ala Arg Gly Lys
                325                 330

<210> SEQ ID NO 124
<211> LENGTH: 463
<212> TYPE: PRT
<213> ORGANISM: Bacillus sp. KSM-330

<400> SEQUENCE: 124

Met Val Glu Lys Arg Lys Ile Phe Thr Val Leu Cys Ala Cys Gly Ile
1               5                   10                  15

Gly Phe Thr Ser Tyr Thr Ser Cys Ile Ser Ala Ala Ile Asp Asn
                20                  25                  30

Asp Thr Leu Ile Asn Asn Gly His Lys Ile Asn Ser Ser Ile Ile Thr
            35                  40                  45

Asn Ser Ser Gln Val Ser Ala Val Ala Lys Glu Met Lys Pro Phe Pro
50                  55                  60

Gln Gln Val Asn Tyr Ser Gly Ile Leu Lys Pro Asn His Val Ser Gln
65                  70                  75                  80

Glu Ser Leu Asn Asn Ala Val Lys Asn Tyr Tyr Asn Asp Trp Lys Lys
                85                  90                  95

Lys Tyr Leu Lys Asn Asp Leu Ser Ser Leu Pro Gly Gly Tyr Tyr Val
                100                 105                 110

Lys Gly Glu Ile Thr Gly Asn Pro Asp Gly Phe Arg Pro Leu Gly Thr
            115                 120                 125

Ser Glu Gly Gln Gly Tyr Gly Met Ile Ile Thr Val Leu Met Ala Gly
        130                 135                 140

His Asp Ser Asn Ala Gln Thr Ile Tyr Asp Gly Leu Phe Lys Thr Ala
145                 150                 155                 160

Arg Ala Phe Lys Ser Ser Ile Asn Pro Asn Leu Met Gly Trp Val Val
                165                 170                 175

Ala Asp Asp Lys Lys Ala Gln Gly His Phe Asp Ser Ala Thr Asp Gly
            180                 185                 190

Asp Leu Asp Ile Ala Tyr Ser Leu Leu Leu Ala His Lys Gln Trp Gly
        195                 200                 205

Ser Ser Gly Lys Ile Asn Tyr Leu Lys Glu Ala Gln Asn Met Ile Thr
    210                 215                 220

Lys Gly Ile Lys Ala Ser Asn Val Thr Lys Asn Asn Gly Leu Asn Leu
225                 230                 235                 240

Gly Asp Trp Gly Asp Lys Ser Thr Phe Asp Thr Arg Pro Ser Asp Trp
                245                 250                 255

Met Met Ser His Leu Arg Ala Phe Tyr Glu Phe Thr Gly Asp Lys Thr
            260                 265                 270

Trp Leu Asn Val Ile Asp Asn Leu Tyr Asn Thr Tyr Thr Asn Phe Thr
        275                 280                 285
```

```
Asn Lys Tyr Ser Pro Lys Thr Gly Leu Ile Ser Asp Phe Val Val Lys
290                 295                 300

Asn Pro Pro Gln Pro Ala Pro Lys Asp Phe Leu Asp Glu Ser Lys Tyr
305                 310                 315                 320

Thr Asp Ser Tyr Tyr Tyr Asn Ala Ser Arg Val Pro Leu Arg Ile Val
            325                 330                 335

Met Asp Tyr Ala Met Tyr Gly Glu Lys Arg Gly Lys Val Ile Ser Asp
            340                 345                 350

Lys Val Ala Thr Trp Ile Lys Ser Lys Thr Lys Gly Asn Pro Ser Lys
                355                 360                 365

Ile Val Asp Gly Tyr Lys Leu Asp Gly Thr Asn Ile Gly Asp Tyr Pro
370                 375                 380

Thr Ala Val Tyr Val Ser Pro Phe Ile Ala Ala Gly Thr Thr Asn Ser
385                 390                 395                 400

Lys Asn Gln Glu Trp Val Asn Ser Gly Trp Asp Trp Met Lys Asn Lys
                405                 410                 415

Lys Glu Ser Tyr Phe Ser Asp Ser Tyr Asn Leu Leu Thr Met Leu Phe
                420                 425                 430

Leu Thr Gly Asn Trp Trp Lys Pro Ile Pro Asp Glu Lys Lys Ile Gln
                435                 440                 445

Ser Pro Ile Asn Leu Glu Val Gln Ser Glu Leu Lys Glu Gln Asp
450                 455                 460

<210> SEQ ID NO 125
<211> LENGTH: 342
<212> TYPE: PRT
<213> ORGANISM: Acetobacter xylinus

<400> SEQUENCE: 125

Met Ser Val Met Ala Ala Met Gly Gly Ala Gln Val Leu Ser Ser Thr
1               5                   10                  15

Gly Ala Phe Ala Asp Pro Ala Pro Asp Ala Val Ala Gln Gln Trp Ala
                20                  25                  30

Ile Phe Arg Ala Lys Tyr Leu Arg Pro Ser Gly Arg Val Val Asp Thr
            35                  40                  45

Gly Asn Gly Gly Glu Ser His Ser Glu Gly Gln Gly Tyr Gly Met Leu
50                  55                  60

Phe Ala Ala Ser Ala Gly Asp Leu Ala Ser Phe Gln Ser Met Trp Met
65                  70                  75                  80

Trp Ala Arg Thr Asn Leu Gln His Thr Asn Asp Lys Leu Phe Ser Trp
                85                  90                  95

Arg Phe Leu Lys Gly His Gln Pro Pro Val Pro Asp Lys Asn Asn Ala
                100                 105                 110

Thr Asp Gly Asp Leu Leu Ile Ala Leu Ala Leu Gly Arg Ala Gly Lys
            115                 120                 125

Arg Phe Gln Arg Pro Asp Tyr Ile Gln Asp Ala Met Ala Ile Tyr Gly
            130                 135                 140

Asp Val Leu Asn Leu Met Thr Met Lys Ala Gly Pro Tyr Val Val Leu
145                 150                 155                 160

Met Pro Gly Ala Val Gly Phe Thr Lys Lys Asp Ser Val Ile Leu Asn
                165                 170                 175

Leu Ser Tyr Tyr Val Met Pro Ser Leu Leu Gln Ala Phe Asp Leu Thr
                180                 185                 190

Ala Asp Pro Arg Trp Arg Gln Val Met Glu Asp Gly Ile Arg Leu Val
            195                 200                 205
```

```
Ser Ala Gly Arg Phe Gly Gln Trp Arg Leu Pro Pro Asp Trp Leu Ala
    210                 215                 220

Val Asn Arg Ala Thr Gly Ala Leu Ser Ile Ala Ser Gly Trp Pro Pro
225                 230                 235                 240

Arg Phe Ser Tyr Asp Ala Ile Arg Val Pro Leu Tyr Phe Tyr Trp Ala
                245                 250                 255

His Met Leu Ala Pro Asn Val Leu Ala Asp Phe Thr Arg Phe Trp Asn
            260                 265                 270

Asn Phe Gly Ala Asn Ala Leu Pro Gly Trp Val Asp Leu Thr Thr Gly
        275                 280                 285

Ala Arg Ser Pro Tyr Asn Ala Pro Pro Gly Tyr Leu Ala Val Ala Glu
    290                 295                 300

Cys Thr Gly Leu Asp Ser Ala Gly Glu Leu Pro Thr Leu Asp His Ala
305                 310                 315                 320

Pro Asp Tyr Tyr Ser Ala Ala Leu Thr Leu Leu Val Tyr Ile Ala Arg
                325                 330                 335

Ala Glu Glu Thr Ile Lys
            340
```

<210> SEQ ID NO 126
<211> LENGTH: 384
<212> TYPE: PRT
<213> ORGANISM: Xanthomonas axonopodis

<400> SEQUENCE: 126

```
Met Thr Arg Arg Arg Leu Leu His Ala Gly Thr Leu Ala Gly Val Ala
1               5                   10                  15

Ala Leu Leu Pro Ala Ala Ala Leu Ala Ala Pro Ser Gln Cys Gly Pro
            20                  25                  30

Trp Pro Leu Trp Ser Ala Phe Val Asp Lys His Ile Gln Arg Asp Gly
        35                  40                  45

Arg Val Val Asp Phe Leu Asn Pro Asp Gln Arg Ser Thr Ser Glu Gly
    50                  55                  60

Gln Ser Tyr Ala Leu Phe Phe Ala Leu Val Asn Asn Asp Gln Val Leu
65                  70                  75                  80

Phe Asp Lys Val Leu Ser Trp Thr Arg His Asn Leu Cys Gly Gly Arg
                85                  90                  95

Pro Asp Leu Asn Leu Pro Ala Trp Leu Trp Gly Arg Asp Gly Ser Gly
            100                 105                 110

Ala Trp Arg Val Leu Asp Ala Asn Thr Ala Ser Asp Gly Glu Leu Trp
        115                 120                 125

Ile Ala Tyr Ala Leu Leu Glu Ala Gly Arg Leu Trp Ser Arg Pro Gly
    130                 135                 140

Phe Leu Lys Ala Gly Gln Gln Met Leu Gln Leu Ile Arg Thr Gln Glu
145                 150                 155                 160

Val Ala Thr Leu Pro Gly Leu Gly Pro Met Leu Leu Pro Gly Arg Thr
                165                 170                 175

Gly Phe Val Asp Asn Gly Arg Trp Thr Leu Asn Pro Ser Tyr Leu Pro
            180                 185                 190

Ile Gln Val Leu Arg Arg Cys Ala Asn Ala Asp Pro Lys Gly Pro Trp
        195                 200                 205

Ala Ala Ile Ala Ala Asn Ser Ala Arg Val Leu Arg Asp Ser Ala Pro
    210                 215                 220

Val Gly Phe Ala Pro Asp Trp Thr Val Trp Asp Gly Lys Thr Phe Asn
```

```
                    225                 230                 235                 240
Ala Asp Pro Lys Arg Gly Asn Val Gly Ser Tyr Asp Ala Ile Arg Val
                245                 250                 255

Tyr Leu Trp Ala Gly Met Leu Asp Ala Gly Glu Pro Leu Arg Ala Arg
                260                 265                 270

Leu Leu Gln Asp Leu Ser Gly Pro Ala Asp Leu Leu Ala Ala Gln Gln
                275                 280                 285

Thr Pro Ala Glu Lys Ile Asp Thr Ala Arg Gly Val Gly Thr Gly Ala
    290                 295                 300

Leu Pro Val Gly Phe Ser Ala Ala Leu Leu Pro Tyr Leu Ser Ala Leu
305                 310                 315                 320

Gly Lys Pro Ala Leu Leu Lys Ala Gln Ala Gln Arg Val Pro Ala Ala
                325                 330                 335

Thr Gln Pro Ala Ala Ala Leu Pro Tyr Phe Glu Arg Thr Leu Ala
                340                 345                 350

Leu Phe Gly Gln Gly Trp Leu Glu Asn Arg Tyr Arg Phe Ala Ala Asp
                355                 360                 365

Gly Arg Leu Leu Pro Ala Trp Arg Thr Pro Ala Cys Ala Ala Thr Thr
370                 375                 380

<210> SEQ ID NO 127
<211> LENGTH: 365
<212> TYPE: PRT
<213> ORGANISM: Fulvimarina pelagi

<400> SEQUENCE: 127

Met Lys Lys Tyr Leu Leu Phe Phe Cys Ala Ala Ala Phe Leu Met Ser
1               5                   10                  15

Gly Thr Ile Asn Ser Arg Ala Val Glu Pro His Thr Glu Asn Thr Glu
                20                  25                  30

Ser Pro Asn Ile Glu Ala Ala Ser Gly Asp Leu Ala Leu Gly Ala Trp
            35                  40                  45

Gln Phe Tyr Arg Ser Val Phe Met Ser Ala Asp Gly Arg Ile Ile Asp
    50                  55                  60

Arg Glu Asn Gly Ser Ile Ser His Ser Glu Gly Gln Gly Tyr Gly Met
65                  70                  75                  80

Leu Ile Ala Ala Met Val Gly Asp Arg Ala Ser Phe Asp Lys Leu Trp
                85                  90                  95

Asp Trp Thr Glu Arg Glu Leu Gln Ile Arg Asp Asn Leu Ser Ala
                100                 105                 110

Trp Lys Trp Asp Pro Ser Ala Thr Pro His Val Thr Asp Arg Asn Asn
            115                 120                 125

Ala Thr Asp Gly Asp Ile Leu Ile Ala Trp Ala Leu Leu Arg Ala Phe
    130                 135                 140

Glu Arg Trp Gly Val Pro Asp His Glu Arg Glu Ala Glu Ala Ile Ile
145                 150                 155                 160

Ala Asp Ile Val Arg Leu Ala Ile Asp Asp Arg Gln Gly Lys Ile
                165                 170                 175

Ile Leu Pro Gly Val Glu Gly Phe Asp Ala Asp Ser Gln Pro Asp Gly
            180                 185                 190

Pro Val Val Asn Leu Ser Tyr Trp Val Phe Pro Ala Leu Ala Glu Ile
    195                 200                 205

Gly Gln His Met Pro Asp Phe Gly Ala Leu Asn Leu Glu Ala Lys Gly
        210                 215                 220
```

Leu Glu Leu Leu Lys Glu Ala Thr Ala Ser Ser Pro His Leu Pro Thr
225                 230                 235                 240

Glu Trp Ser Gly Leu Gly Ser Gly Thr Val Lys Pro Ala Ala Gln Phe
            245                 250                 255

Asp Pro Phe Phe Gly Tyr Asn Ala Leu Arg Ile Pro Leu Tyr Leu Ala
            260                 265                 270

Trp Ser Glu Ile Glu Ala Pro Glu Ile Leu Lys Arg Ile Asp Lys Ala
            275                 280                 285

Trp Glu Gly Lys Thr Glu Thr Gly Leu Ala Val Ile Asp Val Ala Arg
            290                 295                 300

Asp Ala Pro Val Glu Pro Ile Ser Gly Ala Gly Tyr Gln Ala Ile Arg
305                 310                 315                 320

Glu Leu Val Gln Cys Ser Leu Asn Ser Ile Ala Ala Gly Arg Glu Arg
                325                 330                 335

Ala Leu Phe Asp Gly Ser Thr Tyr Tyr Ser Ser Thr Leu His Leu Leu
            340                 345                 350

Ser Leu Leu Ala Ile Ser Glu Arg Tyr Pro Arg Cys Phe
            355                 360                 365

<210> SEQ ID NO 128
<211> LENGTH: 376
<212> TYPE: PRT
<213> ORGANISM: Chlorobium ferrooxidans

<400> SEQUENCE: 128

Met Arg Thr Leu Phe Pro Leu Leu Leu Ser Leu Leu Pro Leu Leu
1               5                   10                  15

Ser Ser Ser Cys Ser Ala Thr Pro Val Asp Pro Glu Glu Ile Val Arg
                20                  25                  30

Gly Ser Trp Val His Tyr Lys Arg Thr Phe Ile Thr Glu Gly Arg Val
            35                  40                  45

Val Arg Pro Gln Asn Ser Asn Asp Thr Val Ser Glu Gly Glu Ala Tyr
        50                  55                  60

Ala Met Leu Arg Ala Val Leu Met Asp Asp Arg Lys Thr Phe Asp Glu
65                  70                  75                  80

Cys Leu Ala Trp Ser Glu Ala Thr Leu Ser Arg Lys Glu Ser His Gly
                85                  90                  95

Asp Asp Leu Leu Ala Trp His Phe Glu Asn Gly Arg Val Ser Asp Ser
            100                 105                 110

Thr Ala Ala Ser Asp Ala Asp Ile Asp Tyr Ala Tyr Ser Leu Leu Leu
        115                 120                 125

Ala Trp Arg Thr Trp Gln Glu Ser Arg Tyr Leu Asp Leu Ala Arg Lys
130                 135                 140

Val Leu Gln Ser Ile Leu Asp Lys Glu Thr Val Leu Val Asn Asn Arg
145                 150                 155                 160

Leu Tyr Leu Leu Pro Trp Pro Ala Gly Glu Gly Gly Ser Thr Pro Pro
                165                 170                 175

Asp Ser Thr Pro Gln Asn Pro Ser Tyr Tyr Ala Pro Ser His Phe Arg
            180                 185                 190

Leu Phe Tyr Ala Val Thr Gly Asp Lys Arg Trp Met Glu Leu Val Asp
        195                 200                 205

Thr Thr Tyr Glu Leu Leu Gly Arg Leu Gln Lys Ser Asn Asp Asn Pro
210                 215                 220

Gly Leu Val Pro Asp Trp Cys Ala Leu Asp Met Gln Glu Asn Ile Ile
225                 230                 235                 240

```
Pro Met Pro Gly Lys Lys Arg Val Tyr Gly Trp Asp Ala Val Arg Val
            245                 250                 255

Pro Leu Arg Val Ala Ala Asp Tyr Arg Leu Asn Asp Asp His Arg Ala
            260                 265                 270

Leu Gln Val Leu Arg Ile Phe Ser Glu Phe Glu Arg Glu Phe Arg
            275                 280                 285

Glu Asn Gly Lys Ile Val Thr Gly Tyr Ser Gly Ser Asp Ala Thr Lys
            290                 295                 300

Ser Ser Met Glu Asn Pro Leu Phe Tyr Ala Ala Tyr Ala Ala Thr
305                 310                 315                 320

Glu Ala Ser Asp Ser Pro Ile Ala Pro Glu Met Leu Gln Arg Val Arg
            325                 330                 335

Asp Phe Ile His Gln Asn Ser Asp Glu Tyr Tyr Asn Glu Ala Asn
            340                 345                 350

Asp Tyr Tyr Val Asn Ser Leu Val Trp Leu Thr Glu Tyr Phe Gln Ile
            355                 360                 365

Thr Lys Lys Thr Ala Thr Asn Asp
    370                 375

<210> SEQ ID NO 129
<211> LENGTH: 1223
<212> TYPE: PRT
<213> ORGANISM: Cytophaga hutchinsonii

<400> SEQUENCE: 129

Met Ile Lys Leu Met Asn Lys Ile Ser Trp Val Ile Ser Val Leu
1               5                   10                  15

Cys Leu Ile His Val Gln Thr His Ala Gln Ile Asn Thr Pro Ala Gly
            20                  25                  30

Ala Thr Val Pro Phe Gly Ser Asn Asn Ser Tyr Ala Tyr Gly Ile Leu
            35                  40                  45

Pro Thr Asn Leu Pro Thr Ser Gly Thr Tyr Gly Lys Gly Thr Glu Val
            50                  55                  60

Ala Ala Lys Tyr Thr Ala Trp Lys Ser Ala Tyr Ile Glu Asn Cys Gly
65                  70                  75                  80

Thr Asp Lys Ala Arg Val Lys Phe Asp Asn Thr Ser Glu Thr Val Ser
                85                  90                  95

Glu Gly Ile Ala Tyr Gly Met Leu Leu Ala Ala Tyr Ala Ala Asp Gln
            100                 105                 110

Asp Leu Phe Asn Arg Leu Trp Ala Tyr Tyr Lys Gln His Arg Asn Ala
            115                 120                 125

Lys Gly Val Met His Trp Lys Ile Ser Gly Cys Asn Ser Val Ile Gly
    130                 135                 140

Gln Asn Gly Ala Thr Asp Ala Glu Leu Asp Ala Ala Met Ala Leu Ile
145                 150                 155                 160

Val Ala Asn Tyr Gln Trp Pro Asn Thr Thr Ser Pro His Asn Tyr Lys
                165                 170                 175

Thr Asp Ala Val Ser Leu Ile Asn Ala Ile Lys Asn Tyr Glu Ile Asn
            180                 185                 190

Ala Thr Asp Phe Thr Phe Glu Asn Gly Asp Ala Trp Lys Pro Ala Cys
            195                 200                 205

Arg Asn Pro Ser Tyr Gln Ala Pro Gly Tyr Ala Arg Val Phe Lys Leu
    210                 215                 220

Phe Met Ala Glu Asn Gly Gln Ala Asn Asn Thr Phe Trp Asp Asn Val
```

-continued

```
            225                 230                 235                 240
        Ile Gln Lys Thr Glu Asn Leu Leu Ile Asn Asn Ala His Thr Thr Ser
                        245                 250                 255

Gly Leu Ser Thr Asn Trp Cys Thr Pro Ala Gly Pro Pro Asn Ser Ser
                        260                 265                 270

Cys Ser Gly Ser Gly Thr Ala Pro Asp Lys Phe Gly Tyr Asp Ala Cys
                        275                 280                 285

Arg Ala Pro Trp Arg Gln Ala Thr Asp Tyr Ile Trp Tyr Gly Pro Ser
                        290                 295                 300

Thr Ile Leu Thr Ile Thr Asn Arg Gln Ala Ala Phe Trp Ile Gly Lys
        305                 310                 315                 320

Gly Gly Ala Gly Ser Val Gln Gly Gly Asp Gly Val Asn His Asp Gly
                        325                 330                 335

Ser Gly Ser Gly Asn His Asn Ala Ala Phe Val Gly Pro Ile Gly Ala
                        340                 345                 350

Leu Ser Leu Ala Thr Thr Asn Thr Thr Ala Asn Gln Gln Phe Cys Asn
                        355                 360                 365

Ala Leu Tyr Ser Glu Asn Lys Asn Asp Gly Leu Ala Ser Gly Tyr Phe
                        370                 375                 380

Thr Lys Ile Leu Gln Met Leu Gly Leu Phe Val Gln Thr Gly Asn Phe
        385                 390                 395                 400

Trp Asn Pro Tyr Ala Val Ser Ser Ala Thr Thr Thr Ser Val Ala Leu
                        405                 410                 415

Thr Ala Pro Thr Val Thr Phe Ala Ala Glu Gly Asp Val Ile Thr Val
                        420                 425                 430

Ser Ala Thr Ala Thr Ala Thr Thr Gly Ala Ile Ser Lys Val Asp Phe
                        435                 440                 445

Tyr Ala Gly Thr Thr Leu Ile Gly Thr Asp Asn Ser Ser Pro Tyr Ser
                        450                 455                 460

Ile Ser Trp Thr Pro Asn Val Ser Gly Thr Val Ser Ile Thr Ala Lys
        465                 470                 475                 480

Ala Thr Asn Thr Asn Gly Asp Val Ala Thr Thr Ala Pro Phe Asn Val
                        485                 490                 495

Ser Ile Tyr Lys Ala Val Asn Gln Thr Asn Thr Ala Pro Thr Ile Asp
                        500                 505                 510

Gly Val Ala Asp Gly Val Trp Gly Gly Thr Asn Thr Ser Ala Ser Leu
                        515                 520                 525

Asn Asn Val Ile Asp Gly Thr Val Ala Asn Ala Ser Asp Leu Ser Ala
        530                 535                 540

Asn Tyr Lys Ala Met Trp Asp Ala Thr Tyr Phe Tyr Val Leu Val Asn
        545                 550                 555                 560

Val Thr Asp Asn Val Lys Thr Asn Asn Gly Gly Thr Asp Tyr Tyr Asn
                        565                 570                 575

Asp Asp Ala Val Glu Val Phe Phe Asp Ile Gly Asn Asn Lys Thr Thr
                        580                 585                 590

Thr Tyr Gly Ala Asn Asp Phe Gln Tyr Thr Phe Arg Trp Asn Asp Asn
                        595                 600                 605

Thr Ile Tyr Glu Lys Asn Asn Lys Thr Thr Gly Val Thr Phe Ala Arg
                        610                 615                 620

Val Asp Asn Ser Thr Gly Tyr Val Met Glu Met Arg Phe Pro Trp Ser
        625                 630                 635                 640

Thr Leu Thr Gly Ser Pro Ala Ile Asn Gln Leu Val Gly Phe Asp Val
                        645                 650                 655
```

```
Ala Val Asn Asp Asp Asp Gly Asn Ala Arg Asp Arg Lys Ile Ser
            660                 665                 670

Trp Ala Ala Thr Ala Asp Gln Ala Trp Thr Asn Pro Ser Tyr Met Gly
        675                 680                 685

Thr Val Ile Leu Lys Gly Ala Pro Ala Cys Thr Leu Pro Ser Ala Ala
690                 695                 700

Gly Thr Ile Thr Gly Thr Thr Thr Cys Ala Asn Ala Ala Gly Ile
705                 710                 715                 720

Thr Tyr Ser Ile Ala Ala Val Thr Gly Ala Thr Gly Tyr Thr Trp Thr
                725                 730                 735

Val Pro Ala Gly Ala Thr Ile Thr Gly Ala Asn Thr Thr Ala Ile
            740                 745                 750

Thr Val Lys Phe Gly Thr Thr Ala Gly Asn Ile Ser Val Thr Pro Ala
        755                 760                 765

Asn Thr Cys Gly Asn Gly Thr Ala Ala Thr Ala Val Thr Leu Asn
770                 775                 780

Ser Leu Pro Ser Ala Ala Gly Ser Ile Thr Gly Ile Thr Thr Cys
785                 790                 795                 800

Ala Asn Ala Ala Gly Ile Thr Tyr Ser Ile Ala Ala Val Thr Gly Ala
                805                 810                 815

Thr Gly Tyr Asn Trp Thr Val Pro Ala Gly Ala Thr Ile Thr Ser Gly
            820                 825                 830

Thr Asn Thr Arg Thr Ile Thr Val Thr Phe Gly Thr Thr Gly Gly Asn
        835                 840                 845

Val Ser Val Thr Pro Thr Asn Thr Cys Gly Asn Gly Thr Ala Ala Ser
850                 855                 860

Thr Ala Val Thr Val Asn Ser Leu Pro Ala Ala Ala Gly Asp Ile Thr
865                 870                 875                 880

Gly Val Thr Thr Thr Cys Ala Asn Thr Ala Gly Val Thr Tyr Ser Ile
                885                 890                 895

Ala Ala Val Thr Gly Ala Thr Gly Tyr Ser Trp Thr Val Pro Ala Gly
            900                 905                 910

Ala Thr Ile Thr Ala Gly Ala Asn Thr Arg Thr Ile Thr Val Thr Phe
        915                 920                 925

Gly Thr Ala Gly Gly Asn Val Thr Val Thr Pro Thr Asn Thr Cys Gly
930                 935                 940

Asn Gly Thr Asn Lys Thr Thr Ala Val Thr Val Asn Ala Ser Gly Gly
945                 950                 955                 960

Asn Ala Ser Val Ser Ile Ala Ala Ser Pro Ser Ser Thr Ile Tyr Thr
                965                 970                 975

Gly Gln Ser Val Thr Phe Thr Ala Thr Pro Val Asn Gly Gly Thr Pro
            980                 985                 990

Thr Tyr Gln Trp Lys Asn Gly Ser Thr Asn Ile Ala Gly Ala Thr Ala
        995                 1000                1005

Ala Thr Tyr Thr Thr Thr Ser Leu Thr Asn Gly Asn Ala Ile Ser
        1010                1015                1020

Val Thr Met Thr Ser Thr Lys Gln Cys Val Ala Asn Thr Thr Ala
        1025                1030                1035

Asn Ser Asn Thr Ile Thr Met Thr Val Thr Ala Ala Pro Ala Phe
        1040                1045                1050

Ser Ser Thr Ile Asn Gly Pro Thr Val Val Ser Pro Asn Gln Ser
        1055                1060                1065
```

-continued

Asn Val Thr Phe Ser Val Ser Asn Gln Ser Gly Met Gln Tyr Gln
    1070                1075                1080

Trp Thr Val Pro Pro Gly Ala Thr Ile Val Ser Gly Ala Asn Thr
    1085                1090                1095

Asn Ser Ile Val Val Asn Phe Gly Thr Ser Gly Asn Val Thr
    1100                1105                1110

Val Lys Glu Thr Asn Pro Ser Asn Gln Thr Thr Thr Ile Thr Lys
    1115                1120                1125

Ala Ile Thr Val Ser Gly Thr Thr Pro Val Tyr Leu Pro Ala Gln
    1130                1135                1140

Glu Val Asn Ile Ser Val Tyr Pro Val Pro Cys Asn Glu Gln Leu
    1145                1150                1155

Met Ile Ala Met Gly Val Glu Ala Ser Thr Lys Val Ser Phe Ser
    1160                1165                1170

Ile Ile Asp Met Thr Gly Asn Thr Ile Gln Ser Gly Ser Phe Glu
    1175                1180                1185

Tyr Asn Ser Met Pro Val Ser Ile Glu Met Pro Val Ala Ala Gly
    1190                1195                1200

Ile Tyr Gln Leu Leu Leu Gln Trp Asp Gly Thr Tyr Ala Met His
    1205                1210                1215

Lys Ile Met Lys Gln
    1220

<210> SEQ ID NO 130
<211> LENGTH: 912
<212> TYPE: PRT
<213> ORGANISM: Pseudoalteromonas atlantica

<400> SEQUENCE: 130

Met Ser Thr Leu Ser Val Ser Asn Thr Val Ser Ser Ala Pro Ser Gly
1               5                   10                  15

Lys Thr Val Ser Leu Ser Lys Ser Val Ala Leu Ala Leu Gly Thr Leu
                20                  25                  30

Leu Leu Thr Ser Phe Ser Met Pro Ser Tyr Ala Glu Val Ser Ile Asp
            35                  40                  45

His Leu Thr Leu Thr Asn Lys Thr Arg Ile Gly Arg Ser Asp Tyr Arg
        50                  55                  60

Tyr Glu Phe Ser Val Phe Val Lys Asn Asp Ala Glu Arg Val Gln Asp
65                  70                  75                  80

Val Gln Ile Asp Val Thr Ser Ser Asn Pro His Ser Arg Ile Glu Ser
                85                  90                  95

Ser Gly Val Ser Leu Ile Glu Ile Pro Ala Asn Ser Val Leu Glu Leu
            100                 105                 110

Thr Glu Pro Phe Val Leu Val Gln Asn Arg Arg Ala Arg Phe Asn Glu
        115                 120                 125

Gln Asp Leu Ser Trp Val Ile Asp Tyr Gln Gln Ser Gly Asn Ala Ile
    130                 135                 140

Ser Asp Asp Phe Ser Pro Asn Ala Ala Tyr His Thr Gly Glu Tyr Lys
145                 150                 155                 160

Asn Phe Phe Val Glu Arg Gly Leu Ala Thr Gln Glu Gln Val Thr Ala
                165                 170                 175

Lys Ile Asp Ala Thr Tyr Gln Gln Leu Phe Glu Leu Val Pro Asp Gln
            180                 185                 190

Ala Leu Pro Gln Pro Ser Lys Gly Glu Arg Ile Tyr His Ala Gly Phe
        195                 200                 205

```
Asp Asp Ser Ile Asp Asn Trp Gln Trp His Ala Asp Asn Gly Ser Gln
    210                 215                 220

Val Gly Ala Thr Leu Ser Gln His Gly Gly Ala Leu Ile Ile Thr Pro
225                 230                 235                 240

Asn Trp Gln Ser Gly Gly Asp Ala Leu Ala Val Leu Ser Ser Ser Phe
                245                 250                 255

Glu Pro Ile Asp Ala Thr Gln Gly Val Asp Val Glu Tyr Lys Met Ala
            260                 265                 270

Val Asp Gln Ala Tyr Ala Asp Gly Ala Met Ala Ala Gln Leu Phe
        275                 280                 285

Ile Gln Asp Ser Ser Gly Gly Ile Gly Phe Phe Ala Tyr Arg Thr Leu
    290                 295                 300

Thr Gln Pro Asp Glu Ser Thr Ile Leu Val Lys Asp Leu Gly Pro Asp
305                 310                 315                 320

Thr Asn Phe Gly Tyr Leu Ser Glu Gly Phe Asp Phe Ser Gln Ile Ser
                325                 330                 335

Thr Leu Gly Phe Gln Phe Leu Ala Asn Gly Lys Ser Ala Asp Ile Gly
                340                 345                 350

Gly Asp Ile Thr Val Ser Glu Val Ser Val Tyr Gln Pro Val Gly Gly
            355                 360                 365

Ser Glu Thr Asp Asn Ser Pro Ser Phe Leu Asp Ser Phe Asp His Gly
370                 375                 380

Ile Ala Gln Trp Asn Ala Gly Ala Asn Asn Gly Ser Ala Ile Glu Pro
385                 390                 395                 400

Ala Leu Thr Val Gly Asn Val Ile Gly Gly Asp Gly Gln Ser Asn Asn
                405                 410                 415

Val Leu Leu Ile Ser Pro Asn Trp Leu Ser Asp Ser Asp Val Phe Thr
            420                 425                 430

Val Lys Tyr Gln Gln Phe Ala Ala Val Asp Ile Thr Asp Gly Arg Asp
        435                 440                 445

Ile Ser Phe Asp Val Lys Ile Pro Ala Asn Tyr Val Val Asp Gly Asn
    450                 455                 460

Leu Val Val Gln Leu Val Leu Glu Asp Ala Asn Tyr Gln Pro Ala Phe
465                 470                 475                 480

Leu Gly Tyr Ile Lys Val Asp Gly Phe Pro Lys Asp Glu Phe Ile Thr
                485                 490                 495

Leu Ser Phe Ser Asp Val Ser Ala Ala Thr Glu Phe Gly Tyr Ile Ser
                500                 505                 510

Asp Ser Phe Asp Phe Ser Gln Leu Arg Gly Ile Gly Val Gln Phe Leu
            515                 520                 525

Ala Asn Gly Lys Leu Pro Glu Leu Thr Gly Asp Ile Gln Ile Asp Asn
530                 535                 540

Val Leu Val Ala Gly Gln Ala Pro Ser Glu Pro Ala Pro Glu Leu Ser
545                 550                 555                 560

Asp Thr Thr Val Leu Tyr Gly Val Gly Asp Asp Met Ala Phe Ile Lys
                565                 570                 575

Ala Ile Asp Ser Asn Asp Ile Arg Ser Glu Gly Met Ser Tyr Gly Met
            580                 585                 590

Met Ile Ser Val Met Met Asp Asp Gln Glu Thr Phe Asn Lys Leu Trp
                595                 600                 605

Arg Phe Thr Lys Ala Lys Met Gln Asn Thr Ser Gly Asn Ser Lys Asp
        610                 615                 620
```

```
Phe Phe Ala Trp Arg Leu Ser Ala Asn Ala Pro Tyr Asn Ala Ile Asp
625                 630                 635                 640

Thr Asn Pro Ala Pro Asp Gly Glu Glu Tyr Phe Ala Met Ala Leu Phe
            645                 650                 655

Phe Ala Asn Asn Arg Trp Gly Ser Ala Asp Gly Ile Phe Asp Tyr Gln
        660                 665                 670

Arg Glu Ala Asn Asp Ile Leu His Asp Met Ile Phe Thr Lys Ser Asp
    675                 680                 685

Asn Ser Ser Thr Arg Leu Met Met His Pro Val Tyr Gln Gln Val Glu
690                 695                 700

Phe Val Thr Thr Thr Asn Val Ala Ser Phe Ser Asp Pro Ser Tyr His
705                 710                 715                 720

Leu Pro Ala Phe Tyr Glu Met Trp Ala Leu Trp Ala Asp Glu Asn Asn
                725                 730                 735

Asp Tyr Trp His Glu Thr Ala Ala Ile Ser Arg Gln Tyr Leu Ala Lys
            740                 745                 750

Ser Ala His Pro Val Thr Gly Leu Phe Ser Asp Tyr Ala Asn His Glu
        755                 760                 765

Gly Glu Pro Gln Thr Thr Ser Phe Asn Pro Asp Ser His Lys Ser Ala
770                 775                 780

Tyr Asp Ser Phe Arg Val Met Gly Asn Met Ala Met Asp Tyr His Trp
785                 790                 795                 800

Val Ser Gln Ser Pro Val Leu Gln Ser Leu Val Glu Gln Val Thr
                805                 810                 815

Phe Phe Ala Gly Glu Val Glu Gln Tyr Gly Asp Phe Ile Ala Val Tyr
            820                 825                 830

Glu Val Asp Gly Thr Arg Glu Pro Gly Ile Asp Tyr Arg Ser His Gly
        835                 840                 845

Arg Thr Ala Met Asn Gly Val Gly Ala Thr Ile Ser Glu Asn Pro Phe
850                 855                 860

Ser Thr Glu Met Leu Asn Tyr Leu Trp Gln Gln Asp Ala Pro Thr Gly
865                 870                 875                 880

Met Tyr Arg Tyr Tyr Asp Gly Leu Leu His Met Phe Gly Leu His
                885                 890                 895

Ala Gly Gly Glu Phe Lys Ile Tyr Lys Pro Asn Glu Asn Glu Pro Glu
            900                 905                 910

<210> SEQ ID NO 131
<211> LENGTH: 292
<212> TYPE: PRT
<213> ORGANISM: Deinococcus geothermalis

<400> SEQUENCE: 131

Met Lys Arg Ser Lys Thr His Leu Ala Val Val Gly Leu Gly Leu Leu
1               5                   10                  15

Ser Leu Leu Gly Ser Cys Gly Gln Ser Val Pro Gly Pro Glu Gln Asn
            20                  25                  30

Ala Ala Phe Tyr Thr Gly Lys Tyr Arg Asn Leu Phe Thr Glu Trp Ser
        35                  40                  45

Ile Ala Thr Glu Ala Gln Val Gln Ala Lys Leu Asp Ala Tyr Trp Glu
    50                  55                  60

Ser Leu Phe Ala Ser Thr Asp Asp Gln Arg Arg Val Tyr Tyr Pro Ala
65                  70                  75                  80

Gly Ser Asn Ala Asn Gly Pro Met Ala Tyr Val Ala Asp Ile Gly Ser
                85                  90                  95
```

Asn Asp Val Arg Thr Glu Gly Met Ser Tyr Gly Met Met Ile Ala Val
            100                 105                 110

Gln Met Asn Lys Gln Ala Glu Phe Asn Ala Leu Trp Asn Tyr Ala Lys
            115                 120                 125

Ser Lys Met Gln His Gln Ser Gly Pro Arg Ala Gly Tyr Phe Ala Trp
        130                 135                 140

His Thr Asp Phe Glu Gly Asn Ile Ile Asp Ala Asn Pro Ala Ser Asp
145                 150                 155                 160

Gly Glu Glu Tyr Phe Ala Thr Ala Leu Phe Phe Ala Ser His Arg Trp
                165                 170                 175

Gly Asp Gly Asn Gly Ile Tyr Asn Tyr Ser Ala Glu Ala Asn Asn Ile
            180                 185                 190

Leu Asn Thr Met Leu His Lys Glu Asp Met Asn Gly Gly Val Val Asn
        195                 200                 205

Gly Val Thr Asn Met Phe Asp Arg Glu His Lys Gln Val Val Phe Val
    210                 215                 220

Pro Glu Gly Asp Asn Ala Ile Phe Thr Asp Pro Ser Tyr His Leu Pro
225                 230                 235                 240

Ala Phe Tyr Glu Leu Trp Ser Arg Trp Ala Thr Gly Trp Asn Gly Gln
                245                 250                 255

Gln Ala Val Asp Arg Lys Phe Trp Ala Glu Ala Gln Val Ser Arg
            260                 265                 270

Asp Tyr Phe Gln Lys Ala Thr His Pro Glu Thr Gly Leu Gly Ser Val
        275                 280                 285

Trp Leu Lys Phe
    290

<210> SEQ ID NO 132
<211> LENGTH: 387
<212> TYPE: PRT
<213> ORGANISM: Ralstonia metallidurans

<400> SEQUENCE: 132

Met Arg Arg Ala Met Ala Trp Leu Leu Arg Ala Thr Val Val Cys Thr
1               5                   10                  15

Leu Ala Gly Thr Val Leu Thr Ser Ala Ala Thr Cys Ala Trp Pro
            20                  25                  30

Asp Trp Asp Ala Phe Arg Arg Ser Thr Ile Ser Gln Asp Gly Arg Val
        35                  40                  45

Ile Asp Asp Ser Thr Asp Gln Gln Val Thr Val Ser Glu Gly Gln Ser
50                  55                  60

Tyr Ala Leu Phe Phe Ala Leu Val Ala Asn Asp Arg Ala Thr Phe Asp
65                  70                  75                  80

Lys Leu Leu Thr Trp Thr Glu Asn Asn Leu Ala Gln Gly Asp Leu Thr
                85                  90                  95

Ala His Leu Pro Ala Trp Ile Trp Gly Lys Thr Glu Gly Glu His
            100                 105                 110

Ala Gly Thr Trp Gly Val Ile Asp Ala Asn Pro Ala Ser Asp Ala Asp
        115                 120                 125

Leu Trp Ile Ala Tyr Ser Leu Leu Glu Ala Gly Arg Leu Trp Asn Glu
    130                 135                 140

Arg Arg Phe Thr Ala Leu Gly Thr Leu Leu Ala Arg Ala Leu Arg
145                 150                 155                 160

Glu Glu Thr Ala Val Leu Pro Gly Leu Gly Arg Thr Leu Leu Pro Gly

```
                    165                 170                 175
Pro Thr Gly Phe His Thr Ser Pro Asp Val Trp Arg Leu Asn Pro Ser
                180                 185                 190

Tyr Val Pro Leu Gln Val Met Arg Arg Leu Ala Ala Met Pro Gly Glu
            195                 200                 205

Asp Ser Ser Trp Lys Thr Leu Val Asp Thr Ser Ala Arg Leu Ile Leu
        210                 215                 220

Asn Thr Ala Pro His Gly Phe Ser Pro Asp Trp Val Glu Tyr His Lys
225                 230                 235                 240

Gly Arg Gly Phe Arg Pro Asp Thr Gln Thr Gln Ala Gly Gly Ser Tyr
                245                 250                 255

Asn Ala Ile Arg Val Tyr Leu Trp Ala Gly Met Met Ala Pro Arg Asp
            260                 265                 270

Pro Leu Arg Thr Ser Val Leu Gln Ala Phe Arg Pro Met Ala Asp Tyr
        275                 280                 285

Val Arg Lys Gln Gly Asp Pro Pro Glu Arg Val Asp Thr Gln Ser Gly
    290                 295                 300

Thr Phe Gly Pro Asn Ser Gly Asn Gly Gly Phe Ser Ala Ala Val Ala
305                 310                 315                 320

Pro Tyr Leu Ala Ala Leu Gly Gln Thr Asp Asp Ala Arg Ala Gln Ala
                325                 330                 335

Gln Arg Ala Arg Asp Leu Ala Ala Gln Lys Pro Ala Gly Tyr Tyr Ser
            340                 345                 350

Gln Val Leu Ala Leu Phe Gly Leu Gly His Leu Asp Gly His Phe Arg
        355                 360                 365

Phe Glu Ala Asp Gly Thr Leu Val Pro Ala Trp Lys Ser Thr Cys Pro
    370                 375                 380

Ala Thr Arg
385

<210> SEQ ID NO 133
<211> LENGTH: 344
<212> TYPE: PRT
<213> ORGANISM: Candidatus Kuenenia stuttgartiensis

<400> SEQUENCE: 133

Met His Lys Lys Leu Ser Cys Ile Val Ile Cys Val Phe Phe Met Leu
1               5                   10                  15

Gly Met Cys Lys Met Thr Tyr Gly Arg Gln Pro Ala Val Trp Glu Ala
            20                  25                  30

Phe Lys Thr Asn Phe Ile Gly Gln Asp Gly Arg Val Val Asp His Tyr
        35                  40                  45

Asn Gly Arg Ile Ser His Ser Glu Gly Gln Gly Tyr Gly Met Leu Leu
    50                  55                  60

Ala Val Lys Tyr Asp Asp Lys Ala Val Phe Asp Lys Leu Leu Gln Trp
65                  70                  75                  80

Thr Gln Asp Asn Ile Ala Val Arg Asn Asp His Leu Phe Ala Trp Lys
                85                  90                  95

Trp Gly Glu Arg Thr Ser Gly Val Trp Gly Val Val Asp Tyr Asn Asn
            100                 105                 110

Ala Thr Asp Gly Asp Ile Leu Ile Ala Tyr Ala Leu Ile Lys Ala Asp
        115                 120                 125

Glu Glu Trp Pro Asn Asn Asn Tyr Lys Asn Thr Ala Leu Lys Ile Val
    130                 135                 140
```

Arg Ser Val Arg Glu Asn Leu Ala Val Glu Trp Asn Gly His Gln Leu
145                 150                 155                 160

Leu Leu Pro Gly Tyr His Gly Phe Ile Arg Glu Asn Asp Arg Phe Ile
            165                 170                 175

Val Asn Pro Ser Tyr Val Ile Phe Ser Ala Tyr Arg Ala Phe Ala Lys
            180                 185                 190

Val Asp Ala Glu Ala Phe Trp Gln Lys Val Tyr Lys Asp Ser Met Leu
        195                 200                 205

Leu Val Ala Lys Ser Cys Phe Gly Ser Leu Lys Met Pro Ala Asp Trp
        210                 215                 220

Val Met Leu Glu Gly Arg Asp Ile Asp Val Cys Asn Glu Arg Lys Pro
225                 230                 235                 240

Tyr Phe Gly Tyr Glu Ala Ile Arg Val Phe Leu Tyr Leu Ser Trp Glu
            245                 250                 255

Glu Asn Pro Leu Phe Pro Glu Gly Leu Ala Lys Met Leu Asp Ile Tyr
            260                 265                 270

Asn Lys Leu Gly Phe Ile Pro Leu Trp Val Asp Val Ala Ser Asp Ser
        275                 280                 285

Ile Ser Leu Gln Asn Ala Pro Pro Gly Phe Tyr Ala Val Phe Ala Arg
290                 295                 300

Ala Ala Glu Lys Met Gly Glu Lys Thr Leu Ser Lys Lys Leu Phe Lys
305                 310                 315                 320

Glu Ala Ser Glu Arg Leu Ala Tyr Asp Lys Lys Asp Tyr Tyr Ser Tyr
            325                 330                 335

Cys Leu Tyr Leu Leu Ala Glu Glu
            340

<210> SEQ ID NO 134
<211> LENGTH: 368
<212> TYPE: PRT
<213> ORGANISM: Vibrio alginolyticus

<400> SEQUENCE: 134

Met Lys Lys Leu Ile Ser Phe Leu Met Leu Phe Val Ser Pro Tyr Leu
1               5                   10                  15

Trp Ala Asn Thr Cys Glu Trp Pro Gln Trp Glu Thr Phe Lys Ser Val
            20                  25                  30

Tyr Met Glu Gln Gly Arg Val Val Asp Gly Ser Asp Glu Arg Met Ile
        35                  40                  45

Thr Thr Ser Glu Gly Gln Ser Tyr Ala Leu Phe Phe Ala Leu Val Ala
    50                  55                  60

Asn Asp Pro Lys Thr Phe Asp Gln Val Leu Lys Trp Thr Gln Ser His
65                  70                  75                  80

Leu Ala Gly Gly Asp Leu Thr Ala Arg Leu Pro Ala Trp Leu Trp Gly
            85                  90                  95

Arg Lys Glu Asn Gly Gln Phe Gly Val Leu Asp Ser Asn Pro Ala Ser
            100                 105                 110

Asp Ser Asp Leu Trp Ile Ala Tyr Ser Leu Val Glu Ala Gly Arg Leu
        115                 120                 125

Trp Asn Asn Tyr Tyr Gln Thr Leu Gly His Leu Ile Ala Ser Arg
        130                 135                 140

Ile Leu Arg Glu Glu Thr Val Asn Ile Ala Gly Val Gly Thr Val Leu
145                 150                 155                 160

Leu Pro Ala Pro Thr Gly Phe Asp Ala Asp Gly Gln Tyr Arg Val Asn
            165                 170                 175

```
Pro Ser Tyr Val Pro Leu Gln Leu Ile Ala Arg Met Gln Ser Leu Tyr
            180                 185                 190

Pro Gln Tyr Asn Trp Asp Ser Met Tyr Lys Ala Ser Val His Met Leu
            195                 200                 205

Glu Lys Thr Met Pro Ala Gly Phe Ser Pro Asp Trp Ala Val Leu Arg
    210                 215                 220

Asn Gly Arg Tyr Ser Ser Asp Val Val Thr Gly Pro Met Gly Ser Tyr
225                 230                 235                 240

Asn Ala Ile Arg Thr Tyr Leu Trp Ala Gly Met Leu Asn Asp Gln Val
                245                 250                 255

Ser Glu Lys Ala Val Leu Val Gln Lys Met Gln Pro Phe Val Ala Ala
            260                 265                 270

Thr Lys Ala Leu Gly Ala Pro Ala Arg Glu Val Asn Thr Glu Thr Gly
            275                 280                 285

Lys Tyr Thr Gln Ala Gly Ser Ala Gly Phe Ser Ala Ala Leu Pro
    290                 295                 300

Leu Leu Ala Ala Ser Gly Glu Ser Thr Leu Leu Glu Thr Gln Phe Arg
305                 310                 315                 320

Arg Ala Gln Asn Glu Leu Val Val Asp Lys Asn Asp His Tyr Tyr Asp
                325                 330                 335

Asn Val Leu Ser Leu Phe Gly Leu Gly Trp His Glu Arg Tyr Arg
                340                 345                 350

Phe Gly Val Gln Gly Glu Leu Leu Pro Val Trp Ser Glu Arg Cys Gln
            355                 360                 365

<210> SEQ ID NO 135
<211> LENGTH: 364
<212> TYPE: PRT
<213> ORGANISM: Aurantimonas sp. SI85-9A1

<400> SEQUENCE: 135

Met Arg Ser Ile Leu Thr Leu Cys Ala Leu Ala Ser Leu Val Pro Ala
1               5                   10                  15

Met Thr Tyr Pro Pro Ala Ala His Ala Thr Pro Val Thr Ala Thr Ser
            20                  25                  30

Ala Ala Pro Glu Val Leu Pro Ala Asp Tyr Ile Val Gly Ser Trp Gln
        35                  40                  45

Leu Tyr Arg Ser Leu Phe Met Ser Ala Glu Gly Arg Ile Ile Asp Arg
    50                  55                  60

Glu Asn Gly Ser Ile Ser His Ser Glu Gly Gln Gly Tyr Gly Met Leu
65                  70                  75                  80

Ile Ala Val Ser Ala Gly Asp Arg Gln Ser Phe Asp Ala Leu Trp Asp
                85                  90                  95

Trp Thr Glu Arg Glu Leu Met Val Arg Asp Asp Asn Leu Ala Ala Trp
            100                 105                 110

Lys Trp Asp Pro Ala Ala Ser Pro His Val Thr Asp Pro Asn Asn Ala
        115                 120                 125

Thr Asp Gly Asp Ile Leu Ile Ala Trp Ala Leu Leu Arg Ala Trp Lys
    130                 135                 140

Leu Trp Gly Val Arg Asp His Leu Arg Glu Ala Arg Ala Ile Val Gly
145                 150                 155                 160

Asp Val Val Ala Leu Ala Thr Thr Asp Ser Arg Tyr Gly Thr Val Leu
                165                 170                 175

Leu Pro Gly Val Gln Gly Phe Thr Val Glu Asp Ser Ala Asp Gly Pro
```

```
                    180                 185                 190
Val Val Asn Met Ser Tyr Trp Val Phe Pro Ala Ile Ser Glu Leu Gly
                195                 200                 205

Glu Ala Met Pro Glu Phe Lys Ala Leu Asn Leu Ala Ala Ser Gly Phe
            210                 215                 220

Ala Leu Leu His Ala Ile Asp Ala Arg Pro Glu Lys Ile Pro Ser Asp
225                 230                 235                 240

Trp Thr Gly Ile Gly Asp Glu Val Pro His Pro Ala Thr Ala Phe Ala
                245                 250                 255

Pro Thr Phe Gly Tyr Asn Ala Val Arg Ile Pro Leu Tyr Ile Ala Trp
            260                 265                 270

Gln Thr Asn Thr Glu Pro Gln Leu Leu Glu Ser Leu Gln Arg Ala Trp
        275                 280                 285

Gly Asp Glu Gly Arg Ser Gly Leu Ala Val Leu Asp Val Thr Thr Gly
        290                 295                 300

Thr Pro Ile Glu Pro Met Val Ser Pro Gly Tyr Asp Ala Ile Leu Asp
305                 310                 315                 320

Val Ile Ala Cys Ser Leu Gly Gln Ser Asn Ser Ala Arg Arg Ala Lys
                325                 330                 335

Ala Phe Glu Pro Ser Thr Tyr Tyr Ala Ser Thr Leu His Ile Leu Ser
                340                 345                 350

Leu Met Ala Leu Ser Glu Arg Tyr Ser Glu Cys Phe
                355                 360
```

<210> SEQ ID NO 136
<211> LENGTH: 369
<212> TYPE: PRT
<213> ORGANISM: Photobacterium profundum

<400> SEQUENCE: 136

```
Met Lys Lys Leu Val Leu Ile Ile Gly Phe Ile Phe Ser Tyr Gln Val
1               5                   10                  15

Asn Ala Ser Thr Cys Ser Trp Pro Glu Trp Glu Gln Phe Lys Ser Thr
            20                  25                  30

Tyr Ile Gln Asn Gly Arg Val Ile Asp Gly Ser Asp Ala Arg Lys Ile
        35                  40                  45

Thr Thr Ser Glu Gly Gln Ser Tyr Gly Leu Phe Phe Ala Leu Val Ala
    50                  55                  60

Asn Asp Pro Thr Ala Phe Lys Ala Met Leu Asn Trp Thr Glu Thr Tyr
65                  70                  75                  80

Leu Ala Asp Gly Asp Leu Thr Ala Arg Leu Pro Ala Trp Leu Trp Gly
                85                  90                  95

Lys Lys Asp Leu Asn Thr Phe Gly Val Leu Asp Asn Asn Pro Ala Ser
            100                 105                 110

Asp Ser Asp Leu Trp Ile Ala Tyr Ser Leu Ile Glu Ala Gly Arg Leu
        115                 120                 125

Trp Gly Glu Tyr Tyr Glu Ser Leu Gly Tyr Leu Leu Ala Ser Arg
    130                 135                 140

Ile Leu Arg Glu Glu Thr Arg Glu Val Lys Gly Ile Gly Thr Val Leu
145                 150                 155                 160

Leu Pro Gly Lys Lys Gly Phe Asp Asn Gly Lys Gly Gln Leu Arg Leu
                165                 170                 175

Asn Pro Ser Tyr Val Pro Leu Phe Leu Ile Lys Asn Met Val Ser His
            180                 185                 190
```

Tyr Pro Asn His Gln Trp Gln Ser Leu Tyr Asn Ser Ser Tyr Thr Met
             195                 200                 205

Leu Glu Lys Thr Met Pro Lys Gly Phe Ser Pro Asp Trp Val Thr Leu
    210                 215                 220

Ser Asn Ala Thr Phe Tyr Ala Asp Ala Glu Thr Gly Pro Ile Gly Ser
225                 230                 235                 240

Tyr Asn Ala Ile Arg Thr Tyr Leu Trp Ala Gly Met Leu Asn Asp Lys
                245                 250                 255

Thr Glu Glu Lys Gln Thr Leu Leu Ser Met Met Ser Pro Met Val Asn
            260                 265                 270

Ala Ile Lys Gln Leu Gln Ala Pro Pro Arg Ser Val Asn Thr Glu Thr
        275                 280                 285

Gly Thr Phe Lys Gly Gly Ser Ala Gly Phe Ser Ala Ala Leu Leu
    290                 295                 300

Pro Leu Leu Gln Ser Leu Gly Glu Lys Glu Leu Ala Ile Glu Gln Ala
305                 310                 315                 320

Lys Ile Ile Ser Ile Ser Leu Gln Ser Asn Ser Asn Asp Tyr Tyr Tyr
                325                 330                 335

Asp Asn Val Leu Ala Leu Phe Gly Met Gly Trp Tyr Gln Gly Lys Tyr
            340                 345                 350

Gln Phe Gly Val Asn Gly Asp Leu Gln Pro Ser Trp Val Glu Gln Cys
        355                 360                 365

Gln

<210> SEQ ID NO 137
<211> LENGTH: 414
<212> TYPE: PRT
<213> ORGANISM: Lysobacter sp. IB-9374

<400> SEQUENCE: 137

Met His His Ala Thr Ala Leu Pro Arg Arg Gly Leu Lys Leu Leu Ser
1               5                   10                  15

Leu Val Leu Ala Thr Ala Ala Leu Gly Ala Ser Leu Ala Ala Gln
            20                  25                  30

Ala Ala Pro Asn Tyr Pro Phe Gly Ser His Arg Gln Ala Tyr Val Ser
        35                  40                  45

Gly Thr Leu Ser Pro Ser Val Gly Arg Ala Ala Asp Gln Ser Thr
    50                  55                  60

Ala Ser Phe Tyr Arg Ala Trp Lys Gln Arg Tyr Leu Val Ala Gly Cys
65                  70                  75                  80

Lys Ala Gly Glu Tyr Arg Val Lys Ala Ser Thr Asp Thr Ala Tyr Val
                85                  90                  95

Val Ser Glu Gly Gln Gly Tyr Gly Met Leu Ile Thr Val Met Met Ala
            100                 105                 110

Gly Asn Asp Pro Asp Ala Gln Ala Leu Phe Asp Gly Leu His Arg Tyr
        115                 120                 125

Asn Arg Gly His Pro Ser Ser Gly Asn Pro Ala Leu Leu Ala Trp Ala
    130                 135                 140

Gln Asp Ala Asn Cys Lys Asn Val Ala Gly Pro Asp Ser Ala Thr Asp
145                 150                 155                 160

Gly Asp Leu Asp Ile Ala Tyr Ala Leu Leu Leu Ala Asp Leu Gln Trp
                165                 170                 175

Gly Ser Ala Gly Ser Ile Asn Tyr Leu Ser Glu Ala Arg Lys Val Ile
            180                 185                 190

```
Ala Ala Ile Arg Ser Ser Asn Val Asn Ala Asn Thr Lys Leu Val Thr
            195                 200                 205

Leu Gly Asp Trp Val Ser Ser Glu Pro Asn Tyr Tyr Asn Ser Thr
210                 215                 220

Arg Ser Ser Asp Trp Met Leu Gly His Phe Arg Gly Phe Ala Ser Lys
225                 230                 235                 240

Leu Gly Asp Ser Tyr Trp Thr Gly Val Leu Asp Ala His Gln Thr Leu
            245                 250                 255

Ile Gly Lys Met Gln Ser Ser Tyr Ala Pro Asn Thr Gly Leu Leu Pro
                260                 265                 270

Asp Phe Ile Val Asn Thr Asn Thr Ala Lys Pro Ala Pro Ala Asn
            275                 280                 285

Phe Leu Glu Ser Glu Tyr Asp Gly Ala Tyr Ser Trp Asn Ala Gly Arg
290                 295                 300

Val Pro Trp Arg Ile Gly Ile Asp Ala Ala Val Ser Gly Asp Ser Arg
305                 310                 315                 320

Ser Arg Asn Ala Ala Arg Lys Leu Ser Gln Trp Ile Lys Val Lys Ala
                325                 330                 335

Gly Asn Asn Ala Asn Asn Ile Arg Ser Gly Tyr Lys Leu Asp Gly Thr
            340                 345                 350

Val Thr Glu Asn Tyr Asn Ser Thr Phe Phe Thr Ala Pro Phe Ala Val
            355                 360                 365

Ala Ala Thr Val Asp Thr Asp Gln Ala Trp Leu Asp Lys Leu Trp Thr
            370                 375                 380

Tyr Leu Ala Asn Gly Ser Thr Ser Asp Tyr Tyr Gly Asp Ser Val Lys
385                 390                 395                 400

Leu Leu Ser Met Leu Ala Val Thr Asn Asn Trp Leu Lys Pro
                405                 410

<210> SEQ ID NO 138
<211> LENGTH: 398
<212> TYPE: PRT
<213> ORGANISM: Bordetella avium

<400> SEQUENCE: 138

Met Met Leu Arg Leu Ala Ala Leu Arg Leu Ala Ala Leu Arg Leu Met
1               5                   10                  15

Ser Leu Val Leu Ala Leu Ile Ala Ala Pro Ala Ser Ala Ala Ala Val
                20                  25                  30

Cys Gln Ala Ala Ser Trp Pro Gln Trp Gln Thr Phe Ala Gln His Phe
            35                  40                  45

Val Gln Ala Asp Gly Arg Val Leu Asp Ala Ser Thr Pro Arg Gln Ile
50                  55                  60

Ser Thr Ser Glu Gly Gln Ser Tyr Ala Met Phe Ala Leu Val Ala
65                  70                  75                  80

Asn Asp Arg Ala Ala Phe Glu Arg Leu Trp Arg Trp Ser Val Ala Asn
                85                  90                  95

Leu Ala Asp Ala Asp Ala Thr Arg Thr Leu Pro Ala Trp Ala Trp Gly
            100                 105                 110

Lys Arg Asp Asp Gly Ser Trp Gly Val Leu Asp Arg Asn Ala Ala Ser
        115                 120                 125

Asp Ala Asp Leu Trp Phe Thr Tyr Ala Leu Leu Glu Ala Gly Arg Leu
    130                 135                 140

Trp Arg Arg Pro Asp Tyr Thr Arg Glu Gly Leu Ala Leu Leu Asn Leu
145                 150                 155                 160
```

```
Ile Gln Asn Gln Glu Leu Ala Asp Leu Pro Asp Phe Gly Pro Met Leu
            165                 170                 175

Leu Pro Ala Pro Phe Gly Phe Val Gln Pro Asp Gly Ile Trp Arg Leu
            180                 185                 190

Asn Pro Ser Tyr Leu Pro Ile Pro Val Leu Arg Arg Leu Ala Leu Ala
            195                 200                 205

Ala Pro Gly Gly Pro Trp Thr Lys Ile Ala Ala Asn Thr Val Arg Leu
    210                 215                 220

Ile Gln Ala Thr Thr Pro Lys Gly Phe Ala Ala Asp Trp Val Ala Tyr
225                 230                 235                 240

Gln Ser Thr Ala Gln Ile Ala Gly Gln Phe Val Ala Asp Pro Val His
                245                 250                 255

Gly Tyr Arg Gly Ser Tyr Asp Ala Ile Arg Thr Tyr Met Trp Ala Gly
            260                 265                 270

Met Thr Pro Ala Ala Asp Pro Ala Ala Gln Pro Leu Arg Ala Ala Leu
        275                 280                 285

Tyr Gly Met Ala Ala Ala Thr Leu Ala Gly Val Pro Pro Glu Ser
    290                 295                 300

Val Gln Thr Asp Thr Gly Val Val Gln Gly Ser Gly Pro Phe Gly Phe
305                 310                 315                 320

Ser Ala Ala Leu Leu Pro Tyr Leu Glu Ala Gly Arg Asp Ala Glu
                325                 330                 335

Leu Arg Thr Gln Leu Ala Arg Val Arg Ala Ala Trp Thr Gln Ser Leu
            340                 345                 350

Glu Pro Gly Asn Leu Ala Leu Arg Gln Pro Ser Tyr Tyr Asp Tyr Val
            355                 360                 365

Leu Ser Leu Phe Gly Thr Gly Trp Tyr Glu Gln Arg Tyr Arg Phe Gly
    370                 375                 380

Thr Thr Gly Arg Leu Ser Leu Glu Trp Glu Lys Lys Cys Pro
385                 390                 395

<210> SEQ ID NO 139
<211> LENGTH: 555
<212> TYPE: PRT
<213> ORGANISM: Hahella chejuensis

<400> SEQUENCE: 139

Met Met Pro Asp Thr Phe Arg Ile Ala Pro Leu Ala Ala Arg Val Ile
1               5                   10                  15

Leu Leu Ser Gly Leu Ala Leu Gly Ala Gln Val Ala Phe Ala Ser Cys
            20                  25                  30

Ala Asp Ser Thr Ala Thr Thr Ala Ser Ala Ala Ala Asp Ala Val Cys
        35                  40                  45

Gln Pro Ala Leu Glu Gln Gln Ala Gln Ala Ala Arg Pro Phe Pro Gln
    50                  55                  60

Ala Leu Glu Phe Ala Gly Lys Ile Lys Pro Asp His Val Ser Gln Thr
65                  70                  75                  80

Gln Met Asn Ala Lys Val Ala Gln Phe Tyr Asp Tyr Trp Lys Ser Ala
                85                  90                  95

Tyr Val Lys Pro Ser Asn Gly Asn Thr Pro Gly Gly Tyr Tyr Val
            100                 105                 110

Asn Met Lys Gly Thr Gly Gly Asp Gly Asn Glu Ile Thr Thr Ser Glu
        115                 120                 125

Ala His Gly Tyr Gly Met Met Leu Phe Ala Leu Met Ala Gly His Asp
```

```
                    130                 135                 140
Ser Glu Ala Lys Gln Tyr Phe Asp Gly Met Tyr Asn Met Tyr Asp Lys
145                 150                 155                 160

His Arg Ser Thr Leu Asn Asn His Leu Met Ser Trp Val Ile Asp Ala
                165                 170                 175

Ser Glu Asn Thr Ser Lys Asp Ser Asp Ser Ala Thr Asp Gly Asp Met
            180                 185                 190

Asp Ile Ala Tyr Ala Leu Leu Leu Ala His Tyr Gln Trp Gly Ser Asp
        195                 200                 205

Gly Ala Ile Asn Tyr Leu Gln Gln Ala Lys Arg Ile Ile Asn Asn Gly
    210                 215                 220

Leu Lys Gly Asp Asp Val His Arg Ser Ser Lys Arg Thr Met Leu Gly
225                 230                 235                 240

Asp Trp Asp Asp Asn Gln Trp Thr Thr Arg Ser Ser Trp Met Thr
                245                 250                 255

Asp His Met His Ala Tyr Gln Gln Ala Thr Gly Asp Ala Phe Trp Gly
                260                 265                 270

Glu Ala Ala Asp Thr Ala Tyr Gly Ile Ile Asp Lys Met Ile Lys Asn
                275                 280                 285

Tyr Ala Ser Ala Thr Gly Leu Met Ser Asp Phe Val Ile Asp Ser Asp
            290                 295                 300

Pro Arg Pro Ala Pro Asn Phe Leu Glu Ala Asp Thr Asp Asp
305                 310                 315                 320

Phe Ser Trp Asn Ala Cys Arg Tyr Pro Leu Arg Ile Ala Ile Asp Ala
                325                 330                 335

Ala His Phe Gly Asp Ser Arg Ala Ser Ala Ala Met Asn Lys Leu Met
                340                 345                 350

Gln Trp Ala Ile Asn Ala Thr Gly Gly Asn Pro Gly Ser Val Met Ala
                355                 360                 365

Gly Tyr Lys Leu Asn Gly Glu Pro Leu Val Gly Tyr Ser Ala Met Ala
            370                 375                 380

Phe Thr Ala Pro Met Val Ala Ala Ser Val Thr Gly His Gln Ser
385                 390                 395                 400

Phe Leu Asn Gln Gly Trp Asp Leu Ile Ser Gly Asn Arg Ser Asp Tyr
                405                 410                 415

Tyr Ser Asp Ser Ile Asn Leu Leu Ser Met Leu Phe Ile Ser Gly Asn
            420                 425                 430

Trp Trp Ser Pro Val Glu Gly Gly Asp Gly Asp Asp Gly
            435                 440                 445

Asp Gly Gly Asp Gly Asp Asp Gly Asp Asn Gly Asp Asp Gly
    450                 455                 460

Ser Asp Asp Gly Gly Asp Gln Asp Asn Pro Ala Gln Thr Thr Leu Ser
465                 470                 475                 480

Lys Thr Asp Asp Trp Gly Gly Gly Tyr Cys Ala Asn Val Arg Val Phe
                485                 490                 495

Asn Ser Ser Asp Ser Asp Leu Val Trp Ser Val Ser Val Pro Ile Glu
            500                 505                 510

Gly Gln Ala Tyr Thr Val Trp Ser Ala Asn Trp Ser Gln Gln Gly Asp
            515                 520                 525

Ala Leu Asn Ala Ser Gly Val His Trp Asn Arg Glu Leu Gly Pro Gln
            530                 535                 540

Glu Ser Thr Glu Phe Gly Phe Cys Ala Asn Arg
545                 550                 555
```

<210> SEQ ID NO 140
<211> LENGTH: 398
<212> TYPE: PRT
<213> ORGANISM: Chlorobium chlorochromatii

<400> SEQUENCE: 140

Met Arg Arg Phe Trp Thr Phe Leu Leu Ile Ser Cys Ala Pro Phe Phe
1               5                   10                  15

Leu Ser Ser Cys Ser Ser Val Pro Gln Asn Pro Glu Lys Ile Ser Thr
            20                  25                  30

Glu Ala Trp His Tyr Tyr Arg Asp Thr Phe Ile Lys Asn Gly Arg Val
        35                  40                  45

Ile Arg Pro Gln Asn Asn Asn Asp Thr Val Ser Glu Gly Gln Ala Tyr
    50                  55                  60

Thr Met Val Arg Ala Val Leu Met Lys Asp Arg Lys Thr Phe Asp Glu
65                  70                  75                  80

Cys Leu Ala Trp Ser Glu Lys Val Leu Ser Arg Lys Asn Ser Asp Gly
                85                  90                  95

Asp Tyr Leu Leu Ala Trp His Tyr Arg Asp Gly Lys Val Thr Asp Thr
            100                 105                 110

Thr Ala Ala Ser Asp Ala Asp Ile Asp Tyr Ala Phe Ser Leu Ile Val
        115                 120                 125

Ala Ser Lys Ile Trp Gln Ala Pro Arg Tyr Leu Glu Leu Ala Lys Glu
    130                 135                 140

Val Leu Ala Ser Ile Leu Glu Ala Glu Thr Thr Arg His Gln Gly Arg
145                 150                 155                 160

Leu Tyr Leu Leu Pro Trp Pro Ala Asn Lys Asn Lys Pro Gly Asp Leu
                165                 170                 175

Leu Ala Gln Asn Leu Ser Tyr Tyr Ala Pro Ser His Phe Lys Leu Phe
            180                 185                 190

Tyr Glu Thr Thr Ser Asp Pro Arg Trp Leu Glu Leu Val Asp Thr Thr
        195                 200                 205

Tyr Tyr Leu Leu Gly Arg Leu Leu His Pro Gly Glu Leu Pro Glu Gly
    210                 215                 220

Pro Ile Val Pro Asp Trp Ile Ala Ile Asn Asp Ala Gly Ala Phe Val
225                 230                 235                 240

His Leu Pro Gly Lys Asp Val Arg Tyr Gly Trp Asp Ala Val Arg Val
                245                 250                 255

Pro Met Arg Ile Ala Ala Asp Tyr His Leu Tyr Gly Asp Lys Arg Ala
            260                 265                 270

Phe Glu Val Leu Ser Trp Leu Ala Val Ser Phe Glu Glu Glu Phe Arg
        275                 280                 285

Gln Gln Ser Lys Phe Leu Leu Gln Arg Asp Ser Thr Leu Gln Val Arg
    290                 295                 300

Asn Asn Ala Leu Phe Tyr Ser Ala Met Tyr Ala Ser Leu Glu Ala Thr
305                 310                 315                 320

Glu Ser Pro Ser Ala Pro Lys Leu Leu Gln Arg Ile Arg Lys Phe Ile
                325                 330                 335

Arg Gln Glu Lys Gln Gly Leu Phe Tyr Asn His Pro Asp Asp Tyr Tyr
            340                 345                 350

Ile Asn Ser Leu Cys Trp Ile Thr Glu Tyr Tyr Glu Gln Asn Lys Lys
        355                 360                 365

His Leu Gln Ala Arg Ser Lys Lys Val Ala Leu Pro Leu Gln Thr His

```
                370                 375                 380
Glu Ser Thr Ala Asn Thr Ala Ser Leu Ser Leu Gln Ala Pro
385                 390                 395

<210> SEQ ID NO 141
<211> LENGTH: 376
<212> TYPE: PRT
<213> ORGANISM: Pelodictyon luteolum

<400> SEQUENCE: 141

Met Leu Ile Val Gly Leu Leu Ala Leu Ala Thr Val Trp Leu Val Ser
1               5                   10                  15

Cys Trp Pro Ala Glu Thr Asp Asp Ala Ile Val Leu Arg Lys Ser Trp
                20                  25                  30

Ala Gly Tyr Leu His Thr Phe Val Gln Asp Gly Arg Val Val Arg Pro
            35                  40                  45

Arg Asn Gly Phe Asp Thr Val Ser Glu Gly Gln Ala Tyr Ala Met Ile
        50                  55                  60

Arg Ala Val Thr Ala Ser Asp Arg Thr Ser Phe Asp Ala Ile Leu Leu
65                  70                  75                  80

Trp Thr Glu Lys Asn Leu Ser Arg Arg Glu Gln Ser Gly Asp Asn Leu
                85                  90                  95

Leu Ala Trp His Tyr Ala Asp Gly Arg Val Val Asp Trp Gln Ala Ala
            100                 105                 110

Ser Asp Ala Asp Ile Asp Tyr Ala Tyr Ser Leu Leu Leu Ala Gly Arg
        115                 120                 125

Lys Trp Gly Asp Pro Ser Tyr Ala Arg Leu Ala Arg Lys Val Leu Ala
130                 135                 140

Asp Ile Leu Arg Leu Glu Thr Ile Ser Tyr Glu Gly Arg Leu Arg Leu
145                 150                 155                 160

Leu Pro Trp Asn Arg Lys Pro Thr Asp Gly Asn Gly Tyr Val Val Gln
                165                 170                 175

Asn Pro Ser Tyr Tyr Ser Pro Ala Gln Phe Lys Leu Phe Phe Ala Glu
            180                 185                 190

Thr Gly Asp Gly Arg Trp Leu Glu Leu Ala Ala Thr Gly Tyr Asp Leu
        195                 200                 205

Leu Asp Arg Leu Gln Glu Pro Ala Gly Gly Ala Phe Leu Val Pro
210                 215                 220

Asp Trp Cys Arg Ile Gly Glu Gly Gly Asp Leu Arg Glu Leu Glu Gly
225                 230                 235                 240

Tyr Ser Ser Leu Tyr Gly Trp Asp Ala Leu Arg Val Pro Met Arg Ile
                245                 250                 255

Ala Leu Asp His Ala Leu Phe Glu Pro Arg Ala Ala Arg Val Leu
            260                 265                 270

Gly Arg Phe Ala Glu Phe Tyr Thr Ser Glu Phe Lys Arg Phe Gly His
        275                 280                 285

Val His Ser Val Tyr Ser Thr Gly Gly Arg Ser Val Val Tyr Asp Glu
            290                 295                 300

Asn Pro Leu Ser Tyr Ala Ala Ala Tyr Ala Ala Leu Glu Ala Ser Gly
305                 310                 315                 320

Ser Pro Leu Ala Glu Thr Ala Tyr Arg Arg Leu Gln Arg Phe Ser His
                325                 330                 335

Leu Lys Lys Gly His Ile Tyr Tyr Leu Asp Arg Lys Asp Tyr Tyr Ala
            340                 345                 350
```

Asn Ser Leu Ser Trp Leu Pro Ser Tyr Tyr Arg Leu Leu Asn Ser
            355                 360                 365

Arg Lys Ser Ser Leu Gln Asp Arg
    370                 375

<210> SEQ ID NO 142
<211> LENGTH: 393
<212> TYPE: PRT
<213> ORGANISM: Xanthomonas euvesicatoria

<400> SEQUENCE: 142

Met Ser Ala His Ala His Thr Gly Gly Met Thr Arg Arg Leu Leu
1               5                   10                  15

His Ala Gly Ala Leu Ala Gly Val Ala Ala Leu Leu Pro Ala Ala Ala
            20                  25                  30

Arg Ala Ala Pro Ser Gln Cys Gly Pro Trp Pro Leu Trp Ser Ala Phe
        35                  40                  45

Val Asp Lys His Ile Gln Pro Asp Gly Arg Val Val Asp Phe Leu Asn
    50                  55                  60

Pro Asp Gln Arg Ser Thr Ser Glu Gly Gln Ser Tyr Ala Leu Phe Phe
65                  70                  75                  80

Ala Leu Val Asn Asn Asp Gln Val Leu Phe Asp Lys Val Leu Ser Trp
                85                  90                  95

Thr Arg His Asn Leu Cys Gly Gly Arg Pro Asp Leu His Leu Pro Ala
            100                 105                 110

Trp Leu Trp Gly Arg Asp Gly Gly Ser Ala Trp Arg Val Leu Asp Ala
        115                 120                 125

Asn Thr Ala Ser Asp Gly Glu Leu Trp Ile Ala Tyr Ala Leu Leu Glu
    130                 135                 140

Ala Gly Arg Leu Trp Ser Arg Pro Gly Tyr Leu Lys Ala Gly Gln Gln
145                 150                 155                 160

Met Leu Gln Leu Ile Arg Thr Gln Glu Val Ala Thr Leu Pro Gly Leu
                165                 170                 175

Gly Pro Met Leu Leu Pro Gly Arg Thr Gly Phe Val Asp Asn Gly Arg
            180                 185                 190

Trp Thr Leu Asn Pro Ser Tyr Leu Pro Ile Gln Val Leu Arg Arg Cys
        195                 200                 205

Ala Asn Ala Asp Pro Lys Gly Pro Trp Ala Ala Ile Ala Ala Asn Ser
    210                 215                 220

Ala Arg Val Leu Arg Asp Ser Ala Pro Val Gly Phe Ala Pro Asp Trp
225                 230                 235                 240

Thr Val Trp Asp Gly Lys Thr Phe Asn Ala Asp Pro Lys Arg Gly Asn
                245                 250                 255

Val Gly Ser Tyr Asp Ala Ile Arg Val Tyr Leu Trp Ala Gly Met Leu
            260                 265                 270

Asp Ala Gly Glu Pro Leu Arg Ala Arg Leu Lys Asp Leu Ser Gly
        275                 280                 285

Pro Ala Asp Leu Leu Ala Ala Gln Gln Thr Pro Ala Glu Lys Ile Asp
    290                 295                 300

Thr Ala Arg Gly Val Gly Thr Gly Ala Leu Pro Val Gly Phe Ser Ala
305                 310                 315                 320

Ala Leu Leu Pro Tyr Leu Ser Ala Leu Gly Lys Pro Ala Leu Leu Lys
                325                 330                 335

Ala Gln Ala Gln Arg Val Pro Ala Ala Thr Gln Pro Ala Ala Ala Ala
            340                 345                 350

```
Leu Pro Tyr Phe Glu Arg Thr Leu Ala Leu Phe Gly Gln Gly Trp Leu
        355                 360                 365

Glu Asn Arg Tyr Arg Phe Ala Ala Asp Gly Arg Leu Leu Pro Ala Trp
        370                 375                 380

Arg Thr Pro Ala Cys Ala Ala Thr Thr
385                 390
```

<210> SEQ ID NO 143
<211> LENGTH: 376
<212> TYPE: PRT
<213> ORGANISM: Pseudoalteromonas haloplanktis

<400> SEQUENCE: 143

```
Met Lys Leu Phe Ile Thr Lys Ala Phe Ile Met Leu Ile Leu Phe Thr
1               5                   10                  15

Pro Leu Ser His Ala Gln Gln Cys Ala Pro Trp Gln Trp Gln Thr
                20                  25                  30

Phe Lys Thr His Phe Met Ser Asp Asp Gly Arg Ile Ile Asp Leu Gly
            35                  40                  45

Ser Glu Gln Asn Ile Thr Thr Ser Glu Gly Gln Ser Tyr Ala Leu Phe
50                  55                  60

Phe Ala Leu Ile Ala Asn Asp Lys Thr Ala Phe Asp Lys Val Leu Asn
65                  70                  75                  80

Trp Thr Glu Glu His Leu Ala Glu Gly Asp Leu Ser Thr Arg Leu Pro
                85                  90                  95

Ala Trp Leu Trp Gly Val Asn Lys Asn Asn Val Gly Asn Ile Leu Asp
            100                 105                 110

Ser Asn Pro Ala Ser Asp Ser Asp Leu Trp Ile Ala Tyr Ser Leu Ser
        115                 120                 125

Gln Ala Ala Ile Leu Trp Asp Asp Arg Arg Tyr Arg Ile Leu Ala Ala
    130                 135                 140

Val Leu Ala Gln Arg Ile Met Arg Glu Glu Thr Ala Tyr Ile Lys Gly
145                 150                 155                 160

Leu Gly Leu Ser Leu Leu Pro Ala Pro Ser Gly Phe Glu Phe Asp Asn
                165                 170                 175

Lys Arg Tyr Lys Leu Asn Pro Ser Tyr Ser Pro Leu Phe Ile Tyr Gln
            180                 185                 190

Gln Phe Ser Lys Leu Tyr Pro His Ser Pro Trp Gln Glu Leu His Asp
        195                 200                 205

Gly Ser Ala Asn Leu Ile Leu Glu Thr Ser Lys Gln Gly Val Ser Pro
    210                 215                 220

Asp Trp Ile Met Phe Asp Thr Asn Lys Gly Phe Tyr Phe Asp Lys Lys
225                 230                 235                 240

Val Thr Asp Leu Gly Ser Tyr Asn Ala Ile Arg Val Tyr Leu Trp Ala
                245                 250                 255

Ser Met Met Ala Glu Asp Ala Pro Tyr Lys Lys Gln Leu Val Thr Gln
            260                 265                 270

Phe Ala Pro Phe Ile Lys Thr Ile Asn Lys Arg Gly Tyr Val Pro Leu
        275                 280                 285

Asn Thr Tyr Ala Gln Thr Gly Asn Ser Asp Lys Arg Gly Pro Val Gly
    290                 295                 300

Phe Asn Ala Ala Leu Leu Pro Leu Leu Ala Thr Ala Asn Asn Asp Asn
305                 310                 315                 320

Asp Ala Val Thr Met Ser Ile Gln Gln Lys Leu Met Val Asp Lys Ser
```

```
                    325                 330                 335
Phe Ser Lys Ser Arg Tyr Tyr Asp Ser Val Leu Asn Leu Phe Gly Ser
                340                 345                 350

Ser Thr Leu Asp Lys Arg Phe Ala Ile Leu Ala Asp Gly Thr Leu Gln
                355                 360                 365

Pro Asn Trp Ser Asp Glu Cys Arg
    370                 375

<210> SEQ ID NO 144
<211> LENGTH: 392
<212> TYPE: PRT
<213> ORGANISM: Cupriavidus pinatubonensis

<400> SEQUENCE: 144

Met Trp Arg Ala Leu Pro Gly Leu Thr Arg Trp Leu Ala Ala Gly Ala
1               5                   10                  15

Leu Ala Cys Ala Cys Val Ala Ala Leu Pro Ala His Ala Ala Thr Cys
                20                  25                  30

Gly Trp Ala Asp Trp Asp Thr Phe Lys Arg Thr Leu Ile Ser Ala Asp
            35                  40                  45

Gly Arg Val Ile Asp Ala Ser Thr Asp Lys Val Thr Val Ser Glu
50                  55                  60

Gly Gln Ala Tyr Gly Leu Phe Phe Ala Leu Val Ala Asn Asp Arg Thr
65                  70                  75                  80

Thr Phe Asp Lys Leu Leu Ala Trp Thr Glu Asn Asn Leu Ala Gln Gly
                85                  90                  95

Asp Leu Ile Ala His Leu Pro Ala Trp Ile Trp Gly Arg Ile Pro Ala
            100                 105                 110

Asp Lys Ala Lys Asp Gly Lys Glu Thr Trp Gly Val Ile Asp Thr Asn
            115                 120                 125

Ser Ala Ser Asp Ala Asp Leu Trp Ile Ala Tyr Thr Leu Leu Glu Ala
        130                 135                 140

Gly Arg Leu Trp Asn Glu Arg Arg Phe Thr Ala Leu Gly Thr Leu Thr
145                 150                 155                 160

Ala Arg Arg Ile Met Arg Glu Glu Thr Ala Ala Met Arg Gly Leu Gly
                165                 170                 175

Arg Thr Val Leu Pro Gly Pro Val Gly Phe Ser Leu Ser Glu Gly Arg
            180                 185                 190

Trp Arg Val Asn Pro Ser Tyr Val Pro Leu Gln Val Met Arg Arg Leu
        195                 200                 205

Ala Val Leu Leu Ala Lys Glu Ser Gly Trp Asp Gln Leu Val Ala Ser
    210                 215                 220

Ser Leu Lys Val Ile Leu Glu Thr Ala Pro Arg Gly Phe Ser Pro Asp
225                 230                 235                 240

Trp Ala Glu Tyr Asp Asn Ser Arg Gly Phe Leu Pro Asp Thr Ala Thr
                245                 250                 255

Lys Ala Glu Ser Ala Tyr Asn Ala Ile Arg Val Tyr Leu Trp Ala Gly
            260                 265                 270

Thr Leu Ala Ala Asp Asp Pro Gln Arg Ala Arg Met Leu Gln Gln Phe
        275                 280                 285

Met Pro Leu Ala Asp Tyr Val Ala Ala His Gly Tyr Ala Pro Glu Arg
    290                 295                 300

Val Asp Thr Gln Thr Gly Gln Pro Gly Pro Asp Ser Gly Asn Ala Gly
305                 310                 315                 320
```

```
Phe Ser Ala Ala Val Ala Pro Tyr Leu Ala Ala Leu Gly Arg Thr Asp
                325                 330                 335
Gln Ala Arg Ala Gln Ala Gln Thr Arg Glu Leu Thr Ala Arg Glu
            340                 345                 350
Pro Leu Gly Tyr Tyr Ser Gln Ala Leu Ala Leu Phe Gly Leu Gly His
            355                 360                 365
Leu Asp Gly Leu Tyr Arg Phe Ala Gly Asp Gly Ala Leu Leu Pro Ala
370                 375                 380
Trp Lys Thr Gly Cys Pro Ala Arg
385                 390
```

<210> SEQ ID NO 145
<211> LENGTH: 361
<212> TYPE: PRT
<213> ORGANISM: Ustilago maydis

<400> SEQUENCE: 145

```
Met Glu Ala Lys Tyr Val Arg Trp Arg Asp Thr Tyr Leu Arg Ser Ser
1               5                   10                  15
Ala Val Gly Leu Tyr Cys Tyr Tyr Asn Gly Lys Gly Asp Asn Gly Asn
                20                  25                  30
Ala Ile Thr Cys Ser Glu Ala His Gly Tyr Ala Met Leu Ile Ser Val
            35                  40                  45
Leu His Arg Asn Arg Ser Asp Phe Asp Gly Leu Leu Ala Phe Phe Gln
50                  55                  60
Gly Phe Arg Asn Glu His Gly Leu Met Cys Trp Gln Ile Arg Ser Pro
65                  70                  75                  80
His Gln Pro Gly Ser Asn Ala Ser Val Glu Pro Tyr Val Glu Glu Asp
                85                  90                  95
Gly Arg Thr Ser Ala Thr Asp Gly Asp Ile Asp Ile Ala Ser Ser Leu
            100                 105                 110
Tyr Leu Gly Ala Lys Thr Phe Gly Asp Gln Arg Tyr Lys Leu Glu Ala
            115                 120                 125
Asp Arg Leu Ala Ser Ala Ile Leu Lys Tyr Thr Ile His Pro His Leu
130                 135                 140
Gly Thr Pro Leu Leu Gly Asp Trp Ala Asn Cys Asp Ser Ala Glu Ala
145                 150                 155                 160
Lys Lys Leu Tyr Asp Ser Thr Arg Thr Ser Asp Phe Ile Leu Ser Ala
                165                 170                 175
Phe Ala Leu Phe Ser Arg Met His Ser Asp Ala Ser Glu Arg Ser Arg
            180                 185                 190
Trp Glu Trp Val Leu Gln Ser Thr Lys Gln Ala Ala Leu Cys Cys Gly
            195                 200                 205
Gly Ser Thr Gly Leu Leu Pro Asp Phe Leu Thr Tyr Asn Thr Met Ser
210                 215                 220
Gln Thr Trp Gln Pro Ala Arg Ala Lys Leu Leu Glu Ser Glu His Asp
225                 230                 235                 240
Gly Ala Leu Asn Trp Asn Ala Cys Arg Thr Pro Trp Arg Leu Ala His
                245                 250                 255
Tyr Leu Ala Thr Thr Gly Asp Pro Ser Ile Val Pro Leu Leu Gln His
            260                 265                 270
Ala His Arg Ser Val Arg Ser Ser Lys Ala Phe Asn Phe Pro Thr Ile
            275                 280                 285
Pro Ala Gly Val Asp Ile Ala Ala Arg Glu Pro Lys Ala Leu Val Asp
            290                 295                 300
```

Tyr Thr Asp Lys Ala Phe Ile Ala Pro Val Gly Tyr Leu Cys Tyr Val
305                 310                 315                 320

Leu Gly Asp Thr Asp Gly His Ser Gln Cys Val Thr Ala Leu Asn His
            325                 330                 335

Gln Glu Pro Gly Tyr Phe Gly Asp Ser Ile Asp Val Cys Ile Ala Glu
        340                 345                 350

Gln Ala Gly His Ala His Glu Trp Phe
        355                 360

<210> SEQ ID NO 146
<211> LENGTH: 339
<212> TYPE: PRT
<213> ORGANISM: Zymomonas mobilis

<400> SEQUENCE: 146

Met Thr Tyr Ser Arg Arg Phe Ile Leu Ser Thr Leu Val Ser Val Pro
1               5                   10                  15

Leu Leu Val Ala Cys Arg Lys Gly Lys Ala Ala Glu Ala Asp Asn Trp
            20                  25                  30

Thr Leu Phe Lys Asn Arg Phe Phe Lys Asp Gly Arg Ile Ser Asp Ser
        35                  40                  45

Gly Asn Gly Asn Ile Ser His Ser Glu Gly Gln Gly Tyr Gly Met Ile
    50                  55                  60

Gln Ala Glu Ala Ala His Asp Lys Ala Thr Phe Asp Ala Leu Trp Gln
65                  70                  75                  80

Trp Thr Lys Thr His Leu Met Arg Pro Asp Met Ala Leu Phe Ala Trp
                85                  90                  95

Arg Phe Asp Pro Ser Gln Ser Asn Pro Val Ser Asp Gln Asn Asn Ala
            100                 105                 110

Thr Asp Gly Asp Ile Leu Ile Ala Trp Ala Leu Leu Arg Ala Glu Lys
        115                 120                 125

Arg Trp Pro Lys Asn Gly Tyr Gly Gln Asp Ser Glu Ala Ile Arg Lys
    130                 135                 140

Ser Ile Gly Lys Lys Leu Val Leu Ser Gly Gly Glu Thr Ile Leu
145                 150                 155                 160

Leu Pro Gly Leu Gln Gly Phe Thr Gly Thr Asp Tyr Val Ile Leu Asn
                165                 170                 175

Phe Ser Tyr Tyr Ile Trp Pro Ala Leu Lys Ala Phe Asn Glu Ala Asp
            180                 185                 190

Asn Gly Ala Trp His Asn Val Ile Glu Ser Gly Lys Lys Leu Leu Ala
        195                 200                 205

Lys Ala Lys Phe Gly Leu Pro Gln Leu Pro Thr Asp Trp Val Ala Phe
    210                 215                 220

Lys Ser Asn Gly Asn Leu Glu Pro Ala Ala Asp Lys Gln Pro Tyr Phe
225                 230                 235                 240

Gly Phe Asp Ala Val Arg Ile Pro Leu Tyr Leu Ile Trp Gly Gly Glu
                245                 250                 255

Asp Ala Leu Ala Ala Pro Phe Ala Ile Tyr Trp Asn Ser Tyr Leu Ser
            260                 265                 270

His Asn Gln Pro Val Pro Ala Trp Val Asp Val Asn Ser Gln Ala Ile
        275                 280                 285

Ala Pro Tyr Pro Leu Ser Lys Gly Gly Met Ala Ile Leu Asp Leu Ala
    290                 295                 300

Met Asn Lys Pro Ile Thr Ala Lys Ile Ala Asp Gln Asp Asp Tyr Tyr

```
305                 310                 315                 320
Ser Ser Ala Leu Leu Ala Leu Ser Glu Ile Ala Ala Lys Glu Arg Pro
                325                 330                 335

His Asn Arg

<210> SEQ ID NO 147
<211> LENGTH: 371
<212> TYPE: PRT
<213> ORGANISM: Erwinia carotovora

<400> SEQUENCE: 147

Met Pro Arg Val Leu Arg Tyr Leu Ile Leu Thr Leu Leu Trp Leu Trp
1               5                   10                  15

Ala Ser Leu Ala Thr Ala Ala Val Cys Asp Trp Pro Ala Trp Glu Gln
                20                  25                  30

Tyr Lys Gln His Tyr Ile Ser Glu Gln Gly Arg Val Ile Asp Thr Ser
                35                  40                  45

Thr Pro Asn Lys Ile Thr Thr Ser Glu Gly Gln Ser Tyr Ala Met Phe
        50                  55                  60

Phe Ala Leu Val Ala Asn Asp Arg Ala Met Phe Asp Arg Leu Leu Lys
65                  70                  75                  80

Trp Thr Glu Asp Asn Leu Ser Ala Gly Asp Leu Arg Ala Asn Leu Pro
                85                  90                  95

Ala Trp Leu Trp Gly Glu Ser Lys Asp Lys Gln Trp Ala Val Leu Asp
                100                 105                 110

Pro Asn Ser Ala Ser Asp Ala Asp Leu Trp Ile Ala Tyr Asn Leu Leu
        115                 120                 125

Glu Ala Gly Arg Leu Trp Lys Glu Ala Arg Tyr Gln Thr Leu Gly Thr
130                 135                 140

Thr Leu Leu Ala Arg Ile Ala Lys Glu Glu Val Val Asn Ile Pro Gly
145                 150                 155                 160

Leu Gly Val Met Leu Leu Pro Gly Lys Val Gly Phe Ala Glu Lys Glu
                165                 170                 175

Ser Trp Arg Val Asn Pro Ser Tyr Leu Pro Pro Gln Leu Leu Ala Arg
                180                 185                 190

Phe Ala Pro Leu Gly Glu Thr Trp Lys Ser Met Gln Arg Thr Thr Gln
        195                 200                 205

Arg Leu Leu Leu Glu Thr Ala Pro Lys Gly Phe Ser Pro Asp Trp Val
210                 215                 220

Ile Trp Gln Lys Gly Lys Gly Trp Gln Pro Asp Thr Thr Lys Pro Asn
225                 230                 235                 240

Ile Gly Ser Tyr Asp Ala Ile Arg Val Tyr Leu Trp Ala Gly Met Met
                245                 250                 255

Ala Asp Ser Ser Arg Gly Lys Ala Asp Leu Leu Lys Gln Phe Gln Pro
                260                 265                 270

Met Ile Gln Gln Thr Leu Gln Gln Gly Leu Pro Pro Glu Lys Ala Asp
        275                 280                 285

Thr Ala Thr Gly Val Val Thr Gly Gln Gly Pro Val Gly Phe Ser Ala
        290                 295                 300

Ser Leu Leu Pro Ile Leu Ser Arg Gln Pro Asp Ala Leu Ala Ala Gln
305                 310                 315                 320

Arg Gln Arg Leu Ala Ala Asn Pro Pro Gly Asp Asp Ala Tyr Phe Ser
                325                 330                 335

Ala Ser Leu Thr Leu Phe Gly Gln Gly Trp Asp Glu Lys Arg Tyr Arg
```

Phe Thr Ser Gln Gly Gln Leu Leu Pro Ser Arg Gly Ser Gln Cys Thr
                355                 360                 365
Thr Thr Pro
    370

<210> SEQ ID NO 148
<211> LENGTH: 369
<212> TYPE: PRT
<213> ORGANISM: Photobacterium profundum

<400> SEQUENCE: 148

Met Lys Lys Leu Val Leu Ile Ile Gly Phe Ile Leu Ser Tyr Gln Val
1               5                   10                  15

Asn Ala Ser Thr Cys Ser Trp Pro Glu Trp Glu Gln Phe Lys Ser Thr
                20                  25                  30

Tyr Ile Gln Ser Gly Arg Val Ile Asp Gly Ser Asp Thr Arg Gln Ile
            35                  40                  45

Thr Thr Ser Glu Gly Gln Ser Tyr Gly Leu Phe Phe Ala Val Val Ala
        50                  55                  60

Asn Asp Pro Thr Ala Phe Lys Ala Val Leu Asn Trp Thr Glu Thr His
65                  70                  75                  80

Leu Ser Gly Gly Asp Leu Thr Ala Arg Leu Pro Ala Trp Leu Trp Gly
                85                  90                  95

Lys Lys Asp Phe Asn Thr Phe Gly Val Leu Asp Asn Asn Pro Ala Ser
                100                 105                 110

Asp Ser Asp Leu Trp Ile Ala Tyr Ser Leu Ile Glu Ala Gly Arg Leu
            115                 120                 125

Trp Gly Glu Tyr Tyr Tyr Glu Ser Leu Gly Tyr Leu Leu Ala Ser Arg
        130                 135                 140

Ile Ile Arg Glu Glu Thr Arg Glu Val Glu Gly Ile Gly Thr Val Leu
145                 150                 155                 160

Leu Pro Gly Lys Lys Gly Phe Asp Asn Gly Lys Gly Gln Leu Arg Leu
                165                 170                 175

Asn Pro Ser Tyr Val Pro Leu Phe Leu Ile Lys Asn Met Ala Ser His
                180                 185                 190

Tyr Pro Asn Asp Gln Trp Gln Ser Leu Tyr Asn Ser Ser Tyr Thr Met
            195                 200                 205

Leu Glu Lys Thr Met Pro Lys Gly Phe Ser Pro Asp Trp Val Thr Leu
        210                 215                 220

Ser Asn Ala Thr Phe Tyr Ala Asp Ala Glu Thr Gly Pro Ile Gly Ser
225                 230                 235                 240

Tyr Asn Ala Ile Arg Thr Tyr Leu Trp Ala Gly Met Leu Asn Asp Lys
                245                 250                 255

Thr Glu Glu Lys Glu Thr Leu Leu Ser Met Met Ser Pro Met Val Asn
                260                 265                 270

Ala Ile Lys Gln Leu Gln Ala Pro Pro Arg Ser Val Asn Thr Glu Thr
            275                 280                 285

Gly Thr Phe Lys Asp Gly Gly Ser Ala Gly Phe Ser Ala Ala Leu Leu
        290                 295                 300

Pro Leu Leu Gln Ser Leu Gly Glu Lys Glu Leu Ala Ile Glu Gln Ala
305                 310                 315                 320

Lys Val Val Ser Met Leu Leu Gln Ser Asn Ser Asn Asp Tyr Tyr Tyr
                325                 330                 335

Asp Asn Val Leu Ala Leu Phe Gly Met Gly Trp Tyr Gln Gly Lys Tyr
            340                 345                 350

His Phe Gly Ile Asn Gly Glu Leu Gln Pro Ser Trp Val Glu Gln Cys
            355                 360                 365

Gln

<210> SEQ ID NO 149
<211> LENGTH: 342
<212> TYPE: PRT
<213> ORGANISM: Acetobacter xylinus

<400> SEQUENCE: 149

Met Ser Val Met Ala Ala Met Gly Gly Ala Gln Val Leu Ser Ser Thr
1               5                   10                  15

Gly Ala Phe Ala Asp Thr Ala Pro Asp Ala Val Ala Gln Gln Trp Ala
            20                  25                  30

Ile Phe Arg Ala Lys Tyr Leu Arg Pro Ser Gly Arg Val Val Asp Thr
        35                  40                  45

Gly Asn Gly Gly Glu Ser His Ser Glu Gly Gln Gly Tyr Gly Met Leu
    50                  55                  60

Phe Ala Ala Ser Ala Gly Asp Leu Ala Ser Phe Gln Ser Met Trp Met
65                  70                  75                  80

Trp Ala Arg Thr Asn Leu Gln His Thr Asn Asp Lys Leu Phe Ser Trp
                85                  90                  95

Arg Phe Leu Lys Gly His Gln Pro Val Pro Asp Lys Asn Asn Ala
            100                 105                 110

Thr Asp Gly Asp Leu Leu Ile Ala Leu Ala Leu Gly Arg Ala Gly Lys
            115                 120                 125

Arg Phe Gln Arg Pro Asp Tyr Ile Gln Asp Ala Met Ala Ile Tyr Gly
        130                 135                 140

Asp Val Leu Asn Leu Met Thr Met Lys Ala Gly Pro Tyr Val Val Leu
145                 150                 155                 160

Met Pro Gly Ala Val Gly Phe Thr Lys Lys Asp Ser Val Ile Leu Asn
                165                 170                 175

Leu Ser Tyr Tyr Val Met Pro Ser Leu Leu Gln Ala Phe Asp Leu Thr
            180                 185                 190

Ala Asp Pro Arg Trp Arg Gln Val Met Glu Asp Gly Ile Arg Leu Val
        195                 200                 205

Ser Ala Gly Arg Phe Gly Gln Trp Arg Leu Pro Pro Asp Trp Leu Ala
    210                 215                 220

Val Asn Arg Ala Thr Gly Ala Leu Ser Ile Ala Ser Gly Trp Pro Pro
225                 230                 235                 240

Arg Phe Ser Tyr Asp Ala Ile Arg Val Pro Leu Tyr Phe Tyr Trp Ala
                245                 250                 255

His Met Leu Ala Pro Asn Val Leu Ala Asp Phe Thr Arg Phe Trp Asn
            260                 265                 270

Asn Phe Gly Ala Asn Ala Leu Pro Gly Trp Val Asp Leu Thr Thr Gly
        275                 280                 285

Ala Arg Ser Pro Tyr Asn Ala Pro Pro Gly Tyr Leu Ala Val Ala Glu
    290                 295                 300

Cys Thr Gly Leu Asp Ser Ala Gly Glu Leu Pro Thr Leu Asp His Ala
305                 310                 315                 320

Pro Asp Tyr Tyr Ser Ala Ala Leu Thr Leu Leu Val Tyr Ile Ala Arg
                325                 330                 335

Ala Glu Glu Thr Ile Lys
            340

<210> SEQ ID NO 150
<211> LENGTH: 382
<212> TYPE: PRT
<213> ORGANISM: Chromobacterium violaceum

<400> SEQUENCE: 150

Met Ser Ala Val Ser Ile Pro Leu Phe Ala Leu Leu Leu Asp Ala
1               5                   10                  15

Leu Pro Ala Leu Ala Ala Pro Cys Asp Gly Trp Pro Asp Trp Gln Ala
                20                  25                  30

Phe Leu Lys Asn Tyr Val Ser Gly Asp Gly Arg Val Val Asp Arg Ser
            35                  40                  45

Gln Asp Ala Arg Pro Thr Thr Ser Glu Gly Gln Ser Tyr Ala Leu Phe
50                  55                  60

Phe Ala Leu Ala Ala Asn Asp Arg Pro Ala Phe Asp Arg Leu Leu Ala
65                  70                  75                  80

Trp Thr Arg Asp Asn Leu Ala Asp Gly Asp Leu Gly Ala Arg Leu Pro
                85                  90                  95

Ala Trp Leu Trp Gly Arg Gly Gln Asp Gly Gly Trp Lys Val Leu Asp
                100                 105                 110

Asp Asn Ser Ala Ser Asp Ser Asp Met Trp Leu Ala Tyr Asp Leu Leu
            115                 120                 125

Glu Ala Gly Arg Leu Trp Arg Glu Pro Ser Tyr Ala Ala Gln Gly Arg
130                 135                 140

Gln Leu Ala Leu Arg Ile Leu Arg Glu Glu Thr Ala Asp Leu Pro Gly
145                 150                 155                 160

Leu Gly Leu Thr Leu Leu Pro Gly Lys Asp Gly Phe Leu Phe Ser Asp
                165                 170                 175

Gly Gly Ala Arg Leu Asn Pro Ser Tyr Leu Pro Pro Gln Leu Leu Ala
                180                 185                 190

Arg Phe Ala Tyr Gly Leu Pro Asp Ser Asp Trp Ala Lys Leu Pro Ser
            195                 200                 205

Gly Ser Glu Arg Val Leu Leu Asp Gly Ala Pro Ala Gly Phe Ala Pro
210                 215                 220

Asp Trp Leu Arg Leu Gln Pro Gly Lys Gly Leu Gln Pro Asp Ala Asp
225                 230                 235                 240

Ser Lys Ala Lys Gly Gly Tyr Ser Ala Ile Arg Val Tyr Leu Trp Ala
                245                 250                 255

Gly Met Leu Ala Pro Ser Ala Pro Leu Arg Ala Ala Leu Leu Ala Arg
                260                 265                 270

Tyr Lys Pro Met Ala Arg Trp Val Ala Arg Glu Gly Ala Pro Pro Glu
            275                 280                 285

Gln Val Asp Thr Arg Asn Gly Lys Ala Gln Gly Arg Ala Pro Thr Gly
290                 295                 300

Phe Ser Phe Ala Leu Leu Pro Phe Leu Gln Ala Gln Gly Glu Thr Glu
305                 310                 315                 320

Ala Leu Arg Ala Leu Leu Gln Arg Leu Arg Ala Met Pro Arg Asp Asp
                325                 330                 335

Arg Ala Asp Ala Tyr Tyr Asp Gln Val Leu Arg Leu Phe Gly Leu Gly
            340                 345                 350

Trp Leu Gln Gly Arg Phe Arg Phe Glu Arg Asn Gly Lys Leu Leu Pro
            355                 360                 365

```
Ala Trp Glu Gly Lys Cys Ser Ala Ser Leu Pro Val Ser Arg
    370                 375                 380
```

<210> SEQ ID NO 151
<211> LENGTH: 403
<212> TYPE: PRT
<213> ORGANISM: Pseudomonas syringae

<400> SEQUENCE: 151

```
Met Pro Thr Leu Val Ile Asn Leu Arg Arg Ala Val Gly Trp Met Thr
1               5                   10                  15

Gly Val Leu Ala Ser Ala Thr Leu Thr Pro Ala Leu Ala Ala Ser Thr
            20                  25                  30

Cys Asp Gly Pro Ala Trp Pro Phe Trp Gln Asp Tyr Ala Thr Arg Tyr
        35                  40                  45

Val Gln Ala Asp Gly Arg Met Leu Glu Ser Ser Leu Lys Ala Asn His
    50                  55                  60

Ser Thr Ser Glu Gly Gln Ser Tyr Gly Met Leu Phe Ala Leu Val Ala
65                  70                  75                  80

Asn Asp Arg Ala Arg Phe Asp Thr Leu Trp Thr Trp Thr Ala Glu Asn
                85                  90                  95

Met Thr Gly Ala Asp Pro Arg Thr Arg Leu Pro Gly Trp Leu Trp Gly
            100                 105                 110

Gln Gly Glu Asp Gly Ser Trp Lys Leu Gln Asp Ala Asn Ser Ala Ser
        115                 120                 125

Asp Ala Asp Leu Trp Ile Ile Tyr Ala Leu Leu Glu Ala Ala Arg Ile
    130                 135                 140

Trp Gln His Pro Ala Tyr Arg Asn Asp Ala Leu Ala Leu Leu Lys Thr
145                 150                 155                 160

Val Glu Ala Arg Leu Val Val Asn Leu Pro Gly Leu Gly Lys Met Leu
                165                 170                 175

Leu Pro Gly Pro Glu Gly Phe Val Gln Pro Asp His Leu Trp Arg Leu
            180                 185                 190

Asn Ser Ser Tyr Leu Pro Val Pro Leu Leu Arg Arg Leu Ala Arg Glu
        195                 200                 205

Glu Pro Ala Gly Pro Trp Lys Glu Ile Ala Asp Asn Thr Ala Lys Leu
    210                 215                 220

Ile Asp Ala Ser Ser Pro Lys Gly Phe Ile Ala Asp Trp Val Gly Tyr
225                 230                 235                 240

Arg Gly Thr Ser Pro Lys Thr Gly Leu Phe Val Val Asp Pro Val Ser
                245                 250                 255

Gly Glu Leu Gly Ser Tyr Asp Ala Ile Arg Val Tyr Leu Trp Ala Gly
            260                 265                 270

Met Thr Pro Ala Ser Asp Pro Leu Ala Ala Arg Leu Leu Ala Arg Leu
        275                 280                 285

Asp Gly Met Ala Val Ser Thr Ala Ser Ser Gly Thr Pro Pro Glu Lys
    290                 295                 300

Val Gln Val Met Ser Gly Ala Ser Gln Gly Gln Ala Pro Phe Gly Tyr
305                 310                 315                 320

Ser Ala Ala Leu Leu Pro Tyr Phe Gln Ala Lys Gly Gln Thr Trp Leu
                325                 330                 335

Ala Glu Gln Gln Gln Arg Arg Val Glu Ala Gly Val Ser Thr Ala Leu
            340                 345                 350

Ala Arg Asp Pro Thr Asp Arg Thr Glu Pro Ala Tyr Tyr Asn Leu Met
```

|   |   | 355 |   |   |   | 360 |   |   |   | 365 |   |

Leu Ser Leu Phe Ala Leu Gly Trp Val Glu Lys Arg Tyr Gln Phe Arg
370             375             380

Glu Asp Gly Thr Leu Lys Leu Ser Trp Glu Thr Ser Cys Pro Arg Ala
385             390             395             400

Ala Thr Arg

<210> SEQ ID NO 152
<211> LENGTH: 370
<212> TYPE: PRT
<213> ORGANISM: Pseudomonas putida

<400> SEQUENCE: 152

Met Arg Gln Met Leu Val Gly Leu Val Ala Leu Gly Leu Pro Val Phe
1               5                   10                  15

Ala Asn Ala Gly Ser Val Cys Pro Trp Pro Ala Trp Glu Arg Phe Lys
            20                  25                  30

Ala Glu Leu Val Ser Val Asp Gly Arg Val Ile Asp Pro Ser Asp Glu
        35                  40                  45

Arg Leu Ile Thr Thr Ser Glu Gly Gln Ser Tyr Ala Leu Phe Phe Ala
50                  55                  60

Leu Val Gly Asn Asp Arg Gln Thr Phe Ala Gln Leu Leu Arg Trp Thr
65                  70                  75                  80

Ser Asn Asn Leu Ala Glu Gly Asp Leu Ala Arg His Leu Pro Ala Trp
                85                  90                  95

Leu Trp Gly Arg Asp Gly Gln Gln Gln Trp Gln Val Leu Asp Ala Asn
            100                 105                 110

Asn Ala Ser Asp Ala Asp Leu Trp Ile Ala Tyr Ser Leu Leu Glu Ala
        115                 120                 125

Gly Arg Leu Trp Asp Gln Pro Ala Tyr Thr Gln Leu Gly Gln His Leu
130                 135                 140

Leu Trp Arg Ile Ala Ala Gln Thr Val Arg Lys Leu Pro Gly Leu Gly
145                 150                 155                 160

Val Met Leu Leu Pro Gly Asp Tyr Gly Phe Glu Asp Ala Gln Gly Thr
                165                 170                 175

Arg Leu Asn Pro Ser Tyr Leu Pro Leu Gln Leu Leu Asp Arg Phe Ser
            180                 185                 190

Asp Val Asp Pro Leu Trp Gly Glu Leu Ala Ala Asn Thr Arg Arg Leu
        195                 200                 205

Trp Leu Ala Ser Ser Pro Lys Gly Phe Ala Pro Asp Trp Leu Leu Trp
210                 215                 220

Thr Pro Ala Gly Lys Pro Ala Ala Asp Thr Lys His Gly Asn Ala Gly
225                 230                 235                 240

Asp Tyr Asp Ala Ile Arg Val Tyr Leu Trp Val Gly Met Leu Ala Glu
                245                 250                 255

Gly Ala Ala Gln Arg Arg Glu Leu Val Ala His Tyr Ala Pro Met Ala
            260                 265                 270

Ala Leu Thr Gln Arg Gln Gly Leu Pro Pro Glu His Leu Asp Ala Arg
        275                 280                 285

Ser Gly Glu Ala Arg Gly His Gly Pro Ala Gly Phe Ser Ala Ala Leu
290                 295                 300

Leu Pro Leu Leu Ala Ala Ser Pro Glu His Val Ala Gly Leu Ala Ala
305                 310                 315                 320

Gln Arg Gln Arg Leu Arg Glu Gln Pro Val Glu Ala Lys Ala Tyr Tyr

```
                     325                 330                 335
Ser Gln Val Leu Ala Leu Phe Gly Gln Gly Phe Asp Glu Ala Arg Tyr
            340                 345                 350

Arg Phe Asp Pro His Gly Arg Leu Leu Pro Ala Trp Ser Ala Pro Cys
            355                 360                 365

Ser Glu
    370

<210> SEQ ID NO 153
<211> LENGTH: 407
<212> TYPE: PRT
<213> ORGANISM: Bacillus circulans

<400> SEQUENCE: 153

Met Lys Val Phe Arg Asn Ser Ile Ile Arg Lys Ser Ala Val Leu Phe
1               5                   10                  15

Cys Ala Val Leu Leu Ile Leu Pro Ala Gly Leu Ser Leu Ala Ala Asn
            20                  25                  30

Lys Pro Phe Pro Gln His Thr Ser Tyr Thr Ser Gly Ser Ile Lys Pro
        35                  40                  45

Asn Asn Val Thr Gln Ser Ala Met Asp Asn Ala Val Lys Ser Lys Trp
    50                  55                  60

Asn Ser Trp Lys Gly Ser Phe Leu Lys Pro Ala Ala Thr Gly Gln Tyr
65                  70                  75                  80

Tyr Val Lys Tyr Asn Ser Ala Gly Glu Thr Val Ser Glu Ala His Gly
                85                  90                  95

Tyr Gly Met Leu Phe Thr Val Leu Met Ala Gly Tyr Asp Ser Asn Ala
            100                 105                 110

Gln Ser Tyr Phe Asp Gly Leu Tyr Arg Tyr Tyr Lys Ala His Pro Ser
        115                 120                 125

Asn Asn Asn Pro Tyr Leu Met Ala Trp Lys Gln Asn Ser Ser Phe Gln
    130                 135                 140

Asn Ile Gly Gly Ala Asn Ser Ala Thr Asp Gly Asp Met Asp Ile Ala
145                 150                 155                 160

Tyr Ala Leu Leu Leu Ala Asp Lys Gln Trp Gly Ser Ser Gly Ser Ile
                165                 170                 175

Asn Tyr Leu Gln Ala Ala Lys Asp Met Ile Asn Ala Ile Met Ser Asn
            180                 185                 190

Asp Val Asn Gln Ser Gln Trp Thr Leu Arg Leu Gly Asp Trp Ala Thr
        195                 200                 205

Ser Gly Ile Phe Asp Thr Ala Thr Arg Pro Ser Asp Phe Met Leu Asn
    210                 215                 220

His Met Lys Ala Phe Arg Ala Thr Gly Asp Ala Arg Trp Glu Asn
225                 230                 235                 240

Val Ile Asn Lys Thr Tyr Thr Ile Ile Asn Ser Ile Tyr Asn Gly Tyr
                245                 250                 255

Ser Ser Asn Thr Gly Leu Leu Pro Asp Phe Val Val Met Ser Gly Gly
            260                 265                 270

Asn Tyr Gln Pro Ala Ala Ala Glu Phe Leu Glu Gly Ala Asn Asp Gly
        275                 280                 285

Lys Tyr Tyr Tyr Asn Ser Ser Arg Thr Pro Trp Arg Ile Thr Thr Asp
    290                 295                 300

Tyr Leu Met Thr Gly Asp Thr Arg Ala Leu Asn Gln Leu Asn Lys Met
305                 310                 315                 320
```

```
Asn Thr Phe Ile Lys Ser Ala Thr Ser Ser Asn Pro Ala Asn Val Lys
            325                 330                 335

Ala Gly Tyr Asn Leu Asn Gly Thr Ala Leu Val Thr Tyr Asn Ser Gly
            340                 345                 350

Ala Phe Tyr Ala Pro Phe Gly Val Ser Ala Met Thr Ser Ser Ser His
            355                 360                 365

Gln Ser Trp Leu Asn Ser Val Trp Ser Tyr Thr Ala Asn Ala Ser Ala
        370                 375                 380

Glu Gly Tyr Tyr Glu Glu Ser Ile Lys Leu Phe Ser Met Ile Val Met
385                 390                 395                 400

Ser Gly Asn Trp Trp Thr Tyr
                405

<210> SEQ ID NO 154
<211> LENGTH: 797
<212> TYPE: PRT
<213> ORGANISM: Paenibacillus fukuinensis

<400> SEQUENCE: 154

Met Phe Thr Ser Ser Leu Ser Gly Ser Pro Arg Leu Lys Ser Ala Phe
1               5                   10                  15

Leu Leu Leu Leu Cys Leu Ala Met Val Val Ser Ile Gly Phe Val Pro
            20                  25                  30

Lys Gly Asn Glu Gly Arg Val His Ala Ala Gly Glu Met Met Pro Phe
        35                  40                  45

Pro Gln Gln Val Ser Tyr Ser Gly Ile Ile Lys Pro Asn His Val Thr
    50                  55                  60

Gln Ala Ala Met Asn Thr Ala Val Ala Ala Tyr Tyr Asp Tyr Trp Lys
65                  70                  75                  80

Gly Lys Tyr Leu Lys Asn Asn Leu Ser Ser Leu Pro Gly Gly Tyr Tyr
                85                  90                  95

Val Lys Gly Glu Ile Thr Gly Ser Pro Glu Gly Phe Val Pro Leu Gly
            100                 105                 110

Thr Ser Glu Gly Gln Gly Tyr Gly Met Ile Ile Thr Ala Leu Met Ala
        115                 120                 125

Gly His Asp Pro Asn Ala Gln Thr Ile Phe Asn Gly Leu Phe Lys Thr
    130                 135                 140

Ala Arg Ala Tyr Lys Ser Ser Gly Asn Pro Asn Leu Met Gly Trp Val
145                 150                 155                 160

Val Ala Asp His Ile Asn Ala Gln Gly His Phe Gly Ser Ala Thr Asp
                165                 170                 175

Gly Asp Leu Asp Ile Ala Tyr Ser Leu Leu Leu Ala His Lys Gln Trp
            180                 185                 190

Gly Ser Asn Gly Thr Val Asn Tyr Leu Ala Glu Ala Gln Asn Met Ile
        195                 200                 205

Thr Asn Gly Ile Lys Ala Ser Tyr Val Thr Thr Asn Asn Arg Leu Asn
    210                 215                 220

Leu Gly Asp Trp Asp Ser Lys Ser Ser Leu Ala Thr Arg Pro Ser Asp
225                 230                 235                 240

Trp Met Leu Ser His Leu Arg Ala Phe Tyr Glu Phe Thr Gly Asp Gln
                245                 250                 255

Thr Trp Ile Asn Val Ile Asn Asn Leu Tyr Asn Val Tyr Thr Gln Val
            260                 265                 270

Ser Asn Asn Tyr Ala Ser Ser Thr Gly Leu Ile Ser Asp Phe Val Val
        275                 280                 285
```

```
Asn Asn Pro Pro Gln Pro Ala Pro Glu Trp Tyr Leu Asn Glu Phe Gln
    290             295                 300
Gln Thr Asn Ala Tyr Tyr Asn Ala Ala Arg Val Pro Leu Arg Ile
305             310              315                 320
Val Met Asp Tyr Ala Met Tyr Gly Asp Thr Arg Gly Lys Thr Ile Ala
                325             330                 335
Asp Lys Ile Ala Val Trp Ile Lys Gly Lys Ala Ser Asn Ser Pro Ala
            340             345             350
Asn Ile Arg Asp Gly Tyr Gln Leu Asn Gly Thr Thr Ile Gly Gly Tyr
        355             360             365
Ala Thr Ala Val Phe Val Ser Pro Phe Ile Ala Ala Ser Thr Thr Ser
    370             375             380
Thr Ser His Gln Ala Trp Val Asn Ala Gly Trp Asp Trp Met Lys Asn
385             390             395                 400
Lys Gln Glu Asn Tyr Phe Ser Asp Ser Tyr Asn Leu Met Thr Met Leu
                405             410             415
Phe Ile Thr Gly Asn Trp Trp Lys Pro Thr Ala Ala Ser Ser Asp Thr
            420             425             430
Gln Ala Pro Thr Val Pro Gly Ser Leu Thr Ala Ala Thr Ser Ser
        435             440             445
Ser Ser Ile Asn Leu Thr Trp Thr Ala Ser Thr Asp Asn Val Gly Val
450             455             460
Thr Gly Tyr Arg Ile Tyr Arg Gly Gly Thr Gln Val Gly Thr Ala Thr
465             470             475             480
Gly Leu Ser Tyr Ala Asp Ser Gly Leu Ser Ala Asn Thr Ser Tyr Ser
                485             490             495
Tyr Thr Val Arg Ala Val Asp Ala Ala Gly Asn Val Ser Gly Asn Ser
            500             505             510
Asn Thr Ala Ser Ala Thr Thr Leu Ser Gly Thr Thr Pro Pro Thr Gly
        515             520             525
Thr Asn Leu Ala Leu Asn Lys Thr Ala Thr Ala Ser Ser Ile Glu Gly
    530             535             540
Ala Gly Phe Glu Ala Ser Arg Ala Phe Asp Gly Ser Ser Thr Thr Arg
545             550             555             560
Trp Ala Ser Ala Glu Gly Val Asp Pro Gln Trp Ile Tyr Val Asn Leu
                565             570             575
Gly Ser Ser Gln Thr Val Asn Arg Val Lys Leu Asn Trp Glu Ala Ala
            580             585             590
Tyr Ala Ser Ser Tyr Thr Ile Gln Val Ser Asn Asp Ser Gly Thr Pro
        595             600             605
Thr Asn Trp Thr Thr Val Tyr Thr Thr Thr Gly Asp Gly Gly Ile
    610             615             620
Asp Asp Ile Thr Phe Thr Ala Arg Thr Ala Lys Tyr Val Arg Val His
625             630             635             640
Gly Thr Val Arg Gly Thr Pro Tyr Gly Tyr Ser Leu Trp Glu Phe Glu
                645             650             655
Val Tyr Gly Gly Ser Thr Ala Pro Ser Asn Leu Ala Leu Asn Lys Ala
            660             665             670
Thr Ala Thr Ser Ser Ile Glu Thr Ala Gly His Glu Gly Asp Lys Ala
        675             680             685
Val Asp Gly Asn Ala Ala Thr Arg Trp Ala Ser Ala Tyr Gly Ala Ser
    690             695             700
```

```
Pro Gln Trp Ile Tyr Ile Asn Leu Gly Ser Thr Gln Ser Ile Ser Arg
705                 710                 715                 720

Val Lys Leu Asn Trp Glu Asp Ala Tyr Ala Thr Ala Tyr Ser Ile Gln
                725                 730                 735

Val Ser Asn Asp Ser Gly Ser Thr Pro Thr Asn Trp Thr Thr Val Tyr
            740                 745                 750

Ser Thr Thr Thr Gly Asp Gly Ala Ile Asp Asp Ile Thr Phe Ala Ala
        755                 760                 765

Thr Asn Ala Lys Phe Val Arg Val Tyr Ala Thr Thr Arg Ala Thr Ala
    770                 775                 780

Tyr Gly Tyr Ser Leu Trp Glu Phe Glu Val Tyr Gly Ala
785                 790                 795

<210> SEQ ID NO 155
<211> LENGTH: 4
<212> TYPE: PRT
<213> ORGANISM: Artificial sequence
<220> FEATURE:
<223> OTHER INFORMATION: GH xylanase conserved motif 2
<220> FEATURE:
<221> NAME/KEY: NON_CONS
<222> LOCATION: (1)..(1)
<223> OTHER INFORMATION: The amino acid in position 1 of the conserved
      motif is either Asparagine (N) or Aspartic acid (D).
<220> FEATURE:
<221> NAME/KEY: NON_CONS
<222> LOCATION: (2)..(2)
<223> OTHER INFORMATION: The amino acid in position 2 of the conserved
      motif is either Alanine (A) or Serine (S).
<220> FEATURE:
<221> NAME/KEY: NON_CONS
<222> LOCATION: (3)..(3)
<223> OTHER INFORMATION: The amino acid in position 3 of the conserved
      motif is any amino acid.
<220> FEATURE:
<221> NAME/KEY: NON_CONS
<222> LOCATION: (4)..(4)
<223> OTHER INFORMATION: The amino acid in position 4 of the conserved
      motif is Arginine (R), Leucine (L), Proline (P) or Glutamine (Q).

<400> SEQUENCE: 155

Xaa Xaa Xaa Xaa
1

<210> SEQ ID NO 156
<211> LENGTH: 42
<212> TYPE: DNA
<213> ORGANISM: Artificial sequence
<220> FEATURE:
<223> OTHER INFORMATION: Primer LBei411f

<400> SEQUENCE: 156
gcttctacaa cagacgctga caaccttggc aacggctatt ac                          42

<210> SEQ ID NO 157
<211> LENGTH: 42
<212> TYPE: DNA
<213> ORGANISM: Artificial sequence
<220> FEATURE:
<223> OTHER INFORMATION: Primer LBei411r

<400> SEQUENCE: 157
gtaatagccg ttgccaaggt tgtcagcgtc tgttgtagaa gc                          42

<210> SEQ ID NO 158
<211> LENGTH: 1299
<212> TYPE: DNA
```

<213> ORGANISM: Pseudoalteromonas haloplanktis
<220> FEATURE:
<221> NAME/KEY: CDS
<222> LOCATION: (1)..(1296)
<220> FEATURE:
<221> NAME/KEY: sig_peptide
<222> LOCATION: (1)..(81)
<220> FEATURE:
<221> NAME/KEY: mat_peptide
<222> LOCATION: (82)..(1296)

<400> SEQUENCE: 158

| | | | | | | | | | | | | | | | | |
|---|---|---|---|---|---|---|---|---|---|---|---|---|---|---|---|---|
| atg | aag | aaa | ccg | ttg | ggg | aaa | att | gtc | gca | agc | acc | gca | cta | ctc | att | 48 |
| Met | Lys | Lys | Pro | Leu | Gly | Lys | Ile | Val | Ala | Ser | Thr | Ala | Leu | Leu | Ile | |
| | | | -25 | | | | -20 | | | | -15 | | | | | |
| tct | gtt | gct | ttt | agt | tca | tcg | atc | gca | tcg | gct | gca | ttt | aat | aat | aac | 96 |
| Ser | Val | Ala | Phe | Ser | Ser | Ser | Ile | Ala | Ser | Ala | Ala | Phe | Asn | Asn | Asn | |
| | | -10 | | | | | -5 | | | | -1 | 1 | | | 5 | |
| cca | tcg | agt | gta | ggc | gcc | gac | agt | tca | gga | gca | tac | cgt | aac | ctc | gca | 144 |
| Pro | Ser | Ser | Val | Gly | Ala | Asp | Ser | Ser | Gly | Ala | Tyr | Arg | Asn | Leu | Ala | |
| | | | | 10 | | | | | 15 | | | | | 20 | | |
| caa | gaa | atg | ggt | aaa | aca | aat | ata | cag | caa | aaa | gtg | aat | agt | act | ttt | 192 |
| Gln | Glu | Met | Gly | Lys | Thr | Asn | Ile | Gln | Gln | Lys | Val | Asn | Ser | Thr | Phe | |
| | | | 25 | | | | | 30 | | | | | 35 | | | |
| gac | aat | atg | ttt | ggc | tat | aac | aac | aca | caa | caa | ctt | tac | tac | ccg | tac | 240 |
| Asp | Asn | Met | Phe | Gly | Tyr | Asn | Asn | Thr | Gln | Gln | Leu | Tyr | Tyr | Pro | Tyr | |
| | | 40 | | | | | 45 | | | | | 50 | | | | |
| acc | gaa | aac | ggt | gtt | tat | aaa | gca | cac | tac | ata | aaa | gca | att | aac | cca | 288 |
| Thr | Glu | Asn | Gly | Val | Tyr | Lys | Ala | His | Tyr | Ile | Lys | Ala | Ile | Asn | Pro | |
| | 55 | | | | | 60 | | | | | 65 | | | | | |
| gac | gaa | ggc | gac | gat | ata | aga | aca | gaa | ggg | caa | tcg | tgg | gga | atg | acc | 336 |
| Asp | Glu | Gly | Asp | Asp | Ile | Arg | Thr | Glu | Gly | Gln | Ser | Trp | Gly | Met | Thr | |
| 70 | | | | | 75 | | | | | 80 | | | | | 85 | |
| gcc | gct | gtc | atg | ctt | aat | aaa | caa | gaa | gaa | ttt | gat | aac | cta | tgg | cgc | 384 |
| Ala | Ala | Val | Met | Leu | Asn | Lys | Gln | Glu | Glu | Phe | Asp | Asn | Leu | Trp | Arg | |
| | | | 90 | | | | | 95 | | | | | 100 | | | |
| ttt | gca | aaa | gcg | tat | caa | aaa | aat | cca | gac | aac | cac | cct | gat | gct | aaa | 432 |
| Phe | Ala | Lys | Ala | Tyr | Gln | Lys | Asn | Pro | Asp | Asn | His | Pro | Asp | Ala | Lys | |
| | | | 105 | | | | | 110 | | | | | 115 | | | |
| aaa | caa | ggc | gtt | tac | gcg | tgg | aaa | cta | aag | ctt | aat | caa | aac | ggc | ttt | 480 |
| Lys | Gln | Gly | Val | Tyr | Ala | Trp | Lys | Leu | Lys | Leu | Asn | Gln | Asn | Gly | Phe | |
| | | 120 | | | | | 125 | | | | | 130 | | | | |
| gtt | tat | aaa | gta | gat | gaa | ggc | ccc | gct | ccc | gat | ggc | gaa | gag | tac | ttt | 528 |
| Val | Tyr | Lys | Val | Asp | Glu | Gly | Pro | Ala | Pro | Asp | Gly | Glu | Glu | Tyr | Phe | |
| | 135 | | | | | 140 | | | | | 145 | | | | | |
| gct | ttt | gca | cta | ctt | aat | gcc | tcc | gct | cgt | tgg | ggc | aat | tcg | ggt | gag | 576 |
| Ala | Phe | Ala | Leu | Leu | Asn | Ala | Ser | Ala | Arg | Trp | Gly | Asn | Ser | Gly | Glu | |
| 150 | | | | | 155 | | | | | 160 | | | | | 165 | |
| ttt | aac | tac | tac | aac | gat | gcc | att | acc | atg | tta | aac | acg | att | aaa | agt | 624 |
| Phe | Asn | Tyr | Tyr | Asn | Asp | Ala | Ile | Thr | Met | Leu | Asn | Thr | Ile | Lys | Ser | |
| | | | 170 | | | | | 175 | | | | | 180 | | | |
| aag | ttg | atg | gaa | aac | caa | ata | atc | cgc | ttt | tca | cct | tac | att | gat | aac | 672 |
| Lys | Leu | Met | Glu | Asn | Gln | Ile | Ile | Arg | Phe | Ser | Pro | Tyr | Ile | Asp | Asn | |
| | | | 185 | | | | | 190 | | | | | 195 | | | |
| cta | aca | gac | cct | tct | tat | cac | ata | cct | gcg | ttt | tat | gac | tac | ttt | gca | 720 |
| Leu | Thr | Asp | Pro | Ser | Tyr | His | Ile | Pro | Ala | Phe | Tyr | Asp | Tyr | Phe | Ala | |
| | | 200 | | | | | 205 | | | | | 210 | | | | |
| aat | aac | gta | act | aac | caa | gca | gac | aaa | act | tac | tgg | cga | caa | gtc | gcc | 768 |
| Asn | Asn | Val | Thr | Asn | Gln | Ala | Asp | Lys | Thr | Tyr | Trp | Arg | Gln | Val | Ala | |
| | | 215 | | | | | 220 | | | | | 225 | | | | |
| aca | aaa | agt | aga | acc | tta | ctt | aaa | aac | cat | ttt | aca | aaa | gta | agt | ggt | 816 |
| Thr | Lys | Ser | Arg | Thr | Leu | Leu | Lys | Asn | His | Phe | Thr | Lys | Val | Ser | Gly | |

```
                            230                 235                 240                 245
agc ccg cat tgg aac tta cct aca ttt tta tca cgc tta gat ggc agc                864
Ser Pro His Trp Asn Leu Pro Thr Phe Leu Ser Arg Leu Asp Gly Ser
            250                 255                 260 cct gtt att ggc tac att ttt aac gac caa gca aac cca ggt caa tgg                912
Pro Val Ile Gly Tyr Ile Phe Asn Asp Gln Ala Asn Pro Gly Gln Trp
            265                 270                 275 tat gaa ttt gat gca tgg cgc gta att atg aat gtg ggt tta gac gcg                960
Tyr Glu Phe Asp Ala Trp Arg Val Ile Met Asn Val Gly Leu Asp Ala
            280                 285                 290 cat tta atg ggt gct caa gcg tgg cat aaa agc gca gta aat aaa gca               1008
His Leu Met Gly Ala Gln Ala Trp His Lys Ser Ala Val Asn Lys Ala
    295                 300                 305 ctg ggc ttt tta agt tat gca aaa act aac aac agt aat aac tgt tac               1056
Leu Gly Phe Leu Ser Tyr Ala Lys Thr Asn Asn Ser Asn Asn Cys Tyr
310                 315                 320                 325 gag caa gtg tat tcg tac ggt ggg gcg caa aac aga ggc tgt gcg ggc               1104
Glu Gln Val Tyr Ser Tyr Gly Gly Ala Gln Asn Arg Gly Cys Ala Gly
                330                 335                 340 gaa ggt caa aaa gcg gct aat gca gta gcg cta ctg gct tca aca aat               1152
Glu Gly Gln Lys Ala Ala Asn Ala Val Ala Leu Leu Ala Ser Thr Asn
            345                 350                 355 gct ggg caa gca act gag ttt ttt aac gaa ttt tgg tct tta tcg caa               1200
Ala Gly Gln Ala Thr Glu Phe Phe Asn Glu Phe Trp Ser Leu Ser Gln
            360                 365                 370 cca aca ggt gat tat cgt tac tac aat ggt tcg ctg tat atg tta gct               1248
Pro Thr Gly Asp Tyr Arg Tyr Tyr Asn Gly Ser Leu Tyr Met Leu Ala
    375                 380                 385 atg ctg cat gta tcg ggt aat ttt aag ttt tat aac aac acg ttt aat               1296
Met Leu His Val Ser Gly Asn Phe Lys Phe Tyr Asn Asn Thr Phe Asn
390                 395                 400                 405 taa                                                                            1299

<210> SEQ ID NO 159
<211> LENGTH: 432
<212> TYPE: PRT
<213> ORGANISM: Pseudoalteromonas haloplanktis

<400> SEQUENCE: 159

Met Lys Lys Pro Leu Gly Lys Ile Val Ala Ser Thr Ala Leu Leu Ile
        -25                 -20                 -15

Ser Val Ala Phe Ser Ser Ile Ala Ser Ala Phe Asn Asn Asn
    -10              -5              -1   1               5

Pro Ser Ser Val Gly Ala Asp Ser Ser Gly Ala Tyr Arg Asn Leu Ala
                10                  15                  20

Gln Glu Met Gly Lys Thr Asn Ile Gln Gln Lys Val Asn Ser Thr Phe
            25                  30                  35

Asp Asn Met Phe Gly Tyr Asn Thr Gln Gln Leu Tyr Tyr Pro Tyr
            40                  45                  50

Thr Glu Asn Gly Val Tyr Lys Ala His Tyr Ile Lys Ala Ile Asn Pro
 55                  60                  65

Asp Glu Gly Asp Ile Arg Thr Glu Gly Gln Ser Trp Gly Met Thr
 70                  75                  80                  85

Ala Ala Val Met Leu Asn Lys Gln Glu Glu Phe Asp Asn Leu Trp Arg
                90                  95                  100

Phe Ala Lys Ala Tyr Gln Lys Asn Pro Asp Asn His Pro Asp Ala Lys
            105                 110                 115
```

-continued

```
Lys Gln Gly Val Tyr Ala Trp Lys Leu Lys Leu Asn Gln Asn Gly Phe
        120                 125                 130
Val Tyr Lys Val Asp Glu Gly Pro Ala Pro Asp Gly Glu Glu Tyr Phe
        135                 140                 145
Ala Phe Ala Leu Leu Asn Ala Ser Ala Arg Trp Gly Asn Ser Gly Glu
150                 155                 160                 165
Phe Asn Tyr Tyr Asn Asp Ala Ile Thr Met Leu Asn Thr Ile Lys Ser
            170                 175                 180
Lys Leu Met Glu Asn Gln Ile Ile Arg Phe Ser Pro Tyr Ile Asp Asn
            185                 190                 195
Leu Thr Asp Pro Ser Tyr His Ile Pro Ala Phe Tyr Asp Tyr Phe Ala
            200                 205                 210
Asn Asn Val Thr Asn Gln Ala Asp Lys Thr Tyr Trp Arg Gln Val Ala
        215                 220                 225
Thr Lys Ser Arg Thr Leu Leu Lys Asn His Phe Thr Lys Val Ser Gly
230                 235                 240                 245
Ser Pro His Trp Asn Leu Pro Thr Phe Leu Ser Arg Leu Asp Gly Ser
            250                 255                 260
Pro Val Ile Gly Tyr Ile Phe Asn Asp Gln Ala Asn Pro Gly Gln Trp
            265                 270                 275
Tyr Glu Phe Asp Ala Trp Arg Val Ile Met Asn Val Gly Leu Asp Ala
            280                 285                 290
His Leu Met Gly Ala Gln Ala Trp His Lys Ser Ala Val Asn Lys Ala
        295                 300                 305
Leu Gly Phe Leu Ser Tyr Ala Lys Thr Asn Asn Ser Asn Asn Cys Tyr
310                 315                 320                 325
Glu Gln Val Tyr Ser Tyr Gly Gly Ala Gln Asn Arg Gly Cys Ala Gly
            330                 335                 340
Glu Gly Gln Lys Ala Ala Asn Ala Val Ala Leu Leu Ala Ser Thr Asn
            345                 350                 355
Ala Gly Gln Ala Thr Glu Phe Phe Asn Glu Phe Trp Ser Leu Ser Gln
            360                 365                 370
Pro Thr Gly Asp Tyr Arg Tyr Tyr Asn Gly Ser Leu Tyr Met Leu Ala
        375                 380                 385
Met Leu His Val Ser Gly Asn Phe Lys Phe Tyr Asn Asn Thr Phe Asn
390                 395                 400                 405
```